United States Patent
Agou et al.

(10) Patent No.: US 8,440,790 B2
(45) Date of Patent: May 14, 2013

(54) CRYSTAL STRUCTURE OF THE CCZ-LZ DOMAIN OF NEMO

(75) Inventors: Fabrice Agou, Paris (FR); Jeanne Chiaravalli, Paris (FR); Stéphane Duquerroy, Paris (FR); Elisabeth Fontan, Boulogne (FR); Olivera Grubisha, Surrey (GB); Monika Dorota Kaminska, Le Plessis Robinson (FR); Michel Veron, Paris (FR); Florence Cordier, Aix les Bains (FR)

(73) Assignees: Les Laboratoires Servier, Suresnes Cedex (FR); Institut Pasteur, Paris Cedex (FR)

( * ) Notice: Subject to any disclaimer, the term of this patent is extended or adjusted under 35 U.S.C. 154(b) by 107 days.

(21) Appl. No.: 12/735,671

(22) PCT Filed: Feb. 5, 2009

(86) PCT No.: PCT/FR2009/000127
§ 371 (c)(1),
(2), (4) Date: Mar. 14, 2011

(87) PCT Pub. No.: WO2009/115664
PCT Pub. Date: Sep. 24, 2009

(65) Prior Publication Data
US 2011/0159598 A1    Jun. 30, 2011

(30) Foreign Application Priority Data
Feb. 5, 2008 (FR) ...................................... 08 00605

(51) Int. Cl.
*C07K 14/00* (2006.01)
*G01N 31/00* (2006.01)
(52) U.S. Cl.
USPC .............................................. 530/300; 436/4
(58) Field of Classification Search .................. None
See application file for complete search history.

(56) References Cited

U.S. PATENT DOCUMENTS
6,864,355 B1    3/2005 May
2005/0220792 A1    10/2005 Agou

FOREIGN PATENT DOCUMENTS
WO    WO 2005/027959    3/2005

OTHER PUBLICATIONS

Moon et al., "A synergistic approach to protein crystallization: Combination of a fixed-arm carrier with surface entropy reduction", Protein Science, 2010, 19:901-913.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Agou, F., et al., "The trimerization domain of nemo is composed of the interacting C-terminal CC2 and LZ coiled-coil subdomins" Journal of Biological Chemistry, Vo. 279, No. 27, p. 27861-27869, Jul. 2, 2004.
Agou, F., et al., :Inhibition of NF-kB activation by peptides targeting NF-kB essential modulator (NEMO) oligomerization: Journal of Biological Chemistry, vol. 279, No. 52, p. 54248-54257, Dec. 24, 2004.
H. Sebban-Benin, et al., "Identification of TRAF6-dependent NEMO polyubiquitination sites through analysis of a new NEMO mutation causing incontinentia pigmenti" Human Molecular Genetics, vol. 16, No. 23, p. 2805-2815, Dec. 1, 2007.
International Search Report for PCT/FR2009/000127 of Sep. 28, 2009.
M. May, et al., "Selective inhibition of NF-kB activation by a peptide that blocks the interaction of NEMO with the IkB kinase complex" Science, vol. 289, p. 1550-1554, Sep. 1, 2000.
M. Rushe, "Structure of a NEMO/IKK-Association domain reveals architecture of the interaction site" Structure, vol. 16, No. 5, p. 798-808, May 7, 2008.
T. Blundell, et al., "High-throughput crystallography for led discovery in drug desing" Nature Reviews. vol. 1, No. 1, p. 45-54, Jan. 1, 2002.
Wyler, E., et al., "Inhibition of NF-kappaB activation with designed ankyrin-repeat proteins targeting the ubiquitin-binding/oligomerization damain of NEMO" Protein Science, vol. 16, No. 9, p. 2013-2022, Sep. 1, 2007.
Written Opinion of the International Searching Authority for PCT/FR2009/000127 of Sep. 16, 2010.

* cited by examiner

*Primary Examiner* — Suzanne M Noakes
(74) *Attorney, Agent, or Firm* — Hueschen and Sage

(57) ABSTRACT

The invention relates to a crystal of the CC2-LZ domain of the NEMO protein, in which the three-dimensional structure has been determined by X-ray diffraction at a resolution of about 3.25 A. The invention also relates to methods for the crystallization of the CC2-LZ domain. The CC2-LZ crystals and the information derived from the crystalline structures thereof are used for identifying and designing compounds interacting with CC2-LZ.

8 Claims, 11 Drawing Sheets

```
43-YHKARQKQIQEDWELAERLQREEEEAFA-70     Rabex-5 (SEQ ID NO:12)
    | :|        \  |||  ||
292 -PVLKAQADIYKADFQAERHAREKLVEKK- 319  NEMO NOA motif
    bcdefgabcdefgabcdefgabcdefga        (a 292-319 of SEQ ID NO:1)
    *  *        **   **  **
```

Figure 6

LKAQADIYKADFQAERHAREKLVEKKEYLQEQLEQLQREFNKL    Wild-type sequence LZ of NEMO (a 294-336 of SEQ ID NO:1)

(N-cap) TVAQLKAQIDIYEAEHQAVEHELEKLEEELEYIKEELEQLQREFNKLSG (C-cap)    Peptide PH4 (SEQ ID NO:6)

(N-cap) TVAQLKAQFDIHQAEHQAVKIELEKIEEDFEYIEEQLEQLQREFNKLKSG (C-cap)    Peptide P8RD (SEQ ID NO:7)

Figure 11

SEQUENCE LISTING

<160> NUMBER OF SEQ ID NOS: 13

<210> SEQ ID NO 1
<211> LENGTH: 412
<212> TYPE: PRT
<213> ORGANISM: Mus musculus

<400> SEQUENCE: 1

Met Asn Lys His Pro Trp Lys Asn Gln Leu Ser Glu Thr Val Gln Pro
1               5                   10                  15

Ser Gly Gly Pro Ala Glu Asp Gln Asp Met Leu Gly Glu Glu Ser Ser
            20                  25                  30

Leu Gly Lys Pro Ala Met Leu His Leu Pro Ser Glu Gln Gly Thr Pro
    35                  40                  45

Glu Thr Leu Gln Arg Cys Leu Glu Glu Asn Gln Glu Leu Arg Asp Ala
50                  55                  60

Ile Arg Gln Ser Asn Gln Met Leu Arg Glu Arg Cys Glu Glu Leu Leu
65                  70                  75                  80

His Phe Gln Val Ser Gln Arg Glu Glu Lys Glu Phe Leu Met Cys Lys
                85                  90                  95

Phe Gln Glu Ala Arg Lys Leu Val Glu Arg Leu Ser Leu Glu Lys Leu
                100                 105                 110

Asp Leu Arg Ser Gln Arg Glu Gln Ala Leu Lys Glu Leu Glu Gln Leu
            115                 120                 125

Lys Lys Cys Gln Gln Gln Met Ala Glu Asp Lys Ala Ser Val Lys Ala
        130                 135                 140

Gln Val Thr Ser Leu Leu Gly Glu Leu Gln Glu Ser Gln Ser Arg Leu
145                 150                 155                 160

Glu Ala Ala Thr Lys Asp Arg Gln Ala Leu Glu Gly Arg Ile Arg Ala
                165                 170                 175

Val Ser Glu Gln Val Arg Gln Leu Glu Ser Arg Glu Val Leu Gln
                180                 185                 190

Gln Gln His Ser Val Gln Val Asp Gln Leu Arg Met Gln Asn Gln Ser
            195                 200                 205

Val Glu Ala Ala Leu Arg Met Glu Arg Gln Ala Ala Ser Glu Glu Lys
        210                 215                 220

Arg Lys Leu Ala Gln Leu Gln Ala Ala Tyr His Gln Leu Phe Gln Asp
225                 230                 235                 240

Tyr Asp Ser His Ile Lys Ser Ser Lys Gly Met Gln Leu Glu Asp Leu
                245                 250                 255

Arg Gln Gln Leu Gln Gln Ala Glu Glu Ala Leu Val Ala Lys Gln Glu
            260                 265                 270

Leu Ile Asp Lys Leu Lys Glu Glu Ala Glu Gln His Lys Ile Val Met
        275                 280                 285

Glu Thr Val Pro Val Leu Lys Ala Gln Ala Asp Ile Tyr Lys Ala Asp
    290                 295                 300

Phe Gln Ala Glu Arg His Ala Arg Glu Lys Leu Val Glu Lys Lys Glu
305                 310                 315                 320

Tyr Leu Gln Glu Gln Leu Glu Gln Leu Gln Arg Glu Phe Asn Lys Leu
                325                 330                 335

Lys Val Gly Cys His Glu Ser Ala Arg Ile Glu Asp Met Arg Lys Arg
            340                 345                 350

His Val Glu Thr Pro Gln Pro Leu Leu Pro Ala Pro Ala His His
        355                 360                 365

Ser Phe His Leu Ala Leu Ser Asn Gln Arg Arg Ser Pro Pro Glu Glu
    370                 375                 380

Pro Pro Asp Phe Cys Cys Pro Lys Cys Gln Tyr Gln Ala Pro Asp Met
385                 390                 395                 400

Asp Thr Leu Gln Ile His Val Met Glu Cys Ile Glu
                405                 410

<210> SEQ ID NO 2
<211> LENGTH: 419
<212> TYPE: PRT
<213> ORGANISM: Homo sapiens

<400> SEQUENCE: 2

-continued

```
Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Ser Pro
            20                  25                  30

Leu Gly Lys Pro Ala Met Leu His Leu Pro Ser Glu Gln Gly Ala Pro
            35                  40                  45

Glu Thr Leu Gln Arg Cys Leu Glu Glu Asn Gln Glu Leu Arg Asp Ala
        50                  55                  60

Ile Arg Gln Ser Asn Gln Ile Leu Arg Glu Arg Cys Glu Glu Leu Leu
65                  70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
                100                 105                 110

Asp Leu Lys Arg Gln Lys Glu Gln Ala Leu Arg Glu Val Glu His Leu
            115                 120                 125

Lys Arg Cys Gln Gln Gln Met Ala Glu Asp Lys Ala Ser Val Lys Ala
            130                 135                 140

Gln Val Thr Ser Leu Leu Gly Glu Leu Gln Glu Ser Gln Ser Arg Leu
145                 150                 155                 160

Glu Ala Ala Thr Lys Glu Cys Gln Ala Leu Glu Gly Arg Ala Arg Ala
                165                 170                 175

Ala Ser Glu Gln Ala Arg Gln Leu Glu Ser Glu Arg Glu Ala Leu Gln
                180                 185                 190

Gln Gln His Ser Val Gln Val Asp Gln Leu Arg Met Gln Gly Gln Ser
            195                 200                 205

Val Glu Ala Ala Leu Arg Met Glu Arg Gln Ala Ala Ser Glu Glu Lys
            210                 215                 220

Arg Lys Leu Ala Gln Leu Gln Val Ala Tyr His Gln Leu Phe Gln Glu
225                 230                 235                 240

Tyr Asp Asn His Ile Lys Ser Ser Val Val Gly Ser Glu Arg Lys Arg
                245                 250                 255

Gly Met Gln Leu Glu Asp Leu Lys Gln Gln Leu Gln Gln Ala Glu Glu
            260                 265                 270

Ala Leu Val Ala Lys Gln Glu Val Ile Asp Lys Leu Lys Glu Glu Ala
            275                 280                 285

Glu Gln His Lys Ile Val Met Glu Thr Val Pro Val Leu Lys Ala Gln
            290                 295                 300

Ala Asp Ile Tyr Lys Ala Asp Phe Gln Ala Glu Arg Gln Ala Arg Glu
305                 310                 315                 320

Lys Leu Ala Glu Lys Lys Glu Leu Leu Gln Glu Gln Leu Glu Gln Leu
                325                 330                 335

Gln Arg Glu Tyr Ser Lys Leu Lys Ala Ser Cys Gln Glu Ser Ala Arg
            340                 345                 350

Ile Glu Asp Met Arg Lys Arg His Val Glu Val Ser Gln Ala Pro Leu
            355                 360                 365

Pro Pro Ala Pro Ala Tyr Leu Ser Ser Pro Leu Ala Leu Pro Ser Gln
            370                 375                 380

Arg Arg Ser Pro Pro Glu Glu Pro Pro Asp Phe Cys Cys Pro Lys Cys
385                 390                 395                 400

Gln Tyr Gln Ala Pro Asp Met Asp Thr Leu Gln Ile His Val Met Glu
                405                 410                 415

Cys Ile Glu
```

```
<210> SEQ ID NO 3
<211> LENGTH: 87
<212> TYPE: PRT
<213> ORGANISM: Mus musculus

<400> SEQUENCE: 3

Met Gln Leu Glu Asp Leu Arg Gln Gln Leu Gln Gln Ala Glu Glu Ala
1               5                   10                  15

Leu Val Ala Lys Gln Glu Leu Ile Asp Lys Leu Lys Glu Glu Ala Glu
            20                  25                  30

Gln His Lys Ile Val Met Glu Thr Val Pro Val Leu Lys Ala Gln Ala
        35                  40                  45

Asp Ile Tyr Lys Ala Asp Phe Gln Ala Glu Arg His Ala Arg Glu Lys
    50                  55                  60

Leu Val Glu Lys Lys Glu Tyr Leu Gln Glu Gln Leu Glu Gln Leu Gln
65                  70                  75                  80

Arg Glu Phe Asn Lys Leu Lys
                85

<210> SEQ ID NO 4
<211> LENGTH: 87
<212> TYPE: PRT
<213> ORGANISM: Homo sapiens

<400> SEQUENCE: 4

Met Gln Leu Glu Asp Leu Lys Gln Gln Leu Gln Gln Ala Glu Glu Ala
1               5                   10                  15

Leu Val Ala Lys Gln Glu Val Ile Asp Lys Leu Lys Glu Glu Ala Glu
            20                  25                  30

Gln His Lys Ile Val Met Glu Thr Val Pro Val Leu Lys Ala Gln Ala
        35                  40                  45

Asp Ile Tyr Lys Ala Asp Phe Gln Ala Glu Arg Gln Ala Arg Glu Lys
    50                  55                  60

Leu Ala Glu Lys Lys Glu Leu Leu Gln Glu Gln Leu Glu Gln Leu Gln
65                  70                  75                  80

Arg Glu Tyr Ser Lys Leu Lys
                85

<210> SEQ ID NO 5
<211> LENGTH: 136
<212> TYPE: PRT
<213> ORGANISM: Artificial
<220> FEATURE:
<223> OTHER INFORMATION: Ankyrin 1D5

<400> SEQUENCE: 5

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Asn Asp Arg Lys Gly Asn
        35                  40                  45

Thr Pro Leu His Leu Ala Ala Asp Tyr Asp His Leu Glu Ile Val Glu
    50                  55                  60

Val Leu Leu Lys His Gly Ala Asp Val Asn Ala His Asp Asn Asp Gly
65                  70                  75                  80

Ser Thr Pro Leu His Leu Ala Ala Leu Phe Gly His Leu Glu Ile Val
                85                  90                  95
```

```
Glu Val Leu Leu Lys His Gly Ala Asp Val Asn Ala Gln Asp Lys Phe
                100                 105                 110
Gly Lys Thr Ala Phe Asp Ile Ser Ile Asp Asn Gly Asn Glu Asp Leu
        115                 120                 125
Ala Glu Ile Leu Gln Lys Leu Asn
        130                 135

<210> SEQ ID NO 6
<211> LENGTH: 49
<212> TYPE: PRT
<213> ORGANISM: Artificial
<220> FEATURE:
<223> OTHER INFORMATION: Peptide probe

<400> SEQUENCE: 6

Thr Val Ala Gln Leu Lys Ala Gln His Asp Ile Tyr Glu Ala Glu His
1               5                   10                  15
Gln Ala Val Glu His Glu Leu Glu Lys Leu Glu Glu Glu Leu Glu Tyr
                20                  25                  30
Ile Lys Glu Glu Leu Glu Gln Leu Gln Arg Glu Phe Asn Lys Leu Ser
        35                  40                  45
Gly

<210> SEQ ID NO 7
<211> LENGTH: 50
<212> TYPE: PRT
<213> ORGANISM: Artificial
<220> FEATURE:
<223> OTHER INFORMATION: Peptide probe

<400> SEQUENCE: 7

Thr Val Ala Gln Leu Lys Ala Gln Phe Asp Ile His Gln Ala Glu His
1               5                   10                  15
Gln Ala Val Lys His Glu Leu Glu Lys Ile Glu Glu Asp Phe Glu Tyr
                20                  25                  30
Ile Glu Glu Gln Leu Glu Gln Leu Gln Arg Glu Phe Asn Lys Leu Lys
        35                  40                  45
Ser Gly
    50

<210> SEQ ID NO 8
<211> LENGTH: 26
<212> TYPE: DNA
<213> ORGANISM: Artificial
<220> FEATURE:
<223> OTHER INFORMATION: Nucleotide primer

<400> SEQUENCE: 8
ccccatatgg agcgccaggc cgcctc                                            26

<210> SEQ ID NO 9
<211> LENGTH: 31
<212> TYPE: DNA
<213> ORGANISM: Artificial
<220> FEATURE:
<223> OTHER INFORMATION: Nucleotide primer

<400> SEQUENCE: 9
tgaggaagcg gatgtcgagt agctcgaggg g                                      31

<210> SEQ ID NO 10
<211> LENGTH: 30
<212> TYPE: DNA
```

-continued

```
<213> ORGANISM: Artificial
<220> FEATURE:
<223> OTHER INFORMATION: Nucleotide primer

<400> SEQUENCE: 10
ggggaattct aataggcacc tctggaagag                                        30

<210> SEQ ID NO 11
<211> LENGTH: 28
<212> TYPE: DNA
<213> ORGANISM: Artificial
<220> FEATURE:
<223> OTHER INFORMATION: Nucleotide primer

<400> SEQUENCE: 11
catggagtgc attgagtagc tcgagggg                                          28

<210> SEQ ID NO 12
<211> LENGTH: 28
<212> TYPE: PRT
<213> ORGANISM: Mus musculus

<400> SEQUENCE: 12

Tyr His Lys Ala Arg Gln Arg Gln Ile Gln Glu Asp Trp Glu Leu Ala
1               5                   10                  15

Glu Arg Leu Gln Arg Glu Glu Glu Glu Ala Phe Ala
            20                  25

<210> SEQ ID NO 13
<211> LENGTH: 8
<212> TYPE: PRT
<213> ORGANISM: Artificial Sequence
<220> FEATURE:
<223> OTHER INFORMATION: FLAG TAG

<400> SEQUENCE: 13

Asp Tyr Lys Asp Asp Asp Asp Lys
1               5
```

CRYSTAL STRUCTURE OF THE CCZ-LZ DOMAIN OF NEMO

The present invention relates to a crystal of the CC2-LZ domain of NEMO of a size and quality sufficient to allow structural data to be obtained by X-ray diffraction crystallography.

The invention relates more particularly to use of the crystallographic data and of the three-dimensional structure of the CC2-LZ domain of NEMO in identifying, modelling and designing compounds modulating the NF-κB signalling pathway.

The NF-κB pathway is activated in response to various extracellular stimuli such as bacterial LPS, proinflammatory cytokines such as IL-1 and TNFα (M. S. Hayden and S. Ghosh, Signaling to NF-kappaB, Genes Dev 18 (2004), no. 18, 2195-2224). The signals are generally transmitted from the cell receptors to the IKK complex, a pivotal regulator of the NE-κB signalling pathway. The IKK complex is composed of two kinases, IKKα and IKKβ, and a regulatory protein, NEMO (NF-κB essential modulator) (S. Yamaoka et al., Complementation cloning of NEMO, a component of the IkappaB kinase complex essential for NF-kappaB activation, Cell 93 (1998), no. 7, 1231-1240). NEMO plays a crucial role in integrating the signals coming from various stimuli and in bringing about activation of the IKK complex.

Figure 1:
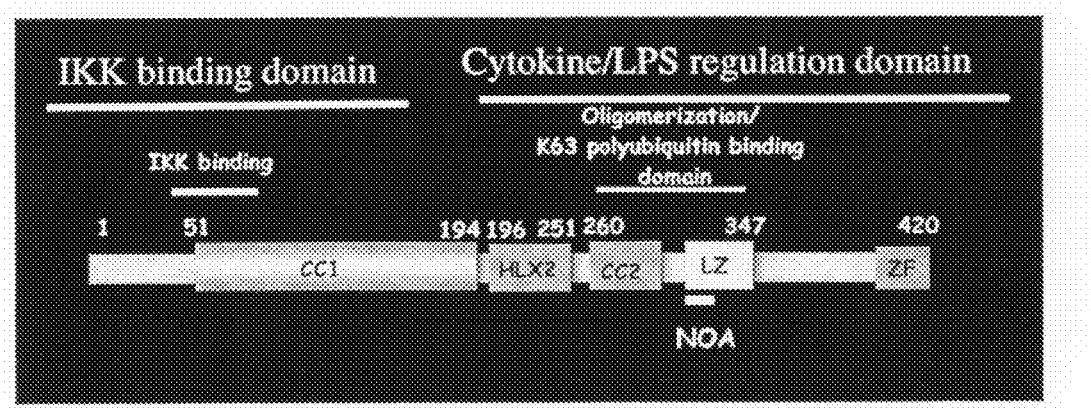

The NEMO protein is composed, at its N-terminal portion, of an IKK complex-binding domain and, at its C-terminal portion, of an oligomerisation domain (FIG. 1). It is to be noted that murine (SEQ ID NO.1) and human (SEQ ID NO:2) NEMO proteins have a high degree of sequence homology except for a 7 amino acid insertion in the human protein just upstream of a specific domain, CC2.

Activation of the IKK complex proceeds by way of a mechanism linked to the capacity of the NEMO protein to oligomerise by trans-activation via an IKKK kinase or by trans-autoactivation via the dimerisation of IKK kinases.

At present, the mechanism of activation of the IKK complex via NEMO has not been completely elucidated although numerous reports show that oligomerisation and binding to K-63 polyubiquitins involving the minimal CC2-LZ domain play an essential role (J. L. Poyet et al., Activation of the IkappaB kinases by RIP via Ikkgamma/NEMO-mediated oligomerization, J Biol Chem 275 (2000), no. 48, 37966-37977) (F. Agou et al., Inhibition of NF-kappab activation by peptides targeting NF-kappaB essential modulator (NEMO) oligomerization, J Biol Chem 279 (2004), no. 52, 54248-54257) (C. K. Ea et al., Activation of IKK by TNFalpha requires site-specific ubiquitination of RIP1 and polyubiquitin binding by NEMO, Mol Cell 22 (2006), no. 2, 245-257) (C. J. Wu, et al., Sensing of lys 63-linked polyubiquitination by NEMO is a key event in NF-kappaB activation, Nat Cell Biol 8 (2006), no. 4, 398-406). All mutations located in CC2-LZ that disrupt the oligomerisation of NEMO or binding to K-63 polyubiquitin chains (polyUb K-63) inhibit IKK activity following stimulation by cytokines (E. Vinolo et al., A point mutation in NEMO associated with anhidrotic ectodermal dysplasia with immunodeficiency pathology results in destabilization of the oligomer and reduces lipopolysaccharide- and tumour necrosis factor-mediated NF-kappaB activation, J Biol Chem 281 (2006), no. 10, 6334-6348).

The minimal oligomerisation domain CC2-LZ of NEMO (aa 251-337 in the mouse, aa 258-344 in humans) is composed of two successive motifs, a coiled-coil motif CC2 (aa 251-290 in the mouse, aa 258-297 in humans) and a leucine zipper motif LZ (aa 293-337 in the mouse, aa 300-344 in humans). Variations of one or two amino acids can be seen at the ends of the CC2-LZ domain depending on the software used for prediction of the CC2 and LZ structures.

Once activated, the IKK complex phosphorylates IκB proteins, thereby triggering degradation of the latter by the 26S proteasome and then releasing the NF-κB transcription factors, which are sequestered into the cytoplasm by IκB proteins. The NF-κB transcription factor then migrates into the nucleus and regulates the expression of genes involved in inflammation, immunity, apoptosis and cell survival. Constitutive activation of the NF-κB pathway is involved in oncogenesis.

It is observed in various solid tumours and leukaemias and also in autoimmune and inflammatory diseases (D. S. Basseres and A. S. Baldwin, Nuclear factor-kappaB and inhibitor of kappaB kinase pathways in oncogenic initiation and progression, Oncogene 25 (2006), no. 51, 6817-6830) (M. S. Hayden et al., NF-kappaB and the immune response, Oncogene 25 (2006), no. 51, 6758-6780) (J. Inoue et al., NF-kappaB activation in development and progression of cancer, Cancer Sci 98 (2007), no. 3, 268-274). Accordingly, the IKK complex has been considered to be a target of great interest for the development of anti-inflammatory and anti-tumour compounds (M. A. Calzado et al., NF-kappaB inhibitors for the treatment of inflammatory diseases and cancer, Curr Med Chem 14 (2007), no. 3, 367-376) (T. D. Gilmore and M. Herscovitch, Inhibitors of NF-kappaB signaling: 785 and counting, Oncogene 25 (2006), no. 51, 6887-6899) (F. D'Acquisto et al., Inhibition of nuclear factor kappa B (NF-kB): An emerging theme in anti-inflammatory therapies, Mol Interv 2 (2002), no. 1, 22-35). Designing compounds that target NEMO rather than kinases makes it possible to selectively suppress the stimuli-dependent IKK activity and thereby to reduce the cytotoxicity of said compounds.

In an effort to elucidate the mechanisms underlying regulation of the NF-κB signalling pathway, the crystalline structure of the IKK complex, and especially of the regulator protein NEMO, is being studied. Knowledge of the three-dimensional structure moreover is an essential advantage in establishing the sites of interaction with ligands resulting from actual screening. This three-dimensional structure is also a source of information in the virtual screening or in silico modelling approach. The crystallisation process of NEMO has been studied, without success, by D. Gopaul et al., M. Delepierre and F. Cordier (not published). There may be mentioned, especially, the fruitless attempts at crystallisation of the CC2-LZ domain bearing the zinc finger motif (aa 251-412 of NEMO) or without that motif (aa 251-388 of NEMO). Therefore, such work directed at obtaining crystals of the NEMO protein and of the CC2-LZ domain in particular has hitherto been unsuccessful.

The present invention is accordingly aimed at proposing a new strategy for obtaining crystallisation of the CC2-LZ domain of the NEMO protein. This alternative strategy is based on increasing the rigidity of the minimal oligomerisation domain of NEMO. The crystal structure was solved by crystallography by X-ray diffraction using a resolution of 3.25 Å. Subsequently, the crystal structure was solved by crystallography by X-ray diffraction using a resolution of 2.9 Å.

The present invention relates also to methods of crystallisation of the CC2-LZ domain. The CC2-LZ crystals and the information derived therefrom can be analysed for the purpose of identifying or designing compounds which enter into interaction with CC2-LZ.

The present invention accordingly relates to a crystal of the CC2-LZ domain of mammalian NEMO, the CC2-LZ peptide domain of which has the amino acid sequence SEQ ID NO.3 and the peptide variants of which derive from said amino acid sequence.

In the context of the invention, the terms "crystal", "crystal of the CC2-LZ domain", "crystal of a CC2-LZ complex" and "co-crystal of the CC2-LZ domain" are used without distinction and refer to a crystal of a complex comprising at least two separate entities, one entity of the crystal according to the invention being the CC2-LZ domain or one of its variants.

The present invention relates also to a crystal of a complex of the CC2-LZ domain of mammalian NEMO, the CC2-LZ peptide domain of which has the amino acid sequence SEQ ID NO.4 and the peptide variants of which derive from said amino acid sequence.

An "amino acid sequence" has to be understood as a peptide sequence isolated from the natural context. It especially comprises sequences that have been isolated, chemically synthesised and/or purified and possibly modified by genetic engineering.

"Variants" are understood to mean amino acid sequences of the peptides described hereinbefore comprising conservative substitutions or conservative point mutations and having substantially the same properties as the peptides respectively encoded by the sequences SEQ ID NO.3 and SEQ ID NO.4 or, that is, the capacity to oligomerise and to bind to K-63 polyubiquitins.

The present invention furthermore relates to a crystal of a complex of the CC2-LZ domain of mammalian NEMO, the unit cell parameters of which are as follows:
 a=b=63.5±5 Å;
 c=437.5±5 Å; and
 $\alpha=\beta=\gamma=90°$;
and the crystal has a space group $P4_32_12$.

According to the common understanding in the context of the invention, the expression "unit cell parameter" denotes the parameters a, b and c of the unit cell of the crystal, corresponding to the lengths of the non-coplanar base vectors (a, b, c) and the angles $\alpha$, $\beta$ and $\gamma$ formed between the vectors (a, b, c). The angle $\alpha$ is the angle between vectors b and c, $\beta$ the angle between vectors a and c, and $\gamma$ the angle between vectors a and c. The unit cell is understood to be the parallelepiped constructed by the vectors (a, b, c).

The symmetry operations which leave a crystal substantially unchanged, a crystal being an infinite object formed by the repetition of a finite motif, are groups. When the crystal is of three dimensions, these are then referred to as "space groups".

It is to be understood that the crystal of a complex of the CC2-LZ domain, according to the present invention, is not limited to the native CC2-LZ domain. The crystal of a complex according to the invention does indeed include mutants of native CC2-LZ. Such mutants are obtained by addition, deletion or substitution of at least one amino acid in the polypeptide sequence of native CC2-LZ and have substantially the same three-dimensional structure as that of the native CC2-LZ domain.

"Having substantially the same three-dimensional structure" is understood to mean having a set of atomic structure coordinates obtained from a crystal which have an average deviation less than or equal to 5 Å, preferably 2 Å, when they are superimposed on the atomic structure coordinates of native CC2-LZ from which the mutant has been derived when at least 50% to about 100% of the alpha carbon atoms of native CC2-LZ are included in the superimposition.

The invention relates preferably to a co-crystal comprising the CC2-LZ domain of mammalian NEMO and at least one ankyrin or a fragment thereof capable of stabilising the complex formed with the CC2-LZ domain, the unit cell parameters of which are as follows:
 a=b=63.5±5 Å;
 c=437.5±5 Å; and
 $\alpha=\beta=\gamma=90$;
and the co-crystal of which has a space group $P4_32_12$.

An "ankyrin" is understood to refer to modular proteins of various sizes involved in numerous protein-protein interactions. The ankyrins are genetically conserved proteins as they are found in bacteria, plants, fungi and animals and their structure is based on repeating structural units of about 33 amino acids.

An "ankyrin fragment" according to the invention is capable of binding and stabilising the complex formed with the CC2-LZ domain of NEMO.

The invention relates preferably to a crystal of the CC2-LZ domain of a mammalian NEMO protein and an ankyrin 1D5 (SEQ ID NO.5). The invention relates also to a crystal of the CC2-LZ domain of a mammalian NEMO protein and an ankyrin 2A1 or 2F6 as described by Wyler et al. (Inhibition of NF-kappaB activation with designed ankyrin-repeat proteins targeting the ubiquitin-binding/oligomerization domain of NEMO, Protein Sci 16 (2007), no. 9, 2013-2022).

In order to facilitate crystallogenesis, the CC2-LZ domain is in fact complexed with an ankyrin 1D5, which binds to the CC2-LZ with a strong affinity and rigidifies the peptide domain. The diffraction profile obtained from crystals of CC2-LZ complexed with, the ankyrin 1D5 is used to determine the three-dimensional structure of the CC2-LZ by molecular replacement.

The ankyrin or ankyrin fragment is preferably complexed with the LZ motif of the CC2-LZ domain, more specifically in order to stabilise it. The LZ motif is in fact more flexible and thermodynamically more unstable than the CC2 motif of the CC2-LZ domain.

The co-crystal of the CC2-LZ domain of NEMO with an ankyrin protein can be obtained by a crystallisation method comprising the following steps:
 incubation of at least one ankyrin or ankyrin fragment and the CC2-LZ domain;
 co-crystallisation of the ankyrin or ankyrin fragment/CC2-LZ protein complex by growing crystals by vapour diffusion.

In a preferred embodiment, the CC2-LZ crystallisation method corresponds to the method as described in Example 1.

The invention relates preferably to the crystal of a complex of the CC2-LZ domain of NEMO or the co-crystal of CC2-LZ having the crystallographic coordinates described in Table 1.

Figure 2:
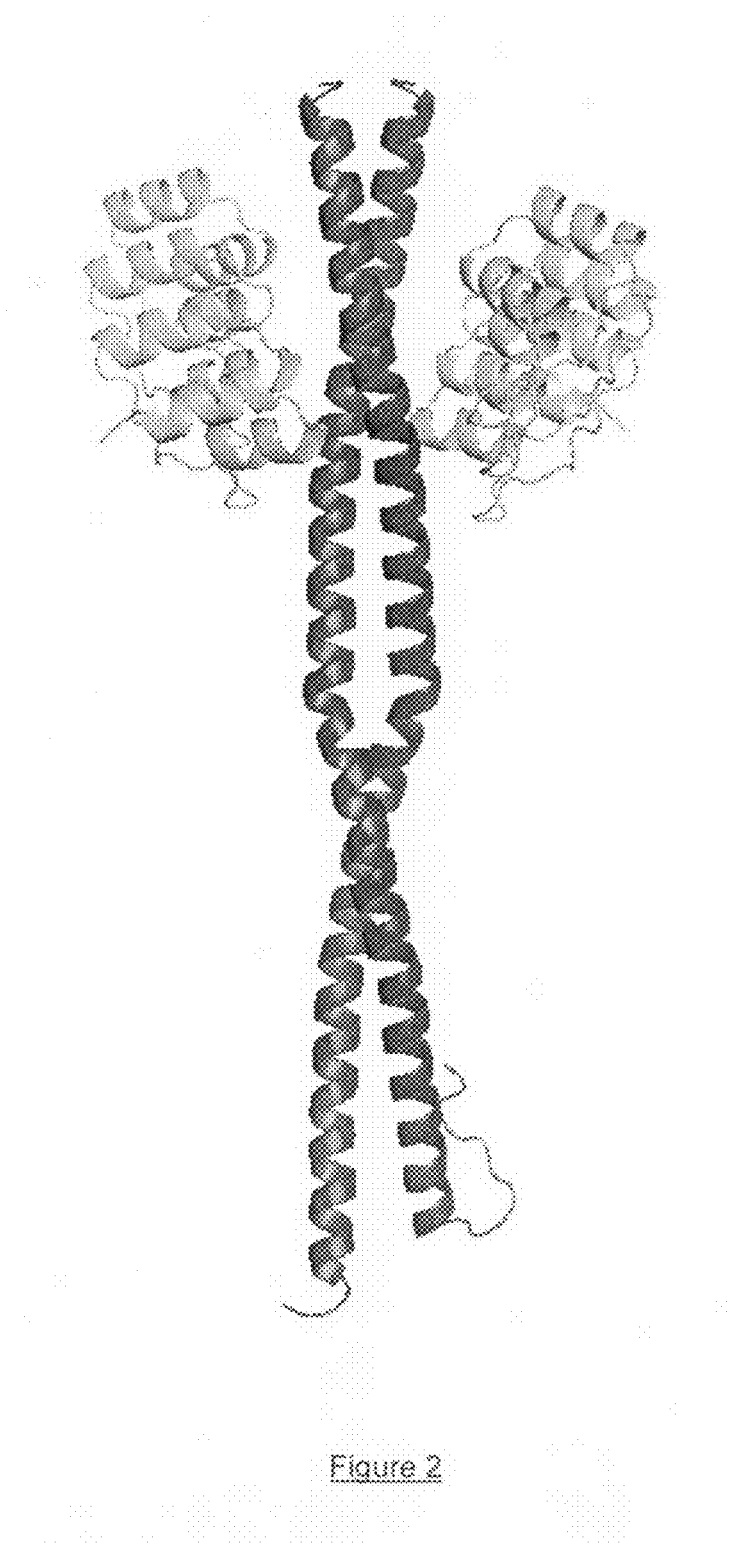
Figure 3:
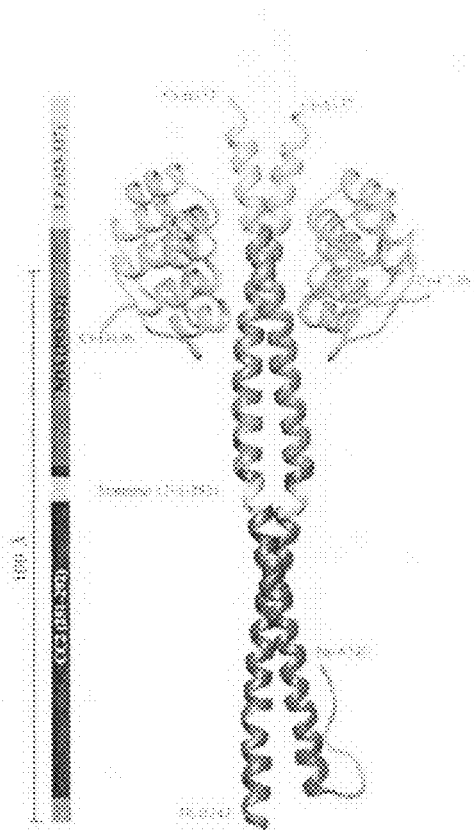

Preferably, the crystal and co-crystal of the CC2-LZ domain according to the invention are in each case defined by their three-dimensional structure obtained by X-ray diffraction, which is shown in FIGS. 2 and 3.

The three-dimensional structure of CC2-LZ forms an elongated dimer composed of two parallel $\alpha$ helices which associate with one another to form a coiled-coil structure (FIG. 2) (FIG. 3). The CC2-LZ dimer interacts with two ankyrin 1D5 molecules, each ankyrin forming contacts with the $\alpha$ helices on the two LZ chains. Three residues located between the CC2 motif and the LZ motif (aa 291-293, mouse numbering) form a pseudo coiled-coil. The domain of binding to the K-63 polyubiquitin chains, which is described in Ea et al., is composed of 67 amino acids (259-325 human numbering, 252-318 mouse numbering) corresponding to the C-terminal region of the CC2 and the N-terminal region of the LZ. By cross-referencing data obtained from the three-dimensional structure, from directed mutagenesis and from CC2-LZ sequence alignment, the region forming the site of binding to the ubiquitins was determined as being between amino acids 293 and 323 in the murine polypeptide sequence of NEMO (aa 300-330 human numbering).

The three-dimensional structure of the CC2-LZ crystal and co-crystal according to the invention is obtained by a method comprising the following steps:
    obtaining a crystal or co-crystal of the CC2-LZ protein;
    exposure of the crystal to X-rays;
    collection of X-ray diffraction data;
    use of that data to calculate the electron density map of said crystal;
    building and refinement of the model starting from the electron density map.

Advantageously, the method of determining the three-dimensional structure of CC2-LZ corresponds to the method as described in Example 1.

The invention relates also, on the one hand, to the crystal of murine CC2-LZ protein comprising the mutation Val316Pro (V316Pro) and/or the mutation Phe305Ala (F305A) and, on the other hand, to the crystal of human CC2-LZ protein likewise comprising the mutation Ala323Pro (A323P) and/or the mutation Phe312Ala (F312A).

Figure 4:
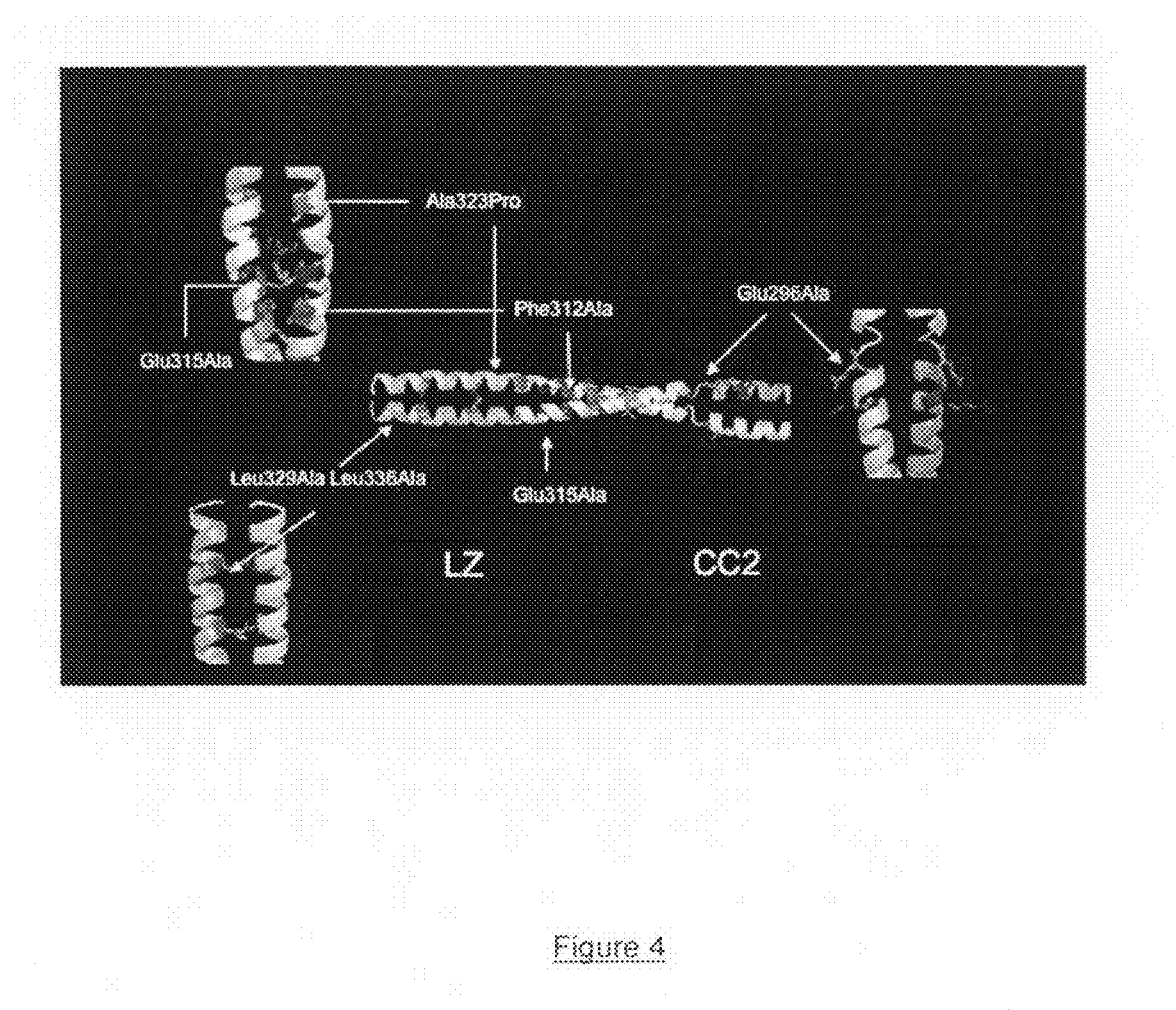

The various mutations obtained by directed mutagenesis in the human CC2-LZ protein are shown in FIG. 4. The mutation Glu296Ala (E296A, position 289 in the mouse) is located at the C-terminal end of the CC2 and is outside the site of interaction with the ubiquitins (position aa 259-325, human numbering, and aa 252-318, mouse numbering). The mutations Phe312Ala (F312A, position 305 in the mouse) and Glu315Ala (E315A, position 308 in the mouse) are located within the site of binding to the ubiquitins. The mutations Glu315Ala and Ala323Pro (A323P, position 316 in the mouse) are implicated in two human pathologies, is respectively anhydrotic ectodermal dysplasia with immunodeficiency (AED-ID) (R. Doffinger et al., Genetic heterogeneity of mendelian susceptibility to mycobacterial infection, Microbes Infect 2 (2000), no. 13, 1553-1557) and incontinentia pigmenti (IP) (A. Smahi et al., Genomic rearrangement in nemo impairs NF-kappaB activation and is a cause of incontinentia pigmenti. The international incontinentia pigmenti (IP) consortium, Nature 405 (2000), no. 6785, 466-472). The double mutation Leu329Ala Leu336Ala (L329A L336A, positions 322 and 329, respectively, in the mouse) is located in the leucine zipper domain of CC2-LZ.

Figure 5:
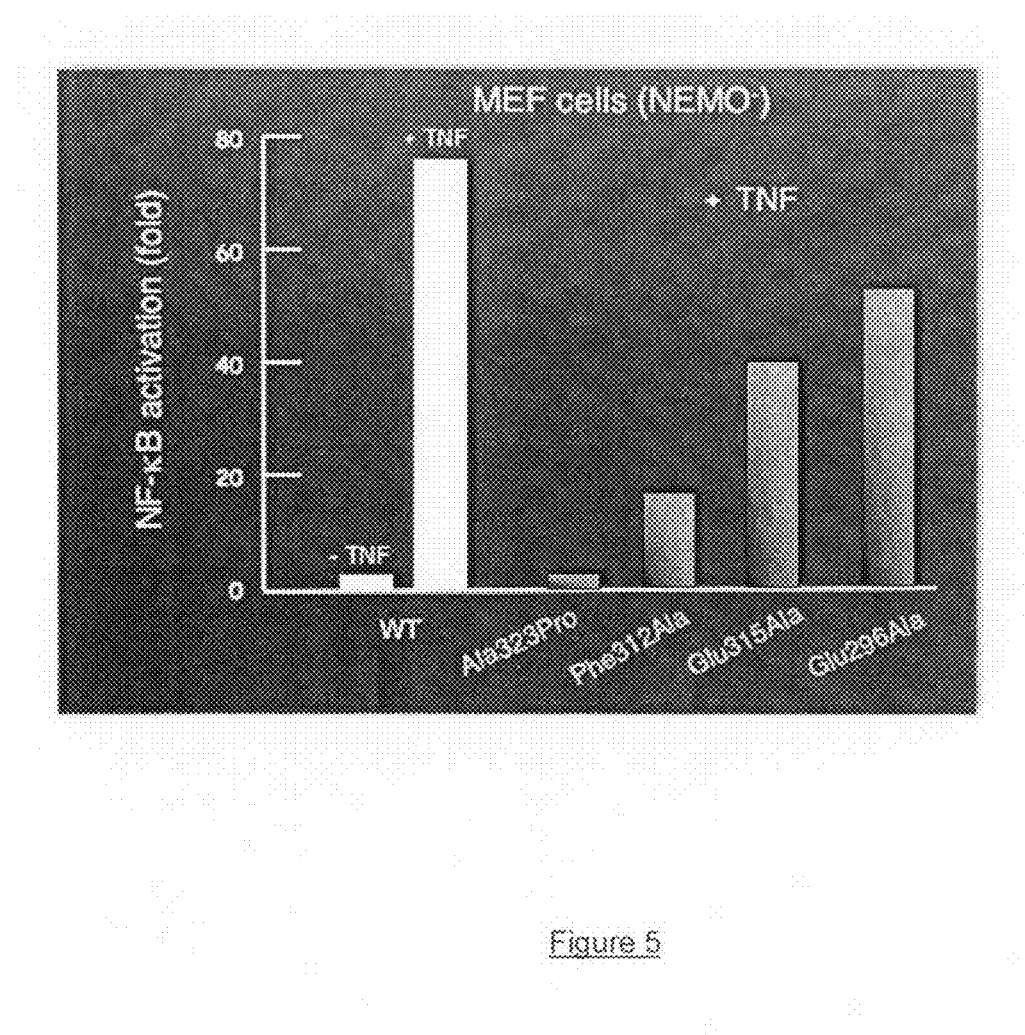

The capabilities of the wild-type NEMO protein and of the above-defined mutant NEMO proteins in restoring activation of the NF-κB pathway in response to the proinflammatory cytokine TNF-α are compared and illustrated in FIG. 5. For that purpose, NEMO-deficient mouse embryo fibroblasts (MEF) are transiently co-transfected on the one hand with the plasmid coding for the Igκ-luciferase reporter gene and on the other hand with the plasmids coding for the various proteins, and then stimulated with TNFα for 24 hours. The wild-type protein completely restores the NF-κB pathway whereas TNFα-dependent activation of the NF-κB pathway is affected by the mutant proteins in differing degrees. The mutations A323P and F312A give rise to the two strongest inhibitions, namely 95% and 78% inhibition, respectively.

For the mutation A323P, which is the cause of a severe form of incontinentia pigmenti, a fault in NEMO dimerisation is the cause of the inactivation of the NE-κB pathway, a result similar to that obtained by Sebban-Benin et al. (Identification of TRAF6-dependent NEMO polyubiquitination sites through analysis of a new NEMO mutation causing incontinentia pigmenti, Hum Mol Genet 16 (2007), no. 23, 2805-2815).

The protein of the CC2-LZ domain of NEMO mutated at position F312A shows an elution profile, on gel filtration, which is the same as that of the wild-type CC2-LZ protein, indicating that this mutation does not affect the stability of the dimer but rather modifies activation of the NF-κB pathway (FIG. 5). Study of this mutant demonstrates for the first time that the fault in activation is not due to a fault in dimerisation of the site of interaction with the ubiquitins but rather to a fault in interaction with K63 polyubiquitin chains, as shown by Ea et al. Consequently, these results underline the possibility of inhibiting the NF-κB pathway, either by modifying the dimerisation of NEMO or by inhibiting the interaction of NEMO with polyubiquitin chains.

The present invention makes possible, on the one hand, the structural validation, by directed mutagenesis, of an active conformation of NEMO and, on the other hand, the determination of the residues that are critical for oligomerisation of the protein and, as a consequence thereof, for activation of the IKK complex as well as those involved in binding to the K-63 polyubiquitins.

The invention relates preferably to a method of identifying compounds capable of binding to the CC2-LZ domain of NEMO, on the basis of crystallographic data obtained in said invention. Peptides mimicking the CC2 or LZ sequence are shown as being capable of disrupting the oligomerisation of NEMO and thereby suppressing activation of the NF-κB pathway in cells in culture. Advantageously, the invention relates to the elaboration and identification of compounds interfering with the oligomerisation of the CC2-LZ domain, which inhibits the binding of said domain to K-63 polyubiquitins.

In the context of the invention, "compounds" are understood to be all chemical molecules which inhibit the dimerisation of the CC2-LZ domain of NEMO or which inhibit the interaction of the CC2-LZ domain of NEMO with the polyubiquitin chains.

The crystallographic data of the domain of NEMO has accordingly made it possible to design peptides having high affinity for this protein. The CC2-LZ: CC2-LZ interactions which make it possible to form in vivo active complexes of NEMO involve numerous non-covalent linkages. As destabilisation of those complexes by small molecules is very difficult to demonstrate in a high-throughput screening context, it is necessary to identify a peptide probe which mimics that interaction, over a reduced portion of the peptide, and which has a greater affinity. Such a peptide probe can then be labelled with a fluorescent group and its association with CC2-LZ demonstrated by a fluorescence polarisation measurement. This system makes it possible to subsequently set up high-throughput screening campaigns. In order to have a rational and effective approach for creating this peptide probe, knowledge of the three-dimensional structure of the CC2-LZ domain is absolutely indispensable. Already two peptides, referred to as P8RD and PH4, have been designed using this principle (FIG. 11).

The peptide probes according to the invention are preferably the peptide PH4 and the peptide P8RD, which have the amino acid sequences SEQ ID NO.6 and SEQ ID NO.7, respectively.

P8RD has an affinity of 60 nM whereas the peptide PH4 has an affinity of 170 nM. These measurements are carried out at pH 7 and at ambient temperature in a stringent buffer corresponding to 20 mM Tris-Acetate-MES containing 200 mM potassium chloride and 0.5% Tween 20. They are carried out by fluorescence polarisation with the aid of peptides coupled at the N-terminal with the fluorophores Fluorescein or Cy5.

For forming the peptide probes of the invention, the peptides can be coupled to any kind of fluorophore.

Finally, the present invention relates to a method of identifying compounds of the dimerisation of NEMO or of the interaction of NEMO with polyubiquitin chains between a peptide probe according to the invention and the CC2-LZ domain of NEMO. This HTS (High-Throughput Screening) method comprises the following steps:
- bringing said peptide and said CC2-LZ domain of NEMO into contact;
- adding the compound under test;
- measuring the fluorescence polarisation in the presence of the compound under test;
- comparing said measurement in the absence of the compound under test.

The structure-activity relationships of these peptides and also the three-dimensional structure of the CC2-LZ target of NEMO will make it possible to design other peptides having affinities of the nM order of magnitude by favouring the zone of interaction of NEMO for ubiquitin and/or polyubiquitin chains having any kind of side chain (K63, K48, K6, N-terminal).

Figure 7:
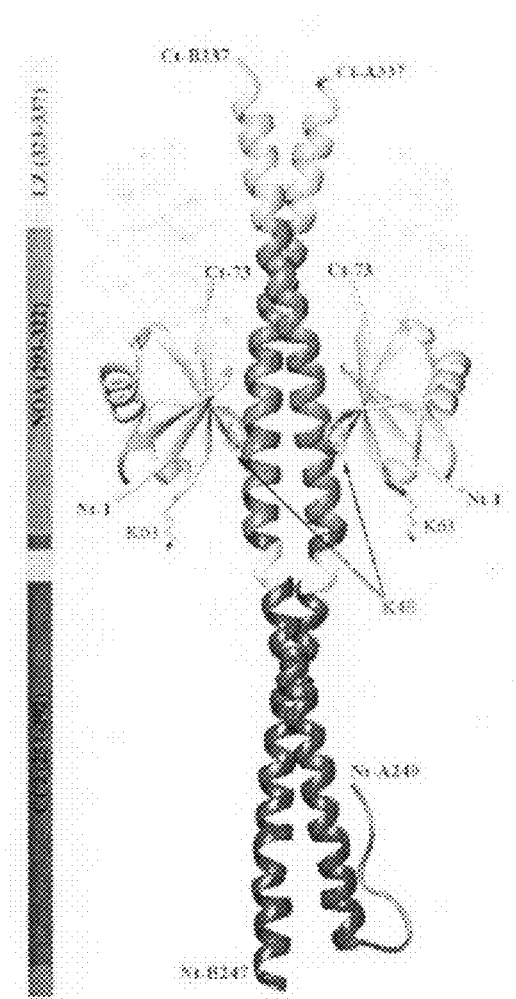
Figure 8:
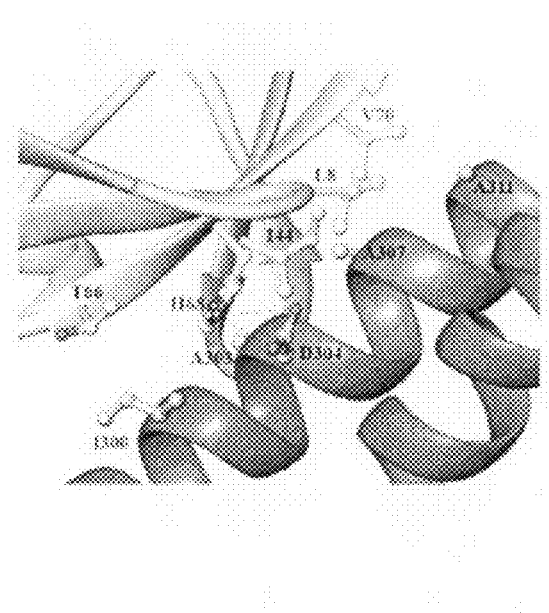
Figure 10:
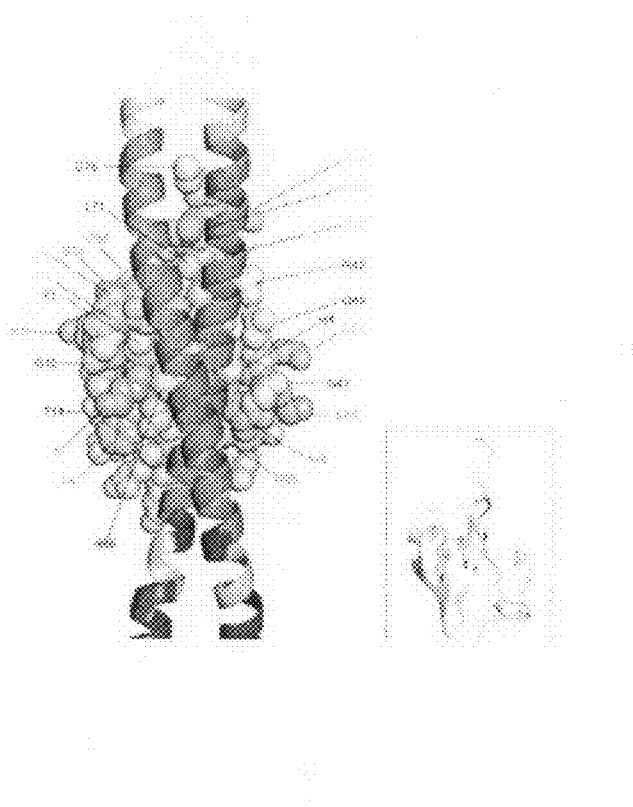

The model of the CC2-LZ domain of NEMO/ubiquitin complex is shown in FIGS. 7, 8 and 10. The "model of the... complex" is understood to mean the three-dimensional structure of the CC2-LZ/ubiquitin complex.

Figure 9:
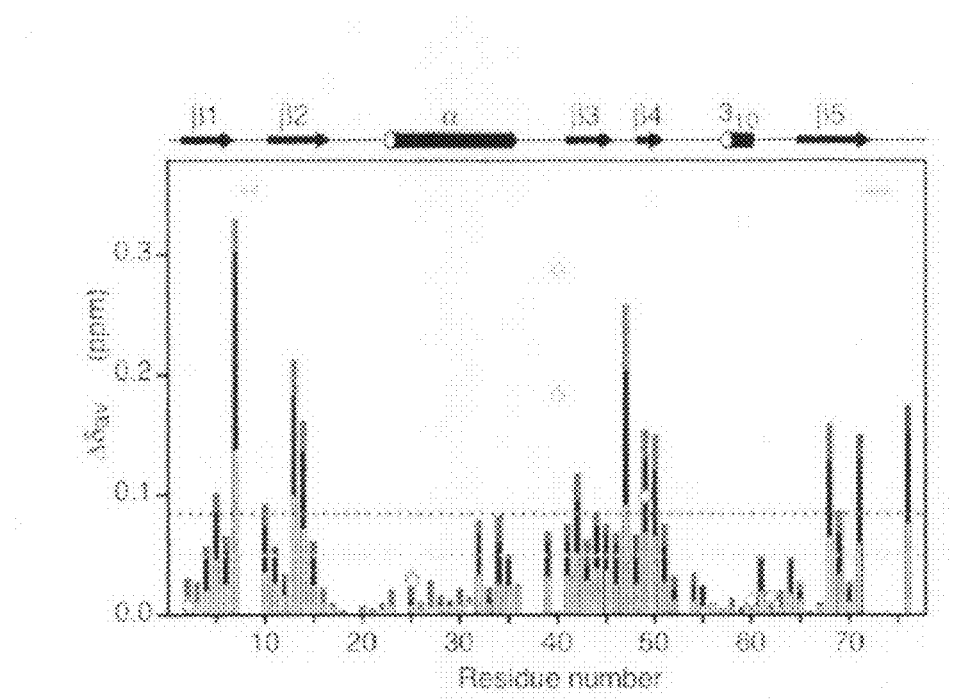

The model of the CC2-LZ of NEMO/ubiquitin complex was built on the basis of structural information obtained from the Rabex-5 IUIM/ubiquitin complex used (Lee S. et al. Structural basis for ubiquitin recognition and autoubiquitination by Rabex-5. Nat Struct Mol Biol 13, 264-271, 2006). The model of the CC2-LZ/ubiquitin complex was verified experimentally by means of the chemical shifts observed by NMR of the interaction between ubiquitin and the CC2-LZ domain of NEMO (FIG. 9).

The three-dimensional structure of the CC2-LZ domain of NEMO is deduced from the model of the CC2-LZ/ubiquitin complex. This three-dimensional structure of CC2-LZ can be used for in silico designing or in silico screening of compounds capable of binding to the CC2-LZ domain of NEMO. The present invention accordingly relates to a method of designing compounds capable of binding to the CC2-LZ domain of NEMO using the three-dimensional structure of the CC2-LZ domain obtained from the crystallographic coordinates of the crystal according to the invention.

Finally, the invention relates to compounds identified by the above identification and design methods. Preferably, these compounds inhibit dimerisation of the CC2-LZ domain of NEMO or inhibit the interaction of the CC2-LZ domain of NEMO with the polyubiquitin chains.

The present invention is illustrated—but without being limited as a result—by the Figures and the Examples that follow:

FIG. 1: Representation of the NEMO protein.

FIG. 2: Three-dimensional structure of the CC2-LZ domain of NEMO complexed with two ankyrin molecules. The two sub-units of the CC2-LZ are in dark grey whilst the ankyrins are in light grey.

FIG. 3: Structure of the CC2-LZ domain of NEMO in the complex with the ankyrins 1D5. Ribbon diagram of the complex in a side view. The NEMO helices are shown in levels of grey depending on the domain: CC2, NOA or LZ. The ankyrin 1D5 chains are in dark grey in a position to the side.

FIG. 4: Locations, within the human CC2-LZ domain, of the various mutations obtained by directed mutagenesis. The domain of binding to the polyubiquitins is shown in white. The numbering used for the amino acids corresponds to that of the human protein.

FIG. 5: Effect of the various mutations on activation of the NF-κB pathway. The numbering of the mutations corresponds to that of the human CC2-LZ protein.

FIG. 6: Model of the CC2-LZ domain of NEMO/ubiquitin complex. Alignment sequence between Rabex-5 (MIU/IUIM) (SEQ ID NO:12) (first line) and NEMO (NOA motif) (amino acids 292-319 of SEQ ID NO:1 (second line), with the positions of the structural motif of NOA (a-g) below. The continuous and broken vertical lines denote identical and similar residues, respectively. The diagonal line indicates spatially similar residues from the aspect of the structural model according to the invention. Strictly conserved residues in the NOA motif are indicated by *.

FIG. 7: Side view of the CC2-LZ of NEMO/ubiquitin complex. The NEMO helices are coloured as in FIG. 3. The ubiquitin molecules are in grey in a position to the side and the ankyrin 1D5 molecules of the co-crystal are in semi-transparent light grey also in a position to the side.

FIG. 8: Close-up view of the NOA/ubiquitin interface. The residues involved in the interaction are drawn in a "ball and stick" type representation, with the carbon atoms in grey (ubiquitin) and white (NEMO).

FIG. 9: Chemical shifts observed by NMR of ubiquitin bound to the CC2-LZ domain of NEMO. Average variations in the chemical shift $\Delta\delta_{av}$ as a function of the chemical residue. The elements of the corresponding secondary structure are shown above the graph of the chemical shifts.

FIG. 10: Representation of the interaction between ubiquitin and the NOA region of the CC2-LZ domain. Dark grey is used for the residues involved in a strong interaction. The residues of ubiquitins are shown in light grey for $0.05<\Delta\delta_{av}<0.085$ ppm.

FIG. 11: Peptide sequences PH4 (SEQ JD NO:6) and P8RD (SEQ ID NO:7), which were designed taking into account the crystallographic structure of the CC2-LZ domain.

EXAMPLE 1

Crystallographic Structure of the CC2-LZ Domain 1.1 Construction of Plasmids, Expression and Purification of Ankyrin 1D5 and CC2-LZ Proteins Evolving the ankyrin 1D5 is carried out by ribosome display using the N2C DARPin (designed ankyrin repeat protein) library (H. K. Binz et al., High-affinity binders selected from designed ankyrin repeat protein libraries, Nat Biotechnol 22 (2004), no. 5, 575-582) for selection. The results of this study and also the amino acids of the ankyrin 1D5 which differ from the initial model are described in the publication of Wyler et al. The cDNA of the ankyrin 1D5 is cloned into the vector pQE30 (Qiagen) in phase with a histidine tag located at the N-terminal end. The pQE30-1D5 plasmid is introduced into a strain of *E. coli* XL-1 blue and expression of the 1D5 protein is induced by adding IPTG 1 mM to the culture medium for 3-3.5 hours at 37° C. The bacteria are recovered by sedimentation, washed in Tris/HCl buffer 50 mM pH 8 and lysed by sonication in a Tris/HCl buffer 50 mM pH8, NaCl 0.5M (buffer A) in the presence of protease inhibitors (Complete free EDTA, Roche). The soluble extract is recovered after centrifuging and is loaded onto a nickel column pre-equilibrated with buffer A. The 1D5 protein is eluted using a linear gradient of imidazole. The fractions containing the protein are collected and then dialysed against a buffer of 20 mM Tris/HCl pH 7.6, 50 mM KCl using dialysis bags having a cut-off threshold of 6-8 kDa (Spectra/Por). The protein is concentrated by ultrafiltration in Amicon tubes (Millipore) having a cut-off threshold of 5 kDa.

The CC2-LZ (SEQ ID NO.3) (aa 251-337 of murine NEMO) is cloned into the plasmid pET28 in phase with a histidine tag located at the N-terminal end. This domain corresponds to residues 258-344 of human NEMO (SEQ ID NO.4). The protein is expressed in a strain of *E. coli*, BL21-gold (DE3) and purified on a nickel column as described for the purification of the ankyrin 1D5. The CC2-LZ protein is then purified on a cation exchange Poros 20-HS column (Perseptive Biosystem). The column is pre-equilibrated in a buffer of 50 mM MES pH 7.1, 50 mM KCl and the proteins are eluted by a linear gradient of KCl. The fractions of interest are collected and dialysed against a buffer of 20 mM Tris/HCl pH 8.0, 100 mM KCl, and then concentrated by ultrafiltration.

The purity of the protein is determined as greater than 98% according to analysis by electrophoresis under denaturing conditions and staining with Coomassie blue. The protein concentration is determined by the method of Bradford and by measurement of the absorption at 280 nm using a coefficient of absorption of 2312 $M^{-1}cm^{-1}$ for CC2-LZ and 1490 $M^{-1}cm^{-1}$ for 1D5.

The 1D5 and CC2-LZ proteins are incubated together for 30 minutes in ice and the complex is purified on a Superdex 200 HR column (Pharmacia) equilibrated in a buffer of 20 mM Tris/HCl pH 8, 100 mM KCl. The binding stoichiometry in the complex is 1:1. The complex is concentrated by ultrafiltration to obtain a protein concentration of 10-13 mg/ml.

1.2 Crystallisation Conditions for the Ankyrin 1D5/CC2-LZ Protein Complex

Crystals grew in reproducible manner under two different conditions (Jena Bioscience ref: 3A4 and 8B5). The reservoir solution 3A4 contains: 10% PEG 40000, 5% isopropanol, 100 mM Na Hepes pH 7.5, and the solution 8B5 contains: 5% MPD (2-methyl-2,4-pentadiol), 5% ethanol, 100 mM Na Hepes pH7.5. The crystals grew under vapour diffusion in suspended droplets seeded with micro-crystals (microseeding). 1 µl of the protein complex is added to 1 µl of the reservoir solution and equilibrated under vapour diffusion at 18-20° C. for more than 36 hours. Micro-crystals (0.1 µl) obtained starting from fragments of crystals are introduced into the drop. After seeding, the crystals grow in a few days to reach a size of 300×150×20 µm. For cryogenic protection, the crystals are plunged for 30 seconds into the reservoir solution additionally Containing PEG 4000 and 20% C glycerol for 3A4 or 30% MPD for 8B5. The crystals are mounted in nylon loops and frozen very rapidly before data collection.

1.3 Analysis of the Ankyrin 1D5/CC2-LZ Protein Complex

The X-ray diffraction data (1=0.9794 Å) are recorded using the PX06SA beamline at the SLS (Swiss Synchrotron Light Source) and a Pilatus 6M hybrid pixel detector (crystal-detector distance: 640 mm and 0.5° oscillations per step at 100° K). The data sets are processed using the XDS program package. All the crystals belong to the same space group $P4_32_12$ with the following crystal unit cell parameters: a=b=63.5 Å and c=437.5 Å.

1.4 Determination and Refinement of the Crystallographic Structure of the CC2-LZ Domain of NEMO The structure was solved by molecular replacement using the AmoRe program using the atomic model of ankyrin 2JAB (Zhand et al., to be published) and a theoretical model for the NEMO helices. The data between 15 and 3.5 Å resolution were used for these calculations. After analysis of the electron density map, manual building of the model was carried out using O. Refinement with TLS Was performed using the Refmac program. The model was refined maintaining non-crystallographic symmetry constraints for the ankyrin (chain C and D) and for the NEMO helices (residues 251 to 290, N-terminal region, and residues 294 to 337, C-terminal region). The final model contains 26 molecules of solvent and one molecule of glycerol, with a resolution $R_{cryst}/R_{free}$ of 20.8%/26.1% at 3.5 Å. The stereochemical data and the R factors are given in Table 1. The stereochemical quality of the model was analysed using PRO-CHECK.

1.5 Obtaining the Model of the CC2-LZ Domain of NEMO/Ubiquitin Complex

The best candidates for modelling the CC2-LZ/ubiquitin complex are structures containing a simple α helix such as UIM (ubiquitin-interacting motif) and inverted UIM (IUIM or MIU) obtained from Rabex-5. After comparison of the sequences, sequence identity of about 20% between the NOA motif of the CC2-LZ domain and the IUIM of Rabex-5 was observed (FIG. 6). The IUIM motif of Rabex-5 binds to the hydrophobic region of ubiquitin centred on the residue Ile 44. It has also been shown that this same residue Ile 44 is necessary in the interaction between NEMO and the polyubiquitin K63 (Bloor S. et al. Signal processing by its coil zipper domain activates IKK gamma, Proc Natl Acad Sci USA 105, 1279-84, 2008), which clearly suggests that ubiquitin binds in equivalent manner to the NOA motif of NEMO and to the Rabex-5 IUIM. Consequently, the known three-dimensional structure of the Rabex-5 IUIM/ubiquitin complex was used as a guide in elaboration of the model of the CC2-LZ/ubiquitin complex.

In order to respect the symmetry, two molecules of ubiquitin are bound to the NEMO helix. The complementarity index for the CC2-LZ/ubiquitin complex is 0.69, which is higher than that of the CC2-LZ/ankyrin 1D5 complex (SC=0.65). The molecules of ubiquitin bind to the hydrophobic region, of NOA, the binding site of which partially overlaps the ankyrins 1D5. The residue D304 of NOA is embedded in the centre of the CC2-LZ/ubiquitin interface and forms H bonds with the H68 residue of the ubiquitin. The other main interactions involve non-polar residues, including Ala 307, corresponding to the invariant Ala residue found in the IUIM motif and the residue F305 involved in the NEMO/polyubiquitin K63 interaction. These interactions mask the hydrophobic surface of NOA, which is not favoured in energy terms, from solvent, which contributes to the stabilisation of this region. The three-dimensional structure of the CC2-LZ/ubiquitin model is further verified by means of various experiments such as directed mutagenesis or chemical shifts observed by NMR (FIG. 9).

| Crystal parameters | |
| --- | --- |
| Parameters of the unit cell (Å) | a = b = 63.5 c = 437.5 |
| Space group | $P4_32_12$ |
| Diffraction data[a] | |
| Temperature (K) | 100 |
| Resolution range (Å) | 30-3.25 |
| Reflections observed (I)0 (I)) | 280.552 (15.169) |
| Unique reflections (I 0 (I)) | 28.729 (2.134) |
| Filling level (%) | 99.1 (99.4) |
| $R_{sym}$[b] | 0.140 (0.449) |
| I/(I) | 5.5 (1.7) |
| Monomers per asymmetric unit | 2 |
| Solvent occupation (%) | 73.3 |
| Matthews coefficient (Å³/Da) | 4.6 |

-continued

| Refinement | |
|---|---|
| Resolution (Å) | 20-3.25 |
| R$_{factor}$ | 0.208 |
| R$_{free}$ | 0.261 |
| rmsd$^c$ of bond lengths (Å) | 0.013 |
| rmsd of bond angles (°) | 1.573 |
| Ramachandran diagram (%) | |
| Residues in the "Most favoured" conformation | 91.8 |
| Residues in the "Additionally allowed" conformation | 8.0 |
| Residues in the "Generously allowed" conformation | 0.2 |
| Residues in the "Disallowed" conformation | 0.0 |
| Data sets and refinement: | |

$^a$Values in parentheses are given for the external resolution envelope: 3.43-3.25 Å.
$^b$Rsym = S |I − (I)|/S (I), where I is the measurement intensity of each reflection and (I) is the mean intensity of that reflection.
$^c$(rmsd) Mean square deviation.

EXAMPLE 2

Structural Validation by Directed Mutagenesis of an Active Conformation of NEMO 2.1 Construction of Plasmids and Directed Mutagenesis The cDNA coding for the human CC2-LZ domain of NEMO, designated Tax CC2-LZ and extending from Met 215 to Glu 362 (human numbering), is obtained by PCR using the following two nucleotide primers: NEMO 1 SEQ ID NO.8 (5'-CCCCATATGGAGCGCCAGGCCGCCTC) and NEMO 2 SEQ ID NO.9 (5'-TGAGGAAGCGGATGTCGAG-TAGCTCGAGGGG). This cDNA is introduced between the NdeI and XhoI restriction sites of a bacterial expression vector, pET-28b (Novagen), to generate the vector pET-NEMO.

The FLAG tag corresponding to the sequence DYKD-DDDK (SEQ ID NO:13) is introduced into a mammalian expression vector, pcDNA3, between the HindIII and EcoRI restriction sties to create the plasmid pcFLAG.

The cDNA coding for the human form of NEMO is amplified by PCR using the following two nucleotide primers, NEMO 3 SEQ ID NO.10 (5'-GGGGAATTCTAATAG-GCACCTCTGGAAGAG) and NEMO 4 SEQ ID NO.11 (5'-CATGGAGTGCATTGAGTAGCTCGAGGGG) and is then introduced into the pcFLAG plasmid between the EcoRI and XhoI restriction sites to create the plasmid pcNEMO-WT.

The point mutations Glu296Ala, Phe312Ala, Glu315Ala, Ala323Pro and the double mutant Leu329Ala Leu336Ala are introduced on the one hand into the bacterial vector pET-NEMO-WT and on the other hand into the mammalian vector pcDNA3/NEMO-WT using the directed mutagenesis technique whose protocol is described in the kit "Quikchange II Site-Directed Mutagenesis" from Stratagene.

2.2 Functional Complementation in Mouse Embryo Fibroblasts

NEMO-deficient mouse embryo fibroblasts (MEF) are cultured in cell culture jars and transiently transfected with a mixture containing: 0.2 µg of a plasmid pEF1 coding for β-galactosidase, 0.5 µg of a plasmid containing the Igk-luciferase reporter gene and 2 µg of plasmids expressing the different variants of NEMO. Twenty-four hours after transfection, the cells are activated with TNFα (20 ng/ml) for 24 hours. The cells are then recovered and then lysed in 110 µl of a buffer of 25 mM Tris/Phosphate pH 7.8, 8 mM MgCl$_2$, 1% Triton, 1 mM dithiothreitol, 15% to glycerol to which a cocktail of proteases is added (Roche). The cell lysate is centrifuged at 13 000 rpm for 20 min at 4° C. The activity of the reporter gene is measured.

2.3 Expression and Purification of the Wild-Type Protein and of the Mutant F312A Purification is carried out using an AKTA Purifier 100 apparatus (Amersham Pharmacia Biotech). Purification of the various proteins is performed starting from a culture of 3 litres of BL21-Gold D3 bacteria (Stratagene) transformed with the various pET 28 plasmids and in the presence of kanamycin (50 µg/ml). Expression of the proteins is induced using 1 mM IPTG at 37° C. for 4 hours. After centrifuging for 20 min at 6000 g at 4° C., the bacteria are washed in a buffer of Tris/HCl 100 mM pH 8 containing 10 mM MgCl$_2$. The bacterial sediments are frozen at −20° C. The sediments are then resuspended in an extraction buffer (Tris/HCl 50 mM pH 8, KCl 20 mM and glycerol 5%) containing a mixture of protease inhibitors (Complete EDTA-free, Roche) at a concentration of 2 ml/g of bacteria and then broken up using a French Press under a pressure of 1500 psi. The bacterial lysate is subjected 3 times to 10 seconds of sonication at 90 W, thereby making it possible to reduce the viscosity of the medium by fragmentation of the DNA. The lysate is then diluted 2.5 times in a buffer of Tris/HCl 50 mM pH8, NaCl 1M and is then centrifuged at 10 000 g for 30 min at 4° C. The supernatant is then placed on a 20 ml Ni-NTA Superflow affinity column (Qiagen) previously equilibrated in the aforesaid buffer. After washing the column over an entire night to remove all the non-adsorbed proteins and also the DNA, the proteins are eluted by a linear gradient (0-500 mM) of imidazole (ACS, Merck) in the equilibration buffer of the column. The fractions containing the protein of interest are collected and dialysed against a buffer of HEPES 20 mM pH 7.5, KCl 50 mM, EDTA 1 mM. The dialysate, whose pH is brought to 6 using MES 1M, is loaded onto a Poros 20-HS cation exchange column (Perseptive Biosystem) previously equilibrated in a buffer of MES 50 mM pH 6, KCl 50 mM. Elution is carried out by means of a linear gradient of KCl (50 mM-1M). The protein fractions are combined and then concentrated by ultrafiltration (Amicon-Ultra with a cut-off threshold of 10 000) and dialysed against a buffer of Tris/HCl 20 mM pH 8, KCl 100 mM. The proteins are stored in aliquots at −80° C. The purity of the various proteins is determined as >98% according to analysis by electrophoresis under denaturing conditions and staining with Coomassie blue. The protein concentration is determined by is measurement of the absorbance at 280 nm using a molar extinction coefficient of 5960 M$^{-1}$ cm$^{-1}$.

2.4 Gel Filtration of the Wild-Type Protein and the Mutant F312A

The gel filtration experiments are carried out at 4° C. on a Superdex 75 HR 10/30 column (Amersham Biosciences). The column is equilibrated in a buffer of Tris/HCl 50 mM pH7.5, NaCl 200 mM, DTE 0.2 mM at 4° C. with a flow rate of 0.5 ml/min. A sample of constant volume (200 µl), at a concentration of 0.3 µM, is injected onto the column at a rate of 0.5 ml/min. The proteins are diluted in the equilibration buffer of the column and allowed to stand at 4° C. for 2 hours before injection in order to allow them to equilibrate. In order to detect elution of the proteins, an RF-10 AXL spectrofluorimeter (Shimadzu) is connected on-line to the AKTA apparatus. The intrinsic fluorescence is recorded, measuring the emission of fluorescence of the tyrosine residues at 310 nm after excitation at 280 nm.

TABLE 1

Chains A & B = Nemo CC2LZ with numbering corresponding to entry O88522
Nemo aa = M251 to L336
chain A starts at 242 and chain B at 247 (extra aa from the his tag)
chains C& D = ankyrin 1D5 (aa 12 to 136)
REMARK Written by O version 11.0.5
REMARK Fri Nov  9 11:30:17 2007

| | | | | | | | | | | |
|---|---|---|---|---|---|---|---|---|---|---|
| CRYST1 | | 63.499 | | 63.499 | 437.472 | 90.00 | 90.00 | 90.00 | | |
| ORIGX1 | | | 1.000000 | 0.000000 | 0.000000 | | 0.00000 | | | |
| ORIGX2 | | | 0.000000 | 1.000000 | 0.000000 | | 0.00000 | | | |
| ORIGX3 | | | 0.000000 | 0.000000 | 1.000000 | | 0.00000 | | | |
| SCALE1 | | | 0.015748 | 0.000000 | 0.000000 | | 0.00000 | | | |
| SCALE2 | | | 0.000000 | 0.015748 | 0.000000 | | 0.00000 | | | |
| SCALE3 | | | 0.000000 | 0.000000 | 0.002286 | | 0.00000 | | | |
| ATOM | 1 | N | VAL | A | 242 | 56.460 | 37.782 | 235.855 | 1.00 | 91.30 | 7 |
| ATOM | 2 | CA | VAL | A | 242 | 57.909 | 38.147 | 235.886 | 1.00 | 90.83 | 6 |
| ATOM | 3 | CB | VAL | A | 242 | 58.315 | 39.047 | 234.639 | 1.00 | 90.87 | 6 |
| ATOM | 4 | CG1 | VAL | A | 242 | 59.704 | 38.671 | 234.120 | 1.00 | 90.25 | 6 |
| ATOM | 5 | CG2 | VAL | A | 242 | 57.284 | 38.950 | 233.503 | 1.00 | 90.33 | 6 |
| ATOM | 6 | C | VAL | A | 242 | 58.376 | 38.794 | 237.240 | 1.00 | 90.98 | 6 |
| ATOM | 7 | O | VAL | A | 242 | 59.397 | 39.509 | 237.240 | 1.00 | 91.19 | 8 |
| ATOM | 8 | N | PRO | A | 243 | 57.655 | 38.548 | 238.390 | 1.00 | 90.67 | 7 |
| ATOM | 9 | CA | PRO | A | 243 | 58.202 | 39.037 | 239.689 | 1.00 | 90.27 | 6 |
| ATOM | 10 | CB | PRO | A | 243 | 57.126 | 38.653 | 240.723 | 1.00 | 90.07 | 6 |
| ATOM | 11 | CG | PRO | A | 243 | 56.375 | 37.540 | 240.096 | 1.00 | 90.45 | 6 |
| ATOM | 12 | CD | PRO | A | 243 | 56.371 | 37.842 | 238.596 | 1.00 | 90.65 | 6 |
| ATOM | 13 | C | PRO | A | 243 | 59.499 | 38.312 | 240.017 | 1.00 | 89.62 | 6 |
| ATOM | 14 | O | PRO | A | 243 | 59.553 | 37.077 | 239.966 | 1.00 | 89.75 | 8 |
| ATOM | 15 | N | ARG | A | 244 | 60.541 | 39.067 | 240.341 | 1.00 | 88.70 | 7 |
| ATOM | 16 | CA | ARG | A | 244 | 61.872 | 38.470 | 240.464 | 1.00 | 87.55 | 6 |
| ATOM | 17 | CB | ARG | A | 244 | 62.947 | 39.465 | 239.995 | 1.00 | 87.84 | 6 |
| ATOM | 18 | CG | ARG | A | 244 | 63.014 | 39.608 | 238.442 | 1.00 | 88.81 | 6 |
| ATOM | 19 | CD | ARG | A | 244 | 63.118 | 41.070 | 237.958 | 1.00 | 90.11 | 6 |
| ATOM | 20 | NE | ARG | A | 244 | 63.866 | 41.926 | 238.892 | 1.00 | 90.83 | 7 |
| ATOM | 21 | CZ | ARG | A | 244 | 64.326 | 43.151 | 238.622 | 1.00 | 90.77 | 6 |
| ATOM | 22 | NH1 | ARG | A | 244 | 64.139 | 43.706 | 237.425 | 1.00 | 90.57 | 7 |
| ATOM | 23 | NH2 | ARG | A | 244 | 64.988 | 43.819 | 239.559 | 1.00 | 90.60 | 7 |
| ATOM | 24 | C | ARG | A | 244 | 62.142 | 37.865 | 241.857 | 1.00 | 86.31 | 6 |
| ATOM | 25 | O | ARG | A | 244 | 63.298 | 37.625 | 242.226 | 1.00 | 86.43 | 8 |
| ATOM | 26 | N | GLY | A | 245 | 61.057 | 37.604 | 242.605 | 1.00 | 84.69 | 7 |
| ATOM | 27 | CA | GLY | A | 245 | 61.092 | 36.869 | 243.883 | 1.00 | 82.05 | 6 |
| ATOM | 28 | C | GLY | A | 245 | 61.335 | 37.747 | 245.101 | 1.00 | 80.21 | 6 |
| ATOM | 29 | O | GLY | A | 245 | 62.456 | 37.794 | 245.628 | 1.00 | 80.36 | 8 |
| ATOM | 30 | N | SER | A | 246 | 60.286 | 38.426 | 245.565 | 1.00 | 77.76 | 7 |
| ATOM | 31 | CA | SER | A | 246 | 60.425 | 39.428 | 246.624 | 1.00 | 75.11 | 6 |
| ATOM | 32 | CB | SER | A | 246 | 59.634 | 40.689 | 246.220 | 1.00 | 75.41 | 6 |
| ATOM | 33 | OG | SER | A | 246 | 59.738 | 41.711 | 247.201 | 1.00 | 75.87 | 8 |
| ATOM | 34 | C | SER | A | 246 | 60.011 | 38.954 | 248.029 | 1.00 | 72.89 | 6 |
| ATOM | 35 | O | SER | A | 246 | 59.422 | 39.727 | 248.773 | 1.00 | 72.73 | 8 |
| ATOM | 36 | N | HIS | A | 247 | 60.322 | 37.708 | 248.392 | 1.00 | 70.26 | 7 |
| ATOM | 37 | CA | HIS | A | 247 | 59.913 | 37.120 | 249.697 | 1.00 | 68.09 | 6 |
| ATOM | 38 | CB | HIS | A | 247 | 60.277 | 35.641 | 249.762 | 1.00 | 67.82 | 6 |
| ATOM | 39 | CG | HIS | A | 247 | 59.186 | 34.734 | 249.301 | 1.00 | 67.04 | 6 |
| ATOM | 40 | ND1 | HIS | A | 247 | 58.145 | 34.350 | 250.118 | 1.00 | 66.33 | 7 |
| ATOM | 41 | CE1 | HIS | A | 247 | 57.331 | 33.558 | 249.446 | 1.00 | 66.01 | 6 |
| ATOM | 42 | NE2 | HIS | A | 247 | 57.810 | 33.409 | 248.224 | 1.00 | 66.25 | 7 |
| ATOM | 43 | CD2 | HIS | A | 247 | 58.969 | 34.136 | 248.107 | 1.00 | 66.19 | 6 |
| ATOM | 44 | C | HIS | A | 247 | 60.439 | 37.801 | 250.974 | 1.00 | 66.82 | 6 |
| ATOM | 45 | O | HIS | A | 247 | 61.560 | 38.276 | 251.027 | 1.00 | 66.82 | 8 |
| ATOM | 46 | N | MET | A | 248 | 59.632 | 37.847 | 252.018 | 1.00 | 65.13 | 7 |
| ATOM | 47 | CA | MET | A | 248 | 60.064 | 38.545 | 253.196 | 1.00 | 63.85 | 6 |
| ATOM | 48 | CB | MET | A | 248 | 58.872 | 39.115 | 253.929 | 1.00 | 63.42 | 6 |
| ATOM | 49 | CG | MET | A | 248 | 58.207 | 40.253 | 253.206 | 1.00 | 61.36 | 6 |
| ATOM | 50 | SD | MET | A | 248 | 58.774 | 41.914 | 253.596 | 1.00 | 57.47 | 16 |
| ATOM | 51 | CE | MET | A | 248 | 60.164 | 41.666 | 254.723 | 1.00 | 57.52 | 6 |
| ATOM | 52 | C | MET | A | 248 | 60.801 | 37.570 | 254.070 | 1.00 | 64.18 | 6 |
| ATOM | 53 | O | MET | A | 248 | 61.670 | 37.954 | 254.840 | 1.00 | 64.07 | 8 |
| ATOM | 54 | N | ALA | A | 249 | 60.452 | 36.294 | 253.928 | 1.00 | 64.58 | 7 |
| ATOM | 55 | CA | ALA | A | 249 | 61.043 | 35.208 | 254.706 | 1.00 | 64.98 | 6 |
| ATOM | 56 | CB | ALA | A | 249 | 59.958 | 34.470 | 255.465 | 1.00 | 64.98 | 6 |
| ATOM | 57 | C | ALA | A | 249 | 61.812 | 34.241 | 253.811 | 1.00 | 65.59 | 6 |
| ATOM | 58 | O | ALA | A | 249 | 62.166 | 34.563 | 252.674 | 1.00 | 65.95 | 8 |
| ATOM | 59 | N | SER | A | 250 | 62.059 | 33.042 | 254.310 | 1.00 | 66.12 | 7 |
| ATOM | 60 | CA | SER | A | 250 | 62.839 | 32.087 | 253.553 | 1.00 | 66.93 | 6 |
| ATOM | 61 | CB | SER | A | 250 | 63.744 | 31.314 | 254.508 | 1.00 | 66.77 | 6 |
| ATOM | 62 | OG | SER | A | 250 | 64.646 | 30.481 | 253.810 | 1.00 | 65.76 | 8 |
| ATOM | 63 | C | SER | A | 250 | 61.970 | 31.123 | 252.738 | 1.00 | 67.78 | 6 |
| ATOM | 64 | O | SER | A | 250 | 61.227 | 30.342 | 253.310 | 1.00 | 68.10 | 8 |
| ATOM | 65 | N | MET | A | 251 | 62.056 | 31.178 | 251.410 | 1.00 | 68.65 | 7 |
| ATOM | 66 | CA | MET | A | 251 | 61.516 | 30.102 | 250.572 | 1.00 | 69.76 | 6 |
| ATOM | 67 | CB | MET | A | 251 | 60.218 | 30.531 | 249.884 | 1.00 | 69.79 | 6 |

TABLE 1-continued

| | | | | | | | | | | |
|---|---|---|---|---|---|---|---|---|---|---|
| ATOM | 68 | CG | MET | A | 251 | 59.165 | 31.143 | 250.777 | 1.00 | 70.09 | 6 |
| ATOM | 69 | SD | MET | A | 251 | 58.290 | 29.962 | 251.810 | 1.00 | 71.12 | 16 |
| ATOM | 70 | CE | MET | A | 251 | 57.647 | 28.875 | 250.577 | 1.00 | 71.11 | 6 |
| ATOM | 71 | C | MET | A | 251 | 62.540 | 29.722 | 249.506 | 1.00 | 70.50 | 6 |
| ATOM | 72 | O | MET | A | 251 | 62.395 | 30.116 | 248.350 | 1.00 | 70.57 | 8 |
| ATOM | 73 | N | GLN | A | 252 | 63.564 | 28.951 | 249.872 | 1.00 | 71.84 | 7 |
| ATOM | 74 | CA | GLN | A | 252 | 64.688 | 28.819 | 248.959 | 1.00 | 72.21 | 6 |
| ATOM | 75 | CB | GLN | A | 252 | 65.925 | 28.261 | 249.676 | 1.00 | 72.09 | 6 |
| ATOM | 76 | CG | GLN | A | 252 | 67.098 | 28.095 | 248.749 | 1.00 | 71.00 | 6 |
| ATOM | 77 | CD | GLN | A | 252 | 68.311 | 28.812 | 249.232 | 1.00 | 69.60 | 6 |
| ATOM | 78 | OE1 | GLN | A | 252 | 69.065 | 28.298 | 250.045 | 1.00 | 70.22 | 8 |
| ATOM | 79 | NE2 | GLN | A | 252 | 68.523 | 30.007 | 248.720 | 1.00 | 69.23 | 7 |
| ATOM | 80 | C | GLN | A | 252 | 64.307 | 27.971 | 247.769 | 1.00 | 72.45 | 6 |
| ATOM | 81 | O | GLN | A | 252 | 64.345 | 28.428 | 246.629 | 1.00 | 72.33 | 8 |
| ATOM | 82 | N | LEU | A | 253 | 63.933 | 26.738 | 248.090 | 1.00 | 72.90 | 7 |
| ATOM | 83 | CA | LEU | A | 253 | 63.577 | 25.691 | 247.155 | 1.00 | 73.09 | 6 |
| ATOM | 84 | CB | LEU | A | 253 | 63.357 | 24.395 | 247.949 | 1.00 | 72.61 | 6 |
| ATOM | 85 | CG | LEU | A | 253 | 62.668 | 23.226 | 247.256 | 1.00 | 71.41 | 6 |
| ATOM | 86 | CD1 | LEU | A | 253 | 63.595 | 22.667 | 246.234 | 1.00 | 70.33 | 6 |
| ATOM | 87 | CD2 | LEU | A | 253 | 62.284 | 22.164 | 248.235 | 1.00 | 72.09 | 6 |
| ATOM | 88 | C | LEU | A | 253 | 62.276 | 26.054 | 246.483 | 1.00 | 73.74 | 6 |
| ATOM | 89 | O | LEU | A | 253 | 62.118 | 25.996 | 245.254 | 1.00 | 73.87 | 8 |
| ATOM | 90 | N | GLU | A | 254 | 61.323 | 26.421 | 247.318 | 1.00 | 74.31 | 7 |
| ATOM | 91 | CA | GLU | A | 254 | 59.992 | 26.671 | 246.823 | 1.00 | 75.04 | 6 |
| ATOM | 92 | CB | GLU | A | 254 | 59.005 | 26.863 | 247.966 | 1.00 | 74.85 | 6 |
| ATOM | 93 | CG | GLU | A | 254 | 57.603 | 27.212 | 247.489 | 1.00 | 75.09 | 6 |
| ATOM | 94 | CD | GLU | A | 254 | 56.927 | 26.092 | 246.722 | 1.00 | 75.76 | 6 |
| ATOM | 95 | OE1 | GLU | A | 254 | 56.661 | 25.012 | 247.298 | 1.00 | 76.58 | 8 |
| ATOM | 96 | OE2 | GLU | A | 254 | 56.644 | 26.301 | 245.532 | 1.00 | 75.99 | 8 |
| ATOM | 97 | C | GLU | A | 254 | 59.957 | 27.875 | 245.904 | 1.00 | 75.25 | 6 |
| ATOM | 98 | O | GLU | A | 254 | 59.127 | 27.941 | 244.996 | 1.00 | 75.30 | 8 |
| ATOM | 99 | N | ASP | A | 255 | 60.850 | 28.825 | 246.140 | 1.00 | 75.42 | 7 |
| ATOM | 100 | CA | ASP | A | 255 | 60.950 | 29.945 | 245.246 | 1.00 | 75.73 | 6 |
| ATOM | 101 | CB | ASP | A | 255 | 61.946 | 30.955 | 245.757 | 1.00 | 75.91 | 6 |
| ATOM | 102 | CG | ASP | A | 255 | 61.599 | 32.354 | 245.335 | 1.00 | 77.56 | 6 |
| ATOM | 103 | OD1 | ASP | A | 255 | 61.563 | 32.620 | 244.112 | 1.00 | 79.25 | 8 |
| ATOM | 104 | OD2 | ASP | A | 255 | 61.348 | 33.195 | 246.227 | 1.00 | 79.41 | 8 |
| ATOM | 105 | C | ASP | A | 255 | 61.330 | 29.449 | 243.859 | 1.00 | 75.60 | 6 |
| ATOM | 106 | O | ASP | A | 255 | 60.526 | 29.514 | 242.933 | 1.00 | 75.72 | 8 |
| ATOM | 107 | N | LEU | A | 256 | 62.537 | 28.920 | 243.728 | 1.00 | 75.34 | 7 |
| ATOM | 108 | CA | LEU | A | 256 | 62.928 | 28.242 | 242.509 | 1.00 | 75.30 | 6 |
| ATOM | 109 | CB | LEU | A | 256 | 64.109 | 27.309 | 242.778 | 1.00 | 75.19 | 6 |
| ATOM | 110 | CG | LEU | A | 256 | 65.514 | 27.903 | 242.786 | 1.00 | 75.23 | 6 |
| ATOM | 111 | CD1 | LEU | A | 256 | 66.534 | 26.772 | 242.738 | 1.00 | 75.17 | 6 |
| ATOM | 112 | CD2 | LEU | A | 256 | 65.729 | 28.881 | 241.617 | 1.00 | 74.99 | 6 |
| ATOM | 113 | C | LEU | A | 256 | 61.774 | 27.431 | 241.925 | 1.00 | 75.31 | 6 |
| ATOM | 114 | O | LEU | A | 256 | 61.341 | 27.649 | 240.800 | 1.00 | 75.30 | 8 |
| ATOM | 115 | N | ARG | A | 257 | 61.272 | 26.501 | 242.718 | 1.00 | 75.47 | 7 |
| ATOM | 116 | CA | ARG | A | 257 | 60.233 | 25.586 | 242.290 | 1.00 | 75.75 | 6 |
| ATOM | 117 | CB | ARG | A | 257 | 59.745 | 24.788 | 243.507 | 1.00 | 75.66 | 6 |
| ATOM | 118 | CG | ARG | A | 257 | 59.159 | 23.466 | 243.150 | 1.00 | 75.77 | 6 |
| ATOM | 119 | CD | ARG | A | 257 | 58.663 | 22.720 | 244.350 | 1.00 | 75.78 | 6 |
| ATOM | 120 | NE | ARG | A | 257 | 58.741 | 21.305 | 244.035 | 1.00 | 77.55 | 7 |
| ATOM | 121 | CZ | ARG | A | 257 | 59.852 | 20.583 | 244.167 | 1.00 | 78.63 | 6 |
| ATOM | 122 | NH1 | ARG | A | 257 | 60.954 | 21.149 | 244.635 | 1.00 | 78.96 | 7 |
| ATOM | 123 | NH2 | ARG | A | 257 | 59.871 | 19.296 | 243.840 | 1.00 | 78.95 | 7 |
| ATOM | 124 | C | ARG | A | 257 | 59.068 | 26.315 | 241.618 | 1.00 | 75.79 | 6 |
| ATOM | 125 | O | ARG | A | 257 | 58.643 | 25.940 | 240.526 | 1.00 | 75.72 | 8 |
| ATOM | 126 | N | GLN | A | 258 | 58.558 | 27.350 | 242.280 | 1.00 | 76.03 | 7 |
| ATOM | 127 | CA | GLN | A | 258 | 57.466 | 28.152 | 241.729 | 1.00 | 76.53 | 6 |
| ATOM | 128 | CB | GLN | A | 258 | 56.919 | 29.156 | 242.741 | 1.00 | 76.59 | 6 |
| ATOM | 129 | CG | GLN | A | 258 | 55.526 | 28.841 | 243.261 | 1.00 | 78.00 | 6 |
| ATOM | 130 | CD | GLN | A | 258 | 55.383 | 29.164 | 244.762 | 1.00 | 80.85 | 6 |
| ATOM | 131 | OE1 | GLN | A | 258 | 55.779 | 30.245 | 245.224 | 1.00 | 81.22 | 8 |
| ATOM | 132 | NE2 | GLN | A | 258 | 54.830 | 28.214 | 245.531 | 1.00 | 81.21 | 7 |
| ATOM | 133 | C | GLN | A | 258 | 57.916 | 28.906 | 240.496 | 1.00 | 76.57 | 6 |
| ATOM | 134 | O | GLN | A | 258 | 57.408 | 28.678 | 239.411 | 1.00 | 76.75 | 8 |
| ATOM | 135 | N | GLN | A | 259 | 58.873 | 29.806 | 240.672 | 1.00 | 76.54 | 7 |
| ATOM | 136 | CA | GLN | A | 259 | 59.466 | 30.559 | 239.579 | 1.00 | 76.73 | 6 |
| ATOM | 137 | CB | GLN | A | 259 | 60.854 | 30.983 | 240.013 | 1.00 | 76.46 | 6 |
| ATOM | 138 | CG | GLN | A | 259 | 61.437 | 32.124 | 239.256 | 1.00 | 77.09 | 6 |
| ATOM | 139 | CD | GLN | A | 259 | 62.109 | 33.116 | 240.183 | 1.00 | 78.35 | 6 |
| ATOM | 140 | OE1 | GLN | A | 259 | 62.761 | 32.735 | 241.153 | 1.00 | 79.03 | 8 |
| ATOM | 141 | NE2 | GLN | A | 259 | 61.941 | 34.403 | 239.898 | 1.00 | 79.78 | 7 |
| ATOM | 142 | C | GLN | A | 259 | 59.582 | 29.768 | 238.276 | 1.00 | 77.02 | 6 |
| ATOM | 143 | O | GLN | A | 259 | 59.241 | 30.259 | 237.204 | 1.00 | 77.36 | 8 |
| ATOM | 144 | N | LEU | A | 260 | 60.087 | 28.547 | 238.385 | 1.00 | 77.32 | 7 |
| ATOM | 145 | CA | LEU | A | 260 | 60.234 | 27.628 | 237.266 | 1.00 | 77.61 | 6 |
| ATOM | 146 | CB | LEU | A | 260 | 60.851 | 26.319 | 237.778 | 1.00 | 77.46 | 6 |
| ATOM | 147 | CG | LEU | A | 260 | 61.475 | 25.205 | 236.920 | 1.00 | 77.15 | 6 |

TABLE 1-continued

| | | | | | | | | | | |
|---|---|---|---|---|---|---|---|---|---|---|
| ATOM | 148 | CD1 | LEU | A | 260 | 60.463 | 24.422 | 236.101 | 1.00 | 76.69 | 6 |
| ATOM | 149 | CD2 | LEU | A | 260 | 62.579 | 25.730 | 236.044 | 1.00 | 76.14 | 6 |
| ATOM | 150 | C | LEU | A | 260 | 58.881 | 27.332 | 236.660 | 1.00 | 78.11 | 6 |
| ATOM | 151 | O | LEU | A | 260 | 58.634 | 27.600 | 235.489 | 1.00 | 78.27 | 8 |
| ATOM | 152 | N | GLN | A | 261 | 57.998 | 26.786 | 237.482 | 1.00 | 78.83 | 7 |
| ATOM | 153 | CA | GLN | A | 261 | 56.678 | 26.388 | 237.041 | 1.00 | 79.56 | 6 |
| ATOM | 154 | CB | GLN | A | 261 | 55.894 | 25.806 | 238.223 | 1.00 | 79.87 | 6 |
| ATOM | 155 | CG | GLN | A | 261 | 55.317 | 24.406 | 237.970 | 1.00 | 81.14 | 6 |
| ATOM | 156 | CD | GLN | A | 261 | 53.927 | 24.449 | 237.344 | 1.00 | 82.68 | 6 |
| ATOM | 157 | OE1 | GLN | A | 261 | 52.924 | 24.570 | 238.055 | 1.00 | 83.22 | 8 |
| ATOM | 158 | NE2 | GLN | A | 261 | 53.861 | 24.343 | 236.013 | 1.00 | 82.41 | 7 |
| ATOM | 159 | C | GLN | A | 261 | 55.972 | 27.583 | 236.421 | 1.00 | 79.62 | 6 |
| ATOM | 160 | O | GLN | A | 261 | 55.300 | 27.456 | 235.403 | 1.00 | 79.75 | 8 |
| ATOM | 161 | N | GLN | A | 262 | 56.171 | 28.753 | 237.011 | 1.00 | 79.91 | 7 |
| ATOM | 162 | CA | GLN | A | 262 | 55.520 | 29.942 | 236.513 | 1.00 | 80.58 | 6 |
| ATOM | 163 | CB | GLN | A | 262 | 55.553 | 31.086 | 237.533 | 1.00 | 80.55 | 6 |
| ATOM | 164 | CG | GLN | A | 262 | 56.669 | 32.105 | 237.335 | 1.00 | 81.54 | 6 |
| ATOM | 165 | CD | GLN | A | 262 | 56.384 | 33.438 | 238.010 | 1.00 | 81.86 | 6 |
| ATOM | 166 | OE1 | GLN | A | 262 | 55.735 | 33.495 | 239.066 | 1.00 | 83.81 | 8 |
| ATOM | 167 | NE2 | GLN | A | 262 | 56.872 | 34.526 | 237.404 | 1.00 | 82.80 | 7 |
| ATOM | 168 | C | GLN | A | 262 | 56.106 | 30.349 | 235.166 | 1.00 | 80.47 | 6 |
| ATOM | 169 | O | GLN | A | 262 | 55.387 | 30.859 | 234.316 | 1.00 | 80.72 | 8 |
| ATOM | 170 | N | ALA | A | 263 | 57.398 | 30.106 | 234.967 | 1.00 | 80.53 | 7 |
| ATOM | 171 | CA | ALA | A | 263 | 58.057 | 30.460 | 233.712 | 1.00 | 80.70 | 6 |
| ATOM | 172 | CB | ALA | A | 263 | 59.544 | 30.496 | 233.899 | 1.00 | 80.51 | 6 |
| ATOM | 173 | C | ALA | A | 263 | 57.688 | 29.497 | 232.588 | 1.00 | 80.85 | 6 |
| ATOM | 174 | O | ALA | A | 263 | 57.431 | 29.908 | 231.466 | 1.00 | 81.05 | 8 |
| ATOM | 175 | N | GLU | A | 264 | 57.664 | 28.213 | 232.902 | 1.00 | 81.06 | 7 |
| ATOM | 176 | CA | GLU | A | 264 | 57.188 | 27.197 | 231.979 | 1.00 | 81.63 | 6 |
| ATOM | 177 | CB | GLU | A | 264 | 57.079 | 25.857 | 232.693 | 1.00 | 81.60 | 6 |
| ATOM | 178 | CG | GLU | A | 264 | 58.146 | 24.850 | 232.314 | 1.00 | 82.66 | 6 |
| ATOM | 179 | CD | GLU | A | 264 | 58.097 | 23.583 | 233.173 | 1.00 | 82.90 | 6 |
| ATOM | 180 | OE1 | GLU | A | 264 | 57.918 | 22.488 | 232.600 | 1.00 | 84.53 | 8 |
| ATOM | 181 | OE2 | GLU | A | 264 | 58.227 | 23.671 | 234.416 | 1.00 | 84.53 | 8 |
| ATOM | 182 | C | GLU | A | 264 | 55.818 | 27.523 | 231.444 | 1.00 | 81.51 | 6 |
| ATOM | 183 | O | GLU | A | 264 | 55.570 | 27.414 | 230.245 | 1.00 | 81.74 | 8 |
| ATOM | 184 | N | GLU | A | 265 | 54.920 | 27.904 | 232.346 | 1.00 | 81.43 | 7 |
| ATOM | 185 | CA | GLU | A | 265 | 53.560 | 28.251 | 231.945 | 1.00 | 81.40 | 6 |
| ATOM | 186 | CB | GLU | A | 265 | 52.613 | 28.305 | 233.157 | 1.00 | 81.27 | 6 |
| ATOM | 187 | CG | GLU | A | 265 | 52.578 | 29.625 | 233.903 | 1.00 | 81.42 | 6 |
| ATOM | 188 | CD | GLU | A | 265 | 51.769 | 29.565 | 235.181 | 1.00 | 81.82 | 6 |
| ATOM | 189 | OE1 | GLU | A | 265 | 51.485 | 30.641 | 235.749 | 1.00 | 82.88 | 8 |
| ATOM | 190 | OE2 | GLU | A | 265 | 51.422 | 28.450 | 235.627 | 1.00 | 82.41 | 8 |
| ATOM | 191 | C | GLU | A | 265 | 53.508 | 29.526 | 231.061 | 1.00 | 81.15 | 6 |
| ATOM | 192 | O | GLU | A | 265 | 52.698 | 29.611 | 230.126 | 1.00 | 81.13 | 8 |
| ATOM | 193 | N | ALA | A | 266 | 54.390 | 30.484 | 231.355 | 1.00 | 80.69 | 7 |
| ATOM | 194 | CA | ALA | A | 266 | 54.572 | 31.683 | 230.551 | 1.00 | 80.22 | 6 |
| ATOM | 195 | CB | ALA | A | 266 | 55.623 | 32.567 | 231.176 | 1.00 | 80.03 | 6 |
| ATOM | 196 | C | ALA | A | 266 | 54.998 | 31.303 | 229.145 | 1.00 | 79.99 | 6 |
| ATOM | 197 | O | ALA | A | 266 | 54.476 | 31.834 | 228.171 | 1.00 | 80.24 | 8 |
| ATOM | 198 | N | LEU | A | 267 | 55.947 | 30.380 | 229.039 | 1.00 | 79.60 | 7 |
| ATOM | 199 | CA | LEU | A | 267 | 56.433 | 29.930 | 227.737 | 1.00 | 79.38 | 6 |
| ATOM | 200 | CB | LEU | A | 267 | 57.411 | 28.769 | 227.876 | 1.00 | 79.44 | 6 |
| ATOM | 201 | CG | LEU | A | 267 | 58.871 | 28.994 | 228.257 | 1.00 | 79.42 | 6 |
| ATOM | 202 | CD1 | LEU | A | 267 | 59.469 | 27.694 | 228.743 | 1.00 | 79.16 | 6 |
| ATOM | 203 | CD2 | LEU | A | 267 | 59.667 | 29.539 | 227.097 | 1.00 | 79.14 | 6 |
| ATOM | 204 | C | LEU | A | 267 | 55.316 | 29.452 | 226.841 | 1.00 | 79.34 | 6 |
| ATOM | 205 | O | LEU | A | 267 | 55.239 | 29.850 | 225.683 | 1.00 | 79.45 | 8 |
| ATOM | 206 | N | VAL | A | 268 | 54.467 | 28.573 | 227.366 | 1.00 | 79.21 | 7 |
| ATOM | 207 | CA | VAL | A | 268 | 53.361 | 28.030 | 226.572 | 1.00 | 79.04 | 6 |
| ATOM | 208 | CB | VAL | A | 268 | 52.613 | 26.883 | 227.300 | 1.00 | 78.93 | 6 |
| ATOM | 209 | CG1 | VAL | A | 268 | 51.418 | 26.402 | 226.487 | 1.00 | 78.36 | 6 |
| ATOM | 210 | CG2 | VAL | A | 268 | 53.564 | 25.725 | 227.558 | 1.00 | 78.85 | 6 |
| ATOM | 211 | C | VAL | A | 268 | 52.424 | 29.161 | 226.157 | 1.00 | 79.09 | 6 |
| ATOM | 212 | O | VAL | A | 268 | 52.099 | 29.294 | 224.985 | 1.00 | 79.08 | 8 |
| ATOM | 213 | N | ALA | A | 269 | 52.035 | 29.988 | 227.123 | 1.00 | 79.16 | 7 |
| ATOM | 214 | CA | ALA | A | 269 | 51.241 | 31.190 | 226.878 | 1.00 | 79.02 | 6 |
| ATOM | 215 | CB | ALA | A | 269 | 51.134 | 32.011 | 228.173 | 1.00 | 79.10 | 6 |
| ATOM | 216 | C | ALA | A | 269 | 51.790 | 32.044 | 225.712 | 1.00 | 78.94 | 6 |
| ATOM | 217 | O | ALA | A | 269 | 51.016 | 32.524 | 224.875 | 1.00 | 78.93 | 8 |
| ATOM | 218 | N | LYS | A | 270 | 53.118 | 32.206 | 225.668 | 1.00 | 78.91 | 7 |
| ATOM | 219 | CA | LYS | A | 270 | 53.831 | 32.939 | 224.603 | 1.00 | 79.11 | 6 |
| ATOM | 220 | CB | LYS | A | 270 | 55.349 | 32.913 | 224.847 | 1.00 | 78.99 | 6 |
| ATOM | 221 | CG | LYS | A | 270 | 55.889 | 33.820 | 225.931 | 1.00 | 78.89 | 6 |
| ATOM | 222 | CD | LYS | A | 270 | 56.069 | 35.237 | 225.432 | 1.00 | 78.84 | 6 |
| ATOM | 223 | CE | LYS | A | 270 | 56.701 | 36.117 | 226.481 | 1.00 | 78.53 | 6 |
| ATOM | 224 | NZ | LYS | A | 270 | 58.147 | 35.838 | 226.532 | 1.00 | 78.40 | 7 |
| ATOM | 225 | C | LYS | A | 270 | 53.629 | 32.276 | 223.259 | 1.00 | 79.26 | 6 |
| ATOM | 226 | O | LYS | A | 270 | 53.286 | 32.921 | 222.266 | 1.00 | 79.27 | 8 |
| ATOM | 227 | N | GLN | A | 271 | 53.900 | 30.977 | 223.239 | 1.00 | 79.44 | 7 |

TABLE 1-continued

| ATOM | 228 | CA  | GLN | A | 271 | 53.703 | 30.146 | 222.065 | 1.00 | 79.70 | 6 |
| ATOM | 229 | CB  | GLN | A | 271 | 54.020 | 28.702 | 222.410 | 1.00 | 79.72 | 6 |
| ATOM | 230 | CG  | GLN | A | 271 | 54.034 | 27.800 | 221.212 | 1.00 | 79.95 | 6 |
| ATOM | 231 | CD  | GLN | A | 271 | 55.299 | 27.960 | 220.416 | 1.00 | 80.65 | 6 |
| ATOM | 232 | OE1 | GLN | A | 271 | 55.254 | 28.250 | 219.231 | 1.00 | 80.79 | 8 |
| ATOM | 233 | NE2 | GLN | A | 271 | 56.444 | 27.786 | 221.071 | 1.00 | 81.31 | 7 |
| ATOM | 234 | C   | GLN | A | 271 | 52.275 | 30.214 | 221.508 | 1.00 | 79.85 | 6 |
| ATOM | 235 | O   | GLN | A | 271 | 52.092 | 30.352 | 220.305 | 1.00 | 79.94 | 8 |
| ATOM | 236 | N   | GLU | A | 272 | 51.274 | 30.090 | 222.386 | 1.00 | 79.87 | 7 |
| ATOM | 237 | CA  | GLU | A | 272 | 49.872 | 30.333 | 222.036 | 1.00 | 79.75 | 6 |
| ATOM | 238 | CB  | GLU | A | 272 | 49.032 | 30.636 | 223.279 | 1.00 | 79.91 | 6 |
| ATOM | 239 | CG  | GLU | A | 272 | 47.978 | 29.614 | 223.638 | 1.00 | 81.15 | 6 |
| ATOM | 240 | CD  | GLU | A | 272 | 48.506 | 28.534 | 224.572 | 1.00 | 83.38 | 6 |
| ATOM | 241 | OE1 | GLU | A | 272 | 48.181 | 28.556 | 225.788 | 1.00 | 84.07 | 8 |
| ATOM | 242 | OE2 | GLU | A | 272 | 49.261 | 27.661 | 224.090 | 1.00 | 84.41 | 8 |
| ATOM | 243 | C   | GLU | A | 272 | 49.788 | 31.543 | 221.137 | 1.00 | 79.48 | 6 |
| ATOM | 244 | O   | GLU | A | 272 | 49.121 | 31.493 | 220.103 | 1.00 | 79.55 | 8 |
| ATOM | 245 | N   | LEU | A | 273 | 50.469 | 32.621 | 221.554 | 1.00 | 79.02 | 7 |
| ATOM | 246 | CA  | LEU | A | 273 | 50.489 | 33.901 | 220.839 | 1.00 | 78.51 | 6 |
| ATOM | 247 | CB  | LEU | A | 273 | 51.075 | 35.027 | 221.700 | 1.00 | 78.34 | 6 |
| ATOM | 248 | CG  | LEU | A | 273 | 51.318 | 36.343 | 220.934 | 1.00 | 77.65 | 6 |
| ATOM | 249 | CD1 | LEU | A | 273 | 50.001 | 37.038 | 220.616 | 1.00 | 77.55 | 6 |
| ATOM | 250 | CD2 | LEU | A | 273 | 52.256 | 37.287 | 221.655 | 1.00 | 77.81 | 6 |
| ATOM | 251 | C   | LEU | A | 273 | 51.279 | 33.840 | 219.538 | 1.00 | 78.55 | 6 |
| ATOM | 252 | O   | LEU | A | 273 | 50.829 | 34.371 | 218.512 | 1.00 | 78.74 | 8 |
| ATOM | 253 | N   | ILE | A | 274 | 52.465 | 33.230 | 219.588 | 1.00 | 78.25 | 7 |
| ATOM | 254 | CA  | ILE | A | 274 | 53.295 | 33.054 | 218.387 | 1.00 | 78.05 | 6 |
| ATOM | 255 | CB  | ILE | A | 274 | 54.445 | 32.022 | 218.582 | 1.00 | 78.15 | 6 |
| ATOM | 256 | CG1 | ILE | A | 274 | 55.511 | 32.529 | 219.564 | 1.00 | 78.91 | 6 |
| ATOM | 257 | CD  | ILE | A | 274 | 56.444 | 33.614 | 218.999 | 1.00 | 79.68 | 6 |
| ATOM | 258 | CG2 | ILE | A | 274 | 55.066 | 31.632 | 217.230 | 1.00 | 77.06 | 6 |
| ATOM | 259 | C   | ILE | A | 274 | 52.461 | 32.491 | 217.263 | 1.00 | 77.87 | 6 |
| ATOM | 260 | O   | ILE | A | 274 | 52.391 | 33.070 | 216.193 | 1.00 | 78.12 | 8 |
| ATOM | 261 | N   | ASP | A | 275 | 51.823 | 31.358 | 217.527 | 1.00 | 77.57 | 7 |
| ATOM | 262 | CA  | ASP | A | 275 | 51.070 | 30.627 | 216.517 | 1.00 | 77.32 | 6 |
| ATOM | 263 | CB  | ASP | A | 275 | 50.685 | 29.250 | 217.037 | 1.00 | 77.35 | 6 |
| ATOM | 264 | CG  | ASP | A | 275 | 51.817 | 28.588 | 217.776 | 1.00 | 78.33 | 6 |
| ATOM | 265 | OD1 | ASP | A | 275 | 52.971 | 29.024 | 217.561 | 1.00 | 79.48 | 8 |
| ATOM | 266 | OD2 | ASP | A | 275 | 51.569 | 27.661 | 218.584 | 1.00 | 78.95 | 8 |
| ATOM | 267 | C   | ASP | A | 275 | 49.831 | 31.368 | 216.064 | 1.00 | 77.10 | 6 |
| ATOM | 268 | O   | ASP | A | 275 | 49.457 | 31.274 | 214.903 | 1.00 | 77.23 | 8 |
| ATOM | 269 | N   | LYS | A | 276 | 49.191 | 32.093 | 216.979 | 1.00 | 76.72 | 7 |
| ATOM | 270 | CA  | LYS | A | 276 | 48.073 | 32.965 | 216.638 | 1.00 | 76.28 | 6 |
| ATOM | 271 | CB  | LYS | A | 276 | 47.521 | 33.630 | 217.906 | 1.00 | 76.24 | 6 |
| ATOM | 272 | CG  | LYS | A | 276 | 46.711 | 34.912 | 217.702 | 1.00 | 76.46 | 6 |
| ATOM | 273 | CD  | LYS | A | 276 | 45.266 | 34.785 | 218.154 | 1.00 | 76.27 | 6 |
| ATOM | 274 | CE  | LYS | A | 276 | 44.766 | 36.135 | 218.644 | 1.00 | 76.13 | 6 |
| ATOM | 275 | NZ  | LYS | A | 276 | 43.317 | 36.130 | 218.942 | 1.00 | 76.37 | 7 |
| ATOM | 276 | C   | LYS | A | 276 | 48.557 | 34.001 | 215.631 | 1.00 | 75.92 | 6 |
| ATOM | 277 | O   | LYS | A | 276 | 47.882 | 34.264 | 214.638 | 1.00 | 76.06 | 8 |
| ATOM | 278 | N   | LEU | A | 277 | 49.744 | 34.552 | 215.887 | 1.00 | 75.43 | 7 |
| ATOM | 279 | CA  | LEU | A | 277 | 50.347 | 35.606 | 215.071 | 1.00 | 75.07 | 6 |
| ATOM | 280 | CB  | LEU | A | 277 | 51.524 | 36.242 | 215.822 | 1.00 | 74.81 | 6 |
| ATOM | 281 | CG  | LEU | A | 277 | 51.343 | 37.516 | 216.648 | 1.00 | 74.54 | 6 |
| ATOM | 282 | CD1 | LEU | A | 277 | 52.698 | 38.142 | 216.886 | 1.00 | 73.76 | 6 |
| ATOM | 283 | CD2 | LEU | A | 277 | 50.410 | 38.536 | 215.974 | 1.00 | 75.19 | 6 |
| ATOM | 284 | C   | LEU | A | 277 | 50.853 | 35.108 | 213.727 | 1.00 | 74.91 | 6 |
| ATOM | 285 | O   | LEU | A | 277 | 50.693 | 35.771 | 212.693 | 1.00 | 74.85 | 8 |
| ATOM | 286 | N   | LYS | A | 278 | 51.506 | 33.953 | 213.781 | 1.00 | 74.84 | 7 |
| ATOM | 287 | CA  | LYS | A | 278 | 52.032 | 33.249 | 212.621 | 1.00 | 74.86 | 6 |
| ATOM | 288 | CB  | LYS | A | 278 | 52.538 | 31.857 | 213.057 | 1.00 | 74.63 | 6 |
| ATOM | 289 | CG  | LYS | A | 278 | 53.711 | 31.258 | 212.282 | 1.00 | 73.54 | 6 |
| ATOM | 290 | CD  | LYS | A | 278 | 55.041 | 31.768 | 212.820 | 1.00 | 72.18 | 6 |
| ATOM | 291 | CE  | LYS | A | 278 | 56.250 | 31.072 | 212.205 | 1.00 | 71.59 | 6 |
| ATOM | 292 | NZ  | LYS | A | 278 | 56.872 | 30.043 | 213.087 | 1.00 | 70.31 | 7 |
| ATOM | 293 | C   | LYS | A | 278 | 50.879 | 33.064 | 211.664 | 1.00 | 75.25 | 6 |
| ATOM | 294 | O   | LYS | A | 278 | 50.921 | 33.503 | 210.517 | 1.00 | 75.38 | 8 |
| ATOM | 295 | N   | GLU | A | 279 | 49.827 | 32.444 | 212.177 | 1.00 | 75.64 | 7 |
| ATOM | 296 | CA  | GLU | A | 279 | 48.639 | 32.143 | 211.414 | 1.00 | 76.14 | 6 |
| ATOM | 297 | CB  | GLU | A | 279 | 47.713 | 31.285 | 212.249 | 1.00 | 76.14 | 6 |
| ATOM | 298 | CG  | GLU | A | 279 | 46.620 | 30.605 | 211.479 | 1.00 | 77.32 | 6 |
| ATOM | 299 | CD  | GLU | A | 279 | 45.497 | 30.185 | 212.395 | 1.00 | 79.14 | 6 |
| ATOM | 300 | OE1 | GLU | A | 279 | 44.382 | 30.722 | 212.233 | 1.00 | 80.40 | 8 |
| ATOM | 301 | OE2 | GLU | A | 279 | 45.730 | 29.346 | 213.298 | 1.00 | 79.74 | 8 |
| ATOM | 302 | C   | GLU | A | 279 | 47.903 | 33.392 | 210.939 | 1.00 | 76.23 | 6 |
| ATOM | 303 | O   | GLU | A | 279 | 47.401 | 33.414 | 209.830 | 1.00 | 76.56 | 8 |
| ATOM | 304 | N   | GLU | A | 280 | 47.825 | 34.425 | 211.770 | 1.00 | 76.32 | 7 |
| ATOM | 305 | CA  | GLU | A | 280 | 47.206 | 35.672 | 211.348 | 1.00 | 76.38 | 6 |
| ATOM | 306 | CB  | GLU | A | 280 | 47.170 | 36.675 | 212.489 | 1.00 | 76.35 | 6 |
| ATOM | 307 | CG  | GLU | A | 280 | 45.956 | 36.539 | 213.381 | 1.00 | 76.80 | 6 |

TABLE 1-continued

| | | | | | | | | | | |
|---|---|---|---|---|---|---|---|---|---|---|
| ATOM | 308 | CD | GLU | A | 280 | 46.104 | 37.297 | 214.691 | 1.00 | 77.93 | 6 |
| ATOM | 309 | OE1 | GLU | A | 280 | 45.309 | 37.030 | 215.618 | 1.00 | 78.26 | 8 |
| ATOM | 310 | OE2 | GLU | A | 280 | 47.013 | 38.156 | 214.803 | 1.00 | 78.36 | 8 |
| ATOM | 311 | C | GLU | A | 280 | 47.962 | 36.261 | 210.172 | 1.00 | 76.62 | 6 |
| ATOM | 312 | O | GLU | A | 280 | 47.357 | 36.647 | 209.167 | 1.00 | 76.82 | 8 |
| ATOM | 313 | N | ALA | A | 281 | 49.288 | 36.309 | 210.297 | 1.00 | 76.86 | 7 |
| ATOM | 314 | CA | ALA | A | 281 | 50.169 | 36.795 | 209.230 | 1.00 | 76.99 | 6 |
| ATOM | 315 | CB | ALA | A | 281 | 51.630 | 36.757 | 209.682 | 1.00 | 77.14 | 6 |
| ATOM | 316 | C | ALA | A | 281 | 49.986 | 35.995 | 207.946 | 1.00 | 76.96 | 6 |
| ATOM | 317 | O | ALA | A | 281 | 50.338 | 36.453 | 206.863 | 1.00 | 77.04 | 8 |
| ATOM | 318 | N | GLU | A | 282 | 49.421 | 34.802 | 208.076 | 1.00 | 76.98 | 7 |
| ATOM | 319 | CA | GLU | A | 282 | 49.109 | 33.975 | 206.920 | 1.00 | 77.23 | 6 |
| ATOM | 320 | CB | GLU | A | 282 | 48.728 | 32.557 | 207.341 | 1.00 | 77.37 | 6 |
| ATOM | 321 | CG | GLU | A | 282 | 48.950 | 31.533 | 206.257 | 1.00 | 78.61 | 6 |
| ATOM | 322 | CD | GLU | A | 282 | 50.385 | 31.552 | 205.750 | 1.00 | 80.14 | 6 |
| ATOM | 323 | OE1 | GLU | A | 282 | 51.248 | 30.934 | 206.411 | 1.00 | 79.79 | 8 |
| ATOM | 324 | OE2 | GLU | A | 282 | 50.645 | 32.191 | 204.699 | 1.00 | 81.09 | 8 |
| ATOM | 325 | C | GLU | A | 282 | 47.997 | 34.556 | 206.059 | 1.00 | 77.07 | 6 |
| ATOM | 326 | O | GLU | A | 282 | 48.166 | 34.681 | 204.850 | 1.00 | 77.14 | 8 |
| ATOM | 327 | N | GLN | A | 283 | 46.858 | 34.883 | 206.673 | 1.00 | 76.94 | 7 |
| ATOM | 328 | CA | GLN | A | 283 | 45.745 | 35.504 | 205.938 | 1.00 | 76.81 | 6 |
| ATOM | 329 | CB | GLN | A | 283 | 44.414 | 35.488 | 206.699 | 1.00 | 77.00 | 6 |
| ATOM | 330 | CG | GLN | A | 283 | 43.709 | 34.155 | 206.792 | 1.00 | 77.77 | 6 |
| ATOM | 331 | CD | GLN | A | 283 | 43.587 | 33.683 | 208.240 | 1.00 | 79.45 | 6 |
| ATOM | 332 | OE1 | GLN | A | 283 | 44.174 | 34.268 | 209.166 | 1.00 | 78.97 | 8 |
| ATOM | 333 | NE2 | GLN | A | 283 | 42.810 | 32.623 | 208.445 | 1.00 | 80.36 | 7 |
| ATOM | 334 | C | GLN | A | 283 | 46.025 | 36.945 | 205.553 | 1.00 | 76.35 | 6 |
| ATOM | 335 | O | GLN | A | 283 | 45.320 | 37.492 | 204.692 | 1.00 | 76.38 | 8 |
| ATOM | 336 | N | HIS | A | 284 | 47.010 | 37.572 | 206.208 | 1.00 | 75.63 | 7 |
| ATOM | 337 | CA | HIS | A | 284 | 47.465 | 38.911 | 205.801 | 1.00 | 75.04 | 6 |
| ATOM | 338 | CB | HIS | A | 284 | 48.363 | 39.586 | 206.848 | 1.00 | 75.13 | 6 |
| ATOM | 339 | CG | HIS | A | 284 | 47.776 | 39.663 | 208.224 | 1.00 | 75.41 | 6 |
| ATOM | 340 | ND1 | HIS | A | 284 | 46.419 | 39.736 | 208.461 | 1.00 | 75.59 | 7 |
| ATOM | 341 | CE1 | HIS | A | 284 | 46.205 | 39.806 | 209.764 | 1.00 | 75.77 | 6 |
| ATOM | 342 | NE2 | HIS | A | 284 | 47.374 | 39.797 | 210.379 | 1.00 | 75.45 | 7 |
| ATOM | 343 | CD2 | HIS | A | 284 | 48.373 | 39.721 | 209.440 | 1.00 | 75.13 | 6 |
| ATOM | 344 | C | HIS | A | 284 | 48.242 | 38.783 | 204.497 | 1.00 | 74.47 | 6 |
| ATOM | 345 | O | HIS | A | 284 | 48.038 | 39.563 | 203.555 | 1.00 | 74.34 | 8 |
| ATOM | 346 | N | LYS | A | 285 | 49.132 | 37.785 | 204.474 | 1.00 | 73.59 | 7 |
| ATOM | 347 | CA | LYS | A | 285 | 49.900 | 37.396 | 203.296 | 1.00 | 72.73 | 6 |
| ATOM | 348 | CB | LYS | A | 285 | 50.613 | 36.058 | 203.587 | 1.00 | 72.85 | 6 |
| ATOM | 349 | CG | LYS | A | 285 | 51.725 | 35.615 | 202.619 | 1.00 | 73.74 | 6 |
| ATOM | 350 | CD | LYS | A | 285 | 51.203 | 34.897 | 201.338 | 1.00 | 75.10 | 6 |
| ATOM | 351 | CE | LYS | A | 285 | 50.670 | 33.452 | 201.571 | 1.00 | 75.35 | 6 |
| ATOM | 352 | NZ | LYS | A | 285 | 51.708 | 32.376 | 201.505 | 1.00 | 75.28 | 7 |
| ATOM | 353 | C | LYS | A | 285 | 48.956 | 37.282 | 202.089 | 1.00 | 71.80 | 6 |
| ATOM | 354 | O | LYS | A | 285 | 49.143 | 37.962 | 201.083 | 1.00 | 71.76 | 8 |
| ATOM | 355 | N | ILE | A | 286 | 47.913 | 36.467 | 202.240 | 1.00 | 70.67 | 7 |
| ATOM | 356 | CA | ILE | A | 286 | 46.969 | 36.136 | 201.166 | 1.00 | 69.68 | 6 |
| ATOM | 357 | CB | ILE | A | 286 | 46.022 | 34.950 | 201.583 | 1.00 | 69.69 | 6 |
| ATOM | 358 | CG1 | ILE | A | 286 | 45.974 | 33.871 | 200.476 | 1.00 | 70.28 | 6 |
| ATOM | 359 | CD | ILE | A | 286 | 46.242 | 32.400 | 200.943 | 1.00 | 70.18 | 6 |
| ATOM | 360 | CG2 | ILE | A | 286 | 44.626 | 35.452 | 201.967 | 1.00 | 68.83 | 6 |
| ATOM | 361 | C | ILE | A | 286 | 46.152 | 37.327 | 200.623 | 1.00 | 68.99 | 6 |
| ATOM | 362 | O | ILE | A | 286 | 45.689 | 37.314 | 199.478 | 1.00 | 69.02 | 8 |
| ATOM | 363 | N | VAL | A | 287 | 45.974 | 38.353 | 201.442 | 1.00 | 68.04 | 7 |
| ATOM | 364 | CA | VAL | A | 287 | 45.303 | 39.572 | 200.999 | 1.00 | 67.05 | 6 |
| ATOM | 365 | CB | VAL | A | 287 | 44.651 | 40.305 | 202.211 | 1.00 | 67.04 | 6 |
| ATOM | 366 | CG1 | VAL | A | 287 | 44.677 | 41.813 | 202.060 | 1.00 | 66.05 | 6 |
| ATOM | 367 | CG2 | VAL | A | 287 | 43.240 | 39.812 | 202.418 | 1.00 | 66.88 | 6 |
| ATOM | 368 | C | VAL | A | 287 | 46.290 | 40.473 | 200.248 | 1.00 | 66.58 | 6 |
| ATOM | 369 | O | VAL | A | 287 | 45.960 | 41.049 | 199.216 | 1.00 | 66.54 | 8 |
| ATOM | 370 | N | MET | A | 288 | 47.508 | 40.570 | 200.776 | 1.00 | 65.76 | 7 |
| ATOM | 371 | CA | MET | A | 288 | 48.574 | 41.382 | 200.195 | 1.00 | 64.98 | 6 |
| ATOM | 372 | CB | MET | A | 288 | 49.837 | 41.251 | 201.041 | 1.00 | 64.94 | 6 |
| ATOM | 373 | CG | MET | A | 288 | 49.663 | 41.683 | 202.469 | 1.00 | 65.34 | 6 |
| ATOM | 374 | SD | MET | A | 288 | 51.073 | 41.339 | 203.554 | 1.00 | 66.03 | 16 |
| ATOM | 375 | CE | MET | A | 288 | 52.398 | 42.312 | 202.814 | 1.00 | 65.40 | 6 |
| ATOM | 376 | C | MET | A | 288 | 48.901 | 40.957 | 198.772 | 1.00 | 63.99 | 6 |
| ATOM | 377 | O | MET | A | 288 | 49.336 | 41.774 | 197.960 | 1.00 | 63.69 | 8 |
| ATOM | 378 | N | GLU | A | 289 | 48.708 | 39.668 | 198.496 | 1.00 | 62.98 | 7 |
| ATOM | 379 | CA | GLU | A | 289 | 48.910 | 39.093 | 197.170 | 1.00 | 62.17 | 6 |
| ATOM | 380 | CB | GLU | A | 289 | 48.692 | 37.597 | 197.204 | 1.00 | 62.12 | 6 |
| ATOM | 381 | CG | GLU | A | 289 | 49.887 | 36.818 | 197.635 | 1.00 | 64.01 | 6 |
| ATOM | 382 | CD | GLU | A | 289 | 49.570 | 35.340 | 197.706 | 1.00 | 67.40 | 6 |
| ATOM | 383 | OE1 | GLU | A | 289 | 48.640 | 34.925 | 196.960 | 1.00 | 67.38 | 8 |
| ATOM | 384 | OE2 | GLU | A | 289 | 50.230 | 34.602 | 198.502 | 1.00 | 68.10 | 8 |
| ATOM | 385 | C | GLU | A | 289 | 47.946 | 39.674 | 196.148 | 1.00 | 61.13 | 6 |
| ATOM | 386 | O | GLU | A | 289 | 48.171 | 39.577 | 194.931 | 1.00 | 61.18 | 8 |
| ATOM | 387 | N | THR | A | 290 | 46.862 | 40.264 | 196.639 | 1.00 | 59.59 | 7 |

TABLE 1-continued

| ATOM | 388 | CA | THR | A | 290 | 45.918 | 40.933 | 195.759 | 1.00 | 57.74 | 6 |
|---|---|---|---|---|---|---|---|---|---|---|---|
| ATOM | 389 | CB | THR | A | 290 | 44.479 | 40.944 | 196.314 | 1.00 | 57.49 | 6 |
| ATOM | 390 | OG1 | THR | A | 290 | 44.310 | 42.073 | 197.164 | 1.00 | 55.48 | 8 |
| ATOM | 391 | CG2 | THR | A | 290 | 44.181 | 39.683 | 197.080 | 1.00 | 57.71 | 6 |
| ATOM | 392 | C | THR | A | 290 | 46.284 | 42.395 | 195.384 | 1.00 | 57.47 | 6 |
| ATOM | 393 | O | THR | A | 290 | 45.584 | 42.952 | 194.540 | 1.00 | 57.42 | 8 |
| ATOM | 394 | N | VAL | A | 291 | 47.321 | 43.026 | 196.001 | 1.00 | 56.52 | 7 |
| ATOM | 395 | CA | VAL | A | 291 | 47.780 | 44.393 | 195.641 | 1.00 | 55.85 | 6 |
| ATOM | 396 | CB | VAL | A | 291 | 48.712 | 44.988 | 196.702 | 1.00 | 55.32 | 6 |
| ATOM | 397 | CG1 | VAL | A | 291 | 49.267 | 46.338 | 196.264 | 1.00 | 55.05 | 6 |
| ATOM | 398 | CG2 | VAL | A | 291 | 47.952 | 45.150 | 197.972 | 1.00 | 54.94 | 6 |
| ATOM | 399 | C | VAL | A | 291 | 48.317 | 44.488 | 194.193 | 1.00 | 55.56 | 6 |
| ATOM | 400 | O | VAL | A | 291 | 47.738 | 45.240 | 193.382 | 1.00 | 55.78 | 8 |
| ATOM | 401 | N | PRO | A | 292 | 49.354 | 43.686 | 193.842 | 1.00 | 54.84 | 7 |
| ATOM | 402 | CA | PRO | A | 292 | 49.844 | 43.624 | 192.470 | 1.00 | 54.30 | 6 |
| ATOM | 403 | CB | PRO | A | 292 | 50.684 | 42.345 | 192.472 | 1.00 | 54.40 | 6 |
| ATOM | 404 | CG | PRO | A | 292 | 50.287 | 41.623 | 193.719 | 1.00 | 54.58 | 6 |
| ATOM | 405 | CD | PRO | A | 292 | 50.062 | 42.716 | 194.682 | 1.00 | 54.67 | 6 |
| ATOM | 406 | C | PRO | A | 292 | 48.664 | 43.468 | 191.510 | 1.00 | 53.71 | 6 |
| ATOM | 407 | O | PRO | A | 292 | 48.637 | 44.116 | 190.447 | 1.00 | 53.44 | 8 |
| ATOM | 408 | N | VAL | A | 293 | 47.696 | 42.634 | 191.918 | 1.00 | 53.07 | 7 |
| ATOM | 409 | CA | VAL | A | 293 | 46.443 | 42.388 | 191.166 | 1.00 | 52.68 | 6 |
| ATOM | 410 | CB | VAL | A | 293 | 45.502 | 41.307 | 191.857 | 1.00 | 52.23 | 6 |
| ATOM | 411 | CG1 | VAL | A | 293 | 44.050 | 41.422 | 191.398 | 1.00 | 51.71 | 6 |
| ATOM | 412 | CG2 | VAL | A | 293 | 45.974 | 39.922 | 191.590 | 1.00 | 51.88 | 6 |
| ATOM | 413 | C | VAL | A | 293 | 45.643 | 43.677 | 190.958 | 1.00 | 52.54 | 6 |
| ATOM | 414 | O | VAL | A | 293 | 45.336 | 44.086 | 189.825 | 1.00 | 52.34 | 8 |
| ATOM | 415 | N | LEU | A | 294 | 45.293 | 44.317 | 192.067 | 1.00 | 52.20 | 7 |
| ATOM | 416 | CA | LEU | A | 294 | 44.479 | 45.517 | 191.965 | 1.00 | 51.54 | 6 |
| ATOM | 417 | CB | LEU | A | 294 | 43.831 | 45.937 | 193.295 | 1.00 | 51.62 | 6 |
| ATOM | 418 | CG | LEU | A | 294 | 42.763 | 44.985 | 193.872 | 1.00 | 51.19 | 6 |
| ATOM | 419 | CD1 | LEU | A | 294 | 41.850 | 45.694 | 194.839 | 1.00 | 48.66 | 6 |
| ATOM | 420 | CD2 | LEU | A | 294 | 41.942 | 44.312 | 192.761 | 1.00 | 52.36 | 6 |
| ATOM | 421 | C | LEU | A | 294 | 45.233 | 46.645 | 191.282 | 1.00 | 51.21 | 6 |
| ATOM | 422 | O | LEU | A | 294 | 44.653 | 47.320 | 190.456 | 1.00 | 51.20 | 8 |
| ATOM | 423 | N | LYS | A | 295 | 46.525 | 46.818 | 191.576 | 1.00 | 50.73 | 7 |
| ATOM | 424 | CA | LYS | A | 295 | 47.325 | 47.786 | 190.837 | 1.00 | 50.37 | 6 |
| ATOM | 425 | CB | LYS | A | 295 | 48.789 | 47.692 | 191.272 | 1.00 | 50.63 | 6 |
| ATOM | 426 | CG | LYS | A | 295 | 49.533 | 49.026 | 191.280 | 1.00 | 52.16 | 6 |
| ATOM | 427 | CD | LYS | A | 295 | 49.194 | 49.934 | 192.516 | 1.00 | 54.46 | 6 |
| ATOM | 428 | CE | LYS | A | 295 | 49.806 | 49.444 | 193.874 | 1.00 | 54.25 | 6 |
| ATOM | 429 | NZ | LYS | A | 295 | 51.231 | 49.832 | 194.136 | 1.00 | 53.36 | 7 |
| ATOM | 430 | C | LYS | A | 295 | 47.140 | 47.524 | 189.331 | 1.00 | 49.83 | 6 |
| ATOM | 431 | O | LYS | A | 295 | 46.723 | 48.408 | 188.591 | 1.00 | 49.39 | 8 |
| ATOM | 432 | N | ALA | A | 296 | 47.394 | 46.282 | 188.914 | 1.00 | 49.63 | 7 |
| ATOM | 433 | CA | ALA | A | 296 | 47.344 | 45.898 | 187.506 | 1.00 | 49.30 | 6 |
| ATOM | 434 | CB | ALA | A | 296 | 47.671 | 44.420 | 187.310 | 1.00 | 49.17 | 6 |
| ATOM | 435 | C | ALA | A | 296 | 45.981 | 46.221 | 186.938 | 1.00 | 49.22 | 6 |
| ATOM | 436 | O | ALA | A | 296 | 45.894 | 46.820 | 185.872 | 1.00 | 49.72 | 8 |
| ATOM | 437 | N | GLN | A | 297 | 44.906 | 45.857 | 187.634 | 1.00 | 48.90 | 7 |
| ATOM | 438 | CA | GLN | A | 297 | 43.581 | 46.189 | 187.087 | 1.00 | 48.85 | 6 |
| ATOM | 439 | CB | GLN | A | 297 | 42.404 | 45.770 | 187.964 | 1.00 | 48.94 | 6 |
| ATOM | 440 | CG | GLN | A | 297 | 41.092 | 46.537 | 187.610 | 1.00 | 49.31 | 6 |
| ATOM | 441 | CD | GLN | A | 297 | 39.894 | 46.206 | 188.516 | 1.00 | 50.34 | 6 |
| ATOM | 442 | OE1 | GLN | A | 297 | 38.945 | 46.995 | 188.622 | 1.00 | 51.69 | 8 |
| ATOM | 443 | NE2 | GLN | A | 297 | 39.934 | 45.038 | 189.169 | 1.00 | 51.71 | 7 |
| ATOM | 444 | C | GLN | A | 297 | 43.469 | 47.675 | 186.861 | 1.00 | 48.33 | 6 |
| ATOM | 445 | O | GLN | A | 297 | 43.156 | 48.104 | 185.756 | 1.00 | 48.54 | 8 |
| ATOM | 446 | N | ALA | A | 298 | 43.719 | 48.457 | 187.909 | 1.00 | 47.62 | 7 |
| ATOM | 447 | CA | ALA | A | 298 | 43.595 | 49.906 | 187.813 | 1.00 | 46.90 | 6 |
| ATOM | 448 | CB | ALA | A | 298 | 44.085 | 50.610 | 189.069 | 1.00 | 46.71 | 6 |
| ATOM | 449 | C | ALA | A | 298 | 44.327 | 50.405 | 186.585 | 1.00 | 46.57 | 6 |
| ATOM | 450 | O | ALA | A | 298 | 43.726 | 51.062 | 185.753 | 1.00 | 46.74 | 8 |
| ATOM | 451 | N | ASP | A | 299 | 45.600 | 50.057 | 186.438 | 1.00 | 46.08 | 7 |
| ATOM | 452 | CA | ASP | A | 299 | 46.352 | 50.478 | 185.260 | 1.00 | 45.84 | 6 |
| ATOM | 453 | CB | ASP | A | 299 | 47.792 | 49.971 | 185.301 | 1.00 | 46.19 | 6 |
| ATOM | 454 | CG | ASP | A | 299 | 48.480 | 50.295 | 186.603 | 1.00 | 47.23 | 6 |
| ATOM | 455 | OD1 | ASP | A | 299 | 48.105 | 51.324 | 187.224 | 1.00 | 48.55 | 8 |
| ATOM | 456 | OD2 | ASP | A | 299 | 49.382 | 49.514 | 186.998 | 1.00 | 47.75 | 8 |
| ATOM | 457 | C | ASP | A | 299 | 45.687 | 50.041 | 183.963 | 1.00 | 45.16 | 6 |
| ATOM | 458 | O | ASP | A | 299 | 45.474 | 50.867 | 183.069 | 1.00 | 45.25 | 8 |
| ATOM | 459 | N | ILE | A | 300 | 45.346 | 48.757 | 183.869 | 1.00 | 44.18 | 7 |
| ATOM | 460 | CA | ILE | A | 300 | 44.756 | 48.222 | 182.649 | 1.00 | 43.77 | 6 |
| ATOM | 461 | CB | ILE | A | 300 | 44.418 | 46.736 | 182.775 | 1.00 | 43.73 | 6 |
| ATOM | 462 | CG1 | ILE | A | 300 | 45.609 | 45.904 | 182.329 | 1.00 | 44.04 | 6 |
| ATOM | 463 | CD | ILE | A | 300 | 45.685 | 44.592 | 183.042 | 1.00 | 44.89 | 6 |
| ATOM | 464 | CG2 | ILE | A | 300 | 43.274 | 46.359 | 181.875 | 1.00 | 43.73 | 6 |
| ATOM | 465 | C | ILE | A | 300 | 43.532 | 49.015 | 182.245 | 1.00 | 43.59 | 6 |
| ATOM | 466 | O | ILE | A | 300 | 43.413 | 49.442 | 181.101 | 1.00 | 43.46 | 8 |
| ATOM | 467 | N | TYR | A | 301 | 42.633 | 49.235 | 183.187 | 1.00 | 43.37 | 7 |

TABLE 1-continued

| | | | | | | | | | | |
|---|---|---|---|---|---|---|---|---|---|---|
| ATOM | 468 | CA | TYR | A | 301 | 41.429 | 49.921 | 182.832 | 1.00 | 43.36 | 6 |
| ATOM | 469 | CB | TYR | A | 301 | 40.294 | 49.605 | 183.797 | 1.00 | 44.03 | 6 |
| ATOM | 470 | CG | TYR | A | 301 | 39.635 | 48.296 | 183.445 | 1.00 | 44.73 | 6 |
| ATOM | 471 | CD1 | TYR | A | 301 | 39.703 | 47.215 | 184.305 | 1.00 | 45.52 | 6 |
| ATOM | 472 | CE1 | TYR | A | 301 | 39.114 | 46.008 | 183.972 | 1.00 | 45.74 | 6 |
| ATOM | 473 | CZ | TYR | A | 301 | 38.447 | 45.881 | 182.770 | 1.00 | 44.85 | 6 |
| ATOM | 474 | OH | TYR | A | 301 | 37.862 | 44.679 | 182.448 | 1.00 | 46.21 | 8 |
| ATOM | 475 | CE2 | TYR | A | 301 | 38.371 | 46.940 | 181.897 | 1.00 | 44.17 | 6 |
| ATOM | 476 | CD2 | TYR | A | 301 | 38.969 | 48.132 | 182.231 | 1.00 | 44.51 | 6 |
| ATOM | 477 | C | TYR | A | 301 | 41.624 | 51.407 | 182.613 | 1.00 | 43.09 | 6 |
| ATOM | 478 | O | TYR | A | 301 | 40.897 | 52.007 | 181.821 | 1.00 | 43.38 | 8 |
| ATOM | 479 | N | LYS | A | 302 | 42.605 | 52.005 | 183.288 | 1.00 | 42.67 | 7 |
| ATOM | 480 | CA | LYS | A | 302 | 42.876 | 53.431 | 183.103 | 1.00 | 42.29 | 6 |
| ATOM | 481 | CB | LYS | A | 302 | 43.945 | 53.925 | 184.072 | 1.00 | 42.22 | 6 |
| ATOM | 482 | CG | LYS | A | 302 | 44.489 | 55.314 | 183.734 | 1.00 | 42.82 | 6 |
| ATOM | 483 | CD | LYS | A | 302 | 45.316 | 55.917 | 184.877 | 1.00 | 43.24 | 6 |
| ATOM | 484 | CE | LYS | A | 302 | 46.152 | 57.089 | 184.385 | 1.00 | 44.85 | 6 |
| ATOM | 485 | NZ | LYS | A | 302 | 47.558 | 56.891 | 184.885 | 1.00 | 48.09 | 7 |
| ATOM | 486 | C | LYS | A | 302 | 43.334 | 53.617 | 181.681 | 1.00 | 41.91 | 6 |
| ATOM | 487 | O | LYS | A | 302 | 42.781 | 54.420 | 180.942 | 1.00 | 41.83 | 8 |
| ATOM | 488 | N | ALA | A | 303 | 44.333 | 52.824 | 181.305 | 1.00 | 41.91 | 7 |
| ATOM | 489 | CA | ALA | A | 303 | 44.837 | 52.743 | 179.936 | 1.00 | 41.67 | 6 |
| ATOM | 490 | CB | ALA | A | 303 | 45.889 | 51.676 | 179.868 | 1.00 | 41.61 | 6 |
| ATOM | 491 | C | ALA | A | 303 | 43.751 | 52.471 | 178.899 | 1.00 | 41.57 | 6 |
| ATOM | 492 | O | ALA | A | 303 | 43.739 | 53.068 | 177.844 | 1.00 | 41.66 | 8 |
| ATOM | 493 | N | ASP | A | 304 | 42.837 | 51.565 | 179.193 | 1.00 | 41.57 | 7 |
| ATOM | 494 | CA | ASP | A | 304 | 41.826 | 51.291 | 178.219 | 1.00 | 41.67 | 6 |
| ATOM | 495 | CB | ASP | A | 304 | 41.199 | 49.939 | 178.433 | 1.00 | 42.26 | 6 |
| ATOM | 496 | CG | ASP | A | 304 | 42.108 | 48.865 | 177.906 | 1.00 | 45.50 | 6 |
| ATOM | 497 | OD1 | ASP | A | 304 | 42.244 | 47.797 | 178.547 | 1.00 | 49.37 | 8 |
| ATOM | 498 | OD2 | ASP | A | 304 | 42.750 | 49.136 | 176.853 | 1.00 | 46.89 | 8 |
| ATOM | 499 | C | ASP | A | 304 | 40.873 | 52.432 | 178.017 | 1.00 | 41.00 | 6 |
| ATOM | 500 | O | ASP | A | 304 | 40.549 | 52.755 | 176.862 | 1.00 | 41.04 | 8 |
| ATOM | 501 | N | PHE | A | 305 | 40.495 | 53.075 | 179.122 | 1.00 | 40.10 | 7 |
| ATOM | 502 | CA | PHE | A | 305 | 39.622 | 54.214 | 179.052 | 1.00 | 39.38 | 6 |
| ATOM | 503 | CB | PHE | A | 305 | 39.447 | 54.895 | 180.390 | 1.00 | 39.47 | 6 |
| ATOM | 504 | CG | PHE | A | 305 | 38.999 | 56.324 | 180.248 | 1.00 | 38.56 | 6 |
| ATOM | 505 | CD1 | PHE | A | 305 | 37.680 | 56.622 | 180.002 | 1.00 | 38.06 | 6 |
| ATOM | 506 | CE1 | PHE | A | 305 | 37.270 | 57.929 | 179.827 | 1.00 | 38.38 | 6 |
| ATOM | 507 | CZ | PHE | A | 305 | 38.170 | 58.944 | 179.885 | 1.00 | 38.12 | 6 |
| ATOM | 508 | CE2 | PHE | A | 305 | 39.493 | 58.657 | 180.120 | 1.00 | 39.16 | 6 |
| ATOM | 509 | CD2 | PHE | A | 305 | 39.905 | 57.352 | 180.291 | 1.00 | 38.01 | 6 |
| ATOM | 510 | C | PHE | A | 305 | 40.248 | 55.237 | 178.159 | 1.00 | 39.02 | 6 |
| ATOM | 511 | O | PHE | A | 305 | 39.594 | 55.830 | 177.305 | 1.00 | 38.98 | 8 |
| ATOM | 512 | N | GLN | A | 306 | 41.520 | 55.480 | 178.401 | 1.00 | 38.74 | 7 |
| ATOM | 513 | CA | GLN | A | 306 | 42.207 | 56.532 | 177.690 | 1.00 | 38.96 | 6 |
| ATOM | 514 | CB | GLN | A | 306 | 43.647 | 56.653 | 178.128 | 1.00 | 38.80 | 6 |
| ATOM | 515 | CG | GLN | A | 306 | 43.808 | 57.295 | 179.486 | 1.00 | 40.68 | 6 |
| ATOM | 516 | CD | GLN | A | 306 | 45.244 | 57.251 | 179.955 | 1.00 | 43.90 | 6 |
| ATOM | 517 | OE1 | GLN | A | 306 | 46.159 | 57.403 | 179.154 | 1.00 | 45.50 | 8 |
| ATOM | 518 | NE2 | GLN | A | 306 | 45.456 | 57.029 | 181.254 | 1.00 | 45.70 | 7 |
| ATOM | 519 | C | GLN | A | 306 | 42.147 | 56.285 | 176.211 | 1.00 | 38.86 | 6 |
| ATOM | 520 | O | GLN | A | 306 | 41.795 | 57.175 | 175.470 | 1.00 | 39.31 | 8 |
| ATOM | 521 | N | ALA | A | 307 | 42.457 | 55.069 | 175.774 | 1.00 | 38.67 | 7 |
| ATOM | 522 | CA | ALA | A | 307 | 42.296 | 54.738 | 174.367 | 1.00 | 38.13 | 6 |
| ATOM | 523 | CB | ALA | A | 307 | 42.852 | 53.400 | 174.054 | 1.00 | 37.84 | 6 |
| ATOM | 524 | C | ALA | A | 307 | 40.834 | 54.861 | 173.913 | 1.00 | 38.20 | 6 |
| ATOM | 525 | O | ALA | A | 307 | 40.600 | 55.327 | 172.808 | 1.00 | 38.71 | 8 |
| ATOM | 526 | N | GLU | A | 308 | 39.860 | 54.470 | 174.742 | 1.00 | 37.63 | 7 |
| ATOM | 527 | CA | GLU | A | 308 | 38.456 | 54.663 | 174.376 | 1.00 | 37.05 | 6 |
| ATOM | 528 | CB | GLU | A | 308 | 37.505 | 54.126 | 175.464 | 1.00 | 37.71 | 6 |
| ATOM | 529 | CG | GLU | A | 308 | 36.247 | 53.502 | 174.901 | 1.00 | 36.69 | 6 |
| ATOM | 530 | CD | GLU | A | 308 | 36.633 | 52.608 | 173.796 | 1.00 | 35.01 | 6 |
| ATOM | 531 | OE1 | GLU | A | 308 | 35.850 | 52.419 | 172.842 | 1.00 | 34.91 | 8 |
| ATOM | 532 | OE2 | GLU | A | 308 | 37.777 | 52.128 | 173.897 | 1.00 | 34.26 | 8 |
| ATOM | 533 | C | GLU | A | 308 | 38.182 | 56.135 | 174.125 | 1.00 | 36.47 | 6 |
| ATOM | 534 | O | GLU | A | 308 | 37.667 | 56.522 | 173.062 | 1.00 | 36.25 | 8 |
| ATOM | 535 | N | ARG | A | 309 | 38.533 | 56.952 | 175.107 | 1.00 | 35.84 | 7 |
| ATOM | 536 | CA | ARG | A | 309 | 38.212 | 58.365 | 175.015 | 1.00 | 35.72 | 6 |
| ATOM | 537 | CB | ARG | A | 309 | 38.801 | 59.178 | 176.162 | 1.00 | 35.31 | 6 |
| ATOM | 538 | CG | ARG | A | 309 | 38.879 | 60.625 | 175.800 | 1.00 | 34.37 | 6 |
| ATOM | 539 | CD | ARG | A | 309 | 37.524 | 61.212 | 175.696 | 1.00 | 35.10 | 6 |
| ATOM | 540 | NE | ARG | A | 309 | 37.040 | 61.643 | 177.005 | 1.00 | 39.10 | 7 |
| ATOM | 541 | CZ | ARG | A | 309 | 35.860 | 61.296 | 177.521 | 1.00 | 40.41 | 6 |
| ATOM | 542 | NH1 | ARG | A | 309 | 35.031 | 60.519 | 176.817 | 1.00 | 40.79 | 7 |
| ATOM | 543 | NH2 | ARG | A | 309 | 35.493 | 61.755 | 178.718 | 1.00 | 39.97 | 7 |
| ATOM | 544 | C | ARG | A | 309 | 38.756 | 58.894 | 173.712 | 1.00 | 35.44 | 6 |
| ATOM | 545 | O | ARG | A | 309 | 38.082 | 59.644 | 172.999 | 1.00 | 35.73 | 8 |
| ATOM | 546 | N | HIS | A | 310 | 39.971 | 58.465 | 173.403 | 1.00 | 34.76 | 7 |
| ATOM | 547 | CA | HIS | A | 310 | 40.661 | 58.966 | 172.248 | 1.00 | 34.42 | 6 |

TABLE 1-continued

| | | | | | | | | | | |
|---|---|---|---|---|---|---|---|---|---|---|
| ATOM | 548 | CB | HIS | A | 310 | 42.085 | 58.458 | 172.211 | 1.00 | 34.33 | 6 |
| ATOM | 549 | CG | HIS | A | 310 | 42.923 | 59.088 | 171.147 | 1.00 | 35.33 | 6 |
| ATOM | 550 | ND1 | HIS | A | 310 | 42.587 | 59.041 | 169.809 | 1.00 | 36.33 | 7 |
| ATOM | 551 | CE1 | HIS | A | 310 | 43.518 | 59.662 | 169.104 | 1.00 | 37.03 | 6 |
| ATOM | 552 | NE2 | HIS | A | 310 | 44.440 | 60.117 | 169.933 | 1.00 | 35.51 | 7 |
| ATOM | 553 | CD2 | HIS | A | 310 | 44.100 | 59.759 | 171.216 | 1.00 | 35.85 | 6 |
| ATOM | 554 | C | HIS | A | 310 | 39.906 | 58.654 | 170.954 | 1.00 | 34.42 | 6 |
| ATOM | 555 | O | HIS | A | 310 | 39.729 | 59.561 | 170.136 | 1.00 | 35.07 | 8 |
| ATOM | 556 | N | ALA | A | 311 | 39.432 | 57.414 | 170.782 | 1.00 | 33.53 | 7 |
| ATOM | 557 | CA | ALA | A | 311 | 38.597 | 57.062 | 169.643 | 1.00 | 32.97 | 6 |
| ATOM | 558 | CB | ALA | A | 311 | 38.331 | 55.635 | 169.638 | 1.00 | 32.83 | 6 |
| ATOM | 559 | C | ALA | A | 311 | 37.292 | 57.807 | 169.700 | 1.00 | 33.26 | 6 |
| ATOM | 560 | O | ALA | A | 311 | 36.860 | 58.387 | 168.692 | 1.00 | 33.19 | 8 |
| ATOM | 561 | N | ARG | A | 312 | 36.681 | 57.797 | 170.890 | 1.00 | 33.54 | 7 |
| ATOM | 562 | CA | ARG | A | 312 | 35.368 | 58.419 | 171.118 | 1.00 | 34.12 | 6 |
| ATOM | 563 | CB | ARG | A | 312 | 34.981 | 58.332 | 172.602 | 1.00 | 34.08 | 6 |
| ATOM | 564 | CG | ARG | A | 312 | 33.564 | 58.795 | 172.904 | 1.00 | 33.75 | 6 |
| ATOM | 565 | CD | ARG | A | 312 | 33.568 | 60.168 | 173.500 | 1.00 | 33.44 | 6 |
| ATOM | 566 | NE | ARG | A | 312 | 32.214 | 60.649 | 173.768 | 1.00 | 34.06 | 7 |
| ATOM | 567 | CZ | ARG | A | 312 | 31.479 | 60.316 | 174.835 | 1.00 | 34.22 | 6 |
| ATOM | 568 | NH1 | ARG | A | 312 | 31.930 | 59.466 | 175.750 | 1.00 | 32.76 | 7 |
| ATOM | 569 | NH2 | ARG | A | 312 | 30.275 | 60.842 | 174.994 | 1.00 | 34.29 | 7 |
| ATOM | 570 | C | ARG | A | 312 | 35.325 | 59.869 | 170.605 | 1.00 | 34.42 | 6 |
| ATOM | 571 | O | ARG | A | 312 | 34.316 | 60.315 | 170.048 | 1.00 | 34.07 | 8 |
| ATOM | 572 | N | GLU | A | 313 | 36.428 | 60.587 | 170.773 | 1.00 | 34.75 | 7 |
| ATOM | 573 | CA | GLU | A | 313 | 36.458 | 61.946 | 170.296 | 1.00 | 36.02 | 6 |
| ATOM | 574 | CB | GLU | A | 313 | 37.708 | 62.689 | 170.745 | 1.00 | 36.55 | 6 |
| ATOM | 575 | CG | GLU | A | 313 | 38.049 | 62.452 | 172.178 | 1.00 | 41.53 | 6 |
| ATOM | 576 | CD | GLU | A | 313 | 38.736 | 63.633 | 172.852 | 1.00 | 47.48 | 6 |
| ATOM | 577 | OE1 | GLU | A | 313 | 39.548 | 64.319 | 172.183 | 1.00 | 49.77 | 8 |
| ATOM | 578 | OE2 | GLU | A | 313 | 38.474 | 63.861 | 174.071 | 1.00 | 51.50 | 8 |
| ATOM | 579 | C | GLU | A | 313 | 36.424 | 61.916 | 168.793 | 1.00 | 35.81 | 6 |
| ATOM | 580 | O | GLU | A | 313 | 35.544 | 62.535 | 168.171 | 1.00 | 35.63 | 8 |
| ATOM | 581 | N | LYS | A | 314 | 37.380 | 61.174 | 168.221 | 1.00 | 35.72 | 7 |
| ATOM | 582 | CA | LYS | A | 314 | 37.626 | 61.218 | 166.791 | 1.00 | 35.35 | 6 |
| ATOM | 583 | CB | LYS | A | 314 | 38.691 | 60.223 | 166.382 | 1.00 | 34.98 | 6 |
| ATOM | 584 | CG | LYS | A | 314 | 40.087 | 60.772 | 166.447 | 1.00 | 35.33 | 6 |
| ATOM | 585 | CD | LYS | A | 314 | 41.051 | 59.859 | 165.734 | 1.00 | 35.09 | 6 |
| ATOM | 586 | CE | LYS | A | 314 | 42.340 | 60.551 | 165.370 | 1.00 | 35.42 | 6 |
| ATOM | 587 | NZ | LYS | A | 314 | 43.481 | 59.603 | 165.698 | 1.00 | 36.91 | 7 |
| ATOM | 588 | C | LYS | A | 314 | 36.338 | 60.933 | 166.078 | 1.00 | 35.71 | 6 |
| ATOM | 589 | O | LYS | A | 314 | 36.074 | 61.546 | 165.043 | 1.00 | 35.61 | 8 |
| ATOM | 590 | N | LEU | A | 315 | 35.538 | 60.024 | 166.652 | 1.00 | 35.83 | 7 |
| ATOM | 591 | CA | LEU | A | 315 | 34.207 | 59.738 | 166.161 | 1.00 | 35.96 | 6 |
| ATOM | 592 | CB | LEU | A | 315 | 33.654 | 58.519 | 166.852 | 1.00 | 36.23 | 6 |
| ATOM | 593 | CG | LEU | A | 315 | 34.464 | 57.235 | 166.666 | 1.00 | 37.28 | 6 |
| ATOM | 594 | CD1 | LEU | A | 315 | 34.300 | 56.299 | 167.872 | 1.00 | 37.09 | 6 |
| ATOM | 595 | CD2 | LEU | A | 315 | 34.081 | 56.519 | 165.369 | 1.00 | 37.93 | 6 |
| ATOM | 596 | C | LEU | A | 315 | 33.276 | 60.922 | 166.367 | 1.00 | 36.22 | 6 |
| ATOM | 597 | O | LEU | A | 315 | 32.689 | 61.383 | 165.410 | 1.00 | 36.53 | 8 |
| ATOM | 598 | N | VAL | A | 316 | 33.152 | 61.440 | 167.590 | 1.00 | 36.39 | 7 |
| ATOM | 599 | CA | VAL | A | 316 | 32.242 | 62.560 | 167.843 | 1.00 | 36.51 | 6 |
| ATOM | 600 | CB | VAL | A | 316 | 32.494 | 63.210 | 169.210 | 1.00 | 36.14 | 6 |
| ATOM | 601 | CG1 | VAL | A | 316 | 32.214 | 64.703 | 169.188 | 1.00 | 35.15 | 6 |
| ATOM | 602 | CG2 | VAL | A | 316 | 31.643 | 62.527 | 170.256 | 1.00 | 36.40 | 6 |
| ATOM | 603 | C | VAL | A | 316 | 32.452 | 63.557 | 166.752 | 1.00 | 37.11 | 6 |
| ATOM | 604 | O | VAL | A | 316 | 31.520 | 64.093 | 166.179 | 1.00 | 37.40 | 8 |
| ATOM | 605 | N | GLU | A | 317 | 33.717 | 63.740 | 166.447 | 1.00 | 38.09 | 7 |
| ATOM | 606 | CA | GLU | A | 317 | 34.185 | 64.668 | 165.461 | 1.00 | 39.29 | 6 |
| ATOM | 607 | CB | GLU | A | 317 | 35.701 | 64.645 | 165.561 | 1.00 | 39.91 | 6 |
| ATOM | 608 | CG | GLU | A | 317 | 36.455 | 64.939 | 164.313 | 1.00 | 43.05 | 6 |
| ATOM | 609 | CD | GLU | A | 317 | 36.686 | 66.421 | 164.139 | 1.00 | 46.07 | 6 |
| ATOM | 610 | OE1 | GLU | A | 317 | 35.764 | 67.099 | 163.611 | 1.00 | 46.37 | 8 |
| ATOM | 611 | OE2 | GLU | A | 317 | 37.801 | 66.882 | 164.525 | 1.00 | 46.81 | 8 |
| ATOM | 612 | C | GLU | A | 317 | 33.683 | 64.266 | 164.069 | 1.00 | 39.27 | 6 |
| ATOM | 613 | O | GLU | A | 317 | 33.067 | 65.057 | 163.375 | 1.00 | 39.27 | 8 |
| ATOM | 614 | N | LYS | A | 318 | 33.926 | 63.030 | 163.666 | 1.00 | 39.74 | 7 |
| ATOM | 615 | CA | LYS | A | 318 | 33.427 | 62.545 | 162.388 | 1.00 | 40.01 | 6 |
| ATOM | 616 | CB | LYS | A | 318 | 33.807 | 61.075 | 162.176 | 1.00 | 39.78 | 6 |
| ATOM | 617 | CG | LYS | A | 318 | 33.545 | 60.518 | 160.781 | 1.00 | 38.10 | 6 |
| ATOM | 618 | CD | LYS | A | 318 | 34.142 | 61.396 | 159.706 | 1.00 | 37.70 | 6 |
| ATOM | 619 | CE | LYS | A | 318 | 35.618 | 61.160 | 159.463 | 1.00 | 36.88 | 6 |
| ATOM | 620 | NZ | LYS | A | 318 | 36.080 | 62.044 | 158.344 | 1.00 | 36.59 | 7 |
| ATOM | 621 | C | LYS | A | 318 | 31.911 | 62.738 | 162.300 | 1.00 | 40.85 | 6 |
| ATOM | 622 | O | LYS | A | 318 | 31.436 | 63.299 | 161.316 | 1.00 | 41.51 | 8 |
| ATOM | 623 | N | LYS | A | 319 | 31.156 | 62.300 | 163.317 | 1.00 | 41.24 | 7 |
| ATOM | 624 | CA | LYS | A | 319 | 29.701 | 62.528 | 163.347 | 1.00 | 41.73 | 6 |
| ATOM | 625 | CB | LYS | A | 319 | 29.084 | 62.138 | 164.697 | 1.00 | 41.47 | 6 |
| ATOM | 626 | CG | LYS | A | 319 | 27.567 | 62.314 | 164.735 | 1.00 | 43.40 | 6 |
| ATOM | 627 | CD | LYS | A | 319 | 27.032 | 62.547 | 166.157 | 1.00 | 46.30 | 6 |

TABLE 1-continued

| | | | | | | | | | | |
|---|---|---|---|---|---|---|---|---|---|---|
| ATOM | 628 | CE | LYS | A | 319 | 27.301 | 63.987 | 166.703 | 1.00 | 48.83 | 6 |
| ATOM | 629 | NZ | LYS | A | 319 | 27.319 | 64.156 | 168.232 | 1.00 | 47.00 | 7 |
| ATOM | 630 | C | LYS | A | 319 | 29.357 | 63.989 | 162.968 | 1.00 | 41.84 | 6 |
| ATOM | 631 | O | LYS | A | 319 | 28.618 | 64.212 | 161.998 | 1.00 | 41.46 | 8 |
| ATOM | 632 | N | GLU | A | 320 | 29.918 | 64.954 | 163.708 | 1.00 | 42.07 | 7 |
| ATOM | 633 | CA | GLU | A | 320 | 29.738 | 66.378 | 163.420 | 1.00 | 43.11 | 6 |
| ATOM | 634 | CB | GLU | A | 320 | 30.742 | 67.278 | 164.178 | 1.00 | 43.58 | 6 |
| ATOM | 635 | CG | GLU | A | 320 | 30.704 | 67.236 | 165.711 | 1.00 | 47.05 | 6 |
| ATOM | 636 | CD | GLU | A | 320 | 29.305 | 67.499 | 166.296 | 1.00 | 52.10 | 6 |
| ATOM | 637 | OE1 | GLU | A | 320 | 28.575 | 68.364 | 165.725 | 1.00 | 53.88 | 8 |
| ATOM | 638 | OE2 | GLU | A | 320 | 28.941 | 66.846 | 167.327 | 1.00 | 52.67 | 8 |
| ATOM | 639 | C | GLU | A | 320 | 29.917 | 66.625 | 161.934 | 1.00 | 43.15 | 6 |
| ATOM | 640 | O | GLU | A | 320 | 29.005 | 67.145 | 161.273 | 1.00 | 43.42 | 8 |
| ATOM | 641 | N | TYR | A | 321 | 31.095 | 66.254 | 161.419 | 1.00 | 42.94 | 7 |
| ATOM | 642 | CA | TYR | A | 321 | 31.440 | 66.468 | 160.019 | 1.00 | 42.74 | 6 |
| ATOM | 643 | CB | TYR | A | 321 | 32.822 | 65.892 | 159.681 | 1.00 | 42.84 | 6 |
| ATOM | 644 | CG | TYR | A | 321 | 33.110 | 65.974 | 158.209 | 1.00 | 42.31 | 6 |
| ATOM | 645 | CD1 | TYR | A | 321 | 33.494 | 67.171 | 157.626 | 1.00 | 42.85 | 6 |
| ATOM | 646 | CE1 | TYR | A | 321 | 33.722 | 67.265 | 156.258 | 1.00 | 42.57 | 6 |
| ATOM | 647 | CZ | TYR | A | 321 | 33.549 | 66.155 | 155.474 | 1.00 | 42.11 | 6 |
| ATOM | 648 | OH | TYR | A | 321 | 33.768 | 66.233 | 154.135 | 1.00 | 41.62 | 8 |
| ATOM | 649 | CE2 | TYR | A | 321 | 33.155 | 64.959 | 156.030 | 1.00 | 42.63 | 6 |
| ATOM | 650 | CD2 | TYR | A | 321 | 32.940 | 64.875 | 157.393 | 1.00 | 42.41 | 6 |
| ATOM | 651 | C | TYR | A | 321 | 30.386 | 65.887 | 159.077 | 1.00 | 43.07 | 6 |
| ATOM | 652 | O | TYR | A | 321 | 30.001 | 66.540 | 158.100 | 1.00 | 43.16 | 8 |
| ATOM | 653 | N | LEU | A | 322 | 29.908 | 64.678 | 159.372 | 1.00 | 43.28 | 7 |
| ATOM | 654 | CA | LEU | A | 322 | 28.896 | 64.066 | 158.533 | 1.00 | 43.76 | 6 |
| ATOM | 655 | CB | LEU | A | 322 | 28.746 | 62.609 | 158.866 | 1.00 | 43.15 | 6 |
| ATOM | 656 | CG | LEU | A | 322 | 29.982 | 61.842 | 158.414 | 1.00 | 42.73 | 6 |
| ATOM | 657 | CD1 | LEU | A | 322 | 29.634 | 60.383 | 158.329 | 1.00 | 43.70 | 6 |
| ATOM | 658 | CD2 | LEU | A | 322 | 30.511 | 62.294 | 157.067 | 1.00 | 41.08 | 6 |
| ATOM | 659 | C | LEU | A | 322 | 27.558 | 64.796 | 158.570 | 1.00 | 44.89 | 6 |
| ATOM | 660 | O | LEU | A | 322 | 26.940 | 64.986 | 157.521 | 1.00 | 44.77 | 8 |
| ATOM | 661 | N | GLN | A | 323 | 27.130 | 65.222 | 159.765 | 1.00 | 46.29 | 7 |
| ATOM | 662 | CA | GLN | A | 323 | 25.897 | 65.992 | 159.923 | 1.00 | 47.61 | 6 |
| ATOM | 663 | CB | GLN | A | 323 | 25.660 | 66.385 | 161.389 | 1.00 | 47.12 | 6 |
| ATOM | 664 | CG | GLN | A | 323 | 24.868 | 65.349 | 162.230 | 1.00 | 48.21 | 6 |
| ATOM | 665 | CD | GLN | A | 323 | 25.298 | 65.253 | 163.746 | 1.00 | 49.49 | 6 |
| ATOM | 666 | OE1 | GLN | A | 323 | 26.009 | 66.118 | 164.271 | 1.00 | 52.44 | 8 |
| ATOM | 667 | NE2 | GLN | A | 323 | 24.853 | 64.191 | 164.432 | 1.00 | 50.57 | 7 |
| ATOM | 668 | C | GLN | A | 323 | 25.936 | 67.198 | 158.991 | 1.00 | 48.24 | 6 |
| ATOM | 669 | O | GLN | A | 323 | 24.972 | 67.450 | 158.280 | 1.00 | 48.14 | 8 |
| ATOM | 670 | N | GLU | A | 324 | 27.069 | 67.898 | 158.954 | 1.00 | 49.58 | 7 |
| ATOM | 671 | CA | GLU | A | 324 | 27.248 | 69.031 | 158.049 | 1.00 | 51.32 | 6 |
| ATOM | 672 | CB | GLU | A | 324 | 28.576 | 69.727 | 158.274 | 1.00 | 51.84 | 6 |
| ATOM | 673 | CG | GLU | A | 324 | 28.583 | 70.635 | 159.464 | 1.00 | 55.85 | 6 |
| ATOM | 674 | CD | GLU | A | 324 | 29.959 | 70.704 | 160.124 | 1.00 | 61.05 | 6 |
| ATOM | 675 | OE1 | GLU | A | 324 | 30.982 | 70.661 | 159.377 | 1.00 | 63.21 | 8 |
| ATOM | 676 | OE2 | GLU | A | 324 | 30.007 | 70.808 | 161.383 | 1.00 | 62.05 | 8 |
| ATOM | 677 | C | GLU | A | 324 | 27.164 | 68.619 | 156.602 | 1.00 | 51.58 | 6 |
| ATOM | 678 | O | GLU | A | 324 | 26.410 | 69.208 | 155.839 | 1.00 | 51.72 | 8 |
| ATOM | 679 | N | GLN | A | 325 | 27.934 | 67.617 | 156.213 | 1.00 | 52.30 | 7 |
| ATOM | 680 | CA | GLN | A | 325 | 27.848 | 67.141 | 154.853 | 1.00 | 53.55 | 6 |
| ATOM | 681 | CB | GLN | A | 325 | 28.648 | 65.869 | 154.678 | 1.00 | 53.62 | 6 |
| ATOM | 682 | CG | GLN | A | 325 | 30.135 | 66.083 | 154.783 | 1.00 | 54.69 | 6 |
| ATOM | 683 | CD | GLN | A | 325 | 30.610 | 67.299 | 154.022 | 1.00 | 55.31 | 6 |
| ATOM | 684 | OE1 | GLN | A | 325 | 30.791 | 68.372 | 154.600 | 1.00 | 56.28 | 8 |
| ATOM | 685 | NE2 | GLN | A | 325 | 30.812 | 67.142 | 152.718 | 1.00 | 55.13 | 7 |
| ATOM | 686 | C | GLN | A | 325 | 26.408 | 66.886 | 154.450 | 1.00 | 54.36 | 6 |
| ATOM | 687 | O | GLN | A | 325 | 25.992 | 67.266 | 153.364 | 1.00 | 54.56 | 8 |
| ATOM | 688 | N | LEU | A | 326 | 25.651 | 66.242 | 155.334 | 1.00 | 55.40 | 7 |
| ATOM | 689 | CA | LEU | A | 326 | 24.231 | 66.011 | 155.116 | 1.00 | 56.16 | 6 |
| ATOM | 690 | CB | LEU | A | 326 | 23.655 | 65.054 | 156.158 | 1.00 | 55.64 | 6 |
| ATOM | 691 | CG | LEU | A | 326 | 23.334 | 63.651 | 155.640 | 1.00 | 54.81 | 6 |
| ATOM | 692 | CD1 | LEU | A | 326 | 22.347 | 62.962 | 156.519 | 1.00 | 54.72 | 6 |
| ATOM | 693 | CD2 | LEU | A | 326 | 22.741 | 63.728 | 154.275 | 1.00 | 55.41 | 6 |
| ATOM | 694 | C | LEU | A | 326 | 23.394 | 67.280 | 155.046 | 1.00 | 57.27 | 6 |
| ATOM | 695 | O | LEU | A | 326 | 22.473 | 67.352 | 154.250 | 1.00 | 57.66 | 8 |
| ATOM | 696 | N | GLU | A | 327 | 23.700 | 68.274 | 155.867 | 1.00 | 58.54 | 7 |
| ATOM | 697 | CA | GLU | A | 327 | 22.969 | 69.523 | 155.786 | 1.00 | 60.05 | 6 |
| ATOM | 698 | CB | GLU | A | 327 | 23.312 | 70.445 | 156.960 | 1.00 | 60.19 | 6 |
| ATOM | 699 | CG | GLU | A | 327 | 22.394 | 71.676 | 157.155 | 1.00 | 61.03 | 6 |
| ATOM | 700 | CD | GLU | A | 327 | 20.925 | 71.335 | 157.421 | 1.00 | 62.03 | 6 |
| ATOM | 701 | OE1 | GLU | A | 327 | 20.573 | 70.136 | 157.386 | 1.00 | 62.52 | 8 |
| ATOM | 702 | OE2 | GLU | A | 327 | 20.119 | 72.271 | 157.654 | 1.00 | 61.96 | 8 |
| ATOM | 703 | C | GLU | A | 327 | 23.223 | 70.171 | 154.430 | 1.00 | 61.19 | 6 |
| ATOM | 704 | O | GLU | A | 327 | 22.296 | 70.280 | 153.630 | 1.00 | 61.54 | 8 |
| ATOM | 705 | N | GLN | A | 328 | 24.471 | 70.552 | 154.162 | 1.00 | 62.53 | 7 |
| ATOM | 706 | CA | GLN | A | 328 | 24.859 | 71.117 | 152.872 | 1.00 | 64.22 | 6 |
| ATOM | 707 | CB | GLN | A | 328 | 26.376 | 71.194 | 152.765 | 1.00 | 64.79 | 6 |

TABLE 1-continued

| | | | | | | | | | | |
|---|---|---|---|---|---|---|---|---|---|---|
| ATOM | 708 | CG | GLN | A | 328 | 26.920 | 72.612 | 152.670 | 1.00 | 67.70 | 6 |
| ATOM | 709 | CD | GLN | A | 328 | 26.291 | 73.586 | 153.686 | 1.00 | 71.01 | 6 |
| ATOM | 710 | OE1 | GLN | A | 328 | 26.909 | 73.906 | 154.721 | 1.00 | 71.92 | 8 |
| ATOM | 711 | NE2 | GLN | A | 328 | 25.070 | 74.074 | 153.384 | 1.00 | 70.50 | 7 |
| ATOM | 712 | C | GLN | A | 328 | 24.301 | 70.399 | 151.657 | 1.00 | 64.82 | 6 |
| ATOM | 713 | O | GLN | A | 328 | 23.890 | 71.048 | 150.701 | 1.00 | 65.09 | 8 |
| ATOM | 714 | N | LEU | A | 329 | 24.284 | 69.070 | 151.697 | 1.00 | 65.64 | 7 |
| ATOM | 715 | CA | LEU | A | 329 | 23.826 | 68.287 | 150.570 | 1.00 | 66.69 | 6 |
| ATOM | 716 | CB | LEU | A | 329 | 24.313 | 66.850 | 150.673 | 1.00 | 66.65 | 6 |
| ATOM | 717 | CG | LEU | A | 329 | 24.342 | 66.023 | 149.383 | 1.00 | 66.07 | 6 |
| ATOM | 718 | CD1 | LEU | A | 329 | 23.112 | 65.170 | 149.269 | 1.00 | 64.76 | 6 |
| ATOM | 719 | CD2 | LEU | A | 329 | 24.538 | 66.908 | 148.133 | 1.00 | 65.81 | 6 |
| ATOM | 720 | C | LEU | A | 329 | 22.329 | 68.297 | 150.460 | 1.00 | 67.81 | 6 |
| ATOM | 721 | O | LEU | A | 329 | 21.803 | 68.298 | 149.367 | 1.00 | 68.11 | 8 |
| ATOM | 722 | N | GLN | A | 330 | 21.645 | 68.290 | 151.593 | 1.00 | 69.44 | 7 |
| ATOM | 723 | CA | GLN | A | 330 | 20.188 | 68.357 | 151.614 | 1.00 | 71.03 | 6 |
| ATOM | 724 | CB | GLN | A | 330 | 19.679 | 67.995 | 153.017 | 1.00 | 71.12 | 6 |
| ATOM | 725 | CG | GLN | A | 330 | 18.174 | 68.148 | 153.273 | 1.00 | 72.41 | 6 |
| ATOM | 726 | CD | GLN | A | 330 | 17.288 | 67.401 | 152.272 | 1.00 | 74.23 | 6 |
| ATOM | 727 | OE1 | GLN | A | 330 | 17.731 | 66.458 | 151.605 | 1.00 | 74.44 | 8 |
| ATOM | 728 | NE2 | GLN | A | 330 | 16.023 | 67.828 | 152.166 | 1.00 | 74.54 | 7 |
| ATOM | 729 | C | GLN | A | 330 | 19.662 | 69.726 | 151.149 | 1.00 | 71.91 | 6 |
| ATOM | 730 | O | GLN | A | 330 | 18.555 | 69.841 | 150.611 | 1.00 | 71.92 | 8 |
| ATOM | 731 | N | ARG | A | 331 | 20.470 | 70.759 | 151.338 | 1.00 | 73.14 | 7 |
| ATOM | 732 | CA | ARG | A | 331 | 20.103 | 72.086 | 150.868 | 1.00 | 74.41 | 6 |
| ATOM | 733 | CB | ARG | A | 331 | 20.850 | 73.164 | 151.648 | 1.00 | 74.06 | 6 |
| ATOM | 734 | CG | ARG | A | 331 | 20.530 | 73.166 | 153.130 | 1.00 | 72.82 | 6 |
| ATOM | 735 | CD | ARG | A | 331 | 21.195 | 74.320 | 153.847 | 1.00 | 70.75 | 6 |
| ATOM | 736 | NE | ARG | A | 331 | 20.934 | 74.285 | 155.281 | 1.00 | 68.50 | 7 |
| ATOM | 737 | CZ | ARG | A | 331 | 21.401 | 75.171 | 156.148 | 1.00 | 67.16 | 6 |
| ATOM | 738 | NH1 | ARG | A | 331 | 22.158 | 76.175 | 155.740 | 1.00 | 66.73 | 7 |
| ATOM | 739 | NH2 | ARG | A | 331 | 21.110 | 75.046 | 157.425 | 1.00 | 66.80 | 7 |
| ATOM | 740 | C | ARG | A | 331 | 20.290 | 72.244 | 149.353 | 1.00 | 75.79 | 6 |
| ATOM | 741 | O | ARG | A | 331 | 19.729 | 73.163 | 148.747 | 1.00 | 76.06 | 8 |
| ATOM | 742 | N | GLU | A | 332 | 21.065 | 71.341 | 148.756 | 1.00 | 77.29 | 7 |
| ATOM | 743 | CA | GLU | A | 332 | 21.313 | 71.315 | 147.315 | 1.00 | 78.99 | 6 |
| ATOM | 744 | CB | GLU | A | 332 | 22.620 | 70.585 | 147.039 | 1.00 | 79.10 | 6 |
| ATOM | 745 | CG | GLU | A | 332 | 23.711 | 71.450 | 146.478 | 1.00 | 80.61 | 6 |
| ATOM | 746 | CD | GLU | A | 332 | 23.989 | 72.646 | 147.343 | 1.00 | 82.74 | 6 |
| ATOM | 747 | OE1 | GLU | A | 332 | 24.867 | 72.518 | 148.227 | 1.00 | 83.96 | 8 |
| ATOM | 748 | OE2 | GLU | A | 332 | 23.320 | 73.696 | 147.151 | 1.00 | 83.56 | 8 |
| ATOM | 749 | C | GLU | A | 332 | 20.204 | 70.606 | 146.571 | 1.00 | 79.91 | 6 |
| ATOM | 750 | O | GLU | A | 332 | 19.723 | 71.079 | 145.544 | 1.00 | 80.08 | 8 |
| ATOM | 751 | N | PHE | A | 333 | 19.844 | 69.444 | 147.101 | 1.00 | 81.18 | 7 |
| ATOM | 752 | CA | PHE | A | 333 | 18.723 | 68.641 | 146.664 | 1.00 | 82.48 | 6 |
| ATOM | 753 | CB | PHE | A | 333 | 18.650 | 67.409 | 147.570 | 1.00 | 82.54 | 6 |
| ATOM | 754 | CG | PHE | A | 333 | 17.756 | 66.304 | 147.064 | 1.00 | 83.09 | 6 |
| ATOM | 755 | CD1 | PHE | A | 333 | 18.246 | 65.346 | 146.166 | 1.00 | 83.45 | 6 |
| ATOM | 756 | CE1 | PHE | A | 333 | 17.415 | 64.305 | 145.706 | 1.00 | 83.73 | 6 |
| ATOM | 757 | CZ | PHE | A | 333 | 16.090 | 64.210 | 146.163 | 1.00 | 83.17 | 6 |
| ATOM | 758 | CE2 | PHE | A | 333 | 15.599 | 65.154 | 147.070 | 1.00 | 83.22 | 6 |
| ATOM | 759 | CD2 | PHE | A | 333 | 16.435 | 66.188 | 147.524 | 1.00 | 83.25 | 6 |
| ATOM | 760 | C | PHE | A | 333 | 17.437 | 69.442 | 146.807 | 1.00 | 83.43 | 6 |
| ATOM | 761 | O | PHE | A | 333 | 16.386 | 69.032 | 146.321 | 1.00 | 83.77 | 8 |
| ATOM | 762 | N | ASN | A | 334 | 17.501 | 70.581 | 147.488 | 1.00 | 84.40 | 7 |
| ATOM | 763 | CA | ASN | A | 334 | 16.296 | 71.386 | 147.639 | 1.00 | 85.15 | 6 |
| ATOM | 764 | CB | ASN | A | 334 | 15.912 | 71.564 | 149.109 | 1.00 | 85.01 | 6 |
| ATOM | 765 | CG | ASN | A | 334 | 15.577 | 70.238 | 149.789 | 1.00 | 84.20 | 6 |
| ATOM | 766 | OD1 | ASN | A | 334 | 15.334 | 69.226 | 149.129 | 1.00 | 82.90 | 8 |
| ATOM | 767 | ND2 | ASN | A | 334 | 15.566 | 70.244 | 151.113 | 1.00 | 83.01 | 7 |
| ATOM | 768 | C | ASN | A | 334 | 16.271 | 72.685 | 146.851 | 1.00 | 85.96 | 6 |
| ATOM | 769 | O | ASN | A | 334 | 15.203 | 73.177 | 146.533 | 1.00 | 86.07 | 8 |
| ATOM | 770 | N | LYS | A | 335 | 17.433 | 73.227 | 146.514 | 1.00 | 87.13 | 7 |
| ATOM | 771 | CA | LYS | A | 335 | 17.478 | 74.371 | 145.609 | 1.00 | 88.32 | 6 |
| ATOM | 772 | CB | LYS | A | 335 | 18.704 | 75.249 | 145.885 | 1.00 | 88.31 | 6 |
| ATOM | 773 | CG | LYS | A | 335 | 18.469 | 76.248 | 147.008 | 1.00 | 88.61 | 6 |
| ATOM | 774 | CD | LYS | A | 335 | 19.747 | 76.581 | 147.736 | 1.00 | 89.01 | 6 |
| ATOM | 775 | CE | LYS | A | 335 | 19.443 | 77.262 | 149.053 | 1.00 | 88.95 | 6 |
| ATOM | 776 | NZ | LYS | A | 335 | 20.688 | 77.591 | 149.787 | 1.00 | 89.07 | 7 |
| ATOM | 777 | C | LYS | A | 335 | 17.393 | 73.904 | 144.152 | 1.00 | 89.02 | 6 |
| ATOM | 778 | O | LYS | A | 335 | 16.719 | 74.527 | 143.331 | 1.00 | 89.20 | 8 |
| ATOM | 779 | N | LEU | A | 336 | 18.056 | 72.784 | 143.866 | 1.00 | 89.96 | 7 |
| ATOM | 780 | CA | LEU | A | 336 | 18.036 | 72.115 | 142.561 | 1.00 | 90.64 | 6 |
| ATOM | 781 | CB | LEU | A | 336 | 19.400 | 71.409 | 142.351 | 1.00 | 90.53 | 6 |
| ATOM | 782 | CG | LEU | A | 336 | 19.972 | 70.837 | 141.042 | 1.00 | 90.21 | 6 |
| ATOM | 783 | CD1 | LEU | A | 336 | 21.423 | 71.285 | 140.821 | 1.00 | 89.63 | 6 |
| ATOM | 784 | CD2 | LEU | A | 336 | 19.876 | 69.315 | 141.019 | 1.00 | 89.73 | 6 |
| ATOM | 785 | C | LEU | A | 336 | 16.859 | 71.116 | 142.514 | 1.00 | 91.24 | 6 |
| ATOM | 786 | O | LEU | A | 336 | 16.832 | 70.217 | 141.674 | 1.00 | 91.39 | 8 |
| ATOM | 787 | N | LYS | A | 337 | 15.882 | 71.300 | 143.409 | 1.00 | 91.82 | 7 |

TABLE 1-continued

| | | | | | | | | | | |
|---|---|---|---|---|---|---|---|---|---|---|
| ATOM | 788 | CA | LYS | A | 337 | 14.740 | 70.380 | 143.547 | 1.00 | 92.31 | 6 |
| ATOM | 789 | CB | LYS | A | 337 | 14.005 | 70.624 | 144.869 | 1.00 | 92.40 | 6 |
| ATOM | 790 | CG | LYS | A | 337 | 13.216 | 69.416 | 145.375 | 1.00 | 92.55 | 6 |
| ATOM | 791 | CD | LYS | A | 337 | 12.668 | 69.637 | 146.776 | 1.00 | 92.33 | 6 |
| ATOM | 792 | CE | LYS | A | 337 | 12.199 | 68.330 | 147.383 | 1.00 | 91.45 | 6 |
| ATOM | 793 | NZ | LYS | A | 337 | 11.469 | 68.579 | 148.642 | 1.00 | 90.92 | 7 |
| ATOM | 794 | C | LYS | A | 337 | 13.747 | 70.442 | 142.382 | 1.00 | 92.61 | 6 |
| ATOM | 795 | O | LYS | A | 337 | 14.096 | 70.638 | 141.218 | 1.00 | 92.91 | 8 |
| ATOM | 796 | OXT | LYS | A | 337 | 12.530 | 70.339 | 142.576 | 1.00 | 92.65 | 8 |
| ATOM | 797 | N | SER | B | 247 | 74.573 | 13.366 | 243.691 | 1.00 | 80.34 | 7 |
| ATOM | 798 | CA | SER | B | 247 | 74.309 | 12.439 | 244.839 | 1.00 | 80.35 | 6 |
| ATOM | 799 | CB | SER | B | 247 | 75.563 | 12.231 | 245.702 | 1.00 | 80.24 | 6 |
| ATOM | 800 | OG | SER | B | 247 | 75.643 | 13.191 | 246.747 | 1.00 | 79.88 | 8 |
| ATOM | 801 | C | SER | B | 247 | 73.158 | 12.935 | 245.711 | 1.00 | 80.47 | 6 |
| ATOM | 802 | O | SER | B | 247 | 73.052 | 14.136 | 246.002 | 1.00 | 80.69 | 8 |
| ATOM | 803 | N | MET | B | 248 | 72.305 | 11.990 | 246.111 | 1.00 | 80.37 | 7 |
| ATOM | 804 | CA | MET | B | 248 | 71.164 | 12.223 | 247.014 | 1.00 | 80.13 | 6 |
| ATOM | 805 | CB | MET | B | 248 | 71.640 | 12.350 | 248.464 | 1.00 | 80.27 | 6 |
| ATOM | 806 | CG | MET | B | 248 | 71.518 | 11.068 | 249.289 | 1.00 | 79.98 | 6 |
| ATOM | 807 | SD | MET | B | 248 | 70.989 | 11.478 | 250.975 | 1.00 | 80.26 | 16 |
| ATOM | 808 | CE | MET | B | 248 | 69.329 | 12.195 | 250.686 | 1.00 | 79.56 | 6 |
| ATOM | 809 | C | MET | B | 248 | 70.196 | 13.367 | 246.647 | 1.00 | 79.85 | 6 |
| ATOM | 810 | O | MET | B | 248 | 69.780 | 13.496 | 245.490 | 1.00 | 79.97 | 8 |
| ATOM | 811 | N | ALA | B | 249 | 69.858 | 14.198 | 247.634 | 1.00 | 79.47 | 7 |
| ATOM | 812 | CA | ALA | B | 249 | 68.688 | 15.087 | 247.548 | 1.00 | 79.06 | 6 |
| ATOM | 813 | CB | ALA | B | 249 | 67.809 | 14.918 | 248.822 | 1.00 | 79.23 | 6 |
| ATOM | 814 | C | ALA | B | 249 | 68.910 | 16.590 | 247.213 | 1.00 | 78.53 | 6 |
| ATOM | 815 | O | ALA | B | 249 | 67.932 | 17.336 | 247.113 | 1.00 | 78.39 | 8 |
| ATOM | 816 | N | SER | B | 250 | 70.165 | 17.029 | 247.043 | 1.00 | 77.83 | 7 |
| ATOM | 817 | CA | SER | B | 250 | 70.461 | 18.421 | 246.613 | 1.00 | 76.92 | 6 |
| ATOM | 818 | CB | SER | B | 250 | 71.441 | 19.134 | 247.556 | 1.00 | 76.81 | 6 |
| ATOM | 819 | OG | SER | B | 250 | 72.159 | 20.157 | 246.883 | 1.00 | 76.19 | 8 |
| ATOM | 820 | C | SER | B | 250 | 70.957 | 18.537 | 245.174 | 1.00 | 76.35 | 6 |
| ATOM | 821 | O | SER | B | 250 | 70.929 | 19.630 | 244.602 | 1.00 | 76.22 | 8 |
| ATOM | 822 | N | MET | B | 251 | 71.423 | 17.429 | 244.598 | 1.00 | 75.47 | 7 |
| ATOM | 823 | CA | MET | B | 251 | 71.623 | 17.393 | 243.156 | 1.00 | 74.63 | 6 |
| ATOM | 824 | CB | MET | B | 251 | 72.286 | 16.088 | 242.700 | 1.00 | 74.73 | 6 |
| ATOM | 825 | CG | MET | B | 251 | 73.773 | 16.275 | 242.344 | 1.00 | 74.68 | 6 |
| ATOM | 826 | SD | MET | B | 251 | 74.208 | 16.478 | 240.572 | 1.00 | 75.60 | 16 |
| ATOM | 827 | CE | MET | B | 251 | 73.183 | 17.815 | 239.951 | 1.00 | 73.52 | 6 |
| ATOM | 828 | C | MET | B | 251 | 70.290 | 17.711 | 242.440 | 1.00 | 74.03 | 6 |
| ATOM | 829 | O | MET | B | 251 | 70.286 | 18.172 | 241.298 | 1.00 | 74.00 | 8 |
| ATOM | 830 | N | GLN | B | 252 | 69.182 | 17.451 | 243.144 | 1.00 | 72.87 | 7 |
| ATOM | 831 | CA | GLN | B | 252 | 67.851 | 18.069 | 242.946 | 1.00 | 72.59 | 6 |
| ATOM | 832 | CB | GLN | B | 252 | 66.945 | 17.790 | 244.146 | 1.00 | 72.33 | 6 |
| ATOM | 833 | CG | GLN | B | 252 | 66.634 | 16.334 | 244.398 | 1.00 | 71.53 | 6 |
| ATOM | 834 | CD | GLN | B | 252 | 65.387 | 16.169 | 245.230 | 1.00 | 70.50 | 6 |
| ATOM | 835 | OE1 | GLN | B | 252 | 65.461 | 15.858 | 246.419 | 1.00 | 70.46 | 8 |
| ATOM | 836 | NE2 | GLN | B | 252 | 64.230 | 16.399 | 244.617 | 1.00 | 69.54 | 7 |
| ATOM | 837 | C | GLN | B | 252 | 67.846 | 19.584 | 242.725 | 1.00 | 72.68 | 6 |
| ATOM | 838 | O | GLN | B | 252 | 66.989 | 20.109 | 242.008 | 1.00 | 72.59 | 8 |
| ATOM | 839 | N | LEU | B | 253 | 68.769 | 20.300 | 243.357 | 1.00 | 72.96 | 7 |
| ATOM | 840 | CA | LEU | B | 253 | 68.833 | 21.736 | 243.122 | 1.00 | 73.18 | 6 |
| ATOM | 841 | CB | LEU | B | 253 | 69.477 | 22.490 | 244.297 | 1.00 | 72.92 | 6 |
| ATOM | 842 | CG | LEU | B | 253 | 69.411 | 24.021 | 244.327 | 1.00 | 72.11 | 6 |
| ATOM | 843 | CD1 | LEU | B | 253 | 69.199 | 24.559 | 245.739 | 1.00 | 70.21 | 6 |
| ATOM | 844 | CD2 | LEU | B | 253 | 70.667 | 24.610 | 243.715 | 1.00 | 71.43 | 6 |
| ATOM | 845 | C | LEU | B | 253 | 69.435 | 22.076 | 241.748 | 1.00 | 73.75 | 6 |
| ATOM | 846 | O | LEU | B | 253 | 69.037 | 23.068 | 241.143 | 1.00 | 73.75 | 8 |
| ATOM | 847 | N | GLU | B | 254 | 70.343 | 21.245 | 241.233 | 1.00 | 74.41 | 7 |
| ATOM | 848 | CA | GLU | B | 254 | 70.856 | 21.493 | 239.886 | 1.00 | 75.13 | 6 |
| ATOM | 849 | CB | GLU | B | 254 | 72.220 | 20.839 | 239.614 | 1.00 | 75.29 | 6 |
| ATOM | 850 | CG | GLU | B | 254 | 73.358 | 21.765 | 240.031 | 1.00 | 75.77 | 6 |
| ATOM | 851 | CD | GLU | B | 254 | 72.914 | 23.240 | 240.063 | 1.00 | 76.49 | 6 |
| ATOM | 852 | OE1 | GLU | B | 254 | 72.725 | 23.833 | 238.973 | 1.00 | 76.50 | 8 |
| ATOM | 853 | OE2 | GLU | B | 254 | 72.734 | 23.792 | 241.178 | 1.00 | 76.16 | 8 |
| ATOM | 854 | C | GLU | B | 254 | 69.831 | 21.299 | 238.772 | 1.00 | 75.31 | 6 |
| ATOM | 855 | O | GLU | B | 254 | 69.895 | 21.981 | 237.748 | 1.00 | 75.32 | 8 |
| ATOM | 856 | N | ASP | B | 255 | 68.885 | 20.383 | 238.997 | 1.00 | 75.53 | 7 |
| ATOM | 857 | CA | ASP | B | 255 | 67.747 | 20.205 | 238.102 | 1.00 | 75.89 | 6 |
| ATOM | 858 | CB | ASP | B | 255 | 66.728 | 19.206 | 238.669 | 1.00 | 76.17 | 6 |
| ATOM | 859 | CG | ASP | B | 255 | 67.374 | 17.947 | 239.232 | 1.00 | 77.38 | 6 |
| ATOM | 860 | OD1 | ASP | B | 255 | 68.585 | 17.722 | 239.014 | 1.00 | 78.27 | 8 |
| ATOM | 861 | OD2 | ASP | B | 255 | 66.657 | 17.172 | 239.903 | 1.00 | 79.00 | 8 |
| ATOM | 862 | C | ASP | B | 255 | 67.093 | 21.565 | 237.994 | 1.00 | 75.80 | 6 |
| ATOM | 863 | O | ASP | B | 255 | 67.115 | 22.198 | 236.924 | 1.00 | 75.90 | 8 |
| ATOM | 864 | N | LEU | B | 256 | 66.548 | 22.018 | 239.124 | 1.00 | 75.52 | 7 |
| ATOM | 865 | CA | LEU | B | 256 | 65.892 | 23.309 | 239.211 | 1.00 | 75.24 | 6 |
| ATOM | 866 | CB | LEU | B | 256 | 65.550 | 23.650 | 240.656 | 1.00 | 75.14 | 6 |
| ATOM | 867 | CG | LEU | B | 256 | 64.603 | 22.714 | 241.416 | 1.00 | 74.95 | 6 |

TABLE 1-continued

| | | | | | | | | | | |
|---|---|---|---|---|---|---|---|---|---|---|
| ATOM | 868 | CD1 | LEU | B | 256 | 64.035 | 23.460 | 242.596 | 1.00 | 74.46 | 6 |
| ATOM | 869 | CD2 | LEU | B | 256 | 63.468 | 22.170 | 240.559 | 1.00 | 74.53 | 6 |
| ATOM | 870 | C | LEU | B | 256 | 66.748 | 24.396 | 238.599 | 1.00 | 75.23 | 6 |
| ATOM | 871 | O | LEU | B | 256 | 66.322 | 25.076 | 237.681 | 1.00 | 75.26 | 8 |
| ATOM | 872 | N | ARG | B | 257 | 67.973 | 24.539 | 239.061 | 1.00 | 75.41 | 7 |
| ATOM | 873 | CA | ARG | B | 257 | 68.760 | 25.623 | 238.529 | 1.00 | 75.72 | 6 |
| ATOM | 874 | CB | ARG | B | 257 | 70.006 | 25.859 | 239.344 | 1.00 | 75.90 | 6 |
| ATOM | 875 | CG | ARG | B | 257 | 69.671 | 26.588 | 240.622 | 1.00 | 76.28 | 6 |
| ATOM | 876 | CD | ARG | B | 257 | 69.917 | 28.087 | 240.509 | 1.00 | 76.40 | 6 |
| ATOM | 877 | NE | ARG | B | 257 | 69.597 | 28.787 | 241.757 | 1.00 | 77.53 | 7 |
| ATOM | 878 | CZ | ARG | B | 257 | 70.125 | 28.525 | 242.960 | 1.00 | 78.51 | 6 |
| ATOM | 879 | NH1 | ARG | B | 257 | 71.016 | 27.554 | 243.140 | 1.00 | 78.70 | 7 |
| ATOM | 880 | NH2 | ARG | B | 257 | 69.748 | 29.240 | 244.009 | 1.00 | 79.07 | 7 |
| ATOM | 881 | C | ARG | B | 257 | 69.018 | 25.546 | 237.035 | 1.00 | 75.87 | 6 |
| ATOM | 882 | O | ARG | B | 257 | 68.981 | 26.580 | 236.387 | 1.00 | 75.77 | 8 |
| ATOM | 883 | N | GLN | B | 258 | 69.226 | 24.341 | 236.491 | 1.00 | 76.21 | 7 |
| ATOM | 884 | CA | GLN | B | 258 | 69.279 | 24.149 | 235.032 | 1.00 | 76.55 | 6 |
| ATOM | 885 | CB | GLN | B | 258 | 69.742 | 22.740 | 234.622 | 1.00 | 76.74 | 6 |
| ATOM | 886 | CG | GLN | B | 258 | 71.192 | 22.662 | 234.152 | 1.00 | 77.32 | 6 |
| ATOM | 887 | CD | GLN | B | 258 | 72.182 | 23.127 | 235.215 | 1.00 | 78.99 | 6 |
| ATOM | 888 | OE1 | GLN | B | 258 | 72.866 | 22.313 | 235.844 | 1.00 | 79.45 | 8 |
| ATOM | 889 | NE2 | GLN | B | 258 | 72.256 | 24.441 | 235.426 | 1.00 | 79.31 | 7 |
| ATOM | 890 | C | GLN | B | 258 | 67.951 | 24.481 | 234.399 | 1.00 | 76.49 | 6 |
| ATOM | 891 | O | GLN | B | 258 | 67.871 | 25.437 | 233.641 | 1.00 | 76.75 | 8 |
| ATOM | 892 | N | GLN | B | 259 | 66.900 | 23.733 | 234.710 | 1.00 | 76.38 | 7 |
| ATOM | 893 | CA | GLN | B | 259 | 65.661 | 24.019 | 234.013 | 1.00 | 76.80 | 6 |
| ATOM | 894 | CB | GLN | B | 259 | 64.502 | 23.099 | 234.358 | 1.00 | 76.80 | 6 |
| ATOM | 895 | CG | GLN | B | 259 | 64.603 | 22.387 | 235.643 | 1.00 | 77.49 | 6 |
| ATOM | 896 | CD | GLN | B | 259 | 64.144 | 20.963 | 235.496 | 1.00 | 78.50 | 6 |
| ATOM | 897 | OE1 | GLN | B | 259 | 63.675 | 20.564 | 234.430 | 1.00 | 78.56 | 8 |
| ATOM | 898 | NE2 | GLN | B | 259 | 64.283 | 20.178 | 236.558 | 1.00 | 79.70 | 7 |
| ATOM | 899 | C | GLN | B | 259 | 65.270 | 25.483 | 234.073 | 1.00 | 77.10 | 6 |
| ATOM | 900 | O | GLN | B | 259 | 64.696 | 25.989 | 233.107 | 1.00 | 77.35 | 8 |
| ATOM | 901 | N | LEU | B | 260 | 65.617 | 26.169 | 235.165 | 1.00 | 77.36 | 7 |
| ATOM | 902 | CA | LEU | B | 260 | 65.368 | 27.606 | 235.256 | 1.00 | 77.65 | 6 |
| ATOM | 903 | CB | LEU | B | 260 | 65.623 | 28.148 | 236.663 | 1.00 | 77.58 | 6 |
| ATOM | 904 | CG | LEU | B | 260 | 64.777 | 29.348 | 237.142 | 1.00 | 77.11 | 6 |
| ATOM | 905 | CD1 | LEU | B | 260 | 65.500 | 30.693 | 236.998 | 1.00 | 76.64 | 6 |
| ATOM | 906 | CD2 | LEU | B | 260 | 63.393 | 29.398 | 236.498 | 1.00 | 75.83 | 6 |
| ATOM | 907 | C | LEU | B | 260 | 66.169 | 28.367 | 234.201 | 1.00 | 78.15 | 6 |
| ATOM | 908 | O | LEU | B | 260 | 65.588 | 29.072 | 233.384 | 1.00 | 78.37 | 8 |
| ATOM | 909 | N | GLN | B | 261 | 67.490 | 28.208 | 234.197 | 1.00 | 78.78 | 7 |
| ATOM | 910 | CA | GLN | B | 261 | 68.328 | 28.800 | 233.141 | 1.00 | 79.49 | 6 |
| ATOM | 911 | CB | GLN | B | 261 | 69.804 | 28.369 | 233.264 | 1.00 | 79.70 | 6 |
| ATOM | 912 | CG | GLN | B | 261 | 70.799 | 29.512 | 233.481 | 1.00 | 80.39 | 6 |
| ATOM | 913 | CD | GLN | B | 261 | 70.504 | 30.712 | 232.595 | 1.00 | 82.13 | 6 |
| ATOM | 914 | OE1 | GLN | B | 261 | 70.458 | 30.602 | 231.365 | 1.00 | 82.63 | 8 |
| ATOM | 915 | NE2 | GLN | B | 261 | 70.285 | 31.865 | 233.219 | 1.00 | 82.64 | 7 |
| ATOM | 916 | C | GLN | B | 261 | 67.825 | 28.469 | 231.733 | 1.00 | 79.64 | 6 |
| ATOM | 917 | O | GLN | B | 261 | 67.853 | 29.316 | 230.841 | 1.00 | 79.71 | 8 |
| ATOM | 918 | N | GLN | B | 262 | 67.376 | 27.231 | 231.552 | 1.00 | 79.89 | 7 |
| ATOM | 919 | CA | GLN | B | 262 | 66.880 | 26.748 | 230.275 | 1.00 | 80.36 | 6 |
| ATOM | 920 | CB | GLN | B | 262 | 66.504 | 25.279 | 230.382 | 1.00 | 80.40 | 6 |
| ATOM | 921 | CG | GLN | B | 262 | 67.649 | 24.319 | 230.179 | 1.00 | 81.23 | 6 |
| ATOM | 922 | CD | GLN | B | 262 | 67.227 | 23.099 | 229.385 | 1.00 | 82.18 | 6 |
| ATOM | 923 | OE1 | GLN | B | 262 | 68.003 | 22.575 | 228.582 | 1.00 | 83.19 | 8 |
| ATOM | 924 | NE2 | GLN | B | 262 | 65.985 | 22.653 | 229.584 | 1.00 | 82.04 | 7 |
| ATOM | 925 | C | GLN | B | 262 | 65.649 | 27.493 | 229.841 | 1.00 | 80.42 | 6 |
| ATOM | 926 | O | GLN | B | 262 | 65.508 | 27.861 | 228.680 | 1.00 | 80.53 | 8 |
| ATOM | 927 | N | ALA | B | 263 | 64.739 | 27.693 | 230.779 | 1.00 | 80.58 | 7 |
| ATOM | 928 | CA | ALA | B | 263 | 63.495 | 28.343 | 230.452 | 1.00 | 80.73 | 6 |
| ATOM | 929 | CB | ALA | B | 263 | 62.431 | 28.013 | 231.473 | 1.00 | 80.83 | 6 |
| ATOM | 930 | C | ALA | B | 263 | 63.668 | 29.853 | 230.256 | 1.00 | 80.96 | 6 |
| ATOM | 931 | O | ALA | B | 263 | 63.103 | 30.401 | 229.309 | 1.00 | 81.15 | 8 |
| ATOM | 932 | N | GLU | B | 264 | 64.458 | 30.519 | 231.104 | 1.00 | 81.16 | 7 |
| ATOM | 933 | CA | GLU | B | 264 | 64.738 | 31.950 | 230.905 | 1.00 | 81.56 | 6 |
| ATOM | 934 | CB | GLU | B | 264 | 65.651 | 32.499 | 231.988 | 1.00 | 81.50 | 6 |
| ATOM | 935 | CG | GLU | B | 264 | 64.907 | 32.850 | 233.240 | 1.00 | 82.27 | 6 |
| ATOM | 936 | CD | GLU | B | 264 | 65.844 | 33.157 | 234.373 | 1.00 | 84.36 | 6 |
| ATOM | 937 | OE1 | GLU | B | 264 | 65.624 | 34.178 | 235.058 | 1.00 | 85.59 | 8 |
| ATOM | 938 | OE2 | GLU | B | 264 | 66.815 | 32.387 | 234.574 | 1.00 | 85.60 | 8 |
| ATOM | 939 | C | GLU | B | 264 | 65.318 | 32.214 | 229.518 | 1.00 | 81.55 | 6 |
| ATOM | 940 | O | GLU | B | 264 | 64.982 | 33.214 | 228.873 | 1.00 | 81.73 | 8 |
| ATOM | 941 | N | GLU | B | 265 | 66.164 | 31.286 | 229.072 | 1.00 | 81.47 | 7 |
| ATOM | 942 | CA | GLU | B | 265 | 66.745 | 31.253 | 227.733 | 1.00 | 81.30 | 6 |
| ATOM | 943 | CB | GLU | B | 265 | 67.619 | 30.008 | 227.641 | 1.00 | 81.19 | 6 |
| ATOM | 944 | CG | GLU | B | 265 | 68.933 | 30.177 | 226.937 | 1.00 | 81.44 | 6 |
| ATOM | 945 | CD | GLU | B | 265 | 69.964 | 29.190 | 227.446 | 1.00 | 81.63 | 6 |
| ATOM | 946 | OE1 | GLU | B | 265 | 70.951 | 28.923 | 226.724 | 1.00 | 81.94 | 8 |
| ATOM | 947 | OE2 | GLU | B | 265 | 69.784 | 28.684 | 228.576 | 1.00 | 81.79 | 8 |

TABLE 1-continued

| | | | | | | | | | | |
|---|---|---|---|---|---|---|---|---|---|---|
| ATOM | 948 | C | GLU | B | 265 | 65.672 | 31.172 | 226.645 | 1.00 | 81.05 | 6 |
| ATOM | 949 | O | GLU | B | 265 | 65.693 | 31.936 | 225.677 | 1.00 | 81.10 | 8 |
| ATOM | 950 | N | ALA | B | 266 | 64.740 | 30.236 | 226.798 | 1.00 | 80.59 | 7 |
| ATOM | 951 | CA | ALA | B | 266 | 63.670 | 30.107 | 225.827 | 1.00 | 80.10 | 6 |
| ATOM | 952 | CB | ALA | B | 266 | 62.871 | 28.856 | 226.047 | 1.00 | 79.83 | 6 |
| ATOM | 953 | C | ALA | B | 266 | 62.791 | 31.346 | 225.858 | 1.00 | 79.95 | 6 |
| ATOM | 954 | O | ALA | B | 266 | 62.359 | 31.820 | 224.822 | 1.00 | 80.15 | 8 |
| ATOM | 955 | N | LEU | B | 267 | 62.559 | 31.905 | 227.034 | 1.00 | 79.65 | 7 |
| ATOM | 956 | CA | LEU | B | 267 | 61.769 | 33.104 | 227.096 | 1.00 | 79.38 | 6 |
| ATOM | 957 | CB | LEU | B | 267 | 61.604 | 33.567 | 228.531 | 1.00 | 79.27 | 6 |
| ATOM | 958 | CG | LEU | B | 267 | 60.693 | 32.580 | 229.237 | 1.00 | 78.77 | 6 |
| ATOM | 959 | CD1 | LEU | B | 267 | 60.468 | 33.027 | 230.675 | 1.00 | 79.02 | 6 |
| ATOM | 960 | CD2 | LEU | B | 267 | 59.390 | 32.454 | 228.464 | 1.00 | 78.39 | 6 |
| ATOM | 961 | C | LEU | B | 267 | 62.334 | 34.186 | 226.176 | 1.00 | 79.46 | 6 |
| ATOM | 962 | O | LEU | B | 267 | 61.573 | 34.756 | 225.387 | 1.00 | 79.66 | 8 |
| ATOM | 963 | N | VAL | B | 268 | 63.648 | 34.447 | 226.234 | 1.00 | 79.24 | 7 |
| ATOM | 964 | CA | VAL | B | 268 | 64.234 | 35.479 | 225.356 | 1.00 | 79.03 | 6 |
| ATOM | 965 | CB | VAL | B | 268 | 65.708 | 35.851 | 225.658 | 1.00 | 78.76 | 6 |
| ATOM | 966 | CG1 | VAL | B | 268 | 65.781 | 37.162 | 226.428 | 1.00 | 78.41 | 6 |
| ATOM | 967 | CG2 | VAL | B | 268 | 66.424 | 34.745 | 226.376 | 1.00 | 78.78 | 6 |
| ATOM | 968 | C | VAL | B | 268 | 64.090 | 35.084 | 223.897 | 1.00 | 79.12 | 6 |
| ATOM | 969 | O | VAL | B | 268 | 63.742 | 35.919 | 223.060 | 1.00 | 79.24 | 8 |
| ATOM | 970 | N | ALA | B | 269 | 64.324 | 33.802 | 223.609 | 1.00 | 79.11 | 7 |
| ATOM | 971 | CA | ALA | B | 269 | 64.153 | 33.250 | 222.261 | 1.00 | 78.86 | 6 |
| ATOM | 972 | CB | ALA | B | 269 | 64.496 | 31.767 | 222.222 | 1.00 | 78.43 | 6 |
| ATOM | 973 | C | ALA | B | 269 | 62.756 | 33.490 | 221.711 | 1.00 | 78.81 | 6 |
| ATOM | 974 | O | ALA | B | 269 | 62.607 | 33.865 | 220.566 | 1.00 | 79.01 | 8 |
| ATOM | 975 | N | LYS | B | 270 | 61.725 | 33.299 | 222.511 | 1.00 | 78.88 | 7 |
| ATOM | 976 | CA | LYS | B | 270 | 60.396 | 33.540 | 221.978 | 1.00 | 79.15 | 6 |
| ATOM | 977 | CB | LYS | B | 270 | 59.330 | 32.685 | 222.685 | 1.00 | 79.22 | 6 |
| ATOM | 978 | CG | LYS | B | 270 | 59.526 | 31.159 | 222.483 | 1.00 | 79.30 | 6 |
| ATOM | 979 | CD | LYS | B | 270 | 58.326 | 30.317 | 223.017 | 1.00 | 79.49 | 6 |
| ATOM | 980 | CE | LYS | B | 270 | 58.714 | 28.872 | 223.468 | 1.00 | 79.40 | 6 |
| ATOM | 981 | NZ | LYS | B | 270 | 59.273 | 27.914 | 222.441 | 1.00 | 78.19 | 7 |
| ATOM | 982 | C | LYS | B | 270 | 60.057 | 35.047 | 221.841 | 1.00 | 79.26 | 6 |
| ATOM | 983 | O | LYS | B | 270 | 59.396 | 35.447 | 220.881 | 1.00 | 79.15 | 8 |
| ATOM | 984 | N | GLN | B | 271 | 60.554 | 35.881 | 222.751 | 1.00 | 79.44 | 7 |
| ATOM | 985 | CA | GLN | B | 271 | 60.407 | 37.320 | 222.590 | 1.00 | 79.74 | 6 |
| ATOM | 986 | CB | GLN | B | 271 | 60.929 | 38.075 | 223.801 | 1.00 | 79.76 | 6 |
| ATOM | 987 | CG | GLN | B | 271 | 60.070 | 39.272 | 224.114 | 1.00 | 80.42 | 6 |
| ATOM | 988 | CD | GLN | B | 271 | 58.629 | 38.865 | 224.375 | 1.00 | 81.53 | 6 |
| ATOM | 989 | OE1 | GLN | B | 271 | 57.967 | 38.297 | 223.507 | 1.00 | 81.18 | 8 |
| ATOM | 990 | NE2 | GLN | B | 271 | 58.140 | 39.146 | 225.584 | 1.00 | 82.89 | 7 |
| ATOM | 991 | C | GLN | B | 271 | 61.069 | 37.830 | 221.304 | 1.00 | 79.93 | 6 |
| ATOM | 992 | O | GLN | B | 271 | 60.507 | 38.686 | 220.612 | 1.00 | 80.16 | 8 |
| ATOM | 993 | N | GLU | B | 272 | 62.248 | 37.291 | 220.989 | 1.00 | 79.88 | 7 |
| ATOM | 994 | CA | GLU | B | 272 | 62.933 | 37.560 | 219.725 | 1.00 | 79.76 | 6 |
| ATOM | 995 | CB | GLU | B | 272 | 64.115 | 36.603 | 219.560 | 1.00 | 80.02 | 6 |
| ATOM | 996 | CG | GLU | B | 272 | 65.454 | 37.266 | 219.247 | 1.00 | 81.01 | 6 |
| ATOM | 997 | CD | GLU | B | 272 | 66.625 | 36.636 | 220.020 | 1.00 | 82.17 | 6 |
| ATOM | 998 | OE1 | GLU | B | 272 | 67.732 | 36.548 | 219.448 | 1.00 | 82.51 | 8 |
| ATOM | 999 | OE2 | GLU | B | 272 | 66.445 | 36.236 | 221.197 | 1.00 | 82.24 | 8 |
| ATOM | 1000 | C | GLU | B | 272 | 61.952 | 37.363 | 218.579 | 1.00 | 79.48 | 6 |
| ATOM | 1001 | O | GLU | B | 272 | 61.899 | 38.176 | 217.663 | 1.00 | 79.61 | 8 |
| ATOM | 1002 | N | LEU | B | 273 | 61.150 | 36.303 | 218.648 | 1.00 | 79.03 | 7 |
| ATOM | 1003 | CA | LEU | B | 273 | 60.191 | 36.028 | 217.588 | 1.00 | 78.54 | 6 |
| ATOM | 1004 | CB | LEU | B | 273 | 59.879 | 34.542 | 217.506 | 1.00 | 78.39 | 6 |
| ATOM | 1005 | CG | LEU | B | 273 | 59.663 | 34.064 | 216.076 | 1.00 | 77.93 | 6 |
| ATOM | 1006 | CD1 | LEU | B | 273 | 60.995 | 34.032 | 215.347 | 1.00 | 77.93 | 6 |
| ATOM | 1007 | CD2 | LEU | B | 273 | 59.007 | 32.695 | 216.056 | 1.00 | 77.26 | 6 |
| ATOM | 1008 | C | LEU | B | 273 | 58.914 | 36.858 | 217.685 | 1.00 | 78.45 | 6 |
| ATOM | 1009 | O | LEU | B | 273 | 58.353 | 37.242 | 216.676 | 1.00 | 78.45 | 8 |
| ATOM | 1010 | N | ILE | B | 274 | 58.457 | 37.139 | 218.893 | 1.00 | 78.25 | 7 |
| ATOM | 1011 | CA | ILE | B | 274 | 57.296 | 37.983 | 219.032 | 1.00 | 78.10 | 6 |
| ATOM | 1012 | CB | ILE | B | 274 | 56.803 | 37.978 | 220.481 | 1.00 | 78.20 | 6 |
| ATOM | 1013 | CG1 | ILE | B | 274 | 55.898 | 36.757 | 220.660 | 1.00 | 78.50 | 6 |
| ATOM | 1014 | CD | ILE | B | 274 | 56.203 | 35.913 | 221.854 | 1.00 | 79.00 | 6 |
| ATOM | 1015 | CG2 | ILE | B | 274 | 56.033 | 39.244 | 220.821 | 1.00 | 78.17 | 6 |
| ATOM | 1016 | C | ILE | B | 274 | 57.560 | 39.357 | 218.408 | 1.00 | 77.96 | 6 |
| ATOM | 1017 | O | ILE | B | 274 | 56.733 | 39.867 | 217.651 | 1.00 | 78.16 | 8 |
| ATOM | 1018 | N | ASP | B | 275 | 58.741 | 39.905 | 218.660 | 1.00 | 77.63 | 7 |
| ATOM | 1019 | CA | ASP | B | 275 | 59.083 | 41.225 | 218.169 | 1.00 | 77.40 | 6 |
| ATOM | 1020 | CB | ASP | B | 275 | 60.301 | 41.749 | 218.931 | 1.00 | 77.56 | 6 |
| ATOM | 1021 | CG | ASP | B | 275 | 60.140 | 41.624 | 220.453 | 1.00 | 77.80 | 6 |
| ATOM | 1022 | OD1 | ASP | B | 275 | 58.997 | 41.709 | 220.960 | 1.00 | 78.11 | 8 |
| ATOM | 1023 | OD2 | ASP | B | 275 | 61.158 | 41.427 | 221.147 | 1.00 | 78.09 | 8 |
| ATOM | 1024 | C | ASP | B | 275 | 59.287 | 41.207 | 216.656 | 1.00 | 77.11 | 6 |
| ATOM | 1025 | O | ASP | B | 275 | 58.951 | 42.173 | 215.970 | 1.00 | 77.25 | 8 |
| ATOM | 1026 | N | LYS | B | 276 | 59.806 | 40.096 | 216.138 | 1.00 | 76.72 | 7 |
| ATOM | 1027 | CA | LYS | B | 276 | 59.898 | 39.909 | 214.688 | 1.00 | 76.40 | 6 |

TABLE 1-continued

| | | | | | | | | | | |
|---|---|---|---|---|---|---|---|---|---|---|
| ATOM | 1028 | CB | LYS | B | 276 | 60.563 | 38.583 | 214.319 | 1.00 | 76.63 | 6 |
| ATOM | 1029 | CG | LYS | B | 276 | 62.009 | 38.691 | 213.866 | 1.00 | 77.43 | 6 |
| ATOM | 1030 | CD | LYS | B | 276 | 62.244 | 39.874 | 212.939 | 1.00 | 77.90 | 6 |
| ATOM | 1031 | CE | LYS | B | 276 | 63.724 | 40.217 | 212.931 | 1.00 | 78.49 | 6 |
| ATOM | 1032 | NZ | LYS | B | 276 | 63.939 | 41.637 | 213.300 | 1.00 | 78.71 | 7 |
| ATOM | 1033 | C | LYS | B | 276 | 58.533 | 39.931 | 214.055 | 1.00 | 75.89 | 6 |
| ATOM | 1034 | O | LYS | B | 276 | 58.350 | 40.504 | 213.004 | 1.00 | 75.94 | 8 |
| ATOM | 1035 | N | LEU | B | 277 | 57.573 | 39.296 | 214.702 | 1.00 | 75.53 | 7 |
| ATOM | 1036 | CA | LEU | B | 277 | 56.263 | 39.160 | 214.110 | 1.00 | 75.08 | 6 |
| ATOM | 1037 | CB | LEU | B | 277 | 55.553 | 37.888 | 214.587 | 1.00 | 75.11 | 6 |
| ATOM | 1038 | CG | LEU | B | 277 | 56.172 | 36.496 | 214.302 | 1.00 | 74.93 | 6 |
| ATOM | 1039 | CD1 | LEU | B | 277 | 55.064 | 35.479 | 213.977 | 1.00 | 74.34 | 6 |
| ATOM | 1040 | CD2 | LEU | B | 277 | 57.226 | 36.516 | 213.165 | 1.00 | 75.23 | 6 |
| ATOM | 1041 | C | LEU | B | 277 | 55.422 | 40.398 | 214.340 | 1.00 | 74.97 | 6 |
| ATOM | 1042 | O | LEU | B | 277 | 54.655 | 40.780 | 213.468 | 1.00 | 75.06 | 8 |
| ATOM | 1043 | N | LYS | B | 278 | 55.567 | 41.040 | 215.491 | 1.00 | 74.88 | 7 |
| ATOM | 1044 | CA | LYS | B | 278 | 54.883 | 42.299 | 215.696 | 1.00 | 74.81 | 6 |
| ATOM | 1045 | CB | LYS | B | 278 | 55.123 | 42.826 | 217.112 | 1.00 | 74.79 | 6 |
| ATOM | 1046 | CG | LYS | B | 278 | 54.331 | 42.073 | 218.194 | 1.00 | 74.11 | 6 |
| ATOM | 1047 | CD | LYS | B | 278 | 54.678 | 42.573 | 219.594 | 1.00 | 74.15 | 6 |
| ATOM | 1048 | CE | LYS | B | 278 | 53.545 | 42.321 | 220.592 | 1.00 | 73.19 | 6 |
| ATOM | 1049 | NZ | LYS | B | 278 | 53.952 | 42.624 | 222.008 | 1.00 | 71.81 | 7 |
| ATOM | 1050 | C | LYS | B | 278 | 55.347 | 43.256 | 214.588 | 1.00 | 75.31 | 6 |
| ATOM | 1051 | O | LYS | B | 278 | 54.527 | 43.828 | 213.863 | 1.00 | 75.33 | 8 |
| ATOM | 1052 | N | GLU | B | 279 | 56.663 | 43.351 | 214.415 | 1.00 | 75.72 | 7 |
| ATOM | 1053 | CA | GLU | B | 279 | 57.269 | 44.196 | 213.397 | 1.00 | 76.38 | 6 |
| ATOM | 1054 | CB | GLU | B | 279 | 58.801 | 44.155 | 213.537 | 1.00 | 76.50 | 6 |
| ATOM | 1055 | CG | GLU | B | 279 | 59.617 | 44.925 | 212.472 | 1.00 | 77.51 | 6 |
| ATOM | 1056 | CD | GLU | B | 279 | 61.117 | 44.572 | 212.490 | 1.00 | 77.60 | 6 |
| ATOM | 1057 | OE1 | GLU | B | 279 | 61.511 | 43.570 | 213.141 | 1.00 | 78.98 | 8 |
| ATOM | 1058 | OE2 | GLU | B | 279 | 61.904 | 45.298 | 211.842 | 1.00 | 78.66 | 8 |
| ATOM | 1059 | C | GLU | B | 279 | 56.818 | 43.807 | 211.986 | 1.00 | 76.31 | 6 |
| ATOM | 1060 | O | GLU | B | 279 | 56.528 | 44.681 | 211.181 | 1.00 | 76.62 | 8 |
| ATOM | 1061 | N | GLU | B | 280 | 56.756 | 42.510 | 211.683 | 1.00 | 76.41 | 7 |
| ATOM | 1062 | CA | GLU | B | 280 | 56.321 | 42.069 | 210.352 | 1.00 | 76.31 | 6 |
| ATOM | 1063 | CB | GLU | B | 280 | 56.563 | 40.590 | 210.126 | 1.00 | 75.98 | 6 |
| ATOM | 1064 | CG | GLU | B | 280 | 57.955 | 40.285 | 209.667 | 1.00 | 75.93 | 6 |
| ATOM | 1065 | CD | GLU | B | 280 | 58.255 | 38.813 | 209.770 | 1.00 | 76.92 | 6 |
| ATOM | 1066 | OE1 | GLU | B | 280 | 57.316 | 38.006 | 209.609 | 1.00 | 76.87 | 8 |
| ATOM | 1067 | OE2 | GLU | B | 280 | 59.424 | 38.455 | 210.026 | 1.00 | 77.78 | 8 |
| ATOM | 1068 | C | GLU | B | 280 | 54.864 | 42.411 | 210.096 | 1.00 | 76.53 | 6 |
| ATOM | 1069 | O | GLU | B | 280 | 54.527 | 42.878 | 209.014 | 1.00 | 76.67 | 8 |
| ATOM | 1070 | N | ALA | B | 281 | 54.003 | 42.207 | 211.088 | 1.00 | 76.73 | 7 |
| ATOM | 1071 | CA | ALA | B | 281 | 52.601 | 42.575 | 210.936 | 1.00 | 76.84 | 6 |
| ATOM | 1072 | CB | ALA | B | 281 | 51.768 | 41.981 | 212.044 | 1.00 | 76.73 | 6 |
| ATOM | 1073 | C | ALA | B | 281 | 52.424 | 44.101 | 210.831 | 1.00 | 76.96 | 6 |
| ATOM | 1074 | O | ALA | B | 281 | 51.355 | 44.592 | 210.462 | 1.00 | 76.99 | 8 |
| ATOM | 1075 | N | GLU | B | 282 | 53.484 | 44.846 | 211.122 | 1.00 | 77.06 | 7 |
| ATOM | 1076 | CA | GLU | B | 282 | 53.467 | 46.276 | 210.887 | 1.00 | 77.26 | 6 |
| ATOM | 1077 | CB | GLU | B | 282 | 54.574 | 46.969 | 211.676 | 1.00 | 77.54 | 6 |
| ATOM | 1078 | CG | GLU | B | 282 | 54.186 | 48.357 | 212.147 | 1.00 | 79.01 | 6 |
| ATOM | 1079 | CD | GLU | B | 282 | 52.893 | 48.366 | 212.963 | 1.00 | 80.49 | 6 |
| ATOM | 1080 | OE1 | GLU | B | 282 | 51.817 | 47.994 | 212.426 | 1.00 | 80.60 | 8 |
| ATOM | 1081 | OE2 | GLU | B | 282 | 52.959 | 48.760 | 214.148 | 1.00 | 81.06 | 8 |
| ATOM | 1082 | C | GLU | B | 282 | 53.525 | 46.626 | 209.396 | 1.00 | 77.10 | 6 |
| ATOM | 1083 | O | GLU | B | 282 | 52.716 | 47.414 | 208.916 | 1.00 | 77.14 | 8 |
| ATOM | 1084 | N | GLN | B | 283 | 54.460 | 46.020 | 208.669 | 1.00 | 77.00 | 7 |
| ATOM | 1085 | CA | GLN | B | 283 | 54.575 | 46.224 | 207.221 | 1.00 | 76.83 | 6 |
| ATOM | 1086 | CB | GLN | B | 283 | 55.939 | 45.740 | 206.707 | 1.00 | 77.18 | 6 |
| ATOM | 1087 | CG | GLN | B | 283 | 57.141 | 46.193 | 207.541 | 1.00 | 77.46 | 6 |
| ATOM | 1088 | CD | GLN | B | 283 | 58.200 | 45.110 | 207.662 | 1.00 | 77.89 | 6 |
| ATOM | 1089 | OE1 | GLN | B | 283 | 58.510 | 44.646 | 208.761 | 1.00 | 78.18 | 8 |
| ATOM | 1090 | NE2 | GLN | B | 283 | 58.751 | 44.692 | 206.529 | 1.00 | 78.35 | 7 |
| ATOM | 1091 | C | GLN | B | 283 | 53.441 | 45.536 | 206.459 | 1.00 | 76.27 | 6 |
| ATOM | 1092 | O | GLN | B | 283 | 53.219 | 45.833 | 205.291 | 1.00 | 76.31 | 8 |
| ATOM | 1093 | N | HIS | B | 284 | 52.743 | 44.611 | 207.118 | 1.00 | 75.52 | 7 |
| ATOM | 1094 | CA | HIS | B | 284 | 51.561 | 43.996 | 206.533 | 1.00 | 74.97 | 6 |
| ATOM | 1095 | CB | HIS | B | 284 | 51.238 | 42.670 | 207.197 | 1.00 | 75.10 | 6 |
| ATOM | 1096 | CG | HIS | B | 284 | 52.332 | 41.665 | 207.079 | 1.00 | 75.87 | 6 |
| ATOM | 1097 | ND1 | HIS | B | 284 | 52.553 | 40.692 | 208.031 | 1.00 | 77.26 | 7 |
| ATOM | 1098 | CE1 | HIS | B | 284 | 53.591 | 39.959 | 207.670 | 1.00 | 76.88 | 6 |
| ATOM | 1099 | NE2 | HIS | B | 284 | 54.057 | 40.428 | 206.525 | 1.00 | 76.21 | 7 |
| ATOM | 1100 | CD2 | HIS | B | 284 | 53.290 | 41.499 | 206.138 | 1.00 | 75.90 | 6 |
| ATOM | 1101 | C | HIS | B | 284 | 50.383 | 44.928 | 206.669 | 1.00 | 74.37 | 6 |
| ATOM | 1102 | O | HIS | B | 284 | 49.545 | 45.033 | 205.771 | 1.00 | 74.33 | 8 |
| ATOM | 1103 | N | LYS | B | 285 | 50.320 | 45.609 | 207.803 | 1.00 | 73.53 | 7 |
| ATOM | 1104 | CA | LYS | B | 285 | 49.268 | 46.563 | 208.032 | 1.00 | 72.60 | 6 |
| ATOM | 1105 | CB | LYS | B | 285 | 49.382 | 47.149 | 209.431 | 1.00 | 72.89 | 6 |
| ATOM | 1106 | CG | LYS | B | 285 | 48.071 | 47.625 | 210.011 | 1.00 | 73.56 | 6 |
| ATOM | 1107 | CD | LYS | B | 285 | 48.311 | 48.410 | 211.284 | 1.00 | 74.04 | 6 |

TABLE 1-continued

| | | | | | | | | | |
|---|---|---|---|---|---|---|---|---|---|
| ATOM | 1108 | CE | LYS | B | 285 | 47.566 | 49.718 | 211.249 | 1.00 | 74.02 | 6 |
| ATOM | 1109 | NZ | LYS | B | 285 | 48.017 | 50.586 | 212.358 | 1.00 | 74.91 | 7 |
| ATOM | 1110 | C | LYS | B | 285 | 49.367 | 47.628 | 206.953 | 1.00 | 71.79 | 6 |
| ATOM | 1111 | O | LYS | B | 285 | 48.396 | 47.859 | 206.231 | 1.00 | 71.75 | 8 |
| ATOM | 1112 | N | ILE | B | 286 | 50.552 | 48.217 | 206.784 | 1.00 | 70.70 | 7 |
| ATOM | 1113 | CA | ILE | B | 286 | 50.706 | 49.314 | 205.818 | 1.00 | 69.62 | 6 |
| ATOM | 1114 | CB | ILE | B | 286 | 51.924 | 50.250 | 206.108 | 1.00 | 69.49 | 6 |
| ATOM | 1115 | CG1 | ILE | B | 286 | 53.165 | 49.438 | 206.498 | 1.00 | 69.93 | 6 |
| ATOM | 1116 | CD | ILE | B | 286 | 54.282 | 50.219 | 207.230 | 1.00 | 69.79 | 6 |
| ATOM | 1117 | CG2 | ILE | B | 286 | 51.547 | 51.270 | 207.186 | 1.00 | 68.93 | 6 |
| ATOM | 1118 | C | ILE | B | 286 | 50.524 | 48.948 | 204.337 | 1.00 | 68.84 | 6 |
| ATOM | 1119 | O | ILE | B | 286 | 50.348 | 49.835 | 203.520 | 1.00 | 68.89 | 8 |
| ATOM | 1120 | N | VAL | B | 287 | 50.514 | 47.661 | 203.995 | 1.00 | 67.87 | 7 |
| ATOM | 1121 | CA | VAL | B | 287 | 50.116 | 47.288 | 202.641 | 1.00 | 66.95 | 6 |
| ATOM | 1122 | CB | VAL | B | 287 | 50.887 | 46.081 | 202.035 | 1.00 | 66.83 | 6 |
| ATOM | 1123 | CG1 | VAL | B | 287 | 52.354 | 46.128 | 202.400 | 1.00 | 66.33 | 6 |
| ATOM | 1124 | CG2 | VAL | B | 287 | 50.273 | 44.789 | 202.449 | 1.00 | 66.81 | 6 |
| ATOM | 1125 | C | VAL | B | 287 | 48.601 | 47.100 | 202.570 | 1.00 | 66.53 | 6 |
| ATOM | 1126 | O | VAL | B | 287 | 47.977 | 47.437 | 201.554 | 1.00 | 66.63 | 8 |
| ATOM | 1127 | N | MET | B | 288 | 48.011 | 46.588 | 203.648 | 1.00 | 65.60 | 7 |
| ATOM | 1128 | CA | MET | B | 288 | 46.571 | 46.338 | 203.674 | 1.00 | 64.90 | 6 |
| ATOM | 1129 | CB | MET | B | 288 | 46.196 | 45.456 | 204.852 | 1.00 | 65.05 | 6 |
| ATOM | 1130 | CG | MET | B | 288 | 46.674 | 44.021 | 204.716 | 1.00 | 65.48 | 6 |
| ATOM | 1131 | SD | MET | B | 288 | 46.458 | 43.062 | 206.238 | 1.00 | 65.82 | 16 |
| ATOM | 1132 | CE | MET | B | 288 | 44.655 | 42.971 | 206.344 | 1.00 | 65.62 | 6 |
| ATOM | 1133 | C | MET | B | 288 | 45.768 | 47.631 | 203.700 | 1.00 | 63.99 | 6 |
| ATOM | 1134 | O | MET | B | 288 | 44.592 | 47.646 | 203.336 | 1.00 | 63.69 | 8 |
| ATOM | 1135 | N | GLU | B | 289 | 46.415 | 48.714 | 204.126 | 1.00 | 63.04 | 7 |
| ATOM | 1136 | CA | GLU | B | 289 | 45.824 | 50.043 | 204.022 | 1.00 | 62.18 | 6 |
| ATOM | 1137 | CB | GLU | B | 289 | 46.610 | 51.084 | 204.832 | 1.00 | 62.43 | 6 |
| ATOM | 1138 | CG | GLU | B | 289 | 47.608 | 50.519 | 205.860 | 1.00 | 64.75 | 6 |
| ATOM | 1139 | CD | GLU | B | 289 | 47.231 | 50.743 | 207.351 | 1.00 | 68.11 | 6 |
| ATOM | 1140 | OE1 | GLU | B | 289 | 46.027 | 50.924 | 207.645 | 1.00 | 69.21 | 8 |
| ATOM | 1141 | OE2 | GLU | B | 289 | 48.145 | 50.730 | 208.234 | 1.00 | 68.26 | 8 |
| ATOM | 1142 | C | GLU | B | 289 | 45.712 | 50.506 | 202.561 | 1.00 | 61.05 | 6 |
| ATOM | 1143 | O | GLU | B | 289 | 44.855 | 51.317 | 202.266 | 1.00 | 61.15 | 8 |
| ATOM | 1144 | N | THR | B | 290 | 46.552 | 50.001 | 201.650 | 1.00 | 59.51 | 7 |
| ATOM | 1145 | CA | THR | B | 290 | 46.584 | 50.563 | 200.299 | 1.00 | 58.05 | 6 |
| ATOM | 1146 | CB | THR | B | 290 | 47.921 | 50.363 | 199.570 | 1.00 | 58.19 | 6 |
| ATOM | 1147 | OG1 | THR | B | 290 | 47.993 | 49.037 | 199.033 | 1.00 | 58.37 | 8 |
| ATOM | 1148 | CG2 | THR | B | 290 | 49.080 | 50.600 | 200.509 | 1.00 | 58.09 | 6 |
| ATOM | 1149 | C | THR | B | 290 | 45.477 | 49.968 | 199.519 | 1.00 | 57.49 | 6 |
| ATOM | 1150 | O | THR | B | 290 | 45.314 | 50.181 | 198.326 | 1.00 | 57.68 | 8 |
| ATOM | 1151 | N | VAL | B | 291 | 44.666 | 49.246 | 200.219 | 1.00 | 56.42 | 7 |
| ATOM | 1152 | CA | VAL | B | 291 | 43.718 | 48.486 | 199.483 | 1.00 | 55.71 | 6 |
| ATOM | 1153 | CB | VAL | B | 291 | 43.220 | 47.261 | 200.256 | 1.00 | 55.56 | 6 |
| ATOM | 1154 | CG1 | VAL | B | 291 | 41.969 | 46.707 | 199.600 | 1.00 | 55.43 | 6 |
| ATOM | 1155 | CG2 | VAL | B | 291 | 44.306 | 46.204 | 200.310 | 1.00 | 54.82 | 6 |
| ATOM | 1156 | C | VAL | B | 291 | 42.552 | 49.347 | 199.060 | 1.00 | 55.33 | 6 |
| ATOM | 1157 | O | VAL | B | 291 | 42.378 | 49.641 | 197.868 | 1.00 | 55.71 | 8 |
| ATOM | 1158 | N | PRO | B | 292 | 41.720 | 49.732 | 200.028 | 1.00 | 54.73 | 7 |
| ATOM | 1159 | CA | PRO | B | 292 | 40.521 | 50.486 | 199.688 | 1.00 | 54.28 | 6 |
| ATOM | 1160 | CB | PRO | B | 292 | 40.145 | 51.120 | 201.018 | 1.00 | 54.38 | 6 |
| ATOM | 1161 | CG | PRO | B | 292 | 40.523 | 50.044 | 202.006 | 1.00 | 54.24 | 6 |
| ATOM | 1162 | CD | PRO | B | 292 | 41.793 | 49.456 | 201.477 | 1.00 | 54.47 | 6 |
| ATOM | 1163 | C | PRO | B | 292 | 40.705 | 51.534 | 198.598 | 1.00 | 53.72 | 6 |
| ATOM | 1164 | O | PRO | B | 292 | 39.911 | 51.592 | 197.675 | 1.00 | 53.29 | 8 |
| ATOM | 1165 | N | VAL | B | 293 | 41.763 | 52.325 | 198.702 | 1.00 | 53.39 | 7 |
| ATOM | 1166 | CA | VAL | B | 293 | 42.062 | 53.332 | 197.705 | 1.00 | 53.05 | 6 |
| ATOM | 1167 | CB | VAL | B | 293 | 43.204 | 54.276 | 198.213 | 1.00 | 53.33 | 6 |
| ATOM | 1168 | CG1 | VAL | B | 293 | 44.530 | 53.502 | 198.503 | 1.00 | 52.63 | 6 |
| ATOM | 1169 | CG2 | VAL | B | 293 | 43.389 | 55.463 | 197.270 | 1.00 | 53.56 | 6 |
| ATOM | 1170 | C | VAL | B | 293 | 42.303 | 52.660 | 196.331 | 1.00 | 52.71 | 6 |
| ATOM | 1171 | O | VAL | B | 293 | 41.619 | 52.992 | 195.346 | 1.00 | 52.66 | 8 |
| ATOM | 1172 | N | LEU | B | 294 | 43.237 | 51.704 | 196.309 | 1.00 | 52.03 | 7 |
| ATOM | 1173 | CA | LEU | B | 294 | 43.530 | 50.872 | 195.166 | 1.00 | 51.42 | 6 |
| ATOM | 1174 | CB | LEU | B | 294 | 44.341 | 49.681 | 195.642 | 1.00 | 51.29 | 6 |
| ATOM | 1175 | CG | LEU | B | 294 | 45.821 | 49.605 | 195.327 | 1.00 | 52.20 | 6 |
| ATOM | 1176 | CD1 | LEU | B | 294 | 45.935 | 49.186 | 193.870 | 1.00 | 53.41 | 6 |
| ATOM | 1177 | CD2 | LEU | B | 294 | 46.581 | 50.926 | 195.614 | 1.00 | 53.79 | 6 |
| ATOM | 1178 | C | LEU | B | 294 | 42.259 | 50.332 | 194.586 | 1.00 | 51.01 | 6 |
| ATOM | 1179 | O | LEU | B | 294 | 41.973 | 50.511 | 193.399 | 1.00 | 51.36 | 8 |
| ATOM | 1180 | N | LYS | B | 295 | 41.482 | 49.668 | 195.425 | 1.00 | 50.27 | 7 |
| ATOM | 1181 | CA | LYS | B | 295 | 40.291 | 49.038 | 194.916 | 1.00 | 49.99 | 6 |
| ATOM | 1182 | CB | LYS | B | 295 | 39.535 | 48.286 | 195.985 | 1.00 | 49.83 | 6 |
| ATOM | 1183 | CG | LYS | B | 295 | 38.105 | 48.030 | 195.568 | 1.00 | 50.37 | 6 |
| ATOM | 1184 | CD | LYS | B | 295 | 37.650 | 46.632 | 195.890 | 1.00 | 52.74 | 6 |
| ATOM | 1185 | CE | LYS | B | 295 | 36.141 | 46.584 | 195.964 | 1.00 | 54.24 | 6 |
| ATOM | 1186 | NZ | LYS | B | 295 | 35.659 | 45.207 | 195.748 | 1.00 | 56.16 | 7 |
| ATOM | 1187 | C | LYS | B | 295 | 39.372 | 50.061 | 194.284 | 1.00 | 49.78 | 6 |

TABLE 1-continued

| | | | | | | | | | | |
|---|---|---|---|---|---|---|---|---|---|---|
| ATOM | 1188 | O | LYS | B | 295 | 38.936 | 49.903 | 193.146 | 1.00 | 49.60 | 8 |
| ATOM | 1189 | N | ALA | B | 296 | 39.088 | 51.125 | 195.020 | 1.00 | 49.58 | 7 |
| ATOM | 1190 | CA | ALA | B | 296 | 38.144 | 52.104 | 194.551 | 1.00 | 49.02 | 6 |
| ATOM | 1191 | CB | ALA | B | 296 | 38.004 | 53.194 | 195.520 | 1.00 | 48.90 | 6 |
| ATOM | 1192 | C | ALA | B | 296 | 38.575 | 52.629 | 193.207 | 1.00 | 49.00 | 6 |
| ATOM | 1193 | O | ALA | B | 296 | 37.763 | 52.661 | 192.298 | 1.00 | 49.49 | 8 |
| ATOM | 1194 | N | GLN | B | 297 | 39.842 | 53.007 | 193.065 | 1.00 | 48.68 | 7 |
| ATOM | 1195 | CA | GLN | B | 297 | 40.349 | 53.458 | 191.786 | 1.00 | 48.80 | 6 |
| ATOM | 1196 | CB | GLN | B | 297 | 41.842 | 53.558 | 191.871 | 1.00 | 48.95 | 6 |
| ATOM | 1197 | CG | GLN | B | 297 | 42.372 | 54.895 | 192.225 | 1.00 | 50.82 | 6 |
| ATOM | 1198 | CD | GLN | B | 297 | 43.883 | 54.802 | 192.392 | 1.00 | 54.01 | 6 |
| ATOM | 1199 | OE1 | GLN | B | 297 | 44.632 | 54.969 | 191.416 | 1.00 | 55.82 | 8 |
| ATOM | 1200 | NE2 | GLN | B | 297 | 44.344 | 54.473 | 193.617 | 1.00 | 53.38 | 7 |
| ATOM | 1201 | C | GLN | B | 297 | 39.985 | 52.466 | 190.672 | 1.00 | 48.49 | 6 |
| ATOM | 1202 | O | GLN | B | 297 | 39.303 | 52.829 | 189.675 | 1.00 | 48.61 | 8 |
| ATOM | 1203 | N | ALA | B | 298 | 40.432 | 51.220 | 190.860 | 1.00 | 47.57 | 7 |
| ATOM | 1204 | CA | ALA | B | 298 | 40.160 | 50.143 | 189.931 | 1.00 | 47.03 | 6 |
| ATOM | 1205 | CB | ALA | B | 298 | 40.479 | 48.830 | 190.580 | 1.00 | 46.90 | 6 |
| ATOM | 1206 | C | ALA | B | 298 | 38.691 | 50.192 | 189.511 | 1.00 | 46.81 | 6 |
| ATOM | 1207 | O | ALA | B | 298 | 38.340 | 50.356 | 188.330 | 1.00 | 47.03 | 8 |
| ATOM | 1208 | N | ASP | B | 299 | 37.822 | 50.102 | 190.495 | 1.00 | 46.29 | 7 |
| ATOM | 1209 | CA | ASP | B | 299 | 36.419 | 50.110 | 190.206 | 1.00 | 46.02 | 6 |
| ATOM | 1210 | CB | ASP | B | 299 | 35.645 | 49.877 | 191.487 | 1.00 | 46.83 | 6 |
| ATOM | 1211 | CG | ASP | B | 299 | 35.892 | 48.485 | 192.037 | 1.00 | 48.73 | 6 |
| ATOM | 1212 | OD1 | ASP | B | 299 | 36.270 | 47.580 | 191.228 | 1.00 | 49.88 | 8 |
| ATOM | 1213 | OD2 | ASP | B | 299 | 35.733 | 48.308 | 193.269 | 1.00 | 51.06 | 8 |
| ATOM | 1214 | C | ASP | B | 299 | 35.981 | 51.349 | 189.469 | 1.00 | 45.12 | 6 |
| ATOM | 1215 | O | ASP | B | 299 | 35.308 | 51.230 | 188.459 | 1.00 | 45.22 | 8 |
| ATOM | 1216 | N | ILE | B | 300 | 36.393 | 52.519 | 189.937 | 1.00 | 44.09 | 7 |
| ATOM | 1217 | CA | ILE | B | 300 | 36.060 | 53.753 | 189.250 | 1.00 | 43.72 | 6 |
| ATOM | 1218 | CB | ILE | B | 300 | 36.694 | 54.977 | 189.931 | 1.00 | 43.59 | 6 |
| ATOM | 1219 | CG1 | ILE | B | 300 | 35.762 | 55.546 | 190.987 | 1.00 | 43.28 | 6 |
| ATOM | 1220 | CD | ILE | B | 300 | 35.743 | 54.793 | 192.284 | 1.00 | 44.16 | 6 |
| ATOM | 1221 | CG2 | ILE | B | 300 | 36.898 | 56.096 | 188.944 | 1.00 | 43.97 | 6 |
| ATOM | 1222 | C | ILE | B | 300 | 36.452 | 53.704 | 187.769 | 1.00 | 43.60 | 6 |
| ATOM | 1223 | O | ILE | B | 300 | 35.635 | 54.011 | 186.898 | 1.00 | 43.41 | 8 |
| ATOM | 1224 | N | TYR | B | 301 | 37.690 | 53.302 | 187.489 | 1.00 | 43.36 | 7 |
| ATOM | 1225 | CA | TYR | B | 301 | 38.197 | 53.302 | 186.123 | 1.00 | 43.35 | 6 |
| ATOM | 1226 | CB | TYR | B | 301 | 39.698 | 53.006 | 186.076 | 1.00 | 43.80 | 6 |
| ATOM | 1227 | CG | TYR | B | 301 | 40.600 | 54.066 | 186.707 | 1.00 | 45.04 | 6 |
| ATOM | 1228 | CD1 | TYR | B | 301 | 41.526 | 53.722 | 187.671 | 1.00 | 44.37 | 6 |
| ATOM | 1229 | CE1 | TYR | B | 301 | 42.342 | 54.671 | 188.251 | 1.00 | 44.78 | 6 |
| ATOM | 1230 | CZ | TYR | B | 301 | 42.259 | 55.988 | 187.870 | 1.00 | 45.46 | 6 |
| ATOM | 1231 | OH | TYR | B | 301 | 43.093 | 56.900 | 188.477 | 1.00 | 46.80 | 8 |
| ATOM | 1232 | CE2 | TYR | B | 301 | 41.357 | 56.384 | 186.906 | 1.00 | 45.30 | 6 |
| ATOM | 1233 | CD2 | TYR | B | 301 | 40.531 | 55.418 | 186.323 | 1.00 | 46.46 | 6 |
| ATOM | 1234 | C | TYR | B | 301 | 37.487 | 52.299 | 185.261 | 1.00 | 43.10 | 6 |
| ATOM | 1235 | O | TYR | B | 301 | 37.150 | 52.590 | 184.123 | 1.00 | 43.59 | 8 |
| ATOM | 1236 | N | LYS | B | 302 | 37.275 | 51.101 | 185.785 | 1.00 | 42.64 | 7 |
| ATOM | 1237 | CA | LYS | B | 302 | 36.596 | 50.097 | 184.995 | 1.00 | 42.03 | 6 |
| ATOM | 1238 | CB | LYS | B | 302 | 36.556 | 48.749 | 185.701 | 1.00 | 41.54 | 6 |
| ATOM | 1239 | CG | LYS | B | 302 | 35.605 | 47.804 | 185.039 | 1.00 | 40.94 | 6 |
| ATOM | 1240 | CD | LYS | B | 302 | 35.862 | 46.391 | 185.411 | 1.00 | 41.71 | 6 |
| ATOM | 1241 | CE | LYS | B | 302 | 34.602 | 45.591 | 185.233 | 1.00 | 42.85 | 6 |
| ATOM | 1242 | NZ | LYS | B | 302 | 34.871 | 44.190 | 185.536 | 1.00 | 44.78 | 7 |
| ATOM | 1243 | C | LYS | B | 302 | 35.205 | 50.639 | 184.653 | 1.00 | 41.79 | 6 |
| ATOM | 1244 | O | LYS | B | 302 | 34.814 | 50.716 | 183.482 | 1.00 | 41.49 | 8 |
| ATOM | 1245 | N | ALA | B | 303 | 34.492 | 51.086 | 185.673 | 1.00 | 41.76 | 7 |
| ATOM | 1246 | CA | ALA | B | 303 | 33.197 | 51.690 | 185.444 | 1.00 | 41.88 | 6 |
| ATOM | 1247 | CB | ALA | B | 303 | 32.612 | 52.285 | 186.722 | 1.00 | 42.11 | 6 |
| ATOM | 1248 | C | ALA | B | 303 | 33.301 | 52.756 | 184.368 | 1.00 | 41.85 | 6 |
| ATOM | 1249 | O | ALA | B | 303 | 32.404 | 52.845 | 183.540 | 1.00 | 42.28 | 8 |
| ATOM | 1250 | N | ASP | B | 304 | 34.381 | 53.548 | 184.369 | 1.00 | 41.58 | 7 |
| ATOM | 1251 | CA | ASP | B | 304 | 34.515 | 54.717 | 183.460 | 1.00 | 41.51 | 6 |
| ATOM | 1252 | CB | ASP | B | 304 | 35.850 | 55.434 | 183.661 | 1.00 | 41.69 | 6 |
| ATOM | 1253 | CG | ASP | B | 304 | 35.735 | 56.697 | 184.519 | 1.00 | 44.65 | 6 |
| ATOM | 1254 | OD1 | ASP | B | 304 | 36.675 | 56.953 | 185.319 | 1.00 | 46.81 | 8 |
| ATOM | 1255 | OD2 | ASP | B | 304 | 34.721 | 57.442 | 184.398 | 1.00 | 46.76 | 8 |
| ATOM | 1256 | C | ASP | B | 304 | 34.550 | 54.274 | 182.047 | 1.00 | 40.98 | 6 |
| ATOM | 1257 | O | ASP | B | 304 | 33.808 | 54.761 | 181.177 | 1.00 | 41.29 | 8 |
| ATOM | 1258 | N | PHE | B | 305 | 35.475 | 53.358 | 181.824 | 1.00 | 40.21 | 7 |
| ATOM | 1259 | CA | PHE | B | 305 | 35.681 | 52.763 | 180.538 | 1.00 | 39.45 | 6 |
| ATOM | 1260 | CB | PHE | B | 305 | 36.807 | 51.738 | 180.652 | 1.00 | 39.05 | 6 |
| ATOM | 1261 | CG | PHE | B | 305 | 36.826 | 50.753 | 179.531 | 1.00 | 38.86 | 6 |
| ATOM | 1262 | CD1 | PHE | B | 305 | 37.541 | 51.019 | 178.374 | 1.00 | 37.47 | 6 |
| ATOM | 1263 | CE1 | PHE | B | 305 | 37.547 | 50.140 | 177.335 | 1.00 | 37.04 | 6 |
| ATOM | 1264 | CZ | PHE | B | 305 | 36.834 | 48.971 | 177.419 | 1.00 | 37.67 | 6 |
| ATOM | 1265 | CE2 | PHE | B | 305 | 36.112 | 48.686 | 178.565 | 1.00 | 38.35 | 6 |
| ATOM | 1266 | CD2 | PHE | B | 305 | 36.104 | 49.573 | 179.615 | 1.00 | 37.84 | 6 |
| ATOM | 1267 | C | PHE | B | 305 | 34.378 | 52.119 | 180.012 | 1.00 | 39.28 | 6 |

TABLE 1-continued

| | | | | | | | | | |
|---|---|---|---|---|---|---|---|---|---|
| ATOM | 1268 | O | PHE | B | 305 | 33.942 | 52.377 | 178.881 | 1.00 | 38.93 | 8 |
| ATOM | 1269 | N | GLN | B | 306 | 33.749 | 51.288 | 180.830 | 1.00 | 39.04 | 7 |
| ATOM | 1270 | CA | GLN | B | 306 | 32.586 | 50.602 | 180.332 | 1.00 | 39.30 | 6 |
| ATOM | 1271 | CB | GLN | B | 306 | 32.007 | 49.734 | 181.419 | 1.00 | 39.64 | 6 |
| ATOM | 1272 | CG | GLN | B | 306 | 32.953 | 48.649 | 181.826 | 1.00 | 40.83 | 6 |
| ATOM | 1273 | CD | GLN | B | 306 | 32.341 | 47.804 | 182.885 | 1.00 | 44.16 | 6 |
| ATOM | 1274 | OE1 | GLN | B | 306 | 31.868 | 46.716 | 182.597 | 1.00 | 46.09 | 8 |
| ATOM | 1275 | NE2 | GLN | B | 306 | 32.283 | 48.319 | 184.126 | 1.00 | 46.74 | 7 |
| ATOM | 1276 | C | GLN | B | 306 | 31.593 | 51.624 | 179.772 | 1.00 | 39.03 | 6 |
| ATOM | 1277 | O | GLN | B | 306 | 31.066 | 51.448 | 178.663 | 1.00 | 39.11 | 8 |
| ATOM | 1278 | N | ALA | B | 307 | 31.409 | 52.714 | 180.521 | 1.00 | 38.65 | 7 |
| ATOM | 1279 | CA | ALA | B | 307 | 30.575 | 53.824 | 180.105 | 1.00 | 38.23 | 6 |
| ATOM | 1280 | CB | ALA | B | 307 | 30.526 | 54.875 | 181.165 | 1.00 | 38.13 | 6 |
| ATOM | 1281 | C | ALA | B | 307 | 31.070 | 54.403 | 178.782 | 1.00 | 38.20 | 6 |
| ATOM | 1282 | O | ALA | B | 307 | 30.256 | 54.580 | 177.860 | 1.00 | 38.84 | 8 |
| ATOM | 1283 | N | GLU | B | 308 | 32.376 | 54.673 | 178.646 | 1.00 | 37.47 | 7 |
| ATOM | 1284 | CA | GLU | B | 308 | 32.892 | 55.133 | 177.324 | 1.00 | 36.90 | 6 |
| ATOM | 1285 | CB | GLU | B | 308 | 34.398 | 55.225 | 177.232 | 1.00 | 36.92 | 6 |
| ATOM | 1286 | CG | GLU | B | 308 | 35.014 | 56.446 | 177.787 | 1.00 | 38.12 | 6 |
| ATOM | 1287 | CD | GLU | B | 308 | 34.592 | 57.750 | 177.130 | 1.00 | 38.09 | 6 |
| ATOM | 1288 | OE1 | GLU | B | 308 | 34.577 | 57.860 | 175.870 | 1.00 | 35.41 | 8 |
| ATOM | 1289 | 0E2 | GLU | B | 308 | 34.316 | 58.685 | 177.936 | 1.00 | 38.58 | 8 |
| ATOM | 1290 | C | GLU | B | 308 | 32.542 | 54.195 | 176.205 | 1.00 | 36.58 | 6 |
| ATOM | 1291 | O | GLU | B | 308 | 31.975 | 54.625 | 175.193 | 1.00 | 36.41 | 8 |
| ATOM | 1292 | N | ARG | B | 309 | 32.908 | 52.914 | 176.364 | 1.00 | 36.19 | 7 |
| ATOM | 1293 | CA | ARG | B | 309 | 32.663 | 51.953 | 175.294 | 1.00 | 35.52 | 6 |
| ATOM | 1294 | CB | ARG | B | 309 | 33.011 | 50.537 | 175.664 | 1.00 | 35.26 | 6 |
| ATOM | 1295 | CG | ARG | B | 309 | 32.884 | 49.632 | 174.477 | 1.00 | 33.84 | 6 |
| ATOM | 1296 | CD | ARG | B | 309 | 34.054 | 49.851 | 173.616 | 1.00 | 33.35 | 6 |
| ATOM | 1297 | NE | ARG | B | 309 | 34.874 | 48.658 | 173.584 | 1.00 | 35.40 | 7 |
| ATOM | 1298 | CZ | ARG | B | 309 | 36.148 | 48.627 | 173.204 | 1.00 | 37.19 | 6 |
| ATOM | 1299 | NH1 | ARG | B | 309 | 36.756 | 49.742 | 172.842 | 1.00 | 37.42 | 7 |
| ATOM | 1300 | NH2 | ARG | B | 309 | 36.815 | 47.473 | 173.160 | 1.00 | 38.83 | 7 |
| ATOM | 1301 | C | ARG | B | 309 | 31.211 | 51.999 | 174.907 | 1.00 | 35.49 | 6 |
| ATOM | 1302 | O | ARG | B | 309 | 30.889 | 52.034 | 173.713 | 1.00 | 35.68 | 8 |
| ATOM | 1303 | N | HIS | B | 310 | 30.341 | 52.034 | 175.917 | 1.00 | 34.98 | 7 |
| ATOM | 1304 | CA | HIS | B | 310 | 28.930 | 52.053 | 175.655 | 1.00 | 34.61 | 6 |
| ATOM | 1305 | CB | HIS | B | 310 | 28.140 | 52.168 | 176.931 | 1.00 | 34.23 | 6 |
| ATOM | 1306 | CG | HIS | B | 310 | 26.684 | 52.125 | 176.685 | 1.00 | 34.16 | 6 |
| ATOM | 1307 | ND1 | HIS | B | 310 | 25.913 | 53.261 | 176.649 | 1.00 | 35.32 | 7 |
| ATOM | 1308 | CE1 | HIS | B | 310 | 24.669 | 52.930 | 176.356 | 1.00 | 37.05 | 6 |
| ATOM | 1309 | NE2 | HIS | B | 310 | 24.620 | 51.624 | 176.166 | 1.00 | 36.92 | 7 |
| ATOM | 1310 | CD2 | HIS | B | 310 | 25.874 | 51.099 | 176.350 | 1.00 | 34.67 | 6 |
| ATOM | 1311 | C | HIS | B | 310 | 28.580 | 53.189 | 174.684 | 1.00 | 34.48 | 6 |
| ATOM | 1312 | O | HIS | B | 310 | 27.908 | 52.958 | 173.650 | 1.00 | 34.89 | 8 |
| ATOM | 1313 | N | ALA | B | 311 | 29.074 | 54.389 | 175.004 | 1.00 | 33.62 | 7 |
| ATOM | 1314 | CA | ALA | B | 311 | 28.875 | 55.565 | 174.164 | 1.00 | 33.41 | 6 |
| ATOM | 1315 | CB | ALA | B | 311 | 29.408 | 56.807 | 174.848 | 1.00 | 33.21 | 6 |
| ATOM | 1316 | C | ALA | B | 311 | 29.565 | 55.378 | 172.815 | 1.00 | 33.50 | 6 |
| ATOM | 1317 | O | ALA | B | 311 | 28.953 | 55.525 | 171.729 | 1.00 | 33.66 | 8 |
| ATOM | 1318 | N | ARG | B | 312 | 30.839 | 55.037 | 172.873 | 1.00 | 33.26 | 7 |
| ATOM | 1319 | CA | ARG | B | 312 | 31.585 | 54.854 | 171.647 | 1.00 | 33.71 | 6 |
| ATOM | 1320 | CB | ARG | B | 312 | 32.993 | 54.390 | 171.963 | 1.00 | 33.44 | 6 |
| ATOM | 1321 | CG | ARG | B | 312 | 33.833 | 54.153 | 170.745 | 1.00 | 32.77 | 6 |
| ATOM | 1322 | CD | ARG | B | 312 | 33.962 | 52.689 | 170.479 | 1.00 | 32.61 | 6 |
| ATOM | 1323 | NE | ARG | B | 312 | 34.778 | 52.445 | 169.300 | 1.00 | 32.74 | 7 |
| ATOM | 1324 | CZ | ARG | B | 312 | 36.073 | 52.167 | 169.316 | 1.00 | 31.55 | 6 |
| ATOM | 1325 | NH1 | ARG | B | 312 | 36.719 | 52.083 | 170.459 | 1.00 | 31.53 | 7 |
| ATOM | 1326 | NH2 | ARG | B | 312 | 36.716 | 51.973 | 168.178 | 1.00 | 31.34 | 7 |
| ATOM | 1327 | C | ARG | B | 312 | 30.907 | 53.921 | 170.614 | 1.00 | 34.20 | 6 |
| ATOM | 1328 | O | ARG | B | 312 | 31.039 | 54.102 | 169.409 | 1.00 | 33.66 | 8 |
| ATOM | 1329 | N | GLU | B | 313 | 30.183 | 52.916 | 171.086 | 1.00 | 34.91 | 7 |
| ATOM | 1330 | CA | GLU | B | 313 | 29.522 | 52.024 | 170.167 | 1.00 | 35.75 | 6 |
| ATOM | 1331 | CB | GLU | B | 313 | 29.069 | 50.765 | 170.876 | 1.00 | 35.96 | 6 |
| ATOM | 1332 | CG | GLU | B | 313 | 30.234 | 49.829 | 171.117 | 1.00 | 38.97 | 6 |
| ATOM | 1333 | CD | GLU | B | 313 | 29.882 | 48.623 | 171.969 | 1.00 | 44.28 | 6 |
| ATOM | 1334 | OE1 | GLU | B | 313 | 29.174 | 48.774 | 172.998 | 1.00 | 46.98 | 8 |
| ATOM | 1335 | OE2 | GLU | B | 313 | 30.343 | 47.517 | 171.624 | 1.00 | 46.65 | 8 |
| ATOM | 1336 | C | GLU | B | 313 | 28.395 | 52.769 | 169.502 | 1.00 | 35.56 | 6 |
| ATOM | 1337 | O | GLU | B | 313 | 28.391 | 52.887 | 168.284 | 1.00 | 35.47 | 8 |
| ATOM | 1338 | N | LYS | B | 314 | 27.502 | 53.340 | 170.316 | 1.00 | 35.58 | 7 |
| ATOM | 1339 | CA | LYS | B | 314 | 26.308 | 54.053 | 169.837 | 1.00 | 35.41 | 6 |
| ATOM | 1340 | CB | LYS | B | 314 | 25.598 | 54.744 | 170.998 | 1.00 | 35.01 | 6 |
| ATOM | 1341 | CG | LYS | B | 314 | 25.139 | 53.788 | 172.054 | 1.00 | 35.61 | 6 |
| ATOM | 1342 | CD | LYS | B | 314 | 24.429 | 54.484 | 173.194 | 1.00 | 36.90 | 6 |
| ATOM | 1343 | CE | LYS | B | 314 | 23.197 | 53.692 | 173.623 | 1.00 | 36.65 | 6 |
| ATOM | 1344 | NZ | LYS | B | 314 | 22.228 | 53.599 | 172.482 | 1.00 | 38.02 | 7 |
| ATOM | 1345 | C | LYS | B | 314 | 26.708 | 55.067 | 168.782 | 1.00 | 35.55 | 6 |
| ATOM | 1346 | O | LYS | B | 314 | 26.005 | 55.253 | 167.782 | 1.00 | 35.05 | 8 |
| ATOM | 1347 | N | LEU | B | 315 | 27.863 | 55.701 | 169.031 | 1.00 | 35.90 | 7 |

TABLE 1-continued

| ATOM | 1348 | CA | LEU | B | 315 | 28.502 | 56.619 | 168.091 | 1.00 | 36.06 | 6 |
| ATOM | 1349 | CB | LEU | B | 315 | 29.733 | 57.273 | 168.712 | 1.00 | 35.55 | 6 |
| ATOM | 1350 | CG | LEU | B | 315 | 29.467 | 58.481 | 169.617 | 1.00 | 36.63 | 6 |
| ATOM | 1351 | CD1 | LEU | B | 315 | 30.711 | 58.935 | 170.328 | 1.00 | 38.75 | 6 |
| ATOM | 1352 | CD2 | LEU | B | 315 | 28.946 | 59.657 | 168.848 | 1.00 | 37.41 | 6 |
| ATOM | 1353 | C | LEU | B | 315 | 28.891 | 55.897 | 166.814 | 1.00 | 36.36 | 6 |
| ATOM | 1354 | O | LEU | B | 315 | 28.367 | 56.195 | 165.740 | 1.00 | 36.68 | 8 |
| ATOM | 1355 | N | VAL | B | 316 | 29.778 | 54.917 | 166.926 | 1.00 | 36.57 | 7 |
| ATOM | 1356 | CA | VAL | B | 316 | 30.230 | 54.213 | 165.745 | 1.00 | 36.73 | 6 |
| ATOM | 1357 | CB | VAL | B | 316 | 30.966 | 52.955 | 166.109 | 1.00 | 36.55 | 6 |
| ATOM | 1358 | CG1 | VAL | B | 316 | 30.926 | 51.962 | 164.967 | 1.00 | 36.31 | 6 |
| ATOM | 1359 | CG2 | VAL | B | 316 | 32.380 | 53.315 | 166.424 | 1.00 | 37.11 | 6 |
| ATOM | 1360 | C | VAL | B | 316 | 29.029 | 53.896 | 164.898 | 1.00 | 37.24 | 6 |
| ATOM | 1361 | O | VAL | B | 316 | 29.011 | 54.104 | 163.699 | 1.00 | 37.65 | 8 |
| ATOM | 1362 | N | GLU | B | 317 | 27.998 | 53.440 | 165.563 | 1.00 | 38.10 | 7 |
| ATOM | 1363 | CA | GLU | B | 317 | 26.768 | 53.058 | 164.935 | 1.00 | 39.28 | 6 |
| ATOM | 1364 | CB | GLU | B | 317 | 25.879 | 52.501 | 166.052 | 1.00 | 40.02 | 6 |
| ATOM | 1365 | CG | GLU | B | 317 | 24.424 | 52.724 | 165.968 | 1.00 | 43.02 | 6 |
| ATOM | 1366 | CD | GLU | B | 317 | 23.772 | 51.699 | 165.094 | 1.00 | 47.74 | 6 |
| ATOM | 1367 | OE1 | GLU | B | 317 | 23.839 | 51.855 | 163.833 | 1.00 | 48.28 | 8 |
| ATOM | 1368 | OE2 | GLU | B | 317 | 23.190 | 50.745 | 165.686 | 1.00 | 49.58 | 8 |
| ATOM | 1369 | C | GLU | B | 317 | 26.175 | 54.263 | 164.210 | 1.00 | 39.25 | 6 |
| ATOM | 1370 | O | GLU | B | 317 | 25.852 | 54.185 | 163.039 | 1.00 | 39.21 | 8 |
| ATOM | 1371 | N | LYS | B | 318 | 26.073 | 55.392 | 164.895 | 1.00 | 39.68 | 7 |
| ATOM | 1372 | CA | LYS | B | 318 | 25.515 | 56.578 | 164.276 | 1.00 | 39.94 | 6 |
| ATOM | 1373 | CB | LYS | B | 318 | 25.435 | 57.738 | 165.264 | 1.00 | 39.65 | 6 |
| ATOM | 1374 | CG | LYS | B | 318 | 24.500 | 58.824 | 164.817 | 1.00 | 37.85 | 6 |
| ATOM | 1375 | CD | LYS | B | 318 | 23.204 | 58.230 | 164.265 | 1.00 | 37.22 | 6 |
| ATOM | 1376 | CE | LYS | B | 318 | 22.189 | 57.915 | 165.345 | 1.00 | 36.18 | 6 |
| ATOM | 1377 | NZ | LYS | B | 318 | 20.828 | 57.948 | 164.797 | 1.00 | 34.71 | 7 |
| ATOM | 1378 | C | LYS | B | 318 | 26.353 | 56.988 | 163.084 | 1.00 | 40.75 | 6 |
| ATOM | 1379 | O | LYS | B | 318 | 25.801 | 57.388 | 162.052 | 1.00 | 41.41 | 8 |
| ATOM | 1380 | N | LYS | B | 319 | 27.676 | 56.901 | 163.219 | 1.00 | 40.96 | 7 |
| ATOM | 1381 | CA | LYS | B | 319 | 28.539 | 57.290 | 162.119 | 1.00 | 41.60 | 6 |
| ATOM | 1382 | CB | LYS | B | 319 | 30.021 | 57.099 | 162.449 | 1.00 | 41.63 | 6 |
| ATOM | 1383 | CG | LYS | B | 319 | 30.963 | 57.401 | 161.257 | 1.00 | 43.27 | 6 |
| ATOM | 1384 | CD | LYS | B | 319 | 32.170 | 56.481 | 161.236 | 1.00 | 45.22 | 6 |
| ATOM | 1385 | CE | LYS | B | 319 | 31.757 | 54.999 | 161.468 | 1.00 | 48.29 | 6 |
| ATOM | 1386 | NZ | LYS | B | 319 | 32.876 | 53.968 | 161.456 | 1.00 | 47.72 | 7 |
| ATOM | 1387 | C | LYS | B | 319 | 28.155 | 56.493 | 160.875 | 1.00 | 41.79 | 6 |
| ATOM | 1388 | O | LYS | B | 319 | 27.875 | 57.075 | 159.825 | 1.00 | 41.47 | 8 |
| ATOM | 1389 | N | GLU | B | 320 | 28.125 | 55.170 | 161.014 | 1.00 | 42.08 | 7 |
| ATOM | 1390 | CA | GLU | B | 320 | 27.737 | 54.291 | 159.933 | 1.00 | 43.06 | 6 |
| ATOM | 1391 | CB | GLU | B | 320 | 27.365 | 52.929 | 160.478 | 1.00 | 43.77 | 6 |
| ATOM | 1392 | CG | GLU | B | 320 | 28.104 | 51.755 | 159.898 | 1.00 | 46.62 | 6 |
| ATOM | 1393 | CD | GLU | B | 320 | 29.072 | 51.175 | 160.914 | 1.00 | 49.77 | 6 |
| ATOM | 1394 | OE1 | GLU | B | 320 | 28.739 | 50.121 | 161.520 | 1.00 | 50.16 | 8 |
| ATOM | 1395 | OE2 | GLU | B | 320 | 30.142 | 51.803 | 161.122 | 1.00 | 50.83 | 8 |
| ATOM | 1396 | C | GLU | B | 320 | 26.493 | 54.846 | 159.286 | 1.00 | 43.02 | 6 |
| ATOM | 1397 | O | GLU | B | 320 | 26.498 | 55.150 | 158.093 | 1.00 | 43.25 | 8 |
| ATOM | 1398 | N | TYR | B | 321 | 25.433 | 54.974 | 160.094 | 1.00 | 42.82 | 7 |
| ATOM | 1399 | CA | TYR | B | 321 | 24.137 | 55.488 | 159.661 | 1.00 | 42.60 | 6 |
| ATOM | 1400 | CB | TYR | B | 321 | 23.237 | 55.840 | 160.865 | 1.00 | 42.18 | 6 |
| ATOM | 1401 | CG | TYR | B | 321 | 21.916 | 56.473 | 160.451 | 1.00 | 41.79 | 6 |
| ATOM | 1402 | CD1 | TYR | B | 321 | 20.853 | 55.683 | 160.002 | 1.00 | 41.67 | 6 |
| ATOM | 1403 | CE1 | TYR | B | 321 | 19.657 | 56.244 | 159.588 | 1.00 | 40.71 | 6 |
| ATOM | 1404 | CZ | TYR | B | 321 | 19.510 | 57.608 | 159.620 | 1.00 | 40.89 | 6 |
| ATOM | 1405 | OH | TYR | B | 321 | 18.328 | 58.152 | 159.211 | 1.00 | 41.16 | 8 |
| ATOM | 1406 | CE2 | TYR | B | 321 | 20.535 | 58.425 | 160.063 | 1.00 | 41.25 | 6 |
| ATOM | 1407 | CD2 | TYR | B | 321 | 21.739 | 57.854 | 160.472 | 1.00 | 41.59 | 6 |
| ATOM | 1408 | C | TYR | B | 321 | 24.294 | 56.714 | 158.776 | 1.00 | 42.94 | 6 |
| ATOM | 1409 | O | TYR | B | 321 | 23.783 | 56.758 | 157.663 | 1.00 | 43.06 | 8 |
| ATOM | 1410 | N | LEU | B | 322 | 25.001 | 57.714 | 159.274 | 1.00 | 43.24 | 7 |
| ATOM | 1411 | CA | LEU | B | 322 | 25.145 | 58.939 | 158.529 | 1.00 | 43.79 | 6 |
| ATOM | 1412 | CB | LEU | B | 322 | 25.827 | 60.003 | 159.383 | 1.00 | 43.47 | 6 |
| ATOM | 1413 | CG | LEU | B | 322 | 25.009 | 60.537 | 160.555 | 1.00 | 42.53 | 6 |
| ATOM | 1414 | CD1 | LEU | B | 322 | 25.768 | 61.620 | 161.279 | 1.00 | 42.81 | 6 |
| ATOM | 1415 | CD2 | LEU | B | 322 | 23.693 | 61.086 | 160.081 | 1.00 | 40.92 | 6 |
| ATOM | 1416 | C | LEU | B | 322 | 25.875 | 58.728 | 157.202 | 1.00 | 44.86 | 6 |
| ATOM | 1417 | O | LEU | B | 322 | 25.481 | 59.307 | 156.194 | 1.00 | 44.52 | 8 |
| ATOM | 1418 | N | GLN | B | 323 | 26.926 | 57.892 | 157.205 | 1.00 | 46.48 | 7 |
| ATOM | 1419 | CA | GLN | B | 323 | 27.697 | 57.580 | 155.979 | 1.00 | 47.79 | 6 |
| ATOM | 1420 | CB | GLN | B | 323 | 28.802 | 56.528 | 156.221 | 1.00 | 47.19 | 6 |
| ATOM | 1421 | CG | GLN | B | 323 | 30.225 | 57.111 | 156.362 | 1.00 | 48.44 | 6 |
| ATOM | 1422 | CD | GLN | B | 323 | 31.124 | 56.369 | 157.418 | 1.00 | 49.39 | 6 |
| ATOM | 1423 | OE1 | GLN | B | 323 | 30.678 | 55.439 | 158.104 | 1.00 | 51.03 | 8 |
| ATOM | 1424 | NE2 | GLN | B | 323 | 32.393 | 56.801 | 157.537 | 1.00 | 50.41 | 7 |
| ATOM | 1425 | C | GLN | B | 323 | 26.705 | 57.119 | 154.926 | 1.00 | 48.27 | 6 |
| ATOM | 1426 | O | GLN | B | 323 | 26.694 | 57.634 | 153.813 | 1.00 | 48.13 | 8 |
| ATOM | 1427 | N | GLU | B | 324 | 25.836 | 56.191 | 155.315 | 1.00 | 49.48 | 7 |

TABLE 1-continued

| ATOM | 1428 | CA  | GLU | B | 324 | 24.833 | 55.651 | 154.421 | 1.00 | 51.23 | 6 |
| ATOM | 1429 | CB  | GLU | B | 324 | 24.071 | 54.495 | 155.085 | 1.00 | 51.47 | 6 |
| ATOM | 1430 | CG  | GLU | B | 324 | 24.853 | 53.157 | 155.036 | 1.00 | 55.79 | 6 |
| ATOM | 1431 | CD  | GLU | B | 324 | 24.664 | 52.230 | 156.281 | 1.00 | 61.40 | 6 |
| ATOM | 1432 | OE1 | GLU | B | 324 | 23.517 | 51.783 | 156.517 | 1.00 | 63.47 | 8 |
| ATOM | 1433 | OE2 | GLU | B | 324 | 25.662 | 51.916 | 157.008 | 1.00 | 63.09 | 8 |
| ATOM | 1434 | C   | GLU | B | 324 | 23.915 | 56.756 | 153.920 | 1.00 | 51.64 | 6 |
| ATOM | 1435 | O   | GLU | B | 324 | 23.775 | 56.938 | 152.725 | 1.00 | 51.92 | 8 |
| ATOM | 1436 | N   | GLN | B | 325 | 23.328 | 57.532 | 154.817 | 1.00 | 52.64 | 7 |
| ATOM | 1437 | CA  | GLN | B | 325 | 22.469 | 58.641 | 154.385 | 1.00 | 53.72 | 6 |
| ATOM | 1438 | CB  | GLN | B | 325 | 21.969 | 59.474 | 155.575 | 1.00 | 53.99 | 6 |
| ATOM | 1439 | CG  | GLN | B | 325 | 21.073 | 58.723 | 156.566 | 1.00 | 54.63 | 6 |
| ATOM | 1440 | CD  | GLN | B | 325 | 19.893 | 58.030 | 155.898 | 1.00 | 55.76 | 6 |
| ATOM | 1441 | OE1 | GLN | B | 325 | 20.054 | 56.980 | 155.270 | 1.00 | 56.31 | 8 |
| ATOM | 1442 | NE2 | GLN | B | 325 | 18.699 | 58.610 | 156.037 | 1.00 | 56.03 | 7 |
| ATOM | 1443 | C   | GLN | B | 325 | 23.163 | 59.535 | 153.363 | 1.00 | 54.30 | 6 |
| ATOM | 1444 | O   | GLN | B | 325 | 22.559 | 59.921 | 152.378 | 1.00 | 54.30 | 8 |
| ATOM | 1445 | N   | LEU | B | 326 | 24.437 | 59.836 | 153.596 | 1.00 | 55.35 | 7 |
| ATOM | 1446 | CA  | LEU | B | 326 | 25.209 | 60.661 | 152.684 | 1.00 | 56.25 | 6 |
| ATOM | 1447 | CB  | LEU | B | 326 | 26.532 | 61.085 | 153.335 | 1.00 | 55.97 | 6 |
| ATOM | 1448 | CG  | LEU | B | 326 | 27.162 | 62.464 | 153.081 | 1.00 | 55.52 | 6 |
| ATOM | 1449 | CD1 | LEU | B | 326 | 28.034 | 62.470 | 151.815 | 1.00 | 56.45 | 6 |
| ATOM | 1450 | CD2 | LEU | B | 326 | 26.136 | 63.607 | 153.065 | 1.00 | 54.51 | 6 |
| ATOM | 1451 | C   | LEU | B | 326 | 25.442 | 59.945 | 151.349 | 1.00 | 57.39 | 6 |
| ATOM | 1452 | O   | LEU | B | 326 | 25.482 | 60.602 | 150.311 | 1.00 | 57.73 | 8 |
| ATOM | 1453 | N   | GLU | B | 327 | 25.591 | 58.615 | 151.368 | 1.00 | 58.58 | 7 |
| ATOM | 1454 | CA  | GLU | B | 327 | 25.681 | 57.845 | 150.128 | 1.00 | 60.00 | 6 |
| ATOM | 1455 | CB  | GLU | B | 327 | 25.895 | 56.361 | 150.384 | 1.00 | 60.00 | 6 |
| ATOM | 1456 | CG  | GLU | B | 327 | 27.175 | 55.802 | 149.812 | 1.00 | 61.00 | 6 |
| ATOM | 1457 | CD  | GLU | B | 327 | 28.338 | 55.861 | 150.796 | 1.00 | 62.50 | 6 |
| ATOM | 1458 | OE1 | GLU | B | 327 | 28.151 | 55.517 | 151.986 | 1.00 | 62.43 | 8 |
| ATOM | 1459 | OE2 | GLU | B | 327 | 29.454 | 56.235 | 150.369 | 1.00 | 63.52 | 8 |
| ATOM | 1460 | C   | GLU | B | 327 | 24.409 | 58.020 | 149.333 | 1.00 | 61.06 | 6 |
| ATOM | 1461 | O   | GLU | B | 327 | 24.414 | 58.680 | 148.303 | 1.00 | 61.52 | 8 |
| ATOM | 1462 | N   | GLN | B | 328 | 23.315 | 57.444 | 149.822 | 1.00 | 62.40 | 7 |
| ATOM | 1463 | CA  | GLN | B | 328 | 21.985 | 57.593 | 149.206 | 1.00 | 64.02 | 6 |
| ATOM | 1464 | CB  | GLN | B | 328 | 20.867 | 57.357 | 150.218 | 1.00 | 63.91 | 6 |
| ATOM | 1465 | CG  | GLN | B | 328 | 21.114 | 56.248 | 151.184 | 1.00 | 66.20 | 6 |
| ATOM | 1466 | CD  | GLN | B | 328 | 20.677 | 54.907 | 150.664 | 1.00 | 68.96 | 6 |
| ATOM | 1467 | OE1 | GLN | B | 328 | 19.941 | 54.187 | 151.341 | 1.00 | 70.32 | 8 |
| ATOM | 1468 | NE2 | GLN | B | 328 | 21.124 | 54.551 | 149.458 | 1.00 | 70.02 | 7 |
| ATOM | 1469 | C   | GLN | B | 328 | 21.719 | 58.972 | 148.641 | 1.00 | 64.74 | 6 |
| ATOM | 1470 | O   | GLN | B | 328 | 21.246 | 59.118 | 147.522 | 1.00 | 64.97 | 8 |
| ATOM | 1471 | N   | LEU | B | 329 | 21.984 | 59.994 | 149.434 | 1.00 | 65.70 | 7 |
| ATOM | 1472 | CA  | LEU | B | 329 | 21.604 | 61.304 | 149.014 | 1.00 | 66.60 | 6 |
| ATOM | 1473 | CB  | LEU | B | 329 | 21.557 | 62.268 | 150.171 | 1.00 | 66.23 | 6 |
| ATOM | 1474 | CG  | LEU | B | 329 | 20.183 | 62.885 | 150.362 | 1.00 | 65.38 | 6 |
| ATOM | 1475 | CD1 | LEU | B | 329 | 20.363 | 64.258 | 150.964 | 1.00 | 65.09 | 6 |
| ATOM | 1476 | CD2 | LEU | B | 329 | 19.409 | 62.954 | 149.059 | 1.00 | 64.54 | 6 |
| ATOM | 1477 | C   | LEU | B | 329 | 22.526 | 61.804 | 147.940 | 1.00 | 67.86 | 6 |
| ATOM | 1478 | O   | LEU | B | 329 | 22.055 | 62.411 | 146.998 | 1.00 | 68.16 | 8 |
| ATOM | 1479 | N   | GLN | B | 330 | 23.826 | 61.538 | 148.048 | 1.00 | 69.76 | 7 |
| ATOM | 1480 | CA  | GLN | B | 330 | 24.759 | 61.993 | 147.000 | 1.00 | 71.11 | 6 |
| ATOM | 1481 | CB  | GLN | B | 330 | 26.235 | 61.977 | 147.457 | 1.00 | 71.23 | 6 |
| ATOM | 1482 | CG  | GLN | B | 330 | 27.277 | 62.386 | 146.364 | 1.00 | 71.34 | 6 |
| ATOM | 1483 | CD  | GLN | B | 330 | 27.436 | 63.910 | 146.110 | 1.00 | 72.70 | 6 |
| ATOM | 1484 | OE1 | GLN | B | 330 | 26.486 | 64.694 | 146.202 | 1.00 | 72.75 | 8 |
| ATOM | 1485 | NE2 | GLN | B | 330 | 28.657 | 64.311 | 145.758 | 1.00 | 72.57 | 7 |
| ATOM | 1486 | C   | GLN | B | 330 | 24.529 | 61.234 | 145.688 | 1.00 | 72.02 | 6 |
| ATOM | 1487 | O   | GLN | B | 330 | 24.907 | 61.710 | 144.618 | 1.00 | 72.08 | 8 |
| ATOM | 1488 | N   | ARG | B | 331 | 23.877 | 60.075 | 145.796 | 1.00 | 73.20 | 7 |
| ATOM | 1489 | CA  | ARG | B | 331 | 23.396 | 59.278 | 144.664 | 1.00 | 74.46 | 6 |
| ATOM | 1490 | CB  | ARG | B | 331 | 22.900 | 57.933 | 145.202 | 1.00 | 74.10 | 6 |
| ATOM | 1491 | CG  | ARG | B | 331 | 22.662 | 56.817 | 144.190 | 1.00 | 73.35 | 6 |
| ATOM | 1492 | CD  | ARG | B | 331 | 23.767 | 55.737 | 144.203 | 1.00 | 71.89 | 6 |
| ATOM | 1493 | NE  | ARG | B | 331 | 24.413 | 55.522 | 145.512 | 1.00 | 70.93 | 7 |
| ATOM | 1494 | CZ  | ARG | B | 331 | 23.920 | 54.808 | 146.534 | 1.00 | 70.02 | 6 |
| ATOM | 1495 | NH1 | ARG | B | 331 | 22.732 | 54.214 | 146.450 | 1.00 | 69.16 | 7 |
| ATOM | 1496 | NH2 | ARG | B | 331 | 24.627 | 54.694 | 147.661 | 1.00 | 69.42 | 7 |
| ATOM | 1497 | C   | ARG | B | 331 | 22.234 | 59.979 | 143.952 | 1.00 | 75.75 | 6 |
| ATOM | 1498 | O   | ARG | B | 331 | 22.019 | 59.796 | 142.751 | 1.00 | 75.92 | 8 |
| ATOM | 1499 | N   | GLU | B | 332 | 21.480 | 60.768 | 144.710 | 1.00 | 77.22 | 7 |
| ATOM | 1500 | CA  | GLU | B | 332 | 20.285 | 61.423 | 144.196 | 1.00 | 78.93 | 6 |
| ATOM | 1501 | CB  | GLU | B | 332 | 19.255 | 61.603 | 145.307 | 1.00 | 78.98 | 6 |
| ATOM | 1502 | CG  | GLU | B | 332 | 17.982 | 60.814 | 145.106 | 1.00 | 79.82 | 6 |
| ATOM | 1503 | CD  | GLU | B | 332 | 18.197 | 59.315 | 145.070 | 1.00 | 81.26 | 6 |
| ATOM | 1504 | OE1 | GLU | B | 332 | 19.313 | 58.863 | 144.735 | 1.00 | 82.51 | 8 |
| ATOM | 1505 | OE2 | GLU | B | 332 | 17.238 | 58.578 | 145.374 | 1.00 | 81.73 | 8 |
| ATOM | 1506 | C   | GLU | B | 332 | 20.572 | 62.750 | 143.537 | 1.00 | 79.91 | 6 |
| ATOM | 1507 | O   | GLU | B | 332 | 20.049 | 63.048 | 142.467 | 1.00 | 80.09 | 8 |

TABLE 1-continued

| | | | | | | | | | |
|---|---|---|---|---|---|---|---|---|---|
| ATOM | 1508 | N | PHE | B | 333 | 21.394 | 63.552 | 144.192 | 1.00 | 81.19 | 7 |
| ATOM | 1509 | CA | PHE | B | 333 | 21.881 | 64.787 | 143.616 | 1.00 | 82.52 | 6 |
| ATOM | 1510 | CB | PHE | B | 333 | 22.660 | 65.545 | 144.693 | 1.00 | 82.67 | 6 |
| ATOM | 1511 | CG | PHE | B | 333 | 22.895 | 66.997 | 144.395 | 1.00 | 82.82 | 6 |
| ATOM | 1512 | CD1 | PHE | B | 333 | 21.834 | 67.895 | 144.333 | 1.00 | 83.07 | 6 |
| ATOM | 1513 | CE1 | PHE | B | 333 | 22.063 | 69.251 | 144.063 | 1.00 | 83.67 | 6 |
| ATOM | 1514 | CZ | PHE | B | 333 | 23.374 | 69.720 | 143.879 | 1.00 | 83.48 | 6 |
| ATOM | 1515 | CE2 | PHE | B | 333 | 24.447 | 68.831 | 143.971 | 1.00 | 83.81 | 6 |
| ATOM | 1516 | CD2 | PHE | B | 333 | 24.199 | 67.477 | 144.233 | 1.00 | 83.48 | 6 |
| ATOM | 1517 | C | PHE | B | 333 | 22.742 | 64.461 | 142.373 | 1.00 | 83.46 | 6 |
| ATOM | 1518 | O | PHE | B | 333 | 23.175 | 65.362 | 141.652 | 1.00 | 83.74 | 8 |
| ATOM | 1519 | N | ASN | B | 334 | 22.943 | 63.161 | 142.123 | 1.00 | 84.37 | 7 |
| ATOM | 1520 | CA | ASN | B | 334 | 23.702 | 62.630 | 140.982 | 1.00 | 85.16 | 6 |
| ATOM | 1521 | CB | ASN | B | 334 | 24.441 | 61.368 | 141.419 | 1.00 | 84.80 | 6 |
| ATOM | 1522 | CG | ASN | B | 334 | 25.913 | 61.583 | 141.580 | 1.00 | 84.10 | 6 |
| ATOM | 1523 | OD1 | ASN | B | 334 | 26.356 | 62.574 | 142.157 | 1.00 | 83.22 | 8 |
| ATOM | 1524 | ND2 | ASN | B | 334 | 26.693 | 60.648 | 141.066 | 1.00 | 83.61 | 7 |
| ATOM | 1525 | C | ASN | B | 334 | 22.847 | 62.236 | 139.784 | 1.00 | 86.03 | 6 |
| ATOM | 1526 | O | ASN | B | 334 | 23.217 | 62.462 | 138.628 | 1.00 | 86.13 | 8 |
| ATOM | 1527 | N | LYS | B | 335 | 21.724 | 61.592 | 140.079 | 1.00 | 87.20 | 7 |
| ATOM | 1528 | CA | LYS | B | 335 | 20.778 | 61.156 | 139.059 | 1.00 | 88.31 | 6 |
| ATOM | 1529 | CB | LYS | B | 335 | 19.863 | 60.053 | 139.602 | 1.00 | 88.28 | 6 |
| ATOM | 1530 | CG | LYS | B | 335 | 20.587 | 58.736 | 139.795 | 1.00 | 88.75 | 6 |
| ATOM | 1531 | CD | LYS | B | 335 | 19.748 | 57.698 | 140.506 | 1.00 | 88.96 | 6 |
| ATOM | 1532 | CE | LYS | B | 335 | 20.604 | 56.470 | 140.773 | 1.00 | 89.05 | 6 |
| ATOM | 1533 | NZ | LYS | B | 335 | 19.804 | 55.314 | 141.231 | 1.00 | 89.30 | 7 |
| ATOM | 1534 | C | LYS | B | 335 | 19.951 | 62.334 | 138.596 | 1.00 | 88.96 | 6 |
| ATOM | 1535 | O | LYS | B | 335 | 19.738 | 62.522 | 137.400 | 1.00 | 89.13 | 8 |
| ATOM | 1536 | N | LEU | B | 336 | 19.494 | 63.132 | 139.553 | 1.00 | 89.86 | 7 |
| ATOM | 1537 | CA | LEU | B | 336 | 18.760 | 64.355 | 139.241 | 1.00 | 90.67 | 6 |
| ATOM | 1538 | CB | LEU | B | 336 | 17.674 | 64.642 | 140.290 | 1.00 | 90.69 | 6 |
| ATOM | 1539 | CG | LEU | B | 336 | 16.579 | 63.599 | 140.557 | 1.00 | 90.76 | 6 |
| ATOM | 1540 | CD1 | LEU | B | 336 | 17.083 | 62.455 | 141.459 | 1.00 | 90.39 | 6 |
| ATOM | 1541 | CD2 | LEU | B | 336 | 15.329 | 64.258 | 141.157 | 1.00 | 90.48 | 6 |
| ATOM | 1542 | C | LEU | B | 336 | 19.731 | 65.539 | 139.093 | 1.00 | 91.31 | 6 |
| ATOM | 1543 | O | LEU | B | 336 | 19.348 | 66.702 | 139.314 | 1.00 | 91.36 | 8 |
| ATOM | 1544 | N | LYS | B | 337 | 20.976 | 65.211 | 138.710 | 1.00 | 91.90 | 7 |
| ATOM | 1545 | CA | LYS | B | 337 | 22.073 | 66.165 | 138.429 | 1.00 | 92.33 | 6 |
| ATOM | 1546 | CB | LYS | B | 337 | 23.207 | 65.473 | 137.638 | 1.00 | 92.29 | 6 |
| ATOM | 1547 | CG | LYS | B | 337 | 24.150 | 66.407 | 136.861 | 1.00 | 91.99 | 6 |
| ATOM | 1548 | CD | LYS | B | 337 | 25.549 | 65.828 | 136.753 | 1.00 | 91.67 | 6 |
| ATOM | 1549 | CE | LYS | B | 337 | 26.487 | 66.799 | 136.059 | 1.00 | 91.01 | 6 |
| ATOM | 1550 | NZ | LYS | B | 337 | 27.893 | 66.364 | 136.238 | 1.00 | 90.54 | 7 |
| ATOM | 1551 | C | LYS | B | 337 | 21.618 | 67.421 | 137.693 | 1.00 | 92.66 | 6 |
| ATOM | 1552 | O | LYS | B | 337 | 20.773 | 67.391 | 136.792 | 1.00 | 92.93 | 8 |
| ATOM | 1553 | OXT | LYS | B | 337 | 22.071 | 68.516 | 138.044 | 1.00 | 92.86 | 8 |
| ATOM | 1554 | N | SER | C | 12 | −1.952 | 44.539 | 167.423 | 1.00 | 71.74 | 7 |
| ATOM | 1555 | CA | SER | C | 12 | −0.990 | 44.950 | 168.497 | 1.00 | 71.74 | 6 |
| ATOM | 1556 | CB | SER | C | 12 | −1.061 | 44.018 | 169.724 | 1.00 | 71.76 | 6 |
| ATOM | 1557 | OG | SER | C | 12 | −1.010 | 42.643 | 169.376 | 1.00 | 71.83 | 8 |
| ATOM | 1558 | C | SER | C | 12 | 0.451 | 45.129 | 167.996 | 1.00 | 71.46 | 6 |
| ATOM | 1559 | O | SER | C | 12 | 1.281 | 45.739 | 168.676 | 1.00 | 71.38 | 8 |
| ATOM | 1560 | N | ASP | C | 13 | 0.744 | 44.617 | 166.802 | 1.00 | 70.95 | 7 |
| ATOM | 1561 | CA | ASP | C | 13 | 2.040 | 44.881 | 166.179 | 1.00 | 70.31 | 6 |
| ATOM | 1562 | CB | ASP | C | 13 | 2.528 | 43.701 | 165.325 | 1.00 | 70.52 | 6 |
| ATOM | 1563 | CG | ASP | C | 13 | 2.379 | 43.951 | 163.829 | 1.00 | 71.36 | 6 |
| ATOM | 1564 | OD1 | ASP | C | 13 | 3.405 | 44.260 | 163.173 | 1.00 | 72.42 | 8 |
| ATOM | 1565 | OD2 | ASP | C | 13 | 1.242 | 43.854 | 163.316 | 1.00 | 71.46 | 8 |
| ATOM | 1566 | C | ASP | C | 13 | 1.993 | 46.220 | 165.411 | 1.00 | 69.34 | 6 |
| ATOM | 1567 | O | ASP | C | 13 | 2.891 | 46.555 | 164.630 | 1.00 | 69.13 | 8 |
| ATOM | 1568 | N | LEU | C | 14 | 0.937 | 46.992 | 165.655 | 1.00 | 67.97 | 7 |
| ATOM | 1569 | CA | LEU | C | 14 | 0.971 | 48.400 | 165.329 | 1.00 | 66.48 | 6 |
| ATOM | 1570 | CB | LEU | C | 14 | −0.312 | 49.109 | 165.753 | 1.00 | 66.48 | 6 |
| ATOM | 1571 | CG | LEU | C | 14 | −1.547 | 48.779 | 164.907 | 1.00 | 66.37 | 6 |
| ATOM | 1572 | CD1 | LEU | C | 14 | −2.667 | 49.803 | 165.128 | 1.00 | 66.16 | 6 |
| ATOM | 1573 | CD2 | LEU | C | 14 | −1.188 | 48.672 | 163.425 | 1.00 | 65.71 | 6 |
| ATOM | 1574 | C | LEU | C | 14 | 2.192 | 49.005 | 166.015 | 1.00 | 65.59 | 6 |
| ATOM | 1575 | O | LEU | C | 14 | 2.867 | 49.857 | 165.434 | 1.00 | 65.73 | 8 |
| ATOM | 1576 | N | GLY | C | 15 | 2.495 | 48.528 | 167.228 | 1.00 | 64.28 | 7 |
| ATOM | 1577 | CA | GLY | C | 15 | 3.707 | 48.922 | 167.961 | 1.00 | 62.51 | 6 |
| ATOM | 1578 | C | GLY | C | 15 | 5.000 | 48.830 | 167.164 | 1.00 | 61.28 | 6 |
| ATOM | 1579 | O | GLY | C | 15 | 5.773 | 49.790 | 167.092 | 1.00 | 61.06 | 8 |
| ATOM | 1580 | N | LYS | C | 16 | 5.218 | 47.667 | 166.556 | 1.00 | 60.20 | 7 |
| ATOM | 1581 | CA | LYS | C | 16 | 6.383 | 47.391 | 165.704 | 1.00 | 58.94 | 6 |
| ATOM | 1582 | CB | LYS | C | 16 | 6.287 | 45.951 | 165.173 | 1.00 | 59.00 | 6 |
| ATOM | 1583 | CG | LYS | C | 16 | 7.571 | 45.351 | 164.641 | 1.00 | 58.67 | 6 |
| ATOM | 1584 | CD | LYS | C | 16 | 7.319 | 43.995 | 164.003 | 1.00 | 58.85 | 6 |
| ATOM | 1585 | CE | LYS | C | 16 | 8.627 | 43.253 | 163.747 | 1.00 | 58.98 | 6 |
| ATOM | 1586 | NZ | LYS | C | 16 | 8.498 | 42.206 | 162.684 | 1.00 | 58.97 | 7 |
| ATOM | 1587 | C | LYS | C | 16 | 6.487 | 48.367 | 164.532 | 1.00 | 58.25 | 6 |

TABLE 1-continued

| | | | | | | | | | |
|---|---|---|---|---|---|---|---|---|---|
| ATOM | 1588 | O | LYS | C | 16 | 7.588 | 48.699 | 164.087 | 1.00 | 57.71 | 8 |
| ATOM | 1589 | N | LYS | C | 17 | 5.333 | 48.809 | 164.028 | 1.00 | 57.78 | 7 |
| ATOM | 1590 | CA | LYS | C | 17 | 5.305 | 49.741 | 162.893 | 1.00 | 57.39 | 6 |
| ATOM | 1591 | CB | LYS | C | 17 | 4.036 | 49.581 | 162.040 | 1.00 | 57.41 | 6 |
| ATOM | 1592 | CG | LYS | C | 17 | 3.897 | 48.204 | 161.356 | 1.00 | 57.84 | 6 |
| ATOM | 1593 | CD | LYS | C | 17 | 5.118 | 47.816 | 160.502 | 1.00 | 58.71 | 6 |
| ATOM | 1594 | CE | LYS | C | 17 | 5.162 | 46.309 | 160.230 | 1.00 | 58.37 | 6 |
| ATOM | 1595 | NZ | LYS | C | 17 | 4.216 | 45.921 | 159.145 | 1.00 | 58.82 | 7 |
| ATOM | 1596 | C | LYS | C | 17 | 5.536 | 51.188 | 163.326 | 1.00 | 56.83 | 6 |
| ATOM | 1597 | O | LYS | C | 17 | 6.221 | 51.951 | 162.624 | 1.00 | 56.52 | 8 |
| ATOM | 1598 | N | LEU | C | 18 | 4.989 | 51.548 | 164.487 | 1.00 | 56.14 | 7 |
| ATOM | 1599 | CA | LEU | C | 18 | 5.225 | 52.861 | 165.056 | 1.00 | 55.66 | 6 |
| ATOM | 1600 | CB | LEU | C | 18 | 4.340 | 53.090 | 166.279 | 1.00 | 55.42 | 6 |
| ATOM | 1601 | CG | LEU | C | 18 | 4.553 | 54.349 | 167.124 | 1.00 | 55.02 | 6 |
| ATOM | 1602 | CD1 | LEU | C | 18 | 4.482 | 55.612 | 166.308 | 1.00 | 54.24 | 6 |
| ATOM | 1603 | CD2 | LEU | C | 18 | 3.530 | 54.396 | 168.245 | 1.00 | 55.55 | 6 |
| ATOM | 1604 | C | LEU | C | 18 | 6.708 | 53.051 | 165.374 | 1.00 | 55.70 | 6 |
| ATOM | 1605 | O | LEU | C | 18 | 7.263 | 54.126 | 165.137 | 1.00 | 55.84 | 8 |
| ATOM | 1606 | N | LEU | C | 19 | 7.355 | 52.005 | 165.876 | 1.00 | 55.62 | 7 |
| ATOM | 1607 | CA | LEU | C | 19 | 8.794 | 52.071 | 166.112 | 1.00 | 55.90 | 6 |
| ATOM | 1608 | CB | LEU | C | 19 | 9.318 | 50.749 | 166.673 | 1.00 | 55.85 | 6 |
| ATOM | 1609 | CG | LEU | C | 19 | 8.833 | 50.292 | 168.046 | 1.00 | 55.50 | 6 |
| ATOM | 1610 | CD1 | LEU | C | 19 | 9.421 | 48.932 | 168.370 | 1.00 | 54.93 | 6 |
| ATOM | 1611 | CD2 | LEU | C | 19 | 9.190 | 51.306 | 169.121 | 1.00 | 55.56 | 6 |
| ATOM | 1612 | C | LEU | C | 19 | 9.548 | 52.432 | 164.832 | 1.00 | 56.28 | 6 |
| ATOM | 1613 | O | LEU | C | 19 | 10.344 | 53.369 | 164.809 | 1.00 | 55.98 | 8 |
| ATOM | 1614 | N | GLU | C | 20 | 9.257 | 51.687 | 163.769 | 1.00 | 57.01 | 7 |
| ATOM | 1615 | CA | GLU | C | 20 | 9.865 | 51.875 | 162.451 | 1.00 | 57.78 | 6 |
| ATOM | 1616 | CB | GLU | C | 20 | 9.246 | 50.909 | 161.444 | 1.00 | 58.21 | 6 |
| ATOM | 1617 | CG | GLU | C | 20 | 10.291 | 50.122 | 160.691 | 1.00 | 61.13 | 6 |
| ATOM | 1618 | CD | GLU | C | 20 | 10.938 | 49.067 | 161.591 | 1.00 | 64.71 | 6 |
| ATOM | 1619 | OE1 | GLU | C | 20 | 10.166 | 48.359 | 162.306 | 1.00 | 67.07 | 8 |
| ATOM | 1620 | OE2 | GLU | C | 20 | 12.198 | 48.961 | 161.594 | 1.00 | 65.04 | 8 |
| ATOM | 1621 | C | GLU | C | 20 | 9.654 | 53.271 | 161.920 | 1.00 | 57.24 | 6 |
| ATOM | 1622 | O | GLU | C | 20 | 10.573 | 53.887 | 161.387 | 1.00 | 57.00 | 8 |
| ATOM | 1623 | N | ALA | C | 21 | 8.417 | 53.742 | 162.055 | 1.00 | 56.95 | 7 |
| ATOM | 1624 | CA | ALA | C | 21 | 8.016 | 55.050 | 161.577 | 1.00 | 56.58 | 6 |
| ATOM | 1625 | CB | ALA | C | 21 | 6.532 | 55.255 | 161.805 | 1.00 | 56.47 | 6 |
| ATOM | 1626 | C | ALA | C | 21 | 8.814 | 56.123 | 162.286 | 1.00 | 56.42 | 6 |
| ATOM | 1627 | O | ALA | C | 21 | 9.279 | 57.072 | 161.663 | 1.00 | 56.26 | 8 |
| ATOM | 1628 | N | ALA | C | 22 | 8.982 | 55.950 | 163.592 | 1.00 | 56.46 | 7 |
| ATOM | 1629 | CA | ALA | C | 22 | 9.727 | 56.895 | 164.413 | 1.00 | 56.50 | 6 |
| ATOM | 1630 | CB | ALA | C | 22 | 9.552 | 56.573 | 165.871 | 1.00 | 56.37 | 6 |
| ATOM | 1631 | C | ALA | C | 22 | 11.215 | 56.959 | 164.048 | 1.00 | 56.64 | 6 |
| ATOM | 1632 | O | ALA | C | 22 | 11.783 | 58.044 | 163.981 | 1.00 | 56.54 | 8 |
| ATOM | 1633 | N | ARG | C | 23 | 11.847 | 55.807 | 163.818 | 1.00 | 56.79 | 7 |
| ATOM | 1634 | CA | ARG | C | 23 | 13.231 | 55.792 | 163.356 | 1.00 | 57.25 | 6 |
| ATOM | 1635 | CB | ARG | C | 23 | 13.777 | 54.367 | 163.242 | 1.00 | 56.85 | 6 |
| ATOM | 1636 | CG | ARG | C | 23 | 15.239 | 54.303 | 162.751 | 1.00 | 58.13 | 6 |
| ATOM | 1637 | CD | ARG | C | 23 | 15.775 | 52.885 | 162.469 | 1.00 | 58.74 | 6 |
| ATOM | 1638 | NE | ARG | C | 23 | 15.285 | 51.911 | 163.446 | 1.00 | 62.17 | 7 |
| ATOM | 1639 | CZ | ARG | C | 23 | 14.436 | 50.919 | 163.168 | 1.00 | 63.14 | 6 |
| ATOM | 1640 | NH1 | ARG | C | 23 | 13.995 | 50.731 | 161.925 | 1.00 | 62.45 | 7 |
| ATOM | 1641 | NH2 | ARG | C | 23 | 14.032 | 50.101 | 164.136 | 1.00 | 63.69 | 7 |
| ATOM | 1642 | C | ARG | C | 23 | 13.326 | 56.481 | 161.999 | 1.00 | 57.16 | 6 |
| ATOM | 1643 | O | ARG | C | 23 | 14.251 | 57.261 | 161.752 | 1.00 | 57.07 | 8 |
| ATOM | 1644 | N | ALA | C | 24 | 12.354 | 56.198 | 161.130 | 1.00 | 57.36 | 7 |
| ATOM | 1645 | CA | ALA | C | 24 | 12.414 | 56.612 | 159.727 | 1.00 | 57.41 | 6 |
| ATOM | 1646 | CB | ALA | C | 24 | 11.484 | 55.778 | 158.891 | 1.00 | 57.20 | 6 |
| ATOM | 1647 | C | ALA | C | 24 | 12.125 | 58.087 | 159.520 | 1.00 | 57.61 | 6 |
| ATOM | 1648 | O | ALA | C | 24 | 12.657 | 58.694 | 158.596 | 1.00 | 57.82 | 8 |
| ATOM | 1649 | N | GLY | C | 25 | 11.294 | 58.666 | 160.375 | 1.00 | 57.82 | 7 |
| ATOM | 1650 | CA | GLY | C | 25 | 10.952 | 60.070 | 160.234 | 1.00 | 58.27 | 6 |
| ATOM | 1651 | C | GLY | C | 25 | 9.623 | 60.268 | 159.540 | 1.00 | 58.64 | 6 |
| ATOM | 1652 | O | GLY | C | 25 | 9.217 | 61.399 | 159.285 | 1.00 | 58.45 | 8 |
| ATOM | 1653 | N | GLN | C | 26 | 8.943 | 59.162 | 159.250 | 1.00 | 59.21 | 7 |
| ATOM | 1654 | CA | GLN | C | 26 | 7.611 | 59.185 | 158.649 | 1.00 | 60.13 | 6 |
| ATOM | 1655 | CB | GLN | C | 26 | 7.119 | 57.767 | 158.323 | 1.00 | 60.19 | 6 |
| ATOM | 1656 | CG | GLN | C | 26 | 8.167 | 56.748 | 157.894 | 1.00 | 61.44 | 6 |
| ATOM | 1657 | CD | GLN | C | 26 | 8.851 | 57.093 | 156.578 | 1.00 | 63.51 | 6 |
| ATOM | 1658 | OE1 | GLN | C | 26 | 8.441 | 58.014 | 155.864 | 1.00 | 64.05 | 8 |
| ATOM | 1659 | NE2 | GLN | C | 26 | 9.903 | 56.340 | 156.244 | 1.00 | 64.54 | 7 |
| ATOM | 1660 | C | GLN | C | 26 | 6.585 | 59.845 | 159.567 | 1.00 | 60.63 | 6 |
| ATOM | 1661 | O | GLN | C | 26 | 5.865 | 59.160 | 160.290 | 1.00 | 60.50 | 8 |
| ATOM | 1662 | N | ASP | C | 27 | 6.531 | 61.175 | 159.518 | 1.00 | 61.51 | 7 |
| ATOM | 1663 | CA | ASP | C | 27 | 5.556 | 61.999 | 160.249 | 1.00 | 62.24 | 6 |
| ATOM | 1664 | CB | ASP | C | 27 | 5.597 | 63.443 | 159.730 | 1.00 | 62.61 | 6 |
| ATOM | 1665 | CG | ASP | C | 27 | 6.743 | 64.249 | 160.313 | 1.00 | 64.07 | 6 |
| ATOM | 1666 | OD1 | ASP | C | 27 | 7.926 | 63.820 | 160.213 | 1.00 | 64.69 | 8 |
| ATOM | 1667 | OD2 | ASP | C | 27 | 6.442 | 65.333 | 160.862 | 1.00 | 65.47 | 8 |

TABLE 1-continued

| | | | | | | | | | | |
|---|---|---|---|---|---|---|---|---|---|---|
| ATOM | 1668 | C | ASP | C | 27 | 4.132 | 61.526 | 160.079 | 1.00 | 62.22 | 6 |
| ATOM | 1669 | O | ASP | C | 27 | 3.412 | 61.327 | 161.053 | 1.00 | 62.46 | 8 |
| ATOM | 1670 | N | ASP | C | 28 | 3.716 | 61.394 | 158.826 | 1.00 | 62.23 | 7 |
| ATOM | 1671 | CA | ASP | C | 28 | 2.347 | 61.002 | 158.519 | 1.00 | 62.39 | 6 |
| ATOM | 1672 | CB | ASP | C | 28 | 2.028 | 61.172 | 157.033 | 1.00 | 62.62 | 6 |
| ATOM | 1673 | CG | ASP | C | 28 | 3.254 | 60.999 | 156.139 | 1.00 | 64.05 | 6 |
| ATOM | 1674 | OD1 | ASP | C | 28 | 3.126 | 61.345 | 154.938 | 1.00 | 65.74 | 8 |
| ATOM | 1675 | OD2 | ASP | C | 28 | 4.330 | 60.537 | 156.617 | 1.00 | 63.80 | 8 |
| ATOM | 1676 | C | ASP | C | 28 | 2.057 | 59.585 | 158.972 | 1.00 | 62.04 | 6 |
| ATOM | 1677 | O | ASP | C | 28 | 0.972 | 59.318 | 159.467 | 1.00 | 62.18 | 8 |
| ATOM | 1678 | N | GLU | C | 29 | 3.028 | 58.687 | 158.818 | 1.00 | 61.72 | 7 |
| ATOM | 1679 | CA | GLU | C | 29 | 2.859 | 57.302 | 159.265 | 1.00 | 61.35 | 6 |
| ATOM | 1680 | CB | GLU | C | 29 | 4.040 | 56.414 | 158.873 | 1.00 | 61.74 | 6 |
| ATOM | 1681 | CG | GLU | C | 29 | 4.126 | 56.080 | 157.383 | 1.00 | 63.75 | 6 |
| ATOM | 1682 | CD | GLU | C | 29 | 3.125 | 55.029 | 156.933 | 1.00 | 65.79 | 6 |
| ATOM | 1683 | OE1 | GLU | C | 29 | 3.146 | 54.693 | 155.724 | 1.00 | 66.39 | 8 |
| ATOM | 1684 | OE2 | GLU | C | 29 | 2.330 | 54.547 | 157.778 | 1.00 | 66.31 | 8 |
| ATOM | 1685 | C | GLU | C | 29 | 2.690 | 57.258 | 160.763 | 1.00 | 60.50 | 6 |
| ATOM | 1686 | O | GLU | C | 29 | 1.881 | 56.492 | 161.271 | 1.00 | 60.56 | 8 |
| ATOM | 1687 | N | VAL | C | 30 | 3.460 | 58.089 | 161.462 | 1.00 | 59.42 | 7 |
| ATOM | 1688 | CA | VAL | C | 30 | 3.371 | 58.194 | 162.913 | 1.00 | 58.17 | 6 |
| ATOM | 1689 | CB | VAL | C | 30 | 4.442 | 59.179 | 163.501 | 1.00 | 58.09 | 6 |
| ATOM | 1690 | CG1 | VAL | C | 30 | 4.045 | 59.695 | 164.872 | 1.00 | 57.33 | 6 |
| ATOM | 1691 | CG2 | VAL | C | 30 | 5.827 | 58.525 | 163.546 | 1.00 | 57.29 | 6 |
| ATOM | 1692 | C | VAL | C | 30 | 1.944 | 58.582 | 163.282 | 1.00 | 57.74 | 6 |
| ATOM | 1693 | O | VAL | C | 30 | 1.274 | 57.837 | 163.991 | 1.00 | 57.46 | 8 |
| ATOM | 1694 | N | ARG | C | 31 | 1.464 | 59.708 | 162.755 | 1.00 | 57.35 | 7 |
| ATOM | 1695 | CA | ARG | C | 31 | 0.131 | 60.184 | 163.124 | 1.00 | 57.25 | 6 |
| ATOM | 1696 | CB | ARG | C | 31 | −0.098 | 61.660 | 162.782 | 1.00 | 57.15 | 6 |
| ATOM | 1697 | CG | ARG | C | 31 | −0.165 | 62.548 | 164.037 | 1.00 | 57.68 | 6 |
| ATOM | 1698 | CD | ARG | C | 31 | −0.448 | 64.000 | 163.708 | 1.00 | 57.91 | 6 |
| ATOM | 1699 | NE | ARG | C | 31 | 0.750 | 64.831 | 163.549 | 1.00 | 59.50 | 7 |
| ATOM | 1700 | CZ | ARG | C | 31 | 1.586 | 64.805 | 162.507 | 1.00 | 60.09 | 6 |
| ATOM | 1701 | NH1 | ARG | C | 31 | 1.404 | 63.960 | 161.503 | 1.00 | 60.61 | 7 |
| ATOM | 1702 | NH2 | ARG | C | 31 | 2.627 | 65.626 | 162.472 | 1.00 | 60.03 | 7 |
| ATOM | 1703 | C | ARG | C | 31 | −1.009 | 59.287 | 162.654 | 1.00 | 56.82 | 6 |
| ATOM | 1704 | O | ARG | C | 31 | −2.057 | 59.243 | 163.300 | 1.00 | 56.57 | 8 |
| ATOM | 1705 | N | ILE | C | 32 | −0.782 | 58.563 | 161.556 | 1.00 | 56.62 | 7 |
| ATOM | 1706 | CA | ILE | C | 32 | −1.696 | 57.509 | 161.084 | 1.00 | 56.34 | 6 |
| ATOM | 1707 | CB | ILE | C | 32 | −1.263 | 56.912 | 159.696 | 1.00 | 56.30 | 6 |
| ATOM | 1708 | CG1 | ILE | C | 32 | −1.784 | 57.773 | 158.537 | 1.00 | 55.84 | 6 |
| ATOM | 1709 | CD | ILE | C | 32 | −3.260 | 57.581 | 158.203 | 1.00 | 55.29 | 6 |
| ATOM | 1710 | CG2 | ILE | C | 32 | −1.709 | 55.439 | 159.534 | 1.00 | 55.88 | 6 |
| ATOM | 1711 | C | ILE | C | 32 | −1.766 | 56.394 | 162.114 | 1.00 | 56.32 | 6 |
| ATOM | 1712 | O | ILE | C | 32 | −2.838 | 55.893 | 162.428 | 1.00 | 56.45 | 8 |
| ATOM | 1713 | N | LEU | C | 33 | −0.610 | 56.015 | 162.642 | 1.00 | 56.35 | 7 |
| ATOM | 1714 | CA | LEU | C | 33 | −0.535 | 54.953 | 163.633 | 1.00 | 56.29 | 6 |
| ATOM | 1715 | CB | LEU | C | 33 | 0.906 | 54.426 | 163.731 | 1.00 | 56.21 | 6 |
| ATOM | 1716 | CG | LEU | C | 33 | 1.262 | 53.436 | 162.601 | 1.00 | 55.63 | 6 |
| ATOM | 1717 | CD1 | LEU | C | 33 | 2.609 | 53.700 | 161.948 | 1.00 | 55.89 | 6 |
| ATOM | 1718 | CD2 | LEU | C | 33 | 1.187 | 52.001 | 163.075 | 1.00 | 54.90 | 6 |
| ATOM | 1719 | C | LEU | C | 33 | −1.094 | 55.425 | 164.978 | 1.00 | 56.42 | 6 |
| ATOM | 1720 | O | LEU | C | 33 | −1.673 | 54.644 | 165.738 | 1.00 | 56.16 | 8 |
| ATOM | 1721 | N | MET | C | 34 | −0.935 | 56.719 | 165.244 | 1.00 | 56.80 | 7 |
| ATOM | 1722 | CA | MET | C | 34 | −1.564 | 57.353 | 166.391 | 1.00 | 57.23 | 6 |
| ATOM | 1723 | CB | MET | C | 34 | −1.148 | 58.823 | 166.504 | 1.00 | 57.51 | 6 |
| ATOM | 1724 | CG | MET | C | 34 | 0.330 | 59.035 | 166.799 | 1.00 | 58.59 | 6 |
| ATOM | 1725 | SD | MET | C | 34 | 0.875 | 58.571 | 168.463 | 1.00 | 61.62 | 16 |
| ATOM | 1726 | CE | MET | C | 34 | 0.026 | 57.005 | 168.760 | 1.00 | 61.15 | 6 |
| ATOM | 1727 | C | MET | C | 34 | −3.078 | 57.235 | 166.301 | 1.00 | 57.18 | 6 |
| ATOM | 1728 | O | MET | C | 34 | −3.704 | 56.781 | 167.249 | 1.00 | 57.49 | 8 |
| ATOM | 1729 | N | ALA | C | 35 | −3.658 | 57.623 | 165.162 | 1.00 | 56.93 | 7 |
| ATOM | 1730 | CA | ALA | C | 35 | −5.112 | 57.553 | 164.971 | 1.00 | 56.54 | 6 |
| ATOM | 1731 | CB | ALA | C | 35 | −5.526 | 58.186 | 163.655 | 1.00 | 56.60 | 6 |
| ATOM | 1732 | C | ALA | C | 35 | −5.677 | 56.129 | 165.093 | 1.00 | 56.34 | 6 |
| ATOM | 1733 | O | ALA | C | 35 | −6.784 | 55.951 | 165.605 | 1.00 | 56.61 | 8 |
| ATOM | 1734 | N | ASN | C | 36 | −4.916 | 55.130 | 164.633 | 1.00 | 55.85 | 7 |
| ATOM | 1735 | CA | ASN | C | 36 | −5.286 | 53.706 | 164.775 | 1.00 | 55.21 | 6 |
| ATOM | 1736 | CB | ASN | C | 36 | −4.566 | 52.822 | 163.738 | 1.00 | 55.03 | 6 |
| ATOM | 1737 | CG | ASN | C | 36 | −5.116 | 52.978 | 162.327 | 1.00 | 54.58 | 6 |
| ATOM | 1738 | OD1 | ASN | C | 36 | −6.290 | 53.287 | 162.121 | 1.00 | 54.61 | 8 |
| ATOM | 1739 | ND2 | ASN | C | 36 | −4.260 | 52.746 | 161.344 | 1.00 | 53.98 | 7 |
| ATOM | 1740 | C | ASN | C | 36 | −4.992 | 53.166 | 166.169 | 1.00 | 55.03 | 6 |
| ATOM | 1741 | O | ASN | C | 36 | −5.064 | 51.961 | 166.398 | 1.00 | 55.13 | 8 |
| ATOM | 1742 | N | GLY | C | 37 | −4.629 | 54.066 | 167.080 | 1.00 | 54.85 | 7 |
| ATOM | 1743 | CA | GLY | C | 37 | −4.318 | 53.731 | 168.472 | 1.00 | 54.31 | 6 |
| ATOM | 1744 | C | GLY | C | 37 | −3.069 | 52.912 | 168.758 | 1.00 | 53.85 | 6 |
| ATOM | 1745 | O | GLY | C | 37 | −3.061 | 52.150 | 169.717 | 1.00 | 53.84 | 8 |
| ATOM | 1746 | N | ALA | C | 38 | −2.012 | 53.056 | 167.957 | 1.00 | 53.56 | 7 |
| ATOM | 1747 | CA | ALA | C | 38 | −0.754 | 52.363 | 168.269 | 1.00 | 53.25 | 6 |

TABLE 1-continued

| | | | | | | | | | |
|---|---|---|---|---|---|---|---|---|---|
| ATOM | 1748 | CB | ALA | C | 38 | 0.274 | 52.552 | 167.173 | 1.00 | 53.22 | 6 |
| ATOM | 1749 | C | ALA | C | 38 | −0.213 | 52.844 | 169.617 | 1.00 | 52.99 | 6 |
| ATOM | 1750 | O | ALA | C | 38 | −0.430 | 53.998 | 170.006 | 1.00 | 53.06 | 8 |
| ATOM | 1751 | N | ASP | C | 39 | 0.459 | 51.952 | 170.338 | 1.00 | 52.56 | 7 |
| ATOM | 1752 | CA | ASP | C | 39 | 0.933 | 52.289 | 171.674 | 1.00 | 52.44 | 6 |
| ATOM | 1753 | CB | ASP | C | 39 | 1.229 | 51.038 | 172.504 | 1.00 | 52.59 | 6 |
| ATOM | 1754 | CG | ASP | C | 39 | 1.752 | 51.377 | 173.896 | 1.00 | 53.05 | 6 |
| ATOM | 1755 | OD1 | ASP | C | 39 | 1.594 | 52.540 | 174.345 | 1.00 | 53.09 | 8 |
| ATOM | 1756 | OD2 | ASP | C | 39 | 2.323 | 50.478 | 174.545 | 1.00 | 54.03 | 8 |
| ATOM | 1757 | C | ASP | C | 39 | 2.162 | 53.189 | 171.632 | 1.00 | 52.15 | 6 |
| ATOM | 1758 | O | ASP | C | 39 | 3.220 | 52.781 | 171.164 | 1.00 | 52.36 | 8 |
| ATOM | 1759 | N | VAL | C | 40 | 2.011 | 54.402 | 172.160 | 1.00 | 51.52 | 7 |
| ATOM | 1760 | CA | VAL | C | 40 | 3.059 | 55.413 | 172.123 | 1.00 | 50.83 | 6 |
| ATOM | 1761 | CB | VAL | C | 40 | 2.538 | 56.763 | 172.686 | 1.00 | 50.85 | 6 |
| ATOM | 1762 | CG1 | VAL | C | 40 | 2.557 | 56.769 | 174.208 | 1.00 | 50.64 | 6 |
| ATOM | 1763 | CG2 | VAL | C | 40 | 3.333 | 57.925 | 172.128 | 1.00 | 50.55 | 6 |
| ATOM | 1764 | C | VAL | C | 40 | 4.329 | 54.939 | 172.848 | 1.00 | 50.52 | 6 |
| ATOM | 1765 | O | VAL | C | 40 | 5.417 | 55.490 | 172.651 | 1.00 | 50.47 | 8 |
| ATOM | 1766 | N | ASN | C | 41 | 4.198 | 53.894 | 173.656 | 1.00 | 50.07 | 7 |
| ATOM | 1767 | CA | ASN | C | 41 | 5.341 | 53.409 | 174.415 | 1.00 | 49.98 | 6 |
| ATOM | 1768 | CB | ASN | C | 41 | 5.033 | 53.442 | 175.899 | 1.00 | 49.79 | 6 |
| ATOM | 1769 | CG | ASN | C | 41 | 4.863 | 54.828 | 176.407 | 1.00 | 49.55 | 6 |
| ATOM | 1770 | OD1 | ASN | C | 41 | 5.432 | 55.782 | 175.872 | 1.00 | 48.90 | 8 |
| ATOM | 1771 | ND2 | ASN | C | 41 | 4.065 | 54.962 | 177.452 | 1.00 | 50.65 | 7 |
| ATOM | 1772 | C | ASN | C | 41 | 5.892 | 52.037 | 174.048 | 1.00 | 50.14 | 6 |
| ATOM | 1773 | O | ASN | C | 41 | 6.725 | 51.497 | 174.773 | 1.00 | 50.29 | 8 |
| ATOM | 1774 | N | ALA | C | 42 | 5.445 | 51.465 | 172.933 | 1.00 | 50.32 | 7 |
| ATOM | 1775 | CA | ALA | C | 42 | 6.014 | 50.200 | 172.442 | 1.00 | 50.41 | 6 |
| ATOM | 1776 | CB | ALA | C | 42 | 5.638 | 49.977 | 170.966 | 1.00 | 50.21 | 6 |
| ATOM | 1777 | C | ALA | C | 42 | 7.545 | 50.147 | 172.630 | 1.00 | 50.47 | 6 |
| ATOM | 1778 | O | ALA | C | 42 | 8.247 | 51.123 | 172.333 | 1.00 | 50.77 | 8 |
| ATOM | 1779 | N | ASN | C | 43 | 8.041 | 49.022 | 173.149 | 1.00 | 50.10 | 7 |
| ATOM | 1780 | CA | ASN | C | 43 | 9.482 | 48.745 | 173.242 | 1.00 | 49.71 | 6 |
| ATOM | 1781 | CB | ASN | C | 43 | 9.781 | 47.955 | 174.519 | 1.00 | 49.84 | 6 |
| ATOM | 1782 | CG | ASN | C | 43 | 9.809 | 48.813 | 175.762 | 1.00 | 50.26 | 6 |
| ATOM | 1783 | OD1 | ASN | C | 43 | 9.439 | 49.988 | 175.754 | 1.00 | 50.77 | 8 |
| ATOM | 1784 | ND2 | ASN | C | 43 | 10.248 | 48.216 | 176.855 | 1.00 | 51.24 | 7 |
| ATOM | 1785 | C | ASN | C | 43 | 9.972 | 47.902 | 172.073 | 1.00 | 49.26 | 6 |
| ATOM | 1786 | O | ASN | C | 43 | 9.260 | 47.013 | 171.627 | 1.00 | 49.60 | 8 |
| ATOM | 1787 | N | ASP | C | 44 | 11.185 | 48.140 | 171.586 | 1.00 | 48.62 | 7 |
| ATOM | 1788 | CA | ASP | C | 44 | 11.832 | 47.114 | 170.761 | 1.00 | 48.21 | 6 |
| ATOM | 1789 | CB | ASP | C | 44 | 12.734 | 47.698 | 169.669 | 1.00 | 48.44 | 6 |
| ATOM | 1790 | CG | ASP | C | 44 | 13.835 | 48.586 | 170.212 | 1.00 | 49.72 | 6 |
| ATOM | 1791 | OD1 | ASP | C | 44 | 14.211 | 48.491 | 171.404 | 1.00 | 51.69 | 8 |
| ATOM | 1792 | OD2 | ASP | C | 44 | 14.342 | 49.393 | 169.416 | 1.00 | 51.27 | 8 |
| ATOM | 1793 | C | ASP | C | 44 | 12.579 | 46.146 | 171.678 | 1.00 | 47.54 | 6 |
| ATOM | 1794 | O | ASP | C | 44 | 12.401 | 46.196 | 172.893 | 1.00 | 47.46 | 8 |
| ATOM | 1795 | N | ARG | C | 45 | 13.411 | 45.275 | 171.106 | 1.00 | 46.84 | 7 |
| ATOM | 1796 | CA | ARG | C | 45 | 14.098 | 44.232 | 171.876 | 1.00 | 46.16 | 6 |
| ATOM | 1797 | CB | ARG | C | 45 | 14.910 | 43.307 | 170.961 | 1.00 | 45.97 | 6 |
| ATOM | 1798 | CG | ARG | C | 45 | 14.248 | 43.071 | 169.581 | 1.00 | 47.44 | 6 |
| ATOM | 1799 | CD | ARG | C | 45 | 15.153 | 42.409 | 168.501 | 1.00 | 47.20 | 6 |
| ATOM | 1800 | NE | ARG | C | 45 | 16.577 | 42.752 | 168.638 | 1.00 | 48.72 | 7 |
| ATOM | 1801 | CZ | ARG | C | 45 | 17.141 | 43.922 | 168.308 | 1.00 | 48.46 | 6 |
| ATOM | 1802 | NH1 | ARG | C | 45 | 16.420 | 44.932 | 167.804 | 1.00 | 48.74 | 7 |
| ATOM | 1803 | NH2 | ARG | C | 45 | 18.448 | 44.081 | 168.495 | 1.00 | 47.64 | 7 |
| ATOM | 1804 | C | ARG | C | 45 | 14.995 | 44.846 | 172.928 | 1.00 | 45.41 | 6 |
| ATOM | 1805 | O | ARG | C | 45 | 15.149 | 44.278 | 174.001 | 1.00 | 45.32 | 8 |
| ATOM | 1806 | N | LYS | C | 46 | 15.566 | 46.014 | 172.626 | 1.00 | 44.92 | 7 |
| ATOM | 1807 | CA | LYS | C | 46 | 16.421 | 46.746 | 173.578 | 1.00 | 44.68 | 6 |
| ATOM | 1808 | CB | LYS | C | 46 | 17.748 | 47.177 | 172.952 | 1.00 | 44.75 | 6 |
| ATOM | 1809 | CG | LYS | C | 46 | 17.631 | 47.766 | 171.562 | 1.00 | 46.50 | 6 |
| ATOM | 1810 | CD | LYS | C | 46 | 18.134 | 46.785 | 170.516 | 1.00 | 49.83 | 6 |
| ATOM | 1811 | CE | LYS | C | 46 | 19.623 | 46.473 | 170.710 | 1.00 | 50.97 | 6 |
| ATOM | 1812 | NZ | LYS | C | 46 | 20.447 | 47.715 | 170.596 | 1.00 | 52.53 | 7 |
| ATOM | 1813 | C | LYS | C | 46 | 15.758 | 47.930 | 174.281 | 1.00 | 44.08 | 6 |
| ATOM | 1814 | O | LYS | C | 46 | 16.408 | 48.874 | 174.671 | 1.00 | 44.20 | 8 |
| ATOM | 1815 | N | GLY | C | 47 | 14.458 | 47.864 | 174.468 | 1.00 | 43.74 | 7 |
| ATOM | 1816 | CA | GLY | C | 47 | 13.803 | 48.769 | 175.393 | 1.00 | 43.31 | 6 |
| ATOM | 1817 | C | GLY | C | 47 | 13.578 | 50.170 | 174.884 | 1.00 | 43.07 | 6 |
| ATOM | 1818 | O | GLY | C | 47 | 13.007 | 50.996 | 175.598 | 1.00 | 43.23 | 8 |
| ATOM | 1819 | N | ASN | C | 48 | 14.023 | 50.439 | 173.660 | 1.00 | 42.69 | 7 |
| ATOM | 1820 | CA | ASN | C | 48 | 13.699 | 51.687 | 172.973 | 1.00 | 42.51 | 6 |
| ATOM | 1821 | CB | ASN | C | 48 | 14.237 | 51.656 | 171.566 | 1.00 | 42.50 | 6 |
| ATOM | 1822 | CG | ASN | C | 48 | 15.677 | 51.917 | 171.523 | 1.00 | 44.06 | 6 |
| ATOM | 1823 | OD1 | ASN | C | 48 | 16.142 | 52.888 | 172.102 | 1.00 | 46.77 | 8 |
| ATOM | 1824 | ND2 | ASN | C | 48 | 16.420 | 51.048 | 170.861 | 1.00 | 45.28 | 7 |
| ATOM | 1825 | C | ASN | C | 48 | 12.227 | 51.894 | 172.825 | 1.00 | 42.06 | 6 |
| ATOM | 1826 | O | ASN | C | 48 | 11.511 | 50.955 | 172.527 | 1.00 | 42.35 | 8 |
| ATOM | 1827 | N | THR | C | 49 | 11.772 | 53.125 | 173.011 | 1.00 | 41.66 | 7 |

TABLE 1-continued

| | | | | | | | | | |
|---|---|---|---|---|---|---|---|---|---|
| ATOM | 1828 | CA | THR | C | 49 | 10.414 | 53.483 | 172.640 | 1.00 | 41.37 | 6 |
| ATOM | 1829 | CB | THR | C | 49 | 9.635 | 54.175 | 173.777 | 1.00 | 41.48 | 6 |
| ATOM | 1830 | OG1 | THR | C | 49 | 10.065 | 55.540 | 173.896 | 1.00 | 42.25 | 8 |
| ATOM | 1831 | CG2 | THR | C | 49 | 9.805 | 53.426 | 175.097 | 1.00 | 41.49 | 6 |
| ATOM | 1832 | C | THR | C | 49 | 10.491 | 54.419 | 171.450 | 1.00 | 41.10 | 6 |
| ATOM | 1833 | O | THR | C | 49 | 11.548 | 54.980 | 171.178 | 1.00 | 41.19 | 8 |
| ATOM | 1834 | N | PRO | C | 50 | 9.364 | 54.630 | 170.753 | 1.00 | 40.93 | 7 |
| ATOM | 1835 | CA | PRO | C | 50 | 9.374 | 55.551 | 169.619 | 1.00 | 40.59 | 6 |
| ATOM | 1836 | CB | PRO | C | 50 | 7.880 | 55.812 | 169.378 | 1.00 | 40.88 | 6 |
| ATOM | 1837 | CG | PRO | C | 50 | 7.164 | 55.255 | 170.619 | 1.00 | 40.89 | 6 |
| ATOM | 1838 | CD | PRO | C | 50 | 8.011 | 54.100 | 170.997 | 1.00 | 41.10 | 6 |
| ATOM | 1839 | C | PRO | C | 50 | 10.077 | 56.863 | 169.965 | 1.00 | 40.26 | 6 |
| ATOM | 1840 | O | PRO | C | 50 | 10.877 | 57.361 | 169.168 | 1.00 | 40.04 | 8 |
| ATOM | 1841 | N | LEU | C | 51 | 9.786 | 57.393 | 171.156 | 1.00 | 39.87 | 7 |
| ATOM | 1842 | CA | LEU | C | 51 | 10.417 | 58.623 | 171.619 | 1.00 | 39.69 | 6 |
| ATOM | 1843 | CB | LEU | C | 51 | 9.870 | 59.057 | 172.986 | 1.00 | 39.87 | 6 |
| ATOM | 1844 | CG | LEU | C | 51 | 10.407 | 60.401 | 173.504 | 1.00 | 39.23 | 6 |
| ATOM | 1845 | CD1 | LEU | C | 51 | 9.846 | 61.554 | 172.699 | 1.00 | 38.27 | 6 |
| ATOM | 1846 | CD2 | LEU | C | 51 | 10.123 | 60.589 | 174.990 | 1.00 | 39.36 | 6 |
| ATOM | 1847 | C | LEU | C | 51 | 11.944 | 58.512 | 171.630 | 1.00 | 39.60 | 6 |
| ATOM | 1848 | O | LEU | C | 51 | 12.637 | 59.418 | 171.147 | 1.00 | 39.45 | 8 |
| ATOM | 1849 | N | HIS | C | 52 | 12.463 | 57.405 | 172.154 | 1.00 | 39.46 | 7 |
| ATOM | 1850 | CA | HIS | C | 52 | 13.887 | 57.133 | 171.997 | 1.00 | 39.80 | 6 |
| ATOM | 1851 | CB | HIS | C | 52 | 14.246 | 55.715 | 172.419 | 1.00 | 39.79 | 6 |
| ATOM | 1852 | CG | HIS | C | 52 | 14.312 | 55.531 | 173.891 | 1.00 | 41.55 | 6 |
| ATOM | 1853 | ND1 | HIS | C | 52 | 13.290 | 54.955 | 174.613 | 1.00 | 43.60 | 7 |
| ATOM | 1854 | CE1 | HIS | C | 52 | 13.622 | 54.922 | 175.893 | 1.00 | 44.57 | 6 |
| ATOM | 1855 | NE2 | HIS | C | 52 | 14.819 | 55.468 | 176.028 | 1.00 | 44.57 | 7 |
| ATOM | 1856 | CD2 | HIS | C | 52 | 15.266 | 55.869 | 174.790 | 1.00 | 43.67 | 6 |
| ATOM | 1857 | C | HIS | C | 52 | 14.287 | 57.320 | 170.543 | 1.00 | 39.55 | 6 |
| ATOM | 1858 | O | HIS | C | 52 | 15.045 | 58.229 | 170.207 | 1.00 | 39.55 | 8 |
| ATOM | 1859 | N | LEU | C | 53 | 13.761 | 56.466 | 169.675 | 1.00 | 39.33 | 7 |
| ATOM | 1860 | CA | LEU | C | 53 | 14.267 | 56.414 | 168.321 | 1.00 | 39.42 | 6 |
| ATOM | 1861 | CB | LEU | C | 53 | 13.504 | 55.413 | 167.475 | 1.00 | 39.20 | 6 |
| ATOM | 1862 | CG | LEU | C | 53 | 13.756 | 53.932 | 167.676 | 1.00 | 38.67 | 6 |
| ATOM | 1863 | CD1 | LEU | C | 53 | 12.764 | 53.424 | 168.623 | 1.00 | 39.69 | 6 |
| ATOM | 1864 | CD2 | LEU | C | 53 | 13.567 | 53.218 | 166.372 | 1.00 | 39.89 | 6 |
| ATOM | 1865 | C | LEU | C | 53 | 14.174 | 57.786 | 167.696 | 1.00 | 39.86 | 6 |
| ATOM | 1866 | O | LEU | C | 53 | 15.091 | 58.214 | 166.998 | 1.00 | 40.33 | 8 |
| ATOM | 1867 | N | ALA | C | 54 | 13.068 | 58.480 | 167.963 | 1.00 | 39.99 | 7 |
| ATOM | 1868 | CA | ALA | C | 54 | 12.844 | 59.798 | 167.391 | 1.00 | 40.11 | 6 |
| ATOM | 1869 | CB | ALA | C | 54 | 11.461 | 60.273 | 167.701 | 1.00 | 40.38 | 6 |
| ATOM | 1870 | C | ALA | C | 54 | 13.884 | 60.779 | 167.916 | 1.00 | 40.33 | 6 |
| ATOM | 1871 | O | ALA | C | 54 | 14.332 | 61.665 | 167.179 | 1.00 | 40.23 | 8 |
| ATOM | 1872 | N | ALA | C | 55 | 14.269 | 60.610 | 169.187 | 1.00 | 40.49 | 7 |
| ATOM | 1873 | CA | ALA | C | 55 | 15.409 | 61.341 | 169.761 | 1.00 | 40.76 | 6 |
| ATOM | 1874 | CB | ALA | C | 55 | 15.544 | 61.055 | 171.245 | 1.00 | 40.30 | 6 |
| ATOM | 1875 | C | ALA | C | 55 | 16.695 | 60.944 | 169.027 | 1.00 | 41.05 | 6 |
| ATOM | 1876 | O | ALA | C | 55 | 17.443 | 61.797 | 168.525 | 1.00 | 41.30 | 8 |
| ATOM | 1877 | N | ASP | C | 56 | 16.923 | 59.641 | 168.938 | 1.00 | 40.97 | 7 |
| ATOM | 1878 | CA | ASP | C | 56 | 18.115 | 59.131 | 168.319 | 1.00 | 41.27 | 6 |
| ATOM | 1879 | CB | ASP | C | 56 | 18.031 | 57.617 | 168.216 | 1.00 | 41.53 | 6 |
| ATOM | 1880 | CG | ASP | C | 56 | 19.385 | 56.977 | 168.127 | 1.00 | 42.42 | 6 |
| ATOM | 1881 | OD1 | ASP | C | 56 | 19.959 | 56.818 | 167.028 | 1.00 | 42.45 | 8 |
| ATOM | 1882 | OD2 | ASP | C | 56 | 19.885 | 56.634 | 169.199 | 1.00 | 45.53 | 8 |
| ATOM | 1883 | C | ASP | C | 56 | 18.407 | 59.714 | 166.929 | 1.00 | 41.32 | 6 |
| ATOM | 1884 | O | ASP | C | 56 | 19.572 | 59.880 | 166.565 | 1.00 | 41.35 | 8 |
| ATOM | 1885 | N | TYR | C | 57 | 17.374 | 60.008 | 166.148 | 1.00 | 41.31 | 7 |
| ATOM | 1886 | CA | TYR | C | 57 | 17.594 | 60.320 | 164.751 | 1.00 | 41.75 | 6 |
| ATOM | 1887 | CB | TYR | C | 57 | 16.847 | 59.320 | 163.884 | 1.00 | 41.69 | 6 |
| ATOM | 1888 | CG | TYR | C | 57 | 17.393 | 57.915 | 163.917 | 1.00 | 41.54 | 6 |
| ATOM | 1889 | CD1 | TYR | C | 57 | 17.100 | 57.057 | 164.970 | 1.00 | 41.80 | 6 |
| ATOM | 1890 | CE1 | TYR | C | 57 | 17.587 | 55.772 | 165.001 | 1.00 | 41.87 | 6 |
| ATOM | 1891 | CZ | TYR | C | 57 | 18.370 | 55.322 | 163.959 | 1.00 | 42.37 | 6 |
| ATOM | 1892 | OH | TYR | C | 57 | 18.869 | 54.046 | 163.989 | 1.00 | 42.86 | 8 |
| ATOM | 1893 | CE2 | TYR | C | 57 | 18.665 | 56.144 | 162.897 | 1.00 | 41.95 | 6 |
| ATOM | 1894 | CD2 | TYR | C | 57 | 18.171 | 57.432 | 162.882 | 1.00 | 41.62 | 6 |
| ATOM | 1895 | C | TYR | C | 57 | 17.119 | 61.717 | 164.433 | 1.00 | 42.35 | 6 |
| ATOM | 1896 | O | TYR | C | 57 | 16.438 | 61.933 | 163.426 | 1.00 | 42.49 | 8 |
| ATOM | 1897 | N | ASP | C | 58 | 17.524 | 62.683 | 165.252 | 1.00 | 42.97 | 7 |
| ATOM | 1898 | CA | ASP | C | 58 | 16.711 | 63.901 | 165.447 | 1.00 | 43.79 | 6 |
| ATOM | 1899 | CB | ASP | C | 58 | 17.505 | 65.184 | 165.822 | 1.00 | 43.91 | 6 |
| ATOM | 1900 | CG | ASP | C | 58 | 18.422 | 65.676 | 164.743 | 1.00 | 43.35 | 6 |
| ATOM | 1901 | OD1 | ASP | C | 58 | 18.631 | 64.954 | 163.766 | 1.00 | 43.95 | 8 |
| ATOM | 1902 | OD2 | ASP | C | 58 | 18.966 | 66.792 | 164.902 | 1.00 | 42.91 | 8 |
| ATOM | 1903 | C | ASP | C | 58 | 15.562 | 64.167 | 164.470 | 1.00 | 44.21 | 6 |
| ATOM | 1904 | O | ASP | C | 58 | 15.736 | 64.651 | 163.373 | 1.00 | 43.85 | 8 |
| ATOM | 1905 | N | HIS | C | 59 | 14.377 | 63.799 | 164.923 | 1.00 | 45.34 | 7 |
| ATOM | 1906 | CA | HIS | C | 59 | 13.156 | 64.100 | 164.244 | 1.00 | 46.35 | 6 |
| ATOM | 1907 | CB | HIS | C | 59 | 12.435 | 62.809 | 163.885 | 1.00 | 46.42 | 6 |

TABLE 1-continued

| | | | | | | | | | | |
|---|---|---|---|---|---|---|---|---|---|---|
| ATOM | 1908 | CG | HIS | C | 59 | 13.191 | 61.955 | 162.915 | 1.00 | 47.08 | 6 |
| ATOM | 1909 | ND1 | HIS | C | 59 | 13.490 | 62.370 | 161.634 | 1.00 | 47.74 | 7 |
| ATOM | 1910 | CE1 | HIS | C | 59 | 14.156 | 61.415 | 161.012 | 1.00 | 47.94 | 6 |
| ATOM | 1911 | NE2 | HIS | C | 59 | 14.297 | 60.395 | 161.840 | 1.00 | 47.52 | 7 |
| ATOM | 1912 | CD2 | HIS | C | 59 | 13.702 | 60.707 | 163.036 | 1.00 | 47.53 | 6 |
| ATOM | 1913 | C | HIS | C | 59 | 12.350 | 64.948 | 165.201 | 1.00 | 46.86 | 6 |
| ATOM | 1914 | O | HIS | C | 59 | 11.447 | 64.464 | 165.867 | 1.00 | 47.16 | 8 |
| ATOM | 1915 | N | LEU | C | 60 | 12.711 | 66.221 | 165.269 | 1.00 | 47.53 | 7 |
| ATOM | 1916 | CA | LEU | C | 60 | 12.121 | 67.163 | 166.206 | 1.00 | 48.37 | 6 |
| ATOM | 1917 | CB | LEU | C | 60 | 12.542 | 68.582 | 165.803 | 1.00 | 48.14 | 6 |
| ATOM | 1918 | CG | LEU | C | 60 | 12.455 | 69.824 | 166.697 | 1.00 | 47.18 | 6 |
| ATOM | 1919 | CD1 | LEU | C | 60 | 11.120 | 69.957 | 167.439 | 1.00 | 47.43 | 6 |
| ATOM | 1920 | CD2 | LEU | C | 60 | 13.598 | 69.867 | 167.669 | 1.00 | 46.68 | 6 |
| ATOM | 1921 | C | LEU | C | 60 | 10.588 | 67.061 | 166.273 | 1.00 | 49.28 | 6 |
| ATOM | 1922 | O | LEU | C | 60 | 10.006 | 66.900 | 167.346 | 1.00 | 49.51 | 8 |
| ATOM | 1923 | N | GLU | C | 61 | 9.943 | 67.163 | 165.122 | 1.00 | 50.22 | 7 |
| ATOM | 1924 | CA | GLU | C | 61 | 8.487 | 67.168 | 165.047 | 1.00 | 51.57 | 6 |
| ATOM | 1925 | CB | GLU | C | 61 | 8.009 | 67.441 | 163.600 | 1.00 | 52.19 | 6 |
| ATOM | 1926 | CG | GLU | C | 61 | 8.695 | 66.590 | 162.476 | 1.00 | 56.17 | 6 |
| ATOM | 1927 | CD | GLU | C | 61 | 10.241 | 66.686 | 162.433 | 1.00 | 60.23 | 6 |
| ATOM | 1928 | OE1 | GLU | C | 61 | 10.920 | 65.656 | 162.655 | 1.00 | 61.20 | 8 |
| ATOM | 1929 | OE2 | GLU | C | 61 | 10.775 | 67.787 | 162.176 | 1.00 | 61.91 | 8 |
| ATOM | 1930 | C | GLU | C | 61 | 7.906 | 65.874 | 165.619 | 1.00 | 51.11 | 6 |
| ATOM | 1931 | O | GLU | C | 61 | 7.076 | 65.913 | 166.533 | 1.00 | 51.38 | 8 |
| ATOM | 1932 | N | ILE | C | 62 | 8.377 | 64.741 | 165.104 | 1.00 | 50.55 | 7 |
| ATOM | 1933 | CA | ILE | C | 62 | 7.938 | 63.430 | 165.563 | 1.00 | 50.11 | 6 |
| ATOM | 1934 | CB | ILE | C | 62 | 8.709 | 62.290 | 164.837 | 1.00 | 50.17 | 6 |
| ATOM | 1935 | CG1 | ILE | C | 62 | 8.206 | 62.175 | 163.394 | 1.00 | 50.18 | 6 |
| ATOM | 1936 | CD | ILE | C | 62 | 9.263 | 61.858 | 162.399 | 1.00 | 49.48 | 6 |
| ATOM | 1937 | CG2 | ILE | C | 62 | 8.540 | 60.943 | 165.537 | 1.00 | 49.42 | 6 |
| ATOM | 1938 | C | ILE | C | 62 | 8.036 | 63.347 | 167.080 | 1.00 | 50.05 | 6 |
| ATOM | 1939 | O | ILE | C | 62 | 7.117 | 62.864 | 167.725 | 1.00 | 50.34 | 8 |
| ATOM | 1940 | N | VAL | C | 63 | 9.125 | 63.863 | 167.643 | 1.00 | 49.92 | 7 |
| ATOM | 1941 | CA | VAL | C | 63 | 9.305 | 63.931 | 169.095 | 1.00 | 49.85 | 6 |
| ATOM | 1942 | CB | VAL | C | 63 | 10.677 | 64.575 | 169.468 | 1.00 | 49.52 | 6 |
| ATOM | 1943 | CG1 | VAL | C | 63 | 10.713 | 65.024 | 170.909 | 1.00 | 49.03 | 6 |
| ATOM | 1944 | CG2 | VAL | C | 63 | 11.786 | 63.608 | 169.208 | 1.00 | 48.80 | 6 |
| ATOM | 1945 | C | VAL | C | 63 | 8.119 | 64.671 | 169.743 | 1.00 | 50.52 | 6 |
| ATOM | 1946 | O | VAL | C | 63 | 7.530 | 64.189 | 170.723 | 1.00 | 50.37 | 8 |
| ATOM | 1947 | N | GLU | C | 64 | 7.752 | 65.816 | 169.171 | 1.00 | 51.25 | 7 |
| ATOM | 1948 | CA | GLU | C | 64 | 6.645 | 66.602 | 169.701 | 1.00 | 52.42 | 6 |
| ATOM | 1949 | CB | GLU | C | 64 | 6.544 | 67.935 | 168.975 | 1.00 | 52.78 | 6 |
| ATOM | 1950 | CG | GLU | C | 64 | 7.551 | 68.957 | 169.447 | 1.00 | 55.48 | 6 |
| ATOM | 1951 | CD | GLU | C | 64 | 7.202 | 70.364 | 168.980 | 1.00 | 59.27 | 6 |
| ATOM | 1952 | OE1 | GLU | C | 64 | 7.506 | 70.711 | 167.809 | 1.00 | 60.55 | 8 |
| ATOM | 1953 | OE2 | GLU | C | 64 | 6.625 | 71.126 | 169.791 | 1.00 | 60.61 | 8 |
| ATOM | 1954 | C | GLU | C | 64 | 5.315 | 65.857 | 169.614 | 1.00 | 52.49 | 6 |
| ATOM | 1955 | O | GLU | C | 64 | 4.544 | 65.821 | 170.581 | 1.00 | 52.52 | 8 |
| ATOM | 1956 | N | VAL | C | 65 | 5.064 | 65.264 | 168.448 | 1.00 | 52.51 | 7 |
| ATOM | 1957 | CA | VAL | C | 65 | 3.887 | 64.431 | 168.204 | 1.00 | 52.43 | 6 |
| ATOM | 1958 | CB | VAL | C | 65 | 3.974 | 63.766 | 166.814 | 1.00 | 52.30 | 6 |
| ATOM | 1959 | CG1 | VAL | C | 65 | 2.683 | 63.040 | 166.475 | 1.00 | 52.45 | 6 |
| ATOM | 1960 | CG2 | VAL | C | 65 | 4.292 | 64.798 | 165.760 | 1.00 | 52.20 | 6 |
| ATOM | 1961 | C | VAL | C | 65 | 3.739 | 63.333 | 169.256 | 1.00 | 52.50 | 6 |
| ATOM | 1962 | O | VAL | C | 65 | 2.639 | 63.079 | 169.753 | 1.00 | 52.43 | 8 |
| ATOM | 1963 | N | LEU | C | 66 | 4.858 | 62.688 | 169.577 | 1.00 | 52.62 | 7 |
| ATOM | 1964 | CA | LEU | C | 66 | 4.887 | 61.605 | 170.549 | 1.00 | 53.09 | 6 |
| ATOM | 1965 | CB | LEU | C | 66 | 6.240 | 60.897 | 170.535 | 1.00 | 53.01 | 6 |
| ATOM | 1966 | CG | LEU | C | 66 | 6.584 | 60.033 | 169.313 | 1.00 | 53.28 | 6 |
| ATOM | 1967 | CD1 | LEU | C | 66 | 8.042 | 59.561 | 169.363 | 1.00 | 53.18 | 6 |
| ATOM | 1968 | CD2 | LEU | C | 66 | 5.627 | 58.853 | 169.152 | 1.00 | 52.89 | 6 |
| ATOM | 1969 | C | LEU | C | 66 | 4.584 | 62.101 | 171.956 | 1.00 | 53.60 | 6 |
| ATOM | 1970 | O | LEU | C | 66 | 3.863 | 61.442 | 172.722 | 1.00 | 53.72 | 8 |
| ATOM | 1971 | N | LEU | C | 67 | 5.136 | 63.264 | 172.291 | 1.00 | 53.88 | 7 |
| ATOM | 1972 | CA | LEU | C | 67 | 4.866 | 63.898 | 173.573 | 1.00 | 53.90 | 6 |
| ATOM | 1973 | CB | LEU | C | 67 | 5.821 | 65.058 | 173.784 | 1.00 | 53.68 | 6 |
| ATOM | 1974 | CG | LEU | C | 67 | 7.252 | 64.554 | 173.916 | 1.00 | 53.65 | 6 |
| ATOM | 1975 | CD1 | LEU | C | 67 | 8.249 | 65.684 | 173.740 | 1.00 | 54.14 | 6 |
| ATOM | 1976 | CD2 | LEU | C | 67 | 7.444 | 63.849 | 175.248 | 1.00 | 53.33 | 6 |
| ATOM | 1977 | C | LEU | C | 67 | 3.414 | 64.361 | 173.681 | 1.00 | 53.98 | 6 |
| ATOM | 1978 | O | LEU | C | 67 | 2.801 | 64.239 | 174.740 | 1.00 | 54.09 | 8 |
| ATOM | 1979 | N | LYS | C | 68 | 2.866 | 64.875 | 172.583 | 1.00 | 53.92 | 7 |
| ATOM | 1980 | CA | LYS | C | 68 | 1.463 | 65.256 | 172.543 | 1.00 | 53.97 | 6 |
| ATOM | 1981 | CB | LYS | C | 68 | 1.088 | 65.955 | 171.232 | 1.00 | 54.03 | 6 |
| ATOM | 1982 | CG | LYS | C | 68 | 1.240 | 67.471 | 171.258 | 1.00 | 54.50 | 6 |
| ATOM | 1983 | CD | LYS | C | 68 | 0.865 | 68.082 | 169.910 | 1.00 | 54.47 | 6 |
| ATOM | 1984 | CE | LYS | C | 68 | 1.161 | 69.584 | 169.846 | 1.00 | 55.14 | 6 |
| ATOM | 1985 | NZ | LYS | C | 68 | 2.534 | 69.914 | 169.359 | 1.00 | 54.89 | 7 |
| ATOM | 1986 | C | LYS | C | 68 | 0.569 | 64.052 | 172.756 | 1.00 | 53.51 | 6 |
| ATOM | 1987 | O | LYS | C | 68 | −0.495 | 64.194 | 173.321 | 1.00 | 53.64 | 8 |

TABLE 1-continued

| | | | | | | | | | |
|---|---|---|---|---|---|---|---|---|---|
| ATOM | 1988 | N | HIS | C | 69 | 0.990 | 62.871 | 172.312 | 1.00 | 53.14 | 7 |
| ATOM | 1989 | CA | HIS | C | 69 | 0.193 | 61.652 | 172.502 | 1.00 | 52.98 | 6 |
| ATOM | 1990 | CB | HIS | C | 69 | 0.344 | 60.706 | 171.301 | 1.00 | 52.96 | 6 |
| ATOM | 1991 | CG | HIS | C | 69 | −0.534 | 61.052 | 170.133 | 1.00 | 53.77 | 6 |
| ATOM | 1992 | ND1 | HIS | C | 69 | −1.806 | 60.537 | 169.976 | 1.00 | 54.15 | 7 |
| ATOM | 1993 | CE1 | HIS | C | 69 | −2.341 | 61.012 | 168.864 | 1.00 | 53.78 | 6 |
| ATOM | 1994 | NE2 | HIS | C | 69 | −1.457 | 61.804 | 168.284 | 1.00 | 54.43 | 7 |
| ATOM | 1995 | CD2 | HIS | C | 69 | −0.316 | 61.843 | 169.054 | 1.00 | 54.46 | 6 |
| ATOM | 1996 | C | HIS | C | 69 | 0.543 | 60.940 | 173.821 | 1.00 | 52.86 | 6 |
| ATOM | 1997 | O | HIS | C | 69 | 0.061 | 59.835 | 174.103 | 1.00 | 52.83 | 8 |
| ATOM | 1998 | N | GLY | C | 70 | 1.389 | 61.587 | 174.618 | 1.00 | 52.62 | 7 |
| ATOM | 1999 | CA | GLY | C | 70 | 1.705 | 61.132 | 175.960 | 1.00 | 52.17 | 6 |
| ATOM | 2000 | C | GLY | C | 70 | 2.706 | 60.000 | 176.022 | 1.00 | 52.07 | 6 |
| ATOM | 2001 | O | GLY | C | 70 | 2.515 | 59.064 | 176.796 | 1.00 | 52.16 | 8 |
| ATOM | 2002 | N | ALA | C | 71 | 3.768 | 60.070 | 175.214 | 1.00 | 51.85 | 7 |
| ATOM | 2003 | CA | ALA | C | 71 | 4.919 | 59.175 | 175.378 | 1.00 | 51.40 | 6 |
| ATOM | 2004 | CB | ALA | C | 71 | 5.917 | 59.372 | 174.254 | 1.00 | 51.45 | 6 |
| ATOM | 2005 | C | ALA | C | 71 | 5.577 | 59.476 | 176.716 | 1.00 | 51.14 | 6 |
| ATOM | 2006 | O | ALA | C | 71 | 5.672 | 60.639 | 177.103 | 1.00 | 51.39 | 8 |
| ATOM | 2007 | N | ASP | C | 72 | 6.008 | 58.436 | 177.428 | 1.00 | 50.69 | 7 |
| ATOM | 2008 | CA | ASP | C | 72 | 6.809 | 58.612 | 178.652 | 1.00 | 50.23 | 6 |
| ATOM | 2009 | CB | ASP | C | 72 | 7.092 | 57.264 | 179.335 | 1.00 | 50.46 | 6 |
| ATOM | 2010 | CG | ASP | C | 72 | 7.960 | 57.394 | 180.593 | 1.00 | 51.08 | 6 |
| ATOM | 2011 | OD1 | ASP | C | 72 | 7.967 | 58.462 | 181.256 | 1.00 | 51.83 | 8 |
| ATOM | 2012 | OD2 | ASP | C | 72 | 8.626 | 56.393 | 180.932 | 1.00 | 52.53 | 8 |
| ATOM | 2013 | C | ASP | C | 72 | 8.120 | 59.284 | 178.289 | 1.00 | 49.60 | 6 |
| ATOM | 2014 | O | ASP | C | 72 | 8.918 | 58.726 | 177.537 | 1.00 | 49.62 | 8 |
| ATOM | 2015 | N | VAL | C | 73 | 8.325 | 60.484 | 178.820 | 1.00 | 48.85 | 7 |
| ATOM | 2016 | CA | VAL | C | 73 | 9.497 | 61.290 | 178.504 | 1.00 | 48.29 | 6 |
| ATOM | 2017 | CB | VAL | C | 73 | 9.284 | 62.768 | 178.932 | 1.00 | 48.25 | 6 |
| ATOM | 2018 | CG1 | VAL | C | 73 | 8.763 | 62.854 | 180.348 | 1.00 | 48.02 | 6 |
| ATOM | 2019 | CG2 | VAL | C | 73 | 10.551 | 63.580 | 178.783 | 1.00 | 47.81 | 6 |
| ATOM | 2020 | C | VAL | C | 73 | 10.769 | 60.708 | 179.117 | 1.00 | 48.13 | 6 |
| ATOM | 2021 | O | VAL | C | 73 | 11.842 | 60.843 | 178.562 | 1.00 | 48.26 | 8 |
| ATOM | 2022 | N | ASN | C | 74 | 10.639 | 60.041 | 180.250 | 1.00 | 47.86 | 7 |
| ATOM | 2023 | CA | ASN | C | 74 | 11.794 | 59.533 | 180.950 | 1.00 | 47.63 | 6 |
| ATOM | 2024 | CB | ASN | C | 74 | 11.687 | 59.891 | 182.428 | 1.00 | 47.90 | 6 |
| ATOM | 2025 | CG | ASN | C | 74 | 11.536 | 61.366 | 182.652 | 1.00 | 47.99 | 6 |
| ATOM | 2026 | OD1 | ASN | C | 74 | 12.484 | 62.137 | 182.466 | 1.00 | 48.86 | 8 |
| ATOM | 2027 | ND2 | ASN | C | 74 | 10.341 | 61.776 | 183.054 | 1.00 | 47.63 | 7 |
| ATOM | 2028 | C | ASN | C | 74 | 11.935 | 58.034 | 180.799 | 1.00 | 47.36 | 6 |
| ATOM | 2029 | O | ASN | C | 74 | 12.514 | 57.367 | 181.656 | 1.00 | 47.46 | 8 |
| ATOM | 2030 | N | ALA | C | 75 | 11.398 | 57.487 | 179.723 | 1.00 | 46.92 | 7 |
| ATOM | 2031 | CA | ALA | C | 75 | 11.521 | 56.056 | 179.515 | 1.00 | 46.93 | 6 |
| ATOM | 2032 | CB | ALA | C | 75 | 10.782 | 55.633 | 178.265 | 1.00 | 46.96 | 6 |
| ATOM | 2033 | C | ALA | C | 75 | 13.011 | 55.686 | 179.434 | 1.00 | 47.10 | 6 |
| ATOM | 2034 | O | ALA | C | 75 | 13.784 | 56.348 | 178.737 | 1.00 | 47.54 | 8 |
| ATOM | 2035 | N | HIS | C | 76 | 13.428 | 54.670 | 180.182 | 1.00 | 46.78 | 7 |
| ATOM | 2036 | CA | HIS | C | 76 | 14.778 | 54.157 | 180.049 | 1.00 | 46.55 | 6 |
| ATOM | 2037 | CB | HIS | C | 76 | 15.323 | 53.684 | 181.393 | 1.00 | 47.13 | 6 |
| ATOM | 2038 | CG | HIS | C | 76 | 15.153 | 54.671 | 182.521 | 1.00 | 50.18 | 6 |
| ATOM | 2039 | ND1 | HIS | C | 76 | 16.207 | 55.395 | 183.051 | 1.00 | 52.42 | 7 |
| ATOM | 2040 | CE1 | HIS | C | 76 | 15.769 | 56.154 | 184.043 | 1.00 | 51.73 | 6 |
| ATOM | 2041 | NE2 | HIS | C | 76 | 14.471 | 55.947 | 184.183 | 1.00 | 52.15 | 7 |
| ATOM | 2042 | CD2 | HIS | C | 76 | 14.063 | 55.014 | 183.255 | 1.00 | 51.95 | 6 |
| ATOM | 2043 | C | HIS | C | 76 | 14.728 | 52.997 | 179.061 | 1.00 | 46.10 | 6 |
| ATOM | 2044 | O | HIS | C | 76 | 13.739 | 52.266 | 178.994 | 1.00 | 45.88 | 8 |
| ATOM | 2045 | N | ASP | C | 77 | 15.778 | 52.838 | 178.265 | 1.00 | 45.73 | 7 |
| ATOM | 2046 | CA | ASP | C | 77 | 15.915 | 51.638 | 177.448 | 1.00 | 45.27 | 6 |
| ATOM | 2047 | CB | ASP | C | 77 | 16.885 | 51.884 | 176.299 | 1.00 | 45.75 | 6 |
| ATOM | 2048 | CG | ASP | C | 77 | 18.305 | 52.212 | 176.782 | 1.00 | 48.00 | 6 |
| ATOM | 2049 | OD1 | ASP | C | 77 | 18.547 | 52.181 | 178.006 | 1.00 | 49.64 | 8 |
| ATOM | 2050 | OD2 | ASP | C | 77 | 19.187 | 52.499 | 175.936 | 1.00 | 51.11 | 8 |
| ATOM | 2051 | C | ASP | C | 77 | 16.426 | 50.560 | 178.392 | 1.00 | 44.35 | 6 |
| ATOM | 2052 | O | ASP | C | 77 | 16.435 | 50.769 | 179.600 | 1.00 | 43.90 | 8 |
| ATOM | 2053 | N | ASN | C | 78 | 16.880 | 49.432 | 177.852 | 1.00 | 43.82 | 7 |
| ATOM | 2054 | CA | ASN | C | 78 | 17.356 | 48.320 | 178.684 | 1.00 | 43.36 | 6 |
| ATOM | 2055 | CB | ASN | C | 78 | 17.477 | 47.028 | 177.872 | 1.00 | 43.33 | 6 |
| ATOM | 2056 | CG | ASN | C | 78 | 16.122 | 46.486 | 177.390 | 1.00 | 45.05 | 6 |
| ATOM | 2057 | OD1 | ASN | C | 78 | 15.049 | 46.672 | 178.005 | 1.00 | 45.62 | 8 |
| ATOM | 2058 | ND2 | ASN | C | 78 | 16.181 | 45.775 | 176.285 | 1.00 | 47.40 | 7 |
| ATOM | 2059 | C | ASN | C | 78 | 18.677 | 48.590 | 179.377 | 1.00 | 42.53 | 6 |
| ATOM | 2060 | O | ASN | C | 78 | 19.008 | 47.940 | 180.357 | 1.00 | 42.61 | 8 |
| ATOM | 2061 | N | ASP | C | 79 | 19.434 | 49.540 | 178.850 | 1.00 | 41.94 | 7 |
| ATOM | 2062 | CA | ASP | C | 79 | 20.707 | 49.933 | 179.436 | 1.00 | 41.54 | 6 |
| ATOM | 2063 | CB | ASP | C | 79 | 21.695 | 50.269 | 178.339 | 1.00 | 41.73 | 6 |
| ATOM | 2064 | CG | ASP | C | 79 | 22.573 | 49.110 | 177.989 | 1.00 | 43.28 | 6 |
| ATOM | 2065 | OD1 | ASP | C | 79 | 22.293 | 47.957 | 178.428 | 1.00 | 43.10 | 8 |
| ATOM | 2066 | OD2 | ASP | C | 79 | 23.559 | 49.362 | 177.267 | 1.00 | 45.59 | 8 |
| ATOM | 2067 | C | ASP | C | 79 | 20.553 | 51.147 | 180.307 | 1.00 | 41.06 | 6 |

TABLE 1-continued

| | | | | | | | | | | |
|---|---|---|---|---|---|---|---|---|---|---|
| ATOM | 2068 | O | ASP | C | 79 | 21.523 | 51.663 | 180.842 | 1.00 | 41.01 | 8 |
| ATOM | 2069 | N | GLY | C | 80 | 19.325 | 51.637 | 180.406 | 1.00 | 40.69 | 7 |
| ATOM | 2070 | CA | GLY | C | 80 | 19.030 | 52.793 | 181.239 | 1.00 | 39.86 | 6 |
| ATOM | 2071 | C | GLY | C | 80 | 19.076 | 54.170 | 180.603 | 1.00 | 39.22 | 6 |
| ATOM | 2072 | O | GLY | C | 80 | 18.754 | 55.141 | 181.274 | 1.00 | 39.39 | 8 |
| ATOM | 2073 | N | SER | C | 81 | 19.467 | 54.276 | 179.332 | 1.00 | 38.75 | 7 |
| ATOM | 2074 | CA | SER | C | 81 | 19.492 | 55.579 | 178.646 | 1.00 | 38.28 | 6 |
| ATOM | 2075 | CB | SER | C | 81 | 20.259 | 55.510 | 177.323 | 1.00 | 37.96 | 6 |
| ATOM | 2076 | OG | SER | C | 81 | 21.379 | 54.637 | 177.408 | 1.00 | 38.47 | 8 |
| ATOM | 2077 | C | SER | C | 81 | 18.069 | 56.060 | 178.392 | 1.00 | 38.05 | 6 |
| ATOM | 2078 | O | SER | C | 81 | 17.218 | 55.303 | 177.896 | 1.00 | 37.96 | 8 |
| ATOM | 2079 | N | THR | C | 82 | 17.797 | 57.310 | 178.755 | 1.00 | 37.83 | 7 |
| ATOM | 2080 | CA | THR | C | 82 | 16.532 | 57.960 | 178.383 | 1.00 | 37.48 | 6 |
| ATOM | 2081 | CB | THR | C | 82 | 16.167 | 58.998 | 179.386 | 1.00 | 37.32 | 6 |
| ATOM | 2082 | OG1 | THR | C | 82 | 17.237 | 59.947 | 179.439 | 1.00 | 37.28 | 8 |
| ATOM | 2083 | CG2 | THR | C | 82 | 15.924 | 58.368 | 180.752 | 1.00 | 36.78 | 6 |
| ATOM | 2084 | C | THR | C | 82 | 16.705 | 58.704 | 177.070 | 1.00 | 37.70 | 6 |
| ATOM | 2085 | O | THR | C | 82 | 17.828 | 58.966 | 176.654 | 1.00 | 38.11 | 8 |
| ATOM | 2086 | N | PRO | C | 83 | 15.609 | 59.070 | 176.405 | 1.00 | 37.69 | 7 |
| ATOM | 2087 | CA | PRO | C | 83 | 15.815 | 59.867 | 175.195 | 1.00 | 37.86 | 6 |
| ATOM | 2088 | CB | PRO | C | 83 | 14.396 | 60.275 | 174.814 | 1.00 | 37.73 | 6 |
| ATOM | 2089 | CG | PRO | C | 83 | 13.573 | 59.153 | 175.293 | 1.00 | 37.94 | 6 |
| ATOM | 2090 | CD | PRO | C | 83 | 14.184 | 58.798 | 176.628 | 1.00 | 37.75 | 6 |
| ATOM | 2091 | C | PRO | C | 83 | 16.742 | 61.100 | 175.403 | 1.00 | 37.90 | 6 |
| ATOM | 2092 | O | PRO | C | 83 | 17.591 | 61.400 | 174.535 | 1.00 | 37.89 | 8 |
| ATOM | 2093 | N | LEU | C | 84 | 16.620 | 61.778 | 176.542 | 1.00 | 37.60 | 7 |
| ATOM | 2094 | CA | LEU | C | 84 | 17.541 | 62.866 | 176.845 | 1.00 | 37.49 | 6 |
| ATOM | 2095 | CB | LEU | C | 84 | 17.316 | 63.433 | 178.247 | 1.00 | 37.61 | 6 |
| ATOM | 2096 | CG | LEU | C | 84 | 17.897 | 64.826 | 178.492 | 1.00 | 37.02 | 6 |
| ATOM | 2097 | CD1 | LEU | C | 84 | 17.428 | 65.798 | 177.435 | 1.00 | 35.89 | 6 |
| ATOM | 2098 | CD2 | LEU | C | 84 | 17.490 | 65.309 | 179.872 | 1.00 | 38.20 | 6 |
| ATOM | 2099 | C | LEU | C | 84 | 18.998 | 62.448 | 176.661 | 1.00 | 37.56 | 6 |
| ATOM | 2100 | O | LEU | C | 84 | 19.745 | 63.154 | 175.963 | 1.00 | 37.67 | 8 |
| ATOM | 2101 | N | HIS | C | 85 | 19.395 | 61.312 | 177.254 | 1.00 | 37.28 | 7 |
| ATOM | 2102 | CA | HIS | C | 85 | 20.743 | 60.755 | 177.008 | 1.00 | 37.48 | 6 |
| ATOM | 2103 | CB | HIS | C | 85 | 20.898 | 59.343 | 177.594 | 1.00 | 38.12 | 6 |
| ATOM | 2104 | CG | HIS | C | 85 | 20.914 | 59.315 | 179.085 | 1.00 | 40.16 | 6 |
| ATOM | 2105 | ND1 | HIS | C | 85 | 19.791 | 59.568 | 179.843 | 1.00 | 42.29 | 7 |
| ATOM | 2106 | CE1 | HIS | C | 85 | 20.105 | 59.492 | 181.125 | 1.00 | 43.32 | 6 |
| ATOM | 2107 | NE2 | HIS | C | 85 | 21.388 | 59.191 | 181.225 | 1.00 | 43.15 | 7 |
| ATOM | 2108 | CD2 | HIS | C | 85 | 21.918 | 59.078 | 179.962 | 1.00 | 41.88 | 6 |
| ATOM | 2109 | C | HIS | C | 85 | 21.083 | 60.728 | 175.517 | 1.00 | 36.69 | 6 |
| ATOM | 2110 | O | HIS | C | 85 | 22.068 | 61.328 | 175.083 | 1.00 | 35.87 | 8 |
| ATOM | 2111 | N | LEU | C | 86 | 20.247 | 60.053 | 174.737 | 1.00 | 36.44 | 7 |
| ATOM | 2112 | CA | LEU | C | 86 | 20.531 | 59.913 | 173.332 | 1.00 | 36.66 | 6 |
| ATOM | 2113 | CB | LEU | C | 86 | 19.449 | 59.138 | 172.587 | 1.00 | 36.73 | 6 |
| ATOM | 2114 | CG | LEU | C | 86 | 19.408 | 57.605 | 172.678 | 1.00 | 36.84 | 6 |
| ATOM | 2115 | CD1 | LEU | C | 86 | 20.722 | 57.006 | 173.202 | 1.00 | 36.68 | 6 |
| ATOM | 2116 | CD2 | LEU | C | 86 | 18.274 | 57.188 | 173.578 | 1.00 | 37.43 | 6 |
| ATOM | 2117 | C | LEU | C | 86 | 20.722 | 61.262 | 172.696 | 1.00 | 36.94 | 6 |
| ATOM | 2118 | O | LEU | C | 86 | 21.746 | 61.502 | 172.047 | 1.00 | 37.14 | 8 |
| ATOM | 2119 | N | ALA | C | 87 | 19.752 | 62.152 | 172.894 | 1.00 | 37.20 | 7 |
| ATOM | 2120 | CA | ALA | C | 87 | 19.821 | 63.482 | 172.288 | 1.00 | 37.51 | 6 |
| ATOM | 2121 | CB | ALA | C | 87 | 18.668 | 64.344 | 172.745 | 1.00 | 37.76 | 6 |
| ATOM | 2122 | C | ALA | C | 87 | 21.150 | 64.126 | 172.643 | 1.00 | 37.57 | 6 |
| ATOM | 2123 | O | ALA | C | 87 | 21.850 | 64.636 | 171.760 | 1.00 | 37.43 | 8 |
| ATOM | 2124 | N | ALA | C | 88 | 21.498 | 64.051 | 173.933 | 1.00 | 37.46 | 7 |
| ATOM | 2125 | CA | ALA | C | 88 | 22.762 | 64.571 | 174.438 | 1.00 | 37.43 | 6 |
| ATOM | 2126 | CB | ALA | C | 88 | 22.902 | 64.283 | 175.905 | 1.00 | 37.42 | 6 |
| ATOM | 2127 | C | ALA | C | 88 | 23.946 | 63.995 | 173.674 | 1.00 | 37.29 | 6 |
| ATOM | 2128 | O | ALA | C | 88 | 24.728 | 64.750 | 173.093 | 1.00 | 37.65 | 8 |
| ATOM | 2129 | N | LEU | C | 89 | 24.066 | 62.671 | 173.656 | 1.00 | 36.76 | 7 |
| ATOM | 2130 | CA | LEU | C | 89 | 25.218 | 62.039 | 173.050 | 1.00 | 36.55 | 6 |
| ATOM | 2131 | CB | LEU | C | 89 | 25.140 | 60.541 | 173.229 | 1.00 | 36.40 | 6 |
| ATOM | 2132 | CG | LEU | C | 89 | 25.989 | 59.583 | 172.405 | 1.00 | 36.40 | 6 |
| ATOM | 2133 | CD1 | LEU | C | 89 | 27.454 | 59.833 | 172.643 | 1.00 | 36.83 | 6 |
| ATOM | 2134 | CD2 | LEU | C | 89 | 25.633 | 58.144 | 172.761 | 1.00 | 36.12 | 6 |
| ATOM | 2135 | C | LEU | C | 89 | 25.373 | 62.418 | 171.586 | 1.00 | 37.28 | 6 |
| ATOM | 2136 | O | LEU | C | 89 | 26.504 | 62.574 | 171.114 | 1.00 | 37.43 | 8 |
| ATOM | 2137 | N | PHE | C | 90 | 24.264 | 62.596 | 170.864 | 1.00 | 37.79 | 7 |
| ATOM | 2138 | CA | PHE | C | 90 | 24.385 | 62.963 | 169.444 | 1.00 | 38.27 | 6 |
| ATOM | 2139 | CB | PHE | C | 90 | 23.380 | 62.250 | 168.538 | 1.00 | 38.44 | 6 |
| ATOM | 2140 | CG | PHE | C | 90 | 23.384 | 60.765 | 168.677 | 1.00 | 39.28 | 6 |
| ATOM | 2141 | CD1 | PHE | C | 90 | 22.235 | 60.096 | 169.066 | 1.00 | 39.62 | 6 |
| ATOM | 2142 | CE1 | PHE | C | 90 | 22.227 | 58.726 | 169.210 | 1.00 | 38.96 | 6 |
| ATOM | 2143 | CZ | PHE | C | 90 | 23.369 | 58.008 | 168.974 | 1.00 | 38.72 | 6 |
| ATOM | 2144 | CE2 | PHE | C | 90 | 24.534 | 58.667 | 168.598 | 1.00 | 39.29 | 6 |
| ATOM | 2145 | CD2 | PHE | C | 90 | 24.538 | 60.035 | 168.453 | 1.00 | 39.56 | 6 |
| ATOM | 2146 | C | PHE | C | 90 | 24.282 | 64.438 | 169.185 | 1.00 | 38.58 | 6 |
| ATOM | 2147 | O | PHE | C | 90 | 24.317 | 64.843 | 168.026 | 1.00 | 39.24 | 8 |

TABLE 1-continued

| ATOM | 2148 | N | GLY | C | 91 | 24.138 | 65.241 | 170.232 | 1.00 | 38.69 | 7 |
|---|---|---|---|---|---|---|---|---|---|---|---|
| ATOM | 2149 | CA | GLY | C | 91 | 24.145 | 66.697 | 170.075 | 1.00 | 39.30 | 6 |
| ATOM | 2150 | C | GLY | C | 91 | 22.935 | 67.331 | 169.402 | 1.00 | 39.82 | 6 |
| ATOM | 2151 | O | GLY | C | 91 | 23.028 | 68.406 | 168.813 | 1.00 | 39.43 | 8 |
| ATOM | 2152 | N | HIS | C | 92 | 21.796 | 66.666 | 169.514 | 1.00 | 40.82 | 7 |
| ATOM | 2153 | CA | HIS | C | 92 | 20.544 | 67.177 | 168.996 | 1.00 | 42.02 | 6 |
| ATOM | 2154 | CB | HIS | C | 92 | 19.609 | 66.011 | 168.746 | 1.00 | 42.01 | 6 |
| ATOM | 2155 | CG | HIS | C | 92 | 20.167 | 65.003 | 167.796 | 1.00 | 42.13 | 6 |
| ATOM | 2156 | ND1 | HIS | C | 92 | 19.855 | 63.664 | 167.861 | 1.00 | 42.74 | 7 |
| ATOM | 2157 | CE1 | HIS | C | 92 | 20.490 | 63.021 | 166.897 | 1.00 | 42.66 | 6 |
| ATOM | 2158 | NE2 | HIS | C | 92 | 21.209 | 63.894 | 166.215 | 1.00 | 41.68 | 7 |
| ATOM | 2159 | CD2 | HIS | C | 92 | 21.029 | 65.139 | 166.760 | 1.00 | 41.95 | 6 |
| ATOM | 2160 | C | HIS | C | 92 | 19.920 | 68.200 | 169.945 | 1.00 | 42.92 | 6 |
| ATOM | 2161 | O | HIS | C | 92 | 18.990 | 67.900 | 170.714 | 1.00 | 42.85 | 8 |
| ATOM | 2162 | N | LEU | C | 93 | 20.434 | 69.424 | 169.875 | 1.00 | 43.91 | 7 |
| ATOM | 2163 | CA | LEU | C | 93 | 20.141 | 70.408 | 170.912 | 1.00 | 45.07 | 6 |
| ATOM | 2164 | CB | LEU | C | 93 | 20.897 | 71.727 | 170.700 | 1.00 | 45.13 | 6 |
| ATOM | 2165 | CG | LEU | C | 93 | 22.425 | 71.701 | 170.509 | 1.00 | 46.93 | 6 |
| ATOM | 2166 | CD1 | LEU | C | 93 | 23.158 | 70.530 | 171.249 | 1.00 | 47.92 | 6 |
| ATOM | 2167 | CD2 | LEU | C | 93 | 22.805 | 71.706 | 169.024 | 1.00 | 48.28 | 6 |
| ATOM | 2168 | C | LEU | C | 93 | 18.668 | 70.656 | 170.980 | 1.00 | 45.47 | 6 |
| ATOM | 2169 | O | LEU | C | 93 | 18.025 | 70.358 | 171.969 | 1.00 | 45.32 | 8 |
| ATOM | 2170 | N | GLU | C | 94 | 18.138 | 71.177 | 169.891 | 1.00 | 46.32 | 7 |
| ATOM | 2171 | CA | GLU | C | 94 | 16.739 | 71.515 | 169.819 | 1.00 | 47.42 | 6 |
| ATOM | 2172 | CB | GLU | C | 94 | 16.304 | 71.933 | 168.390 | 1.00 | 47.58 | 6 |
| ATOM | 2173 | CG | GLU | C | 94 | 16.888 | 71.113 | 167.234 | 1.00 | 50.17 | 6 |
| ATOM | 2174 | CD | GLU | C | 94 | 18.385 | 70.793 | 167.392 | 1.00 | 53.61 | 6 |
| ATOM | 2175 | OE1 | GLU | C | 94 | 18.720 | 69.646 | 167.809 | 1.00 | 54.04 | 8 |
| ATOM | 2176 | OE2 | GLU | C | 94 | 19.214 | 71.694 | 167.108 | 1.00 | 54.33 | 8 |
| ATOM | 2177 | C | GLU | C | 94 | 15.896 | 70.408 | 170.457 | 1.00 | 47.47 | 6 |
| ATOM | 2178 | O | GLU | C | 94 | 14.964 | 70.715 | 171.197 | 1.00 | 48.02 | 8 |
| ATOM | 2179 | N | ILE | C | 95 | 16.254 | 69.140 | 170.261 | 1.00 | 47.32 | 7 |
| ATOM | 2180 | CA | ILE | C | 95 | 15.453 | 68.071 | 170.874 | 1.00 | 47.28 | 6 |
| ATOM | 2181 | CB | ILE | C | 95 | 15.757 | 66.709 | 170.272 | 1.00 | 47.59 | 6 |
| ATOM | 2182 | CG1 | ILE | C | 95 | 15.358 | 66.718 | 168.785 | 1.00 | 48.24 | 6 |
| ATOM | 2183 | CD | ILE | C | 95 | 14.957 | 65.358 | 168.229 | 1.00 | 50.27 | 6 |
| ATOM | 2184 | CG2 | ILE | C | 95 | 15.087 | 65.587 | 171.120 | 1.00 | 46.89 | 6 |
| ATOM | 2185 | C | ILE | C | 95 | 15.613 | 68.023 | 172.388 | 1.00 | 47.24 | 6 |
| ATOM | 2186 | O | ILE | C | 95 | 14.632 | 67.980 | 173.149 | 1.00 | 47.07 | 8 |
| ATOM | 2187 | N | VAL | C | 96 | 16.865 | 68.040 | 172.811 | 1.00 | 47.19 | 7 |
| ATOM | 2188 | CA | VAL | C | 96 | 17.189 | 68.213 | 174.202 | 1.00 | 47.32 | 6 |
| ATOM | 2189 | CB | VAL | C | 96 | 18.639 | 68.677 | 174.307 | 1.00 | 47.43 | 6 |
| ATOM | 2190 | CG1 | VAL | C | 96 | 18.906 | 69.317 | 175.651 | 1.00 | 47.63 | 6 |
| ATOM | 2191 | CG2 | VAL | C | 96 | 19.589 | 67.505 | 174.019 | 1.00 | 47.60 | 6 |
| ATOM | 2192 | C | VAL | C | 96 | 16.244 | 69.242 | 174.843 | 1.00 | 47.32 | 6 |
| ATOM | 2193 | O | VAL | C | 96 | 15.580 | 68.964 | 175.838 | 1.00 | 47.33 | 8 |
| ATOM | 2194 | N | GLU | C | 97 | 16.160 | 70.417 | 174.241 | 1.00 | 47.32 | 7 |
| ATOM | 2195 | CA | GLU | C | 97 | 15.344 | 71.476 | 174.796 | 1.00 | 47.47 | 6 |
| ATOM | 2196 | CB | GLU | C | 97 | 15.454 | 72.731 | 173.964 | 1.00 | 47.78 | 6 |
| ATOM | 2197 | CG | GLU | C | 97 | 16.871 | 73.053 | 173.589 | 1.00 | 49.63 | 6 |
| ATOM | 2198 | CD | GLU | C | 97 | 17.003 | 74.461 | 173.093 | 1.00 | 52.37 | 6 |
| ATOM | 2199 | OE1 | GLU | C | 97 | 16.365 | 74.791 | 172.061 | 1.00 | 53.22 | 8 |
| ATOM | 2200 | OE2 | GLU | C | 97 | 17.737 | 75.238 | 173.747 | 1.00 | 53.08 | 8 |
| ATOM | 2201 | C | GLU | C | 97 | 13.894 | 71.074 | 174.910 | 1.00 | 47.03 | 6 |
| ATOM | 2202 | O | GLU | C | 97 | 13.359 | 71.057 | 176.008 | 1.00 | 47.28 | 8 |
| ATOM | 2203 | N | VAL | C | 98 | 13.258 | 70.739 | 173.793 | 1.00 | 46.46 | 7 |
| ATOM | 2204 | CA | VAL | C | 98 | 11.863 | 70.281 | 173.844 | 1.00 | 46.18 | 6 |
| ATOM | 2205 | CB | VAL | C | 98 | 11.257 | 69.922 | 172.434 | 1.00 | 46.11 | 6 |
| ATOM | 2206 | CG1 | VAL | C | 98 | 12.262 | 70.097 | 171.333 | 1.00 | 46.16 | 6 |
| ATOM | 2207 | CG2 | VAL | C | 98 | 10.622 | 68.519 | 172.408 | 1.00 | 45.61 | 6 |
| ATOM | 2208 | C | VAL | C | 98 | 11.620 | 69.166 | 174.882 | 1.00 | 46.03 | 6 |
| ATOM | 2209 | O | VAL | C | 98 | 10.575 | 69.159 | 175.564 | 1.00 | 46.08 | 8 |
| ATOM | 2210 | N | LEU | C | 99 | 12.583 | 68.251 | 175.014 | 1.00 | 45.44 | 7 |
| ATOM | 2211 | CA | LEU | C | 99 | 12.486 | 67.196 | 176.014 | 1.00 | 44.79 | 6 |
| ATOM | 2212 | CB | LEU | C | 99 | 13.623 | 66.204 | 175.860 | 1.00 | 44.41 | 6 |
| ATOM | 2213 | CG | LEU | C | 99 | 13.490 | 65.159 | 174.761 | 1.00 | 43.50 | 6 |
| ATOM | 2214 | CD1 | LEU | C | 99 | 14.792 | 64.418 | 174.654 | 1.00 | 43.61 | 6 |
| ATOM | 2215 | CD2 | LEU | C | 99 | 12.369 | 64.187 | 175.061 | 1.00 | 42.42 | 6 |
| ATOM | 2216 | C | LEU | C | 99 | 12.467 | 67.774 | 177.422 | 1.00 | 44.79 | 6 |
| ATOM | 2217 | O | LEU | C | 99 | 11.629 | 67.394 | 178.244 | 1.00 | 44.36 | 8 |
| ATOM | 2218 | N | LEU | C | 100 | 13.380 | 68.708 | 177.684 | 1.00 | 44.88 | 7 |
| ATOM | 2219 | CA | LEU | C | 100 | 13.417 | 69.424 | 178.953 | 1.00 | 45.06 | 6 |
| ATOM | 2220 | CB | LEU | C | 100 | 14.531 | 70.459 | 178.946 | 1.00 | 44.71 | 6 |
| ATOM | 2221 | CG | LEU | C | 100 | 15.903 | 69.824 | 178.840 | 1.00 | 43.97 | 6 |
| ATOM | 2222 | CD1 | LEU | C | 100 | 16.958 | 70.863 | 178.570 | 1.00 | 43.81 | 6 |
| ATOM | 2223 | CD2 | LEU | C | 100 | 16.195 | 69.073 | 180.109 | 1.00 | 43.51 | 6 |
| ATOM | 2224 | C | LEU | C | 100 | 12.099 | 70.113 | 179.206 | 1.00 | 45.56 | 6 |
| ATOM | 2225 | O | LEU | C | 100 | 11.518 | 69.970 | 180.277 | 1.00 | 44.98 | 8 |
| ATOM | 2226 | N | LYS | C | 101 | 11.642 | 70.851 | 178.191 | 1.00 | 46.67 | 7 |
| ATOM | 2227 | CA | LYS | C | 101 | 10.376 | 71.586 | 178.223 | 1.00 | 48.03 | 6 |

TABLE 1-continued

| | | | | | | | | | |
|---|---|---|---|---|---|---|---|---|---|
| ATOM | 2228 | CB | LYS | C | 101 | 10.035 | 72.188 | 176.844 | 1.00 | 47.97 | 6 |
| ATOM | 2229 | CG | LYS | C | 101 | 8.770 | 73.083 | 176.818 | 1.00 | 48.91 | 6 |
| ATOM | 2230 | CD | LYS | C | 101 | 8.161 | 73.219 | 175.416 | 1.00 | 49.16 | 6 |
| ATOM | 2231 | CE | LYS | C | 101 | 8.738 | 74.396 | 174.640 | 1.00 | 51.06 | 6 |
| ATOM | 2232 | NZ | LYS | C | 101 | 8.521 | 74.238 | 173.174 | 1.00 | 51.85 | 7 |
| ATOM | 2233 | C | LYS | C | 101 | 9.256 | 70.669 | 178.683 | 1.00 | 48.34 | 6 |
| ATOM | 2234 | O | LYS | C | 101 | 8.460 | 71.038 | 179.533 | 1.00 | 48.37 | 8 |
| ATOM | 2235 | N | HIS | C | 102 | 9.211 | 69.467 | 178.121 | 1.00 | 49.10 | 7 |
| ATOM | 2236 | CA | HIS | C | 102 | 8.221 | 68.474 | 178.518 | 1.00 | 49.76 | 6 |
| ATOM | 2237 | CB | HIS | C | 102 | 7.949 | 67.504 | 177.364 | 1.00 | 50.06 | 6 |
| ATOM | 2238 | CG | HIS | C | 102 | 7.093 | 68.069 | 176.277 | 1.00 | 50.98 | 6 |
| ATOM | 2239 | ND1 | HIS | C | 102 | 5.836 | 67.577 | 175.990 | 1.00 | 51.82 | 7 |
| ATOM | 2240 | CE1 | HIS | C | 102 | 5.322 | 68.253 | 174.980 | 1.00 | 52.14 | 6 |
| ATOM | 2241 | NE2 | HIS | C | 102 | 6.199 | 69.165 | 174.602 | 1.00 | 52.60 | 7 |
| ATOM | 2242 | CD2 | HIS | C | 102 | 7.317 | 69.070 | 175.395 | 1.00 | 51.82 | 6 |
| ATOM | 2243 | C | HIS | C | 102 | 8.653 | 67.694 | 179.765 | 1.00 | 49.77 | 6 |
| ATOM | 2244 | O | HIS | C | 102 | 8.142 | 66.603 | 180.022 | 1.00 | 49.90 | 8 |
| ATOM | 2245 | N | GLY | C | 103 | 9.608 | 68.242 | 180.516 | 1.00 | 49.76 | 7 |
| ATOM | 2246 | CA | GLY | C | 103 | 9.953 | 67.728 | 181.839 | 1.00 | 49.69 | 6 |
| ATOM | 2247 | C | GLY | C | 103 | 10.832 | 66.494 | 181.890 | 1.00 | 49.55 | 6 |
| ATOM | 2248 | O | GLY | C | 103 | 10.753 | 65.719 | 182.844 | 1.00 | 49.94 | 8 |
| ATOM | 2249 | N | ALA | C | 104 | 11.670 | 66.293 | 180.880 | 1.00 | 49.09 | 7 |
| ATOM | 2250 | CA | ALA | C | 104 | 12.710 | 65.275 | 180.983 | 1.00 | 48.39 | 6 |
| ATOM | 2251 | CB | ALA | C | 104 | 13.644 | 65.325 | 179.774 | 1.00 | 48.65 | 6 |
| ATOM | 2252 | C | ALA | C | 104 | 13.489 | 65.504 | 182.276 | 1.00 | 47.83 | 6 |
| ATOM | 2253 | O | ALA | C | 104 | 13.787 | 66.640 | 182.645 | 1.00 | 47.75 | 8 |
| ATOM | 2254 | N | ASP | C | 105 | 13.786 | 64.424 | 182.976 | 1.00 | 47.34 | 7 |
| ATOM | 2255 | CA | ASP | C | 105 | 14.571 | 64.512 | 184.181 | 1.00 | 47.34 | 6 |
| ATOM | 2256 | CB | ASP | C | 105 | 14.344 | 63.246 | 185.000 | 1.00 | 47.94 | 6 |
| ATOM | 2257 | CG | ASP | C | 105 | 14.988 | 63.300 | 186.374 | 1.00 | 49.66 | 6 |
| ATOM | 2258 | OD1 | ASP | C | 105 | 15.249 | 64.414 | 186.894 | 1.00 | 52.12 | 8 |
| ATOM | 2259 | OD2 | ASP | C | 105 | 15.219 | 62.204 | 186.939 | 1.00 | 51.07 | 8 |
| ATOM | 2260 | C | ASP | C | 105 | 16.042 | 64.658 | 183.803 | 1.00 | 46.72 | 6 |
| ATOM | 2261 | O | ASP | C | 105 | 16.634 | 63.731 | 183.271 | 1.00 | 46.93 | 8 |
| ATOM | 2262 | N | VAL | C | 106 | 16.624 | 65.824 | 184.059 | 1.00 | 45.97 | 7 |
| ATOM | 2263 | CA | VAL | C | 106 | 18.026 | 66.081 | 183.721 | 1.00 | 45.49 | 6 |
| ATOM | 2264 | CB | VAL | C | 106 | 18.409 | 67.567 | 183.938 | 1.00 | 45.52 | 6 |
| ATOM | 2265 | CG1 | VAL | C | 106 | 17.467 | 68.211 | 184.952 | 1.00 | 46.22 | 6 |
| ATOM | 2266 | CG2 | VAL | C | 106 | 19.879 | 67.735 | 184.373 | 1.00 | 44.70 | 6 |
| ATOM | 2267 | C | VAL | C | 106 | 18.923 | 65.178 | 184.554 | 1.00 | 45.38 | 6 |
| ATOM | 2268 | O | VAL | C | 106 | 20.049 | 64.828 | 184.147 | 1.00 | 46.06 | 8 |
| ATOM | 2269 | N | ASN | C | 107 | 18.411 | 64.772 | 185.707 | 1.00 | 44.49 | 7 |
| ATOM | 2270 | CA | ASN | C | 107 | 19.209 | 63.989 | 186.635 | 1.00 | 43.88 | 6 |
| ATOM | 2271 | CB | ASN | O | 107 | 18.873 | 64.376 | 188.060 | 1.00 | 43.93 | 6 |
| ATOM | 2272 | CG | ASN | C | 107 | 19.599 | 65.601 | 188.465 | 1.00 | 44.00 | 6 |
| ATOM | 2273 | OD1 | ASN | C | 107 | 20.613 | 65.960 | 187.840 | 1.00 | 43.75 | 8 |
| ATOM | 2274 | ND2 | ASN | C | 107 | 19.095 | 66.284 | 189.484 | 1.00 | 43.61 | 7 |
| ATOM | 2275 | C | ASN | C | 107 | 19.138 | 62.498 | 186.457 | 1.00 | 43.34 | 6 |
| ATOM | 2276 | O | ASN | C | 107 | 19.879 | 61.745 | 187.096 | 1.00 | 43.48 | 8 |
| ATOM | 2277 | N | ALA | C | 108 | 18.242 | 62.069 | 185.586 | 1.00 | 42.63 | 7 |
| ATOM | 2278 | CA | ALA | C | 108 | 18.106 | 60.659 | 185.321 | 1.00 | 42.04 | 6 |
| ATOM | 2279 | CB | ALA | C | 108 | 16.959 | 60.410 | 184.365 | 1.00 | 42.24 | 6 |
| ATOM | 2280 | C | ALA | C | 108 | 19.431 | 60.101 | 184.785 | 1.00 | 41.75 | 6 |
| ATOM | 2281 | O | ALA | C | 108 | 20.115 | 60.735 | 183.940 | 1.00 | 41.66 | 8 |
| ATOM | 2282 | N | GLN | C | 109 | 19.794 | 58.932 | 185.314 | 1.00 | 41.20 | 7 |
| ATOM | 2283 | CA | GLN | C | 109 | 21.062 | 58.275 | 184.975 | 1.00 | 40.82 | 6 |
| ATOM | 2284 | CB | GLN | C | 109 | 22.000 | 58.258 | 186.195 | 1.00 | 40.78 | 6 |
| ATOM | 2285 | CG | GLN | C | 109 | 21.313 | 58.553 | 187.533 | 1.00 | 40.28 | 6 |
| ATOM | 2286 | CD | GLN | C | 109 | 22.289 | 58.666 | 188.701 | 1.00 | 40.51 | 6 |
| ATOM | 2287 | OE1 | GLN | C | 109 | 21.885 | 58.969 | 189.822 | 1.00 | 41.49 | 8 |
| ATOM | 2288 | NE2 | GLN | C | 109 | 23.570 | 58.425 | 188.446 | 1.00 | 39.36 | 7 |
| ATOM | 2289 | C | GLN | C | 109 | 20.919 | 56.877 | 184.344 | 1.00 | 40.48 | 6 |
| ATOM | 2290 | O | GLN | C | 109 | 20.026 | 56.110 | 184.692 | 1.00 | 40.71 | 8 |
| ATOM | 2291 | N | ASP | C | 110 | 21.795 | 56.565 | 183.397 | 1.00 | 40.06 | 7 |
| ATOM | 2292 | CA | ASP | C | 110 | 21.796 | 55.249 | 182.768 | 1.00 | 40.04 | 6 |
| ATOM | 2293 | CB | ASP | C | 110 | 22.547 | 55.289 | 181.444 | 1.00 | 40.23 | 6 |
| ATOM | 2294 | CG | ASP | C | 110 | 23.968 | 55.778 | 181.604 | 1.00 | 41.63 | 6 |
| ATOM | 2295 | OD1 | ASP | C | 110 | 24.624 | 55.436 | 182.623 | 1.00 | 41.18 | 8 |
| ATOM | 2296 | OD2 | ASP | C | 110 | 24.427 | 56.512 | 180.699 | 1.00 | 44.25 | 8 |
| ATOM | 2297 | C | ASP | C | 110 | 22.457 | 54.264 | 183.708 | 1.00 | 39.48 | 6 |
| ATOM | 2298 | O | ASP | C | 110 | 22.767 | 54.617 | 184.831 | 1.00 | 39.47 | 8 |
| ATOM | 2299 | N | LYS | C | 111 | 22.701 | 53.050 | 183.227 | 1.00 | 39.02 | 7 |
| ATOM | 2300 | CA | LYS | C | 111 | 23.208 | 51.961 | 184.056 | 1.00 | 38.58 | 6 |
| ATOM | 2301 | CB | LYS | C | 111 | 23.100 | 50.624 | 183.310 | 1.00 | 38.76 | 6 |
| ATOM | 2302 | CG | LYS | C | 111 | 24.258 | 50.323 | 182.325 | 1.00 | 38.60 | 6 |
| ATOM | 2303 | CD | LYS | C | 111 | 23.978 | 49.119 | 181.451 | 1.00 | 38.59 | 6 |
| ATOM | 2304 | CE | LYS | C | 111 | 25.226 | 48.269 | 181.331 | 1.00 | 40.61 | 6 |
| ATOM | 2305 | NZ | LYS | C | 111 | 25.109 | 47.136 | 180.357 | 1.00 | 41.56 | 7 |
| ATOM | 2306 | C | LYS | C | 111 | 24.640 | 52.172 | 184.538 | 1.00 | 38.35 | 6 |
| ATOM | 2307 | O | LYS | C | 111 | 25.102 | 51.443 | 185.401 | 1.00 | 38.35 | 8 |

TABLE 1-continued

| | | | | | | | | | | |
|---|---|---|---|---|---|---|---|---|---|---|
| ATOM | 2308 | N | PHE | C | 112 | 25.348 | 53.149 | 183.975 | 1.00 | 38.15 | 7 |
| ATOM | 2309 | CA | PHE | C | 112 | 26.703 | 53.482 | 184.442 | 1.00 | 37.88 | 6 |
| ATOM | 2310 | CB | PHE | C | 112 | 27.620 | 53.815 | 183.260 | 1.00 | 37.96 | 6 |
| ATOM | 2311 | CG | PHE | C | 112 | 27.489 | 52.868 | 182.115 | 1.00 | 38.22 | 6 |
| ATOM | 2312 | CD1 | PHE | C | 112 | 28.258 | 51.693 | 182.073 | 1.00 | 38.38 | 6 |
| ATOM | 2313 | CE1 | PHE | C | 112 | 28.140 | 50.791 | 181.017 | 1.00 | 37.81 | 6 |
| ATOM | 2314 | CZ | PHE | C | 112 | 27.231 | 51.065 | 179.991 | 1.00 | 38.60 | 6 |
| ATOM | 2315 | CE2 | PHE | C | 112 | 26.448 | 52.238 | 180.028 | 1.00 | 38.16 | 6 |
| ATOM | 2316 | CD2 | PHE | C | 112 | 26.584 | 53.126 | 181.087 | 1.00 | 37.86 | 6 |
| ATOM | 2317 | C | PHE | C | 112 | 26.663 | 54.669 | 185.391 | 1.00 | 37.69 | 6 |
| ATOM | 2318 | O | PHE | C | 112 | 27.697 | 55.160 | 185.820 | 1.00 | 37.50 | 8 |
| ATOM | 2319 | N | GLY | C | 113 | 25.457 | 55.138 | 185.687 | 1.00 | 37.67 | 7 |
| ATOM | 2320 | CA | GLY | C | 113 | 25.254 | 56.335 | 186.484 | 1.00 | 37.58 | 6 |
| ATOM | 2321 | C | GLY | C | 113 | 25.480 | 57.664 | 185.775 | 1.00 | 37.44 | 6 |
| ATOM | 2322 | O | GLY | C | 113 | 25.557 | 58.708 | 186.437 | 1.00 | 37.78 | 8 |
| ATOM | 2323 | N | LYS | C | 114 | 25.589 | 57.643 | 184.448 | 1.00 | 37.00 | 7 |
| ATOM | 2324 | CA | LYS | C | 114 | 25.865 | 58.872 | 183.709 | 1.00 | 36.88 | 6 |
| ATOM | 2325 | CB | LYS | C | 114 | 26.584 | 58.582 | 182.405 | 1.00 | 36.44 | 6 |
| ATOM | 2326 | CG | LYS | C | 114 | 28.069 | 58.312 | 182.607 | 1.00 | 35.94 | 6 |
| ATOM | 2327 | CD | LYS | C | 114 | 28.843 | 58.493 | 181.312 | 1.00 | 34.40 | 6 |
| ATOM | 2328 | CE | LYS | C | 114 | 30.312 | 58.304 | 181.512 | 1.00 | 31.77 | 6 |
| ATOM | 2329 | NZ | LYS | C | 114 | 30.881 | 59.495 | 182.125 | 1.00 | 32.45 | 7 |
| ATOM | 2330 | C | LYS | C | 114 | 24.594 | 59.628 | 183.435 | 1.00 | 37.41 | 6 |
| ATOM | 2331 | O | LYS | C | 114 | 23.572 | 59.024 | 183.129 | 1.00 | 37.84 | 8 |
| ATOM | 2332 | N | THR | C | 115 | 24.649 | 60.946 | 183.559 | 1.00 | 38.00 | 7 |
| ATOM | 2333 | CA | THR | C | 115 | 23.508 | 61.796 | 183.233 | 1.00 | 38.74 | 6 |
| ATOM | 2334 | CB | THR | C | 115 | 23.352 | 62.921 | 184.254 | 1.00 | 38.86 | 6 |
| ATOM | 2335 | OG1 | THR | C | 115 | 24.568 | 63.696 | 184.316 | 1.00 | 38.00 | 8 |
| ATOM | 2336 | CG2 | THR | C | 115 | 23.046 | 62.324 | 185.617 | 1.00 | 38.98 | 6 |
| ATOM | 2337 | C | THR | C | 115 | 23.806 | 62.443 | 181.907 | 1.00 | 39.20 | 6 |
| ATOM | 2338 | O | THR | C | 115 | 24.978 | 62.489 | 181.501 | 1.00 | 39.29 | 8 |
| ATOM | 2339 | N | ALA | C | 116 | 22.780 | 62.973 | 181.239 | 1.00 | 39.35 | 7 |
| ATOM | 2340 | CA | ALA | C | 116 | 23.035 | 63.736 | 180.007 | 1.00 | 39.41 | 6 |
| ATOM | 2341 | CB | ALA | C | 116 | 21.764 | 64.388 | 179.475 | 1.00 | 39.66 | 6 |
| ATOM | 2342 | C | ALA | C | 116 | 24.153 | 64.776 | 180.192 | 1.00 | 39.29 | 6 |
| ATOM | 2343 | O | ALA | C | 116 | 25.015 | 64.906 | 179.324 | 1.00 | 39.10 | 8 |
| ATOM | 2344 | N | PHE | C | 117 | 24.158 | 65.484 | 181.328 | 1.00 | 39.22 | 7 |
| ATOM | 2345 | CA | PHE | C | 117 | 25.224 | 66.456 | 181.584 | 1.00 | 38.99 | 6 |
| ATOM | 2346 | CB | PHE | C | 117 | 25.097 | 67.146 | 182.938 | 1.00 | 38.75 | 6 |
| ATOM | 2347 | CG | PHE | C | 117 | 26.283 | 68.037 | 183.270 | 1.00 | 38.22 | 6 |
| ATOM | 2348 | CD1 | PHE | C | 117 | 26.400 | 69.308 | 182.712 | 1.00 | 38.91 | 6 |
| ATOM | 2349 | CE1 | PHE | C | 117 | 27.491 | 70.132 | 183.002 | 1.00 | 37.81 | 6 |
| ATOM | 2350 | CZ | PHE | C | 117 | 28.461 | 69.687 | 183.846 | 1.00 | 37.25 | 6 |
| ATOM | 2351 | CE2 | PHE | C | 117 | 28.357 | 68.422 | 184.402 | 1.00 | 36.91 | 6 |
| ATOM | 2352 | CD2 | PHE | C | 117 | 27.280 | 67.606 | 184.117 | 1.00 | 36.76 | 6 |
| ATOM | 2353 | C | PHE | C | 117 | 26.605 | 65.836 | 181.478 | 1.00 | 38.96 | 6 |
| ATOM | 2354 | O | PHE | C | 117 | 27.509 | 66.407 | 180.878 | 1.00 | 38.81 | 8 |
| ATOM | 2355 | N | ASP | C | 118 | 26.775 | 64.675 | 182.078 | 1.00 | 39.07 | 7 |
| ATOM | 2356 | CA | ASP | C | 118 | 28.040 | 64.010 | 181.963 | 1.00 | 39.54 | 6 |
| ATOM | 2357 | CB | ASP | C | 118 | 28.014 | 62.700 | 182.722 | 1.00 | 39.96 | 6 |
| ATOM | 2358 | CG | ASP | C | 118 | 27.830 | 62.904 | 184.201 | 1.00 | 41.79 | 6 |
| ATOM | 2359 | OD1 | ASP | C | 118 | 28.352 | 63.903 | 184.749 | 1.00 | 43.06 | 8 |
| ATOM | 2360 | OD2 | ASP | C | 118 | 27.162 | 62.055 | 184.819 | 1.00 | 44.49 | 8 |
| ATOM | 2361 | C | ASP | C | 118 | 28.344 | 63.801 | 180.493 | 1.00 | 39.20 | 6 |
| ATOM | 2362 | O | ASP | C | 118 | 29.375 | 64.262 | 179.996 | 1.00 | 39.16 | 8 |
| ATOM | 2363 | N | ILE | C | 119 | 27.416 | 63.149 | 179.795 | 1.00 | 38.64 | 7 |
| ATOM | 2364 | CA | ILE | C | 119 | 27.554 | 62.852 | 178.376 | 1.00 | 37.94 | 6 |
| ATOM | 2365 | CB | ILE | C | 119 | 26.228 | 62.367 | 177.807 | 1.00 | 37.56 | 6 |
| ATOM | 2366 | CG1 | ILE | C | 119 | 26.032 | 60.908 | 178.186 | 1.00 | 37.32 | 6 |
| ATOM | 2367 | CD | ILE | C | 119 | 24.761 | 60.289 | 177.639 | 1.00 | 38.02 | 6 |
| ATOM | 2368 | CG2 | ILE | C | 119 | 26.216 | 62.493 | 176.324 | 1.00 | 37.65 | 6 |
| ATOM | 2369 | C | ILE | C | 119 | 28.085 | 64.050 | 177.593 | 1.00 | 37.90 | 6 |
| ATOM | 2370 | O | ILE | C | 119 | 29.060 | 63.939 | 176.865 | 1.00 | 37.62 | 8 |
| ATOM | 2371 | N | SER | C | 120 | 27.462 | 65.203 | 177.783 | 1.00 | 38.22 | 7 |
| ATOM | 2372 | CA | SER | C | 120 | 27.850 | 66.417 | 177.067 | 1.00 | 38.94 | 6 |
| ATOM | 2373 | CB | SER | C | 120 | 26.886 | 67.539 | 177.388 | 1.00 | 39.23 | 6 |
| ATOM | 2374 | OG | SER | C | 120 | 26.699 | 67.588 | 178.792 | 1.00 | 41.18 | 8 |
| ATOM | 2375 | C | SER | C | 120 | 29.254 | 66.859 | 177.409 | 1.00 | 39.07 | 6 |
| ATOM | 2376 | O | SER | C | 120 | 29.989 | 67.304 | 176.533 | 1.00 | 38.94 | 8 |
| ATOM | 2377 | N | ILE | C | 121 | 29.610 | 66.749 | 178.690 | 1.00 | 39.44 | 7 |
| ATOM | 2378 | CA | ILE | C | 121 | 30.978 | 66.975 | 179.130 | 1.00 | 39.57 | 6 |
| ATOM | 2379 | CB | ILE | C | 121 | 31.075 | 66.847 | 180.642 | 1.00 | 39.30 | 6 |
| ATOM | 2380 | CG1 | ILE | C | 121 | 30.477 | 68.094 | 181.284 | 1.00 | 39.30 | 6 |
| ATOM | 2381 | CD | ILE | C | 121 | 31.284 | 69.375 | 181.037 | 1.00 | 40.20 | 6 |
| ATOM | 2382 | CG2 | ILE | C | 121 | 32.510 | 66.589 | 181.080 | 1.00 | 39.02 | 6 |
| ATOM | 2383 | C | ILE | C | 121 | 31.905 | 65.987 | 178.444 | 1.00 | 40.03 | 6 |
| ATOM | 2384 | O | ILE | C | 121 | 32.908 | 66.398 | 177.863 | 1.00 | 39.94 | 8 |
| ATOM | 2385 | N | ASP | C | 122 | 31.532 | 64.702 | 178.487 | 1.00 | 40.70 | 7 |
| ATOM | 2386 | CA | ASP | C | 122 | 32.362 | 63.612 | 177.955 | 1.00 | 41.46 | 6 |
| ATOM | 2387 | CB | ASP | C | 122 | 31.785 | 62.216 | 178.227 | 1.00 | 41.47 | 6 |

TABLE 1-continued

| | | | | | | | | | |
|---|---|---|---|---|---|---|---|---|---|
| ATOM | 2388 | CG | ASP | C | 122 | 31.816 | 61.860 | 179.689 | 1.00 | 42.33 | 6 |
| ATOM | 2389 | OD1 | ASP | C | 122 | 30.866 | 61.206 | 180.158 | 1.00 | 42.98 | 8 |
| ATOM | 2390 | OD2 | ASP | C | 122 | 32.774 | 62.265 | 180.380 | 1.00 | 43.75 | 8 |
| ATOM | 2391 | C | ASP | C | 122 | 32.645 | 63.766 | 176.492 | 1.00 | 41.62 | 6 |
| ATOM | 2392 | O | ASP | C | 122 | 33.742 | 63.464 | 176.064 | 1.00 | 42.05 | 8 |
| ATOM | 2393 | N | ASN | C | 123 | 31.694 | 64.222 | 175.698 | 1.00 | 41.91 | 7 |
| ATOM | 2394 | CA | ASN | C | 123 | 32.099 | 64.491 | 174.336 | 1.00 | 42.51 | 6 |
| ATOM | 2395 | CB | ASN | C | 123 | 31.347 | 63.674 | 173.255 | 1.00 | 42.56 | 6 |
| ATOM | 2396 | CG | ASN | C | 123 | 29.843 | 63.874 | 173.264 | 1.00 | 43.22 | 6 |
| ATOM | 2397 | OD1 | ASN | C | 123 | 29.340 | 64.932 | 173.640 | 1.00 | 44.53 | 8 |
| ATOM | 2398 | ND2 | ASN | C | 123 | 29.111 | 62.853 | 172.813 | 1.00 | 42.66 | 7 |
| ATOM | 2399 | C | ASN | C | 123 | 32.275 | 65.959 | 174.052 | 1.00 | 42.84 | 6 |
| ATOM | 2400 | O | ASN | C | 123 | 32.102 | 66.416 | 172.940 | 1.00 | 42.80 | 8 |
| ATOM | 2401 | N | GLY | C | 124 | 32.651 | 66.679 | 175.099 | 1.00 | 43.71 | 7 |
| ATOM | 2402 | CA | GLY | C | 124 | 33.152 | 68.041 | 174.979 | 1.00 | 44.95 | 6 |
| ATOM | 2403 | C | GLY | C | 124 | 32.221 | 69.059 | 174.367 | 1.00 | 45.71 | 6 |
| ATOM | 2404 | O | GLY | C | 124 | 32.664 | 70.095 | 173.931 | 1.00 | 45.65 | 8 |
| ATOM | 2405 | N | ASN | C | 125 | 30.928 | 68.768 | 174.344 | 1.00 | 46.94 | 7 |
| ATOM | 2406 | CA | ASN | C | 125 | 29.949 | 69.669 | 173.763 | 1.00 | 48.04 | 6 |
| ATOM | 2407 | CB | ASN | C | 125 | 28.818 | 68.855 | 173.107 | 1.00 | 47.86 | 6 |
| ATOM | 2408 | CG | ASN | C | 125 | 27.621 | 69.699 | 172.724 | 1.00 | 47.75 | 6 |
| ATOM | 2409 | OD1 | ASN | C | 125 | 27.572 | 70.908 | 172.967 | 1.00 | 47.92 | 8 |
| ATOM | 2410 | ND2 | ASN | C | 125 | 26.634 | 69.057 | 172.130 | 1.00 | 47.94 | 7 |
| ATOM | 2411 | C | ASN | C | 125 | 29.452 | 70.600 | 174.855 | 1.00 | 49.07 | 6 |
| ATOM | 2412 | O | ASN | C | 125 | 28.439 | 70.322 | 175.504 | 1.00 | 49.36 | 8 |
| ATOM | 2413 | N | GLU | C | 126 | 30.168 | 71.699 | 175.082 | 1.00 | 50.61 | 7 |
| ATOM | 2414 | CA | GLU | C | 126 | 29.826 | 72.527 | 176.249 | 1.00 | 52.32 | 6 |
| ATOM | 2415 | CB | GLU | C | 126 | 31.051 | 73.125 | 176.981 | 1.00 | 52.16 | 6 |
| ATOM | 2416 | CG | GLU | C | 126 | 31.394 | 74.555 | 176.620 | 1.00 | 53.52 | 6 |
| ATOM | 2417 | CD | GLU | C | 126 | 31.956 | 74.696 | 175.214 | 1.00 | 54.93 | 6 |
| ATOM | 2418 | OE1 | GLU | C | 126 | 33.174 | 74.947 | 175.105 | 1.00 | 56.03 | 8 |
| ATOM | 2419 | OE2 | GLU | C | 126 | 31.194 | 74.558 | 174.225 | 1.00 | 55.11 | 8 |
| ATOM | 2420 | C | GLU | C | 126 | 28.656 | 73.503 | 176.041 | 1.00 | 52.80 | 6 |
| ATOM | 2421 | O | GLU | C | 126 | 28.088 | 73.983 | 177.017 | 1.00 | 52.93 | 8 |
| ATOM | 2422 | N | ASP | C | 127 | 28.272 | 73.756 | 174.790 | 1.00 | 53.62 | 7 |
| ATOM | 2423 | CA | ASP | C | 127 | 27.014 | 74.453 | 174.526 | 1.00 | 54.39 | 6 |
| ATOM | 2424 | CB | ASP | C | 127 | 26.756 | 74.617 | 173.019 | 1.00 | 54.71 | 6 |
| ATOM | 2425 | CG | ASP | C | 127 | 27.574 | 75.748 | 172.397 | 1.00 | 55.52 | 6 |
| ATOM | 2426 | OD1 | ASP | C | 127 | 28.495 | 76.257 | 173.079 | 1.00 | 56.85 | 8 |
| ATOM | 2427 | OD2 | ASP | C | 127 | 27.299 | 76.123 | 171.228 | 1.00 | 56.04 | 8 |
| ATOM | 2428 | C | ASP | C | 127 | 25.885 | 73.680 | 175.198 | 1.00 | 54.69 | 6 |
| ATOM | 2429 | O | ASP | C | 127 | 25.122 | 74.261 | 175.976 | 1.00 | 54.92 | 8 |
| ATOM | 2430 | N | LEU | C | 128 | 25.826 | 72.372 | 174.916 | 1.00 | 54.90 | 7 |
| ATOM | 2431 | CA | LEU | C | 128 | 24.866 | 71.444 | 175.511 | 1.00 | 55.09 | 6 |
| ATOM | 2432 | CB | LEU | C | 128 | 25.130 | 70.034 | 175.003 | 1.00 | 55.04 | 6 |
| ATOM | 2433 | CG | LEU | C | 128 | 23.934 | 69.114 | 174.773 | 1.00 | 55.63 | 6 |
| ATOM | 2434 | CD1 | LEU | C | 128 | 23.960 | 67.946 | 175.733 | 1.00 | 56.08 | 6 |
| ATOM | 2435 | CD2 | LEU | C | 128 | 22.609 | 69.862 | 174.847 | 1.00 | 55.55 | 6 |
| ATOM | 2436 | C | LEU | C | 128 | 24.962 | 71.466 | 177.017 | 1.00 | 55.27 | 6 |
| ATOM | 2437 | O | LEU | C | 128 | 23.951 | 71.587 | 177.706 | 1.00 | 55.36 | 8 |
| ATOM | 2438 | N | ALA | C | 129 | 26.190 | 71.371 | 177.515 | 1.00 | 55.68 | 7 |
| ATOM | 2439 | CA | ALA | C | 129 | 26.460 | 71.434 | 178.948 | 1.00 | 56.41 | 6 |
| ATOM | 2440 | CB | ALA | C | 129 | 27.951 | 71.398 | 179.205 | 1.00 | 56.27 | 6 |
| ATOM | 2441 | C | ALA | C | 129 | 25.827 | 72.660 | 179.617 | 1.00 | 57.01 | 6 |
| ATOM | 2442 | O | ALA | C | 129 | 25.137 | 72.537 | 180.628 | 1.00 | 56.94 | 8 |
| ATOM | 2443 | N | GLU | C | 130 | 26.047 | 73.838 | 179.044 | 1.00 | 57.83 | 7 |
| ATOM | 2444 | CA | GLU | C | 130 | 25.456 | 75.049 | 179.591 | 1.00 | 58.73 | 6 |
| ATOM | 2445 | CB | GLU | C | 130 | 26.062 | 76.299 | 178.962 | 1.00 | 59.17 | 6 |
| ATOM | 2446 | CG | GLU | C | 130 | 27.411 | 76.674 | 179.549 | 1.00 | 61.40 | 6 |
| ATOM | 2447 | CD | GLU | C | 130 | 28.456 | 76.967 | 178.470 | 1.00 | 63.99 | 6 |
| ATOM | 2448 | OE1 | GLU | C | 130 | 28.172 | 77.803 | 177.569 | 1.00 | 64.68 | 8 |
| ATOM | 2449 | OE2 | GLU | C | 130 | 29.556 | 76.352 | 178.530 | 1.00 | 64.72 | 8 |
| ATOM | 2450 | C | GLU | C | 130 | 23.941 | 75.083 | 179.478 | 1.00 | 58.52 | 6 |
| ATOM | 2451 | O | GLU | C | 130 | 23.293 | 75.738 | 180.285 | 1.00 | 58.74 | 8 |
| ATOM | 2452 | N | ILE | C | 131 | 23.360 | 74.396 | 178.500 | 1.00 | 58.47 | 7 |
| ATOM | 2453 | CA | ILE | C | 131 | 21.909 | 74.401 | 178.437 | 1.00 | 58.57 | 6 |
| ATOM | 2454 | CB | ILE | C | 131 | 21.297 | 74.127 | 177.020 | 1.00 | 58.50 | 6 |
| ATOM | 2455 | CG1 | ILE | C | 131 | 20.574 | 72.781 | 176.978 | 1.00 | 58.29 | 6 |
| ATOM | 2456 | CD | ILE | C | 131 | 19.296 | 72.819 | 176.189 | 1.00 | 58.30 | 6 |
| ATOM | 2457 | CG2 | ILE | C | 131 | 22.318 | 74.297 | 175.893 | 1.00 | 57.78 | 6 |
| ATOM | 2458 | C | ILE | C | 131 | 21.381 | 73.441 | 179.484 | 1.00 | 58.97 | 6 |
| ATOM | 2459 | O | ILE | C | 131 | 20.226 | 73.514 | 179.878 | 1.00 | 59.06 | 8 |
| ATOM | 2460 | N | LEU | C | 132 | 22.240 | 72.554 | 179.955 | 1.00 | 59.62 | 7 |
| ATOM | 2461 | CA | LEU | C | 132 | 21.829 | 71.635 | 181.000 | 1.00 | 60.65 | 6 |
| ATOM | 2462 | CB | LEU | C | 132 | 22.459 | 70.253 | 180.777 | 1.00 | 60.38 | 6 |
| ATOM | 2463 | CG | LEU | C | 132 | 21.629 | 69.320 | 179.874 | 1.00 | 59.60 | 6 |
| ATOM | 2464 | CD1 | LEU | C | 132 | 22.475 | 68.387 | 179.014 | 1.00 | 58.29 | 6 |
| ATOM | 2465 | CD2 | LEU | C | 132 | 20.582 | 68.533 | 180.681 | 1.00 | 58.81 | 6 |
| ATOM | 2466 | C | LEU | C | 132 | 22.082 | 72.199 | 182.405 | 1.00 | 61.76 | 6 |
| ATOM | 2467 | O | LEU | C | 132 | 21.358 | 71.881 | 183.351 | 1.00 | 61.82 | 8 |

TABLE 1-continued

| | | | | | | | | | |
|---|---|---|---|---|---|---|---|---|---|
| ATOM | 2468 | N | GLN | C | 133 | 23.098 | 73.055 | 182.517 | 1.00 63.20 7 |
| ATOM | 2469 | CA | GLN | C | 133 | 23.368 | 73.828 | 183.734 | 1.00 64.65 6 |
| ATOM | 2470 | CB | GLN | C | 133 | 24.693 | 74.594 | 183.616 | 1.00 64.54 6 |
| ATOM | 2471 | CG | GLN | C | 133 | 25.919 | 73.732 | 183.599 | 1.00 64.14 6 |
| ATOM | 2472 | CD | GLN | C | 133 | 25.929 | 72.737 | 184.724 | 1.00 63.49 6 |
| ATOM | 2473 | OE1 | GLN | C | 133 | 26.983 | 72.435 | 185.288 | 1.00 63.65 8 |
| ATOM | 2474 | NE2 | GLN | C | 133 | 24.752 | 72.214 | 185.065 | 1.00 62.66 7 |
| ATOM | 2475 | C | GLN | C | 133 | 22.278 | 74.850 | 183.999 | 1.00 66.11 6 |
| ATOM | 2476 | O | GLN | C | 133 | 21.960 | 75.145 | 185.151 | 1.00 66.37 8 |
| ATOM | 2477 | N | LYS | C | 134 | 21.724 | 75.397 | 182.918 | 1.00 67.89 7 |
| ATOM | 2478 | CA | LYS | C | 134 | 20.731 | 76.469 | 182.977 | 1.00 69.50 6 |
| ATOM | 2479 | CB | LYS | C | 134 | 20.417 | 76.969 | 181.553 | 1.00 69.38 6 |
| ATOM | 2480 | CG | LYS | C | 134 | 20.526 | 78.476 | 181.327 | 1.00 69.23 6 |
| ATOM | 2481 | CD | LYS | C | 134 | 21.972 | 78.904 | 181.070 | 1.00 68.71 6 |
| ATOM | 2482 | CE | LYS | C | 134 | 22.099 | 79.745 | 179.806 | 1.00 68.48 6 |
| ATOM | 2483 | NZ | LYS | C | 134 | 21.155 | 80.901 | 179.749 | 1.00 68.07 7 |
| ATOM | 2484 | C | LYS | C | 134 | 19.446 | 76.001 | 183.677 | 1.00 70.74 6 |
| ATOM | 2485 | O | LYS | C | 134 | 18.473 | 76.771 | 183.775 | 1.00 71.11 8 |
| ATOM | 2486 | N | LEU | C | 135 | 19.453 | 74.751 | 184.166 | 1.00 72.01 7 |
| ATOM | 2487 | CA | LEU | C | 135 | 18.269 | 74.145 | 184.794 | 1.00 73.28 6 |
| ATOM | 2488 | CB | LEU | C | 135 | 17.948 | 72.771 | 184.192 | 1.00 73.24 6 |
| ATOM | 2489 | CG | LEU | C | 135 | 17.071 | 72.844 | 182.931 | 1.00 74.03 6 |
| ATOM | 2490 | CD1 | LEU | C | 135 | 17.255 | 71.594 | 182.093 | 1.00 74.85 6 |
| ATOM | 2491 | CD2 | LEU | C | 135 | 15.572 | 73.129 | 183.211 | 1.00 73.66 6 |
| ATOM | 2492 | C | LEU | C | 135 | 18.312 | 74.031 | 186.308 | 1.00 74.01 6 |
| ATOM | 2493 | O | LEU | C | 135 | 19.358 | 73.744 | 186.890 | 1.00 74.20 8 |
| ATOM | 2494 | N | ASN | C | 136 | 17.153 | 74.312 | 186.913 | 1.00 74.92 7 |
| ATOM | 2495 | CA | ASN | C | 136 | 16.761 | 73.874 | 188.252 | 1.00 75.40 6 |
| ATOM | 2496 | CB | ASN | C | 136 | 15.236 | 73.729 | 188.280 | 1.00 75.53 6 |
| ATOM | 2497 | CG | ASN | C | 136 | 14.652 | 73.218 | 186.927 | 1.00 76.44 6 |
| ATOM | 2498 | OD1 | ASN | C | 136 | 13.745 | 73.849 | 186.366 | 1.00 77.16 8 |
| ATOM | 2499 | ND2 | ASN | C | 136 | 15.175 | 72.081 | 186.411 | 1.00 76.82 7 |
| ATOM | 2500 | C | ASN | C | 136 | 17.384 | 72.536 | 188.634 | 1.00 75.59 6 |
| ATOM | 2501 | O | ASN | C | 136 | 17.386 | 71.574 | 187.845 | 1.00 75.85 8 |
| ATOM | 2502 | N | SER | D | 12 | 57.072 | 76.469 | 149.223 | 1.00 71.66 7 |
| ATOM | 2503 | CA | SER | D | 12 | 57.218 | 75.497 | 150.357 | 1.00 72.01 6 |
| ATOM | 2504 | CB | SER | D | 12 | 58.177 | 76.071 | 151.421 | 1.00 72.13 6 |
| ATOM | 2505 | OG | SER | D | 12 | 59.438 | 76.408 | 150.868 | 1.00 72.16 8 |
| ATOM | 2506 | C | SER | D | 12 | 55.865 | 75.183 | 151.012 | 1.00 71.64 6 |
| ATOM | 2507 | O | SER | D | 12 | 55.631 | 74.080 | 151.579 | 1.00 71.37 8 |
| ATOM | 2508 | N | ASP | D | 13 | 55.004 | 76.196 | 150.919 | 1.00 71.06 7 |
| ATOM | 2509 | CA | ASP | D | 13 | 53.670 | 76.236 | 151.512 | 1.00 70.55 6 |
| ATOM | 2510 | CB | ASP | D | 13 | 53.358 | 77.731 | 151.756 | 1.00 71.06 6 |
| ATOM | 2511 | CG | ASP | D | 13 | 52.015 | 77.989 | 152.458 | 1.00 72.21 6 |
| ATOM | 2512 | OD1 | ASP | D | 13 | 52.045 | 78.420 | 153.649 | 1.00 73.06 8 |
| ATOM | 2513 | OD2 | ASP | D | 13 | 50.947 | 77.817 | 151.802 | 1.00 71.77 8 |
| ATOM | 2514 | C | ASP | D | 13 | 52.684 | 75.523 | 150.545 | 1.00 69.48 6 |
| ATOM | 2515 | O | ASP | D | 13 | 51.462 | 75.430 | 150.785 | 1.00 69.05 8 |
| ATOM | 2516 | N | LEU | D | 14 | 53.254 | 75.029 | 149.441 | 1.00 68.09 7 |
| ATOM | 2517 | CA | LEU | D | 14 | 52.637 | 74.008 | 148.609 | 1.00 66.41 6 |
| ATOM | 2518 | CB | LEU | D | 14 | 53.666 | 73.437 | 147.636 | 1.00 66.29 6 |
| ATOM | 2519 | CG | LEU | D | 14 | 53.966 | 74.228 | 146.369 | 1.00 65.59 6 |
| ATOM | 2520 | CD1 | LEU | D | 14 | 55.222 | 73.727 | 145.680 | 1.00 65.76 6 |
| ATOM | 2521 | CD2 | LEU | D | 14 | 52.808 | 74.103 | 145.452 | 1.00 64.98 6 |
| ATOM | 2522 | C | LEU | D | 14 | 52.107 | 72.890 | 149.493 | 1.00 65.51 6 |
| ATOM | 2523 | O | LEU | D | 14 | 50.976 | 72.463 | 149.319 | 1.00 65.77 8 |
| ATOM | 2524 | N | GLY | D | 15 | 52.923 | 72.435 | 150.449 | 1.00 64.23 7 |
| ATOM | 2525 | CA | GLY | D | 15 | 52.501 | 71.453 | 151.460 | 1.00 62.41 6 |
| ATOM | 2526 | C | GLY | D | 15 | 51.178 | 71.709 | 152.174 | 1.00 61.18 6 |
| ATOM | 2527 | O | GLY | D | 15 | 50.329 | 70.828 | 152.243 | 1.00 60.79 8 |
| ATOM | 2528 | N | LYS | D | 16 | 50.994 | 72.918 | 152.698 | 1.00 60.20 7 |
| ATOM | 2529 | CA | LYS | D | 16 | 49.745 | 73.272 | 153.382 | 1.00 58.81 6 |
| ATOM | 2530 | CB | LYS | D | 16 | 49.862 | 74.629 | 154.071 | 1.00 58.79 6 |
| ATOM | 2531 | CG | LYS | D | 16 | 48.662 | 75.033 | 154.922 | 1.00 58.52 6 |
| ATOM | 2532 | CD | LYS | D | 16 | 48.936 | 76.320 | 155.708 | 1.00 58.76 6 |
| ATOM | 2533 | CE | LYS | D | 16 | 47.724 | 76.754 | 156.535 | 1.00 58.71 6 |
| ATOM | 2534 | NZ | LYS | D | 16 | 48.103 | 77.727 | 157.589 | 1.00 57.71 7 |
| ATOM | 2535 | C | LYS | D | 16 | 48.557 | 73.242 | 152.438 | 1.00 58.00 6 |
| ATOM | 2536 | O | LYS | D | 16 | 47.454 | 72.947 | 152.846 | 1.00 57.61 8 |
| ATOM | 2537 | N | LYS | D | 17 | 48.796 | 73.536 | 151.172 | 1.00 57.54 7 |
| ATOM | 2538 | CA | LYS | D | 17 | 47.756 | 73.458 | 150.144 | 1.00 57.33 6 |
| ATOM | 2539 | CB | LYS | D | 17 | 48.242 | 74.157 | 148.854 | 1.00 57.47 6 |
| ATOM | 2540 | CG | LYS | D | 17 | 48.360 | 75.682 | 148.918 | 1.00 57.59 6 |
| ATOM | 2541 | CD | LYS | D | 17 | 47.077 | 76.337 | 148.462 | 1.00 58.43 6 |
| ATOM | 2542 | CE | LYS | D | 17 | 46.732 | 77.561 | 149.310 | 1.00 60.29 6 |
| ATOM | 2543 | NZ | LYS | D | 17 | 46.653 | 78.874 | 148.554 | 1.00 61.03 7 |
| ATOM | 2544 | C | LYS | D | 17 | 47.346 | 71.995 | 149.843 | 1.00 56.68 6 |
| ATOM | 2545 | O | LYS | D | 17 | 46.162 | 71.648 | 149.756 | 1.00 56.26 8 |
| ATOM | 2546 | N | LEU | D | 18 | 48.348 | 71.147 | 149.677 | 1.00 56.01 7 |
| ATOM | 2547 | CA | LEU | D | 18 | 48.114 | 69.750 | 149.427 | 1.00 55.59 6 |

TABLE 1-continued

| | | | | | | | | | |
|---|---|---|---|---|---|---|---|---|---|
| ATOM | 2548 | CB | LEU | D | 18 | 49.432 | 69.015 | 149.255 | 1.00 | 55.04 | 6 |
| ATOM | 2549 | CG | LEU | D | 18 | 49.290 | 67.529 | 148.944 | 1.00 | 54.58 | 6 |
| ATOM | 2550 | CD1 | LEU | D | 18 | 48.236 | 67.250 | 147.865 | 1.00 | 54.03 | 6 |
| ATOM | 2551 | CD2 | LEU | D | 18 | 50.633 | 66.931 | 148.538 | 1.00 | 55.07 | 6 |
| ATOM | 2552 | C | LEU | D | 18 | 47.297 | 69.128 | 150.550 | 1.00 | 55.76 | 6 |
| ATOM | 2553 | O | LEU | D | 18 | 46.322 | 68.403 | 150.297 | 1.00 | 55.89 | 8 |
| ATOM | 2554 | N | LEU | D | 19 | 47.683 | 69.423 | 151.787 | 1.00 | 55.74 | 7 |
| ATOM | 2555 | CA | LEU | D | 19 | 46.954 | 68.918 | 152.937 | 1.00 | 55.74 | 6 |
| ATOM | 2556 | CB | LEU | D | 19 | 47.542 | 69.451 | 154.244 | 1.00 | 55.23 | 6 |
| ATOM | 2557 | CG | LEU | D | 19 | 48.845 | 68.723 | 154.600 | 1.00 | 54.59 | 6 |
| ATOM | 2558 | CD1 | LEU | D | 19 | 49.729 | 69.448 | 155.607 | 1.00 | 53.41 | 6 |
| ATOM | 2559 | CD2 | LEU | D | 19 | 48.542 | 67.307 | 155.067 | 1.00 | 54.86 | 6 |
| ATOM | 2560 | C | LEU | D | 19 | 45.485 | 69.257 | 152.784 | 1.00 | 56.26 | 6 |
| ATOM | 2561 | O | LEU | D | 19 | 44.638 | 68.355 | 152.778 | 1.00 | 55.97 | 8 |
| ATOM | 2562 | N | GLU | D | 20 | 45.202 | 70.547 | 152.588 | 1.00 | 56.94 | 7 |
| ATOM | 2563 | CA | GLU | D | 20 | 43.822 | 71.035 | 152.464 | 1.00 | 58.02 | 6 |
| ATOM | 2564 | CB | GLU | D | 20 | 43.769 | 72.578 | 152.421 | 1.00 | 57.73 | 6 |
| ATOM | 2565 | CG | GLU | D | 20 | 44.234 | 73.253 | 153.754 | 1.00 | 60.07 | 6 |
| ATOM | 2566 | CD | GLU | D | 20 | 44.638 | 74.769 | 153.653 | 1.00 | 61.13 | 6 |
| ATOM | 2567 | OE1 | GLU | D | 20 | 45.124 | 75.269 | 152.589 | 1.00 | 64.85 | 8 |
| ATOM | 2568 | OE2 | GLU | D | 20 | 44.488 | 75.469 | 154.684 | 1.00 | 64.45 | 8 |
| ATOM | 2569 | C | GLU | D | 20 | 43.065 | 70.370 | 151.300 | 1.00 | 57.32 | 6 |
| ATOM | 2570 | O | GLU | D | 20 | 41.883 | 70.032 | 151.434 | 1.00 | 57.14 | 8 |
| ATOM | 2571 | N | ALA | D | 21 | 43.762 | 70.136 | 150.189 | 1.00 | 56.99 | 7 |
| ATOM | 2572 | CA | ALA | D | 21 | 43.118 | 69.578 | 149.017 | 1.00 | 56.48 | 6 |
| ATOM | 2573 | CB | ALA | D | 21 | 43.973 | 69.769 | 147.815 | 1.00 | 56.52 | 6 |
| ATOM | 2574 | C | ALA | D | 21 | 42.822 | 68.118 | 149.263 | 1.00 | 56.48 | 6 |
| ATOM | 2575 | O | ALA | D | 21 | 41.782 | 67.619 | 148.845 | 1.00 | 56.37 | 8 |
| ATOM | 2576 | N | ALA | D | 22 | 43.723 | 67.439 | 149.971 | 1.00 | 56.56 | 7 |
| ATOM | 2577 | CA | ALA | D | 22 | 43.479 | 66.051 | 150.345 | 1.00 | 56.55 | 6 |
| ATOM | 2578 | CB | ALA | D | 22 | 44.715 | 65.424 | 150.925 | 1.00 | 56.59 | 6 |
| ATOM | 2579 | C | ALA | D | 22 | 42.276 | 65.909 | 151.288 | 1.00 | 56.59 | 6 |
| ATOM | 2580 | O | ALA | D | 22 | 41.430 | 65.070 | 151.049 | 1.00 | 56.50 | 8 |
| ATOM | 2581 | N | ARG | D | 23 | 42.173 | 66.740 | 152.325 | 1.00 | 56.73 | 7 |
| ATOM | 2582 | CA | ARG | D | 23 | 40.974 | 66.729 | 153.182 | 1.00 | 57.41 | 6 |
| ATOM | 2583 | CB | ARG | D | 23 | 41.049 | 67.803 | 154.286 | 1.00 | 57.14 | 6 |
| ATOM | 2584 | CG | ARG | D | 23 | 39.795 | 67.850 | 155.195 | 1.00 | 57.96 | 6 |
| ATOM | 2585 | CD | ARG | D | 23 | 39.749 | 69.085 | 156.109 | 1.00 | 59.45 | 6 |
| ATOM | 2586 | NE | ARG | D | 23 | 40.494 | 68.922 | 157.373 | 1.00 | 64.37 | 7 |
| ATOM | 2587 | CZ | ARG | D | 23 | 41.731 | 69.385 | 157.623 | 1.00 | 65.22 | 6 |
| ATOM | 2588 | NH1 | ARG | D | 23 | 42.439 | 70.068 | 156.707 | 1.00 | 64.16 | 7 |
| ATOM | 2589 | NH2 | ARG | D | 23 | 42.272 | 69.151 | 158.812 | 1.00 | 64.98 | 7 |
| ATOM | 2590 | C | ARG | D | 23 | 39.690 | 66.928 | 152.364 | 1.00 | 57.10 | 6 |
| ATOM | 2591 | O | ARG | D | 23 | 38.664 | 66.275 | 152.587 | 1.00 | 56.90 | 8 |
| ATOM | 2592 | N | ALA | D | 24 | 39.770 | 67.836 | 151.408 | 1.00 | 57.16 | 7 |
| ATOM | 2593 | CA | ALA | D | 24 | 38.597 | 68.296 | 150.720 | 1.00 | 57.23 | 6 |
| ATOM | 2594 | CB | ALA | D | 24 | 38.868 | 69.626 | 150.087 | 1.00 | 57.24 | 6 |
| ATOM | 2595 | C | ALA | D | 24 | 38.113 | 67.306 | 149.687 | 1.00 | 57.52 | 6 |
| ATOM | 2596 | O | ALA | D | 24 | 36.926 | 67.254 | 149.399 | 1.00 | 57.76 | 8 |
| ATOM | 2597 | N | GLY | D | 25 | 39.019 | 66.515 | 149.131 | 1.00 | 57.87 | 7 |
| ATOM | 2598 | CA | GLY | D | 25 | 38.652 | 65.638 | 148.028 | 1.00 | 58.24 | 6 |
| ATOM | 2599 | C | GLY | D | 25 | 38.828 | 66.258 | 146.647 | 1.00 | 58.65 | 6 |
| ATOM | 2600 | O | GLY | D | 25 | 38.422 | 65.671 | 145.653 | 1.00 | 58.41 | 8 |
| ATOM | 2601 | N | GLN | D | 26 | 39.449 | 67.431 | 146.576 | 1.00 | 59.14 | 7 |
| ATOM | 2602 | CA | GLN | D | 26 | 39.786 | 68.038 | 145.304 | 1.00 | 60.00 | 6 |
| ATOM | 2603 | CB | GLN | D | 26 | 40.098 | 69.505 | 145.513 | 1.00 | 60.16 | 6 |
| ATOM | 2604 | CG | GLN | D | 26 | 39.250 | 70.142 | 146.605 | 1.00 | 61.63 | 6 |
| ATOM | 2605 | CD | GLN | D | 26 | 37.923 | 70.738 | 146.128 | 1.00 | 64.20 | 6 |
| ATOM | 2606 | OE1 | GLN | D | 26 | 37.344 | 70.323 | 145.114 | 1.00 | 65.91 | 8 |
| ATOM | 2607 | NE2 | GLN | D | 26 | 37.427 | 71.719 | 146.879 | 1.00 | 64.88 | 7 |
| ATOM | 2608 | C | GLN | D | 26 | 40.932 | 67.292 | 144.596 | 1.00 | 60.60 | 6 |
| ATOM | 2609 | O | GLN | D | 26 | 42.117 | 67.608 | 144.765 | 1.00 | 60.40 | 8 |
| ATOM | 2610 | N | ASP | D | 27 | 40.549 | 66.291 | 143.799 | 1.00 | 61.48 | 7 |
| ATOM | 2611 | CA | ASP | D | 27 | 41.500 | 65.421 | 143.102 | 1.00 | 62.13 | 6 |
| ATOM | 2612 | CB | ASP | D | 27 | 40.830 | 64.190 | 142.480 | 1.00 | 62.51 | 6 |
| ATOM | 2613 | CG | ASP | D | 27 | 39.481 | 63.858 | 143.110 | 1.00 | 64.47 | 6 |
| ATOM | 2614 | OD1 | ASP | D | 27 | 39.342 | 62.777 | 143.749 | 1.00 | 66.51 | 8 |
| ATOM | 2615 | OD2 | ASP | D | 27 | 38.549 | 64.682 | 142.952 | 1.00 | 66.12 | 8 |
| ATOM | 2616 | C | ASP | D | 27 | 42.302 | 66.159 | 142.045 | 1.00 | 62.16 | 6 |
| ATOM | 2617 | O | ASP | D | 27 | 43.477 | 65.864 | 141.879 | 1.00 | 62.57 | 8 |
| ATOM | 2618 | N | ASP | D | 28 | 41.694 | 67.103 | 141.335 | 1.00 | 61.96 | 7 |
| ATOM | 2619 | CA | ASP | D | 28 | 42.454 | 67.896 | 140.390 | 1.00 | 62.30 | 6 |
| ATOM | 2620 | CB | ASP | D | 28 | 41.548 | 68.786 | 139.591 | 1.00 | 62.90 | 6 |
| ATOM | 2621 | CG | ASP | D | 28 | 40.866 | 68.041 | 138.496 | 1.00 | 65.47 | 6 |
| ATOM | 2622 | OD1 | ASP | D | 28 | 41.244 | 66.857 | 138.274 | 1.00 | 67.62 | 8 |
| ATOM | 2623 | OD2 | ASP | D | 28 | 39.951 | 68.633 | 137.867 | 1.00 | 66.86 | 8 |
| ATOM | 2624 | C | ASP | D | 28 | 43.452 | 68.759 | 141.077 | 1.00 | 61.98 | 6 |
| ATOM | 2625 | O | ASP | D | 28 | 44.583 | 68.863 | 140.629 | 1.00 | 62.11 | 8 |
| ATOM | 2626 | N | GLU | D | 29 | 43.011 | 69.392 | 142.159 | 1.00 | 61.73 | 7 |
| ATOM | 2627 | CA | GLU | D | 29 | 43.860 | 70.228 | 142.999 | 1.00 | 61.32 | 6 |

TABLE 1-continued

| | | | | | | | | | |
|---|---|---|---|---|---|---|---|---|---|
| ATOM | 2628 | CB | GLU | D | 29 | 43.061 | 70.738 | 144.204 | 1.00 | 61.59 | 6 |
| ATOM | 2629 | CG | GLU | D | 29 | 42.714 | 72.205 | 144.181 | 1.00 | 63.74 | 6 |
| ATOM | 2630 | CD | GLU | D | 29 | 43.975 | 73.058 | 144.244 | 1.00 | 68.32 | 6 |
| ATOM | 2631 | OE1 | GLU | D | 29 | 44.634 | 73.193 | 143.176 | 1.00 | 69.59 | 8 |
| ATOM | 2632 | OE2 | GLU | D | 29 | 44.318 | 73.579 | 145.350 | 1.00 | 69.36 | 8 |
| ATOM | 2633 | C | GLU | D | 29 | 45.073 | 69.437 | 143.467 | 1.00 | 60.51 | 6 |
| ATOM | 2634 | O | GLU | D | 29 | 46.201 | 69.941 | 143.456 | 1.00 | 60.69 | 8 |
| ATOM | 2635 | N | VAL | D | 30 | 44.832 | 68.188 | 143.858 | 1.00 | 59.25 | 7 |
| ATOM | 2636 | CA | VAL | D | 30 | 45.892 | 67.313 | 144.306 | 1.00 | 58.04 | 6 |
| ATOM | 2637 | CB | VAL | D | 30 | 45.315 | 65.986 | 144.832 | 1.00 | 57.79 | 6 |
| ATOM | 2638 | CG1 | VAL | D | 30 | 46.428 | 65.005 | 145.224 | 1.00 | 57.27 | 6 |
| ATOM | 2639 | CG2 | VAL | D | 30 | 44.446 | 66.260 | 146.021 | 1.00 | 57.41 | 6 |
| ATOM | 2640 | C | VAL | D | 30 | 46.896 | 67.106 | 143.176 | 1.00 | 57.60 | 6 |
| ATOM | 2641 | O | VAL | D | 30 | 48.079 | 67.355 | 143.333 | 1.00 | 57.42 | 8 |
| ATOM | 2642 | N | ARG | D | 31 | 46.386 | 66.695 | 142.031 | 1.00 | 57.24 | 7 |
| ATOM | 2643 | CA | ARG | D | 31 | 47.159 | 66.392 | 140.843 | 1.00 | 57.14 | 6 |
| ATOM | 2644 | CB | ARG | D | 31 | 46.153 | 66.085 | 139.757 | 1.00 | 57.14 | 6 |
| ATOM | 2645 | CG | ARG | D | 31 | 46.359 | 64.798 | 139.064 | 1.00 | 58.78 | 6 |
| ATOM | 2646 | CD | ARG | D | 31 | 45.099 | 64.491 | 138.286 | 1.00 | 61.86 | 6 |
| ATOM | 2647 | NE | ARG | D | 31 | 44.077 | 63.782 | 139.076 | 1.00 | 63.51 | 7 |
| ATOM | 2648 | CZ | ARG | D | 31 | 42.771 | 63.758 | 138.777 | 1.00 | 63.63 | 6 |
| ATOM | 2649 | NH1 | ARG | D | 31 | 42.294 | 64.425 | 137.725 | 1.00 | 62.62 | 7 |
| ATOM | 2650 | NH2 | ARG | D | 31 | 41.927 | 63.072 | 139.540 | 1.00 | 64.17 | 7 |
| ATOM | 2651 | C | ARG | D | 31 | 47.989 | 67.576 | 140.385 | 1.00 | 56.73 | 6 |
| ATOM | 2652 | O | ARG | D | 31 | 49.127 | 67.430 | 139.911 | 1.00 | 56.39 | 8 |
| ATOM | 2653 | N | ILE | D | 32 | 47.373 | 68.749 | 140.512 | 1.00 | 56.50 | 7 |
| ATOM | 2654 | CA | ILE | D | 32 | 47.971 | 70.008 | 140.126 | 1.00 | 56.15 | 6 |
| ATOM | 2655 | CB | ILE | D | 32 | 46.921 | 71.142 | 140.059 | 1.00 | 56.07 | 6 |
| ATOM | 2656 | CG1 | ILE | D | 32 | 45.991 | 70.962 | 138.858 | 1.00 | 55.42 | 6 |
| ATOM | 2657 | CD | ILE | D | 32 | 44.830 | 71.940 | 138.839 | 1.00 | 55.57 | 6 |
| ATOM | 2658 | CG2 | ILE | D | 32 | 47.590 | 72.487 | 139.926 | 1.00 | 56.57 | 6 |
| ATOM | 2659 | C | ILE | D | 32 | 49.106 | 70.337 | 141.083 | 1.00 | 56.23 | 6 |
| ATOM | 2660 | O | ILE | D | 32 | 50.166 | 70.757 | 140.646 | 1.00 | 56.54 | 8 |
| ATOM | 2661 | N | LEU | D | 33 | 48.898 | 70.118 | 142.379 | 1.00 | 56.26 | 7 |
| ATOM | 2662 | CA | LEU | D | 33 | 49.977 | 70.265 | 143.370 | 1.00 | 56.10 | 6 |
| ATOM | 2663 | CB | LEU | D | 33 | 49.409 | 70.214 | 144.767 | 1.00 | 55.63 | 6 |
| ATOM | 2664 | CG | LEU | D | 33 | 48.540 | 71.432 | 144.996 | 1.00 | 55.06 | 6 |
| ATOM | 2665 | CD1 | LEU | D | 33 | 47.580 | 71.158 | 146.123 | 1.00 | 56.17 | 6 |
| ATOM | 2666 | CD2 | LEU | D | 33 | 49.414 | 72.611 | 145.297 | 1.00 | 53.85 | 6 |
| ATOM | 2667 | C | LEU | D | 33 | 51.102 | 69.244 | 143.206 | 1.00 | 56.15 | 6 |
| ATOM | 2668 | O | LEU | D | 33 | 52.262 | 69.548 | 143.385 | 1.00 | 56.01 | 8 |
| ATOM | 2669 | N | MET | D | 34 | 50.748 | 68.031 | 142.841 | 1.00 | 56.56 | 7 |
| ATOM | 2670 | CA | MET | D | 34 | 51.736 | 67.056 | 142.472 | 1.00 | 57.10 | 6 |
| ATOM | 2671 | CB | MET | D | 34 | 51.065 | 65.756 | 142.042 | 1.00 | 57.30 | 6 |
| ATOM | 2672 | CG | MET | D | 34 | 50.190 | 65.176 | 143.142 | 1.00 | 58.41 | 6 |
| ATOM | 2673 | SD | MET | D | 34 | 51.150 | 64.520 | 144.521 | 1.00 | 62.08 | 16 |
| ATOM | 2674 | CE | MET | D | 34 | 51.913 | 65.938 | 145.301 | 1.00 | 60.18 | 6 |
| ATOM | 2675 | C | MET | D | 34 | 52.602 | 67.611 | 141.369 | 1.00 | 57.05 | 6 |
| ATOM | 2676 | O | MET | D | 34 | 53.819 | 67.665 | 141.512 | 1.00 | 57.43 | 8 |
| ATOM | 2677 | N | ALA | D | 35 | 51.969 | 68.044 | 140.284 | 1.00 | 56.82 | 7 |
| ATOM | 2678 | CA | ALA | D | 35 | 52.677 | 68.571 | 139.123 | 1.00 | 56.49 | 6 |
| ATOM | 2679 | CB | ALA | D | 35 | 51.696 | 69.124 | 138.129 | 1.00 | 56.34 | 6 |
| ATOM | 2680 | C | ALA | D | 35 | 53.673 | 69.646 | 139.523 | 1.00 | 56.33 | 6 |
| ATOM | 2681 | O | ALA | D | 35 | 54.782 | 69.673 | 139.000 | 1.00 | 56.69 | 8 |
| ATOM | 2682 | N | ASN | D | 36 | 53.268 | 70.510 | 140.458 | 1.00 | 55.73 | 7 |
| ATOM | 2683 | CA | ASN | D | 36 | 54.103 | 71.565 | 141.007 | 1.00 | 54.98 | 6 |
| ATOM | 2684 | CB | ASN | D | 36 | 53.235 | 72.595 | 141.649 | 1.00 | 54.62 | 6 |
| ATOM | 2685 | CG | ASN | D | 36 | 52.666 | 73.508 | 140.666 | 1.00 | 55.34 | 6 |
| ATOM | 2686 | OD1 | ASN | D | 36 | 53.399 | 74.244 | 140.014 | 1.00 | 57.80 | 8 |
| ATOM | 2687 | ND2 | ASN | D | 36 | 51.347 | 73.483 | 140.519 | 1.00 | 54.88 | 7 |
| ATOM | 2688 | C | ASN | D | 36 | 55.042 | 71.098 | 142.067 | 1.00 | 54.87 | 6 |
| ATOM | 2689 | O | ASN | D | 36 | 55.607 | 71.921 | 142.786 | 1.00 | 55.18 | 8 |
| ATOM | 2690 | N | GLY | D | 37 | 55.171 | 69.782 | 142.192 | 1.00 | 54.57 | 7 |
| ATOM | 2691 | CA | GLY | D | 37 | 56.092 | 69.159 | 143.128 | 1.00 | 54.08 | 6 |
| ATOM | 2692 | C | GLY | D | 37 | 55.829 | 69.345 | 144.613 | 1.00 | 53.79 | 6 |
| ATOM | 2693 | O | GLY | D | 37 | 56.765 | 69.369 | 145.391 | 1.00 | 53.85 | 8 |
| ATOM | 2694 | N | ALA | D | 38 | 54.568 | 69.469 | 145.019 | 1.00 | 53.57 | 7 |
| ATOM | 2695 | CA | ALA | D | 38 | 54.216 | 69.541 | 146.440 | 1.00 | 53.06 | 6 |
| ATOM | 2696 | CB | ALA | D | 38 | 52.723 | 69.626 | 146.618 | 1.00 | 52.86 | 6 |
| ATOM | 2697 | C | ALA | D | 38 | 54.738 | 68.300 | 147.118 | 1.00 | 52.85 | 6 |
| ATOM | 2698 | O | ALA | D | 38 | 54.835 | 67.247 | 146.473 | 1.00 | 53.01 | 8 |
| ATOM | 2699 | N | ASP | D | 39 | 55.081 | 68.425 | 148.401 | 1.00 | 52.44 | 7 |
| ATOM | 2700 | CA | ASP | D | 39 | 55.623 | 67.309 | 149.166 | 1.00 | 52.26 | 6 |
| ATOM | 2701 | CB | ASP | D | 39 | 56.372 | 67.809 | 150.393 | 1.00 | 52.02 | 6 |
| ATOM | 2702 | CG | ASP | D | 39 | 56.714 | 66.686 | 151.388 | 1.00 | 53.04 | 6 |
| ATOM | 2703 | OD1 | ASP | D | 39 | 56.710 | 65.472 | 151.040 | 1.00 | 52.47 | 8 |
| ATOM | 2704 | OD2 | ASP | D | 39 | 57.001 | 67.037 | 152.548 | 1.00 | 54.96 | 8 |
| ATOM | 2705 | C | ASP | D | 39 | 54.522 | 66.343 | 149.591 | 1.00 | 52.11 | 6 |
| ATOM | 2706 | O | ASP | D | 39 | 53.676 | 66.690 | 150.427 | 1.00 | 52.33 | 8 |
| ATOM | 2707 | N | VAL | D | 40 | 54.568 | 65.123 | 149.046 | 1.00 | 51.38 | 7 |

TABLE 1-continued

| | | | | | | | | | |
|---|---|---|---|---|---|---|---|---|---|
| ATOM | 2708 | CA | VAL | D | 40 | 53.517 | 64.135 | 149.254 | 1.00 | 50.70 | 6 |
| ATOM | 2709 | CB | VAL | D | 40 | 53.732 | 62.874 | 148.342 | 1.00 | 50.57 | 6 |
| ATOM | 2710 | CG1 | VAL | D | 40 | 54.702 | 61.950 | 148.948 | 1.00 | 50.64 | 6 |
| ATOM | 2711 | CG2 | VAL | D | 40 | 52.451 | 62.121 | 148.097 | 1.00 | 50.05 | 6 |
| ATOM | 2712 | C | VAL | D | 40 | 53.422 | 63.785 | 150.741 | 1.00 | 50.44 | 6 |
| ATOM | 2713 | O | VAL | D | 40 | 52.436 | 63.206 | 151.196 | 1.00 | 50.33 | 8 |
| ATOM | 2714 | N | ASN | D | 41 | 54.433 | 64.173 | 151.506 | 1.00 | 50.12 | 7 |
| ATOM | 2715 | CA | ASN | D | 41 | 54.445 | 63.833 | 152.919 | 1.00 | 50.06 | 6 |
| ATOM | 2716 | CB | ASN | D | 41 | 55.639 | 62.941 | 153.247 | 1.00 | 49.98 | 6 |
| ATOM | 2717 | CG | ASN | D | 41 | 55.477 | 61.547 | 152.697 | 1.00 | 49.62 | 6 |
| ATOM | 2718 | OD1 | ASN | D | 41 | 54.365 | 61.091 | 152.439 | 1.00 | 50.47 | 8 |
| ATOM | 2719 | ND2 | ASN | D | 41 | 56.584 | 60.865 | 152.502 | 1.00 | 49.83 | 7 |
| ATOM | 2720 | C | ASN | D | 41 | 54.339 | 64.973 | 153.900 | 1.00 | 50.08 | 6 |
| ATOM | 2721 | O | ASN | D | 41 | 54.575 | 64.801 | 155.088 | 1.00 | 50.24 | 8 |
| ATOM | 2722 | N | ALA | D | 42 | 53.955 | 66.136 | 153.412 | 1.00 | 50.00 | 7 |
| ATOM | 2723 | CA | ALA | D | 42 | 53.717 | 67.262 | 154.284 | 1.00 | 50.36 | 6 |
| ATOM | 2724 | CB | ALA | D | 42 | 52.917 | 68.259 | 153.525 | 1.00 | 50.44 | 6 |
| ATOM | 2725 | C | ALA | D | 42 | 52.970 | 66.859 | 155.581 | 1.00 | 50.66 | 6 |
| ATOM | 2726 | O | ALA | D | 42 | 51.997 | 66.086 | 155.496 | 1.00 | 51.10 | 8 |
| ATOM | 2727 | N | ASN | D | 43 | 53.412 | 67.351 | 156.758 | 1.00 | 50.17 | 7 |
| ATOM | 2728 | CA | ASN | D | 43 | 52.612 | 67.199 | 158.000 | 1.00 | 49.75 | 6 |
| ATOM | 2729 | CB | ASN | D | 43 | 53.467 | 66.907 | 159.219 | 1.00 | 50.10 | 6 |
| ATOM | 2730 | CG | ASN | D | 43 | 54.285 | 65.667 | 159.078 | 1.00 | 51.24 | 6 |
| ATOM | 2731 | OD1 | ASN | D | 43 | 54.319 | 65.069 | 158.000 | 1.00 | 53.03 | 8 |
| ATOM | 2732 | ND2 | ASN | D | 43 | 54.980 | 65.269 | 160.166 | 1.00 | 51.07 | 7 |
| ATOM | 2733 | C | ASN | D | 43 | 51.822 | 68.432 | 158.347 | 1.00 | 49.34 | 6 |
| ATOM | 2734 | O | ASN | D | 43 | 52.269 | 69.538 | 158.073 | 1.00 | 49.80 | 8 |
| ATOM | 2735 | N | ASP | D | 44 | 50.665 | 68.249 | 158.975 | 1.00 | 48.59 | 7 |
| ATOM | 2736 | CA | ASP | D | 44 | 49.991 | 69.351 | 159.642 | 1.00 | 48.29 | 6 |
| ATOM | 2737 | CB | ASP | D | 44 | 48.491 | 69.140 | 159.620 | 1.00 | 48.73 | 6 |
| ATOM | 2738 | CG | ASP | D | 44 | 48.062 | 67.918 | 160.408 | 1.00 | 51.34 | 6 |
| ATOM | 2739 | OD1 | ASP | D | 44 | 48.877 | 67.308 | 161.140 | 1.00 | 53.22 | 8 |
| ATOM | 2740 | OD2 | ASP | D | 44 | 46.876 | 67.563 | 160.298 | 1.00 | 54.79 | 8 |
| ATOM | 2741 | C | ASP | D | 44 | 50.535 | 69.382 | 161.065 | 1.00 | 47.49 | 6 |
| ATOM | 2742 | O | ASP | D | 44 | 51.431 | 68.616 | 161.372 | 1.00 | 47.43 | 8 |
| ATOM | 2743 | N | ARG | D | 45 | 50.023 | 70.233 | 161.952 | 1.00 | 46.84 | 7 |
| ATOM | 2744 | CA | ARG | D | 45 | 50.706 | 70.332 | 163.251 | 1.00 | 46.04 | 6 |
| ATOM | 2745 | CB | ARG | D | 45 | 50.417 | 71.600 | 164.059 | 1.00 | 45.97 | 6 |
| ATOM | 2746 | CG | ARG | D | 45 | 49.075 | 71.701 | 164.644 | 1.00 | 45.40 | 6 |
| ATOM | 2747 | CD | ARG | D | 45 | 49.037 | 72.816 | 165.619 | 1.00 | 43.85 | 6 |
| ATOM | 2748 | NE | ARG | D | 45 | 48.817 | 72.309 | 166.953 | 1.00 | 43.16 | 7 |
| ATOM | 2749 | CZ | ARG | D | 45 | 47.688 | 71.747 | 167.369 | 1.00 | 43.41 | 6 |
| ATOM | 2750 | NH1 | ARG | D | 45 | 46.667 | 71.579 | 166.555 | 1.00 | 44.48 | 7 |
| ATOM | 2751 | NH2 | ARG | D | 45 | 47.579 | 71.329 | 168.613 | 1.00 | 44.79 | 7 |
| ATOM | 2752 | C | ARG | D | 45 | 50.540 | 69.121 | 164.093 | 1.00 | 45.37 | 6 |
| ATOM | 2753 | O | ARG | D | 45 | 51.354 | 68.888 | 164.962 | 1.00 | 45.16 | 8 |
| ATOM | 2754 | N | LYS | D | 46 | 49.511 | 68.332 | 163.832 | 1.00 | 44.85 | 7 |
| ATOM | 2755 | CA | LYS | D | 46 | 49.412 | 67.077 | 164.535 | 1.00 | 44.82 | 6 |
| ATOM | 2756 | CB | LYS | D | 46 | 48.093 | 66.936 | 165.275 | 1.00 | 44.58 | 6 |
| ATOM | 2757 | CG | LYS | D | 46 | 47.004 | 67.704 | 164.632 | 1.00 | 47.35 | 6 |
| ATOM | 2758 | CD | LYS | D | 46 | 45.649 | 67.019 | 164.834 | 1.00 | 52.56 | 6 |
| ATOM | 2759 | CE | LYS | D | 46 | 44.959 | 67.475 | 166.138 | 1.00 | 53.29 | 6 |
| ATOM | 2760 | NZ | LYS | D | 46 | 45.855 | 67.391 | 167.329 | 1.00 | 53.75 | 7 |
| ATOM | 2761 | C | LYS | D | 46 | 49.759 | 65.878 | 163.643 | 1.00 | 44.52 | 6 |
| ATOM | 2762 | O | LYS | D | 46 | 49.085 | 64.841 | 163.681 | 1.00 | 44.87 | 8 |
| ATOM | 2763 | N | GLY | D | 47 | 50.838 | 66.033 | 162.867 | 1.00 | 44.00 | 7 |
| ATOM | 2764 | CA | GLY | D | 47 | 51.527 | 64.936 | 162.185 | 1.00 | 43.24 | 6 |
| ATOM | 2765 | C | GLY | D | 47 | 50.797 | 64.191 | 161.082 | 1.00 | 43.13 | 6 |
| ATOM | 2766 | O | GLY | D | 47 | 51.317 | 63.211 | 160.536 | 1.00 | 43.35 | 8 |
| ATOM | 2767 | N | ASN | D | 48 | 49.592 | 64.630 | 160.750 | 1.00 | 42.76 | 7 |
| ATOM | 2768 | CA | ASN | D | 48 | 48.877 | 64.046 | 159.643 | 1.00 | 42.83 | 6 |
| ATOM | 2769 | CB | ASN | D | 48 | 47.467 | 64.600 | 159.611 | 1.00 | 43.56 | 6 |
| ATOM | 2770 | CG | ASN | D | 48 | 46.596 | 64.019 | 160.720 | 1.00 | 47.03 | 6 |
| ATOM | 2771 | OD1 | ASN | D | 48 | 46.662 | 62.790 | 161.032 | 1.00 | 50.61 | 8 |
| ATOM | 2772 | ND2 | ASN | D | 48 | 45.782 | 64.886 | 161.344 | 1.00 | 48.47 | 7 |
| ATOM | 2773 | C | ASN | D | 48 | 49.568 | 64.303 | 158.325 | 1.00 | 42.22 | 6 |
| ATOM | 2774 | O | ASN | D | 48 | 50.169 | 65.342 | 158.144 | 1.00 | 42.65 | 8 |
| ATOM | 2775 | N | THR | D | 49 | 49.513 | 63.347 | 157.416 | 1.00 | 41.68 | 7 |
| ATOM | 2776 | CA | THR | D | 49 | 49.959 | 63.581 | 156.057 | 1.00 | 41.50 | 6 |
| ATOM | 2777 | CB | THR | D | 49 | 50.777 | 62.403 | 155.517 | 1.00 | 41.96 | 6 |
| ATOM | 2778 | OG1 | THR | D | 49 | 49.956 | 61.221 | 155.443 | 1.00 | 41.45 | 8 |
| ATOM | 2779 | CG2 | THR | D | 49 | 52.039 | 62.166 | 156.362 | 1.00 | 42.52 | 6 |
| ATOM | 2780 | C | THR | D | 49 | 48.743 | 63.717 | 155.162 | 1.00 | 41.13 | 6 |
| ATOM | 2781 | O | THR | D | 49 | 47.621 | 63.473 | 155.591 | 1.00 | 41.16 | 8 |
| ATOM | 2782 | N | PRO | D | 50 | 48.956 | 64.100 | 153.905 | 1.00 | 40.74 | 7 |
| ATOM | 2783 | CA | PRO | D | 50 | 47.848 | 64.047 | 152.975 | 1.00 | 40.47 | 6 |
| ATOM | 2784 | CB | PRO | D | 50 | 48.507 | 64.273 | 151.632 | 1.00 | 40.26 | 6 |
| ATOM | 2785 | CG | PRO | D | 50 | 49.719 | 65.051 | 151.962 | 1.00 | 40.72 | 6 |
| ATOM | 2786 | CD | PRO | D | 50 | 50.190 | 64.592 | 153.281 | 1.00 | 40.54 | 6 |
| ATOM | 2787 | C | PRO | D | 50 | 47.216 | 62.675 | 152.978 | 1.00 | 40.30 | 6 |

TABLE 1-continued

| | | | | | | | | | | |
|---|---|---|---|---|---|---|---|---|---|---|
| ATOM | 2788 | O | PRO | D | 50 | 45.981 | 62.588 | 152.989 | 1.00 | 40.43 | 8 |
| ATOM | 2789 | N | LEU | D | 51 | 48.031 | 61.613 | 152.991 | 1.00 | 39.72 | 7 |
| ATOM | 2790 | CA | LEU | D | 51 | 47.459 | 60.272 | 152.922 | 1.00 | 39.50 | 6 |
| ATOM | 2791 | CB | LEU | D | 51 | 48.498 | 59.178 | 152.655 | 1.00 | 39.61 | 6 |
| ATOM | 2792 | CG | LEU | D | 51 | 48.005 | 57.711 | 152.693 | 1.00 | 39.41 | 6 |
| ATOM | 2793 | CD1 | LEU | D | 51 | 47.220 | 57.340 | 151.464 | 1.00 | 38.04 | 6 |
| ATOM | 2794 | CD2 | LEU | D | 51 | 49.126 | 56.692 | 152.932 | 1.00 | 39.18 | 6 |
| ATOM | 2795 | C | LEU | D | 51 | 46.615 | 59.971 | 154.154 | 1.00 | 39.58 | 6 |
| ATOM | 2796 | O | LEU | D | 51 | 45.551 | 59.383 | 154.022 | 1.00 | 39.70 | 8 |
| ATOM | 2797 | N | HIS | D | 52 | 47.063 | 60.389 | 155.334 | 1.00 | 39.49 | 7 |
| ATOM | 2798 | CA | HIS | D | 52 | 46.198 | 60.367 | 156.501 | 1.00 | 39.72 | 6 |
| ATOM | 2799 | CB | HIS | D | 52 | 46.792 | 61.139 | 157.664 | 1.00 | 39.89 | 6 |
| ATOM | 2800 | CG | HIS | D | 52 | 47.821 | 60.384 | 158.438 | 1.00 | 42.02 | 6 |
| ATOM | 2801 | ND1 | HIS | D | 52 | 49.143 | 60.777 | 158.500 | 1.00 | 43.64 | 7 |
| ATOM | 2802 | CE1 | HIS | D | 52 | 49.815 | 59.933 | 159.261 | 1.00 | 44.05 | 6 |
| ATOM | 2803 | NE2 | HIS | D | 52 | 48.978 | 59.005 | 159.694 | 1.00 | 43.73 | 7 |
| ATOM | 2804 | CD2 | HIS | D | 52 | 47.724 | 59.267 | 159.197 | 1.00 | 43.38 | 6 |
| ATOM | 2805 | C | HIS | D | 52 | 44.871 | 61.017 | 156.172 | 1.00 | 39.71 | 6 |
| ATOM | 2806 | O | HIS | D | 52 | 43.827 | 60.372 | 156.258 | 1.00 | 39.97 | 8 |
| ATOM | 2807 | N | LEU | D | 53 | 44.886 | 62.292 | 155.795 | 1.00 | 39.54 | 7 |
| ATOM | 2808 | CA | LEU | D | 53 | 43.622 | 63.000 | 155.682 | 1.00 | 39.69 | 6 |
| ATOM | 2809 | CB | LEU | D | 53 | 43.801 | 64.482 | 155.395 | 1.00 | 39.80 | 6 |
| ATOM | 2810 | CG | LEU | D | 53 | 44.704 | 65.268 | 156.330 | 1.00 | 40.31 | 6 |
| ATOM | 2811 | CD1 | LEU | D | 53 | 44.856 | 66.684 | 155.821 | 1.00 | 41.23 | 6 |
| ATOM | 2812 | CD2 | LEU | D | 53 | 44.162 | 65.251 | 157.754 | 1.00 | 41.39 | 6 |
| ATOM | 2813 | C | LEU | D | 53 | 42.760 | 62.368 | 154.626 | 1.00 | 39.96 | 6 |
| ATOM | 2814 | O | LEU | D | 53 | 41.546 | 62.239 | 154.817 | 1.00 | 40.69 | 8 |
| ATOM | 2815 | N | ALA | D | 54 | 43.370 | 61.949 | 153.526 | 1.00 | 39.83 | 7 |
| ATOM | 2816 | CA | ALA | D | 54 | 42.590 | 61.323 | 152.474 | 1.00 | 40.18 | 6 |
| ATOM | 2817 | CB | ALA | D | 54 | 43.438 | 61.085 | 151.280 | 1.00 | 40.73 | 6 |
| ATOM | 2818 | C | ALA | D | 54 | 41.937 | 60.022 | 152.963 | 1.00 | 40.43 | 6 |
| ATOM | 2819 | O | ALA | D | 54 | 40.779 | 59.734 | 152.637 | 1.00 | 40.45 | 8 |
| ATOM | 2820 | N | ALA | D | 55 | 42.675 | 59.247 | 153.755 | 1.00 | 40.53 | 7 |
| ATOM | 2821 | CA | ALA | D | 55 | 42.098 | 58.085 | 154.427 | 1.00 | 40.76 | 6 |
| ATOM | 2822 | CB | ALA | D | 55 | 43.144 | 57.367 | 155.255 | 1.00 | 40.58 | 6 |
| ATOM | 2823 | C | ALA | D | 55 | 40.962 | 58.548 | 155.312 | 1.00 | 41.05 | 6 |
| ATOM | 2824 | O | ALA | D | 55 | 39.850 | 58.050 | 155.209 | 1.00 | 41.23 | 8 |
| ATOM | 2825 | N | ASP | D | 56 | 41.256 | 59.528 | 156.161 | 1.00 | 41.19 | 7 |
| ATOM | 2826 | CA | ASP | D | 56 | 40.314 | 60.038 | 157.130 | 1.00 | 41.51 | 6 |
| ATOM | 2827 | CB | ASP | D | 56 | 40.938 | 61.226 | 157.874 | 1.00 | 41.73 | 6 |
| ATOM | 2828 | CG | ASP | D | 56 | 40.240 | 61.512 | 159.199 | 1.00 | 43.95 | 6 |
| ATOM | 2829 | OD1 | ASP | D | 56 | 39.016 | 61.797 | 159.198 | 1.00 | 46.40 | 8 |
| ATOM | 2830 | OD2 | ASP | D | 56 | 40.905 | 61.454 | 160.260 | 1.00 | 46.26 | 8 |
| ATOM | 2831 | C | ASP | D | 56 | 38.942 | 60.394 | 156.534 | 1.00 | 41.43 | 6 |
| ATOM | 2832 | O | ASP | D | 56 | 37.928 | 60.204 | 157.200 | 1.00 | 41.20 | 8 |
| ATOM | 2833 | N | TYR | D | 57 | 38.917 | 60.882 | 155.286 | 1.00 | 41.74 | 7 |
| ATOM | 2834 | CA | TYR | D | 57 | 37.680 | 61.416 | 154.640 | 1.00 | 42.19 | 6 |
| ATOM | 2835 | CB | TYR | D | 57 | 37.930 | 62.869 | 154.209 | 1.00 | 41.96 | 6 |
| ATOM | 2836 | CG | TYR | D | 57 | 38.023 | 63.787 | 155.379 | 1.00 | 41.76 | 6 |
| ATOM | 2837 | CD1 | TYR | D | 57 | 39.115 | 63.738 | 156.230 | 1.00 | 41.22 | 6 |
| ATOM | 2838 | CE1 | TYR | D | 57 | 39.200 | 64.562 | 157.336 | 1.00 | 41.61 | 6 |
| ATOM | 2839 | CZ | TYR | D | 57 | 38.186 | 65.460 | 157.601 | 1.00 | 42.46 | 6 |
| ATOM | 2840 | OH | TYR | D | 57 | 38.294 | 66.277 | 158.703 | 1.00 | 43.34 | 8 |
| ATOM | 2841 | CE2 | TYR | D | 57 | 37.072 | 65.531 | 156.773 | 1.00 | 42.25 | 6 |
| ATOM | 2842 | CD2 | TYR | D | 57 | 36.998 | 64.685 | 155.668 | 1.00 | 42.19 | 6 |
| ATOM | 2843 | C | TYR | D | 57 | 37.206 | 60.585 | 153.433 | 1.00 | 42.47 | 6 |
| ATOM | 2844 | O | TYR | D | 57 | 36.822 | 61.132 | 152.411 | 1.00 | 42.33 | 8 |
| ATOM | 2845 | N | ASP | D | 58 | 37.185 | 59.267 | 153.587 | 1.00 | 43.05 | 7 |
| ATOM | 2846 | CA | ASP | D | 58 | 37.600 | 58.402 | 152.491 | 1.00 | 43.89 | 6 |
| ATOM | 2847 | CB | ASP | D | 58 | 37.034 | 56.984 | 152.575 | 1.00 | 43.92 | 6 |
| ATOM | 2848 | CG | ASP | D | 58 | 35.583 | 56.954 | 152.365 | 1.00 | 44.00 | 6 |
| ATOM | 2849 | OD1 | ASP | D | 58 | 35.018 | 58.054 | 152.376 | 1.00 | 44.16 | 8 |
| ATOM | 2850 | OD2 | ASP | D | 58 | 35.015 | 55.863 | 152.174 | 1.00 | 44.65 | 8 |
| ATOM | 2851 | C | ASP | D | 58 | 37.481 | 59.024 | 151.103 | 1.00 | 44.35 | 6 |
| ATOM | 2852 | O | ASP | D | 58 | 36.404 | 59.294 | 150.583 | 1.00 | 43.98 | 8 |
| ATOM | 2853 | N | HIS | D | 59 | 38.656 | 59.241 | 150.541 | 1.00 | 45.45 | 7 |
| ATOM | 2854 | CA | HIS | D | 59 | 38.826 | 59.765 | 149.223 | 1.00 | 46.45 | 6 |
| ATOM | 2855 | CB | HIS | D | 59 | 39.527 | 61.111 | 149.332 | 1.00 | 46.36 | 6 |
| ATOM | 2856 | CG | HIS | D | 59 | 38.633 | 62.201 | 149.837 | 1.00 | 47.07 | 6 |
| ATOM | 2857 | ND1 | HIS | D | 59 | 37.352 | 62.387 | 149.369 | 1.00 | 47.38 | 7 |
| ATOM | 2858 | CE1 | HIS | D | 59 | 36.801 | 63.417 | 149.986 | 1.00 | 47.75 | 6 |
| ATOM | 2859 | NE2 | HIS | D | 59 | 37.680 | 63.913 | 150.835 | 1.00 | 47.98 | 7 |
| ATOM | 2860 | CD2 | HIS | D | 59 | 38.835 | 63.170 | 150.761 | 1.00 | 48.40 | 6 |
| ATOM | 2861 | C | HIS | D | 59 | 39.661 | 58.742 | 148.492 | 1.00 | 46.98 | 6 |
| ATOM | 2862 | O | HIS | D | 59 | 40.877 | 58.879 | 148.377 | 1.00 | 47.24 | 8 |
| ATOM | 2863 | N | LEU | D | 60 | 38.989 | 57.703 | 148.019 | 1.00 | 47.63 | 7 |
| ATOM | 2864 | CA | LEU | D | 60 | 39.667 | 56.527 | 147.508 | 1.00 | 48.47 | 6 |
| ATOM | 2865 | CB | LEU | D | 60 | 38.676 | 55.559 | 146.854 | 1.00 | 48.69 | 6 |
| ATOM | 2866 | CG | LEU | D | 60 | 39.214 | 54.183 | 146.452 | 1.00 | 47.75 | 6 |
| ATOM | 2867 | CD1 | LEU | D | 60 | 39.881 | 53.552 | 147.639 | 1.00 | 47.41 | 6 |

TABLE 1-continued

| | | | | | | | | | | |
|---|---|---|---|---|---|---|---|---|---|---|
| ATOM | 2868 | CD2 | LEU | D | 60 | 38.104 | 53.270 | 145.940 | 1.00 | 48.12 | 6 |
| ATOM | 2869 | C | LEU | D | 60 | 40.709 | 56.889 | 146.497 | 1.00 | 49.37 | 6 |
| ATOM | 2870 | O | LEU | D | 60 | 41.850 | 56.479 | 146.629 | 1.00 | 49.75 | 8 |
| ATOM | 2871 | N | GLU | D | 61 | 40.306 | 57.645 | 145.479 | 1.00 | 50.35 | 7 |
| ATOM | 2872 | CA | GLU | D | 61 | 41.176 | 57.927 | 144.327 | 1.00 | 51.65 | 6 |
| ATOM | 2873 | CB | GLU | D | 61 | 40.435 | 58.503 | 143.096 | 1.00 | 52.16 | 6 |
| ATOM | 2874 | CG | GLU | D | 61 | 39.328 | 59.530 | 143.409 | 1.00 | 57.83 | 6 |
| ATOM | 2875 | CD | GLU | D | 61 | 38.344 | 59.058 | 144.527 | 1.00 | 64.50 | 6 |
| ATOM | 2876 | OE1 | GLU | D | 61 | 38.537 | 59.433 | 145.741 | 1.00 | 65.38 | 8 |
| ATOM | 2877 | OE2 | GLU | D | 61 | 37.403 | 58.284 | 144.178 | 1.00 | 66.25 | 8 |
| ATOM | 2878 | C | GLU | D | 61 | 42.343 | 58.770 | 144.764 | 1.00 | 51.09 | 6 |
| ATOM | 2879 | O | GLU | D | 61 | 43.487 | 58.403 | 144.476 | 1.00 | 51.37 | 8 |
| ATOM | 2880 | N | ILE | D | 62 | 42.076 | 59.847 | 145.509 | 1.00 | 50.59 | 7 |
| ATOM | 2881 | CA | ILE | D | 62 | 43.175 | 60.640 | 146.082 | 1.00 | 50.05 | 6 |
| ATOM | 2882 | CB | ILE | D | 62 | 42.717 | 61.735 | 147.046 | 1.00 | 49.93 | 6 |
| ATOM | 2883 | CG1 | ILE | D | 62 | 41.946 | 62.832 | 146.297 | 1.00 | 49.95 | 6 |
| ATOM | 2884 | CD | ILE | D | 62 | 41.808 | 64.172 | 147.092 | 1.00 | 49.66 | 6 |
| ATOM | 2885 | CG2 | ILE | D | 62 | 43.924 | 62.312 | 147.791 | 1.00 | 48.28 | 6 |
| ATOM | 2886 | C | ILE | D | 62 | 44.175 | 59.747 | 146.815 | 1.00 | 50.09 | 6 |
| ATOM | 2887 | O | ILE | D | 62 | 45.391 | 59.902 | 146.649 | 1.00 | 50.31 | 8 |
| ATOM | 2888 | N | VAL | D | 63 | 43.668 | 58.800 | 147.601 | 1.00 | 49.72 | 7 |
| ATOM | 2889 | CA | VAL | D | 63 | 44.549 | 57.879 | 148.292 | 1.00 | 49.62 | 6 |
| ATOM | 2890 | CB | VAL | D | 63 | 43.788 | 56.814 | 149.086 | 1.00 | 49.10 | 6 |
| ATOM | 2891 | CG1 | VAL | D | 63 | 44.723 | 55.739 | 149.554 | 1.00 | 48.31 | 6 |
| ATOM | 2892 | CG2 | VAL | D | 63 | 43.131 | 57.425 | 150.267 | 1.00 | 48.71 | 6 |
| ATOM | 2893 | C | VAL | D | 63 | 45.472 | 57.232 | 147.280 | 1.00 | 50.33 | 6 |
| ATOM | 2894 | O | VAL | D | 63 | 46.689 | 57.192 | 147.472 | 1.00 | 50.30 | 8 |
| ATOM | 2895 | N | GLU | D | 64 | 44.901 | 56.765 | 146.178 | 1.00 | 51.16 | 7 |
| ATOM | 2896 | CA | GLU | D | 64 | 45.698 | 56.058 | 145.197 | 1.00 | 52.39 | 6 |
| ATOM | 2897 | CB | GLU | D | 64 | 44.801 | 55.356 | 144.206 | 1.00 | 52.50 | 6 |
| ATOM | 2898 | CG | GLU | D | 64 | 45.290 | 53.947 | 143.915 | 1.00 | 55.95 | 6 |
| ATOM | 2899 | CD | GLU | D | 64 | 44.135 | 52.950 | 143.750 | 1.00 | 60.39 | 6 |
| ATOM | 2900 | OE1 | GLU | D | 64 | 42.954 | 53.396 | 143.883 | 1.00 | 60.76 | 8 |
| ATOM | 2901 | OE2 | GLU | D | 64 | 44.416 | 51.734 | 143.493 | 1.00 | 61.33 | 8 |
| ATOM | 2902 | C | GLU | D | 64 | 46.721 | 56.977 | 144.510 | 1.00 | 52.50 | 6 |
| ATOM | 2903 | O | GLU | D | 64 | 47.905 | 56.620 | 144.337 | 1.00 | 52.42 | 8 |
| ATOM | 2904 | N | VAL | D | 65 | 46.263 | 58.176 | 144.163 | 1.00 | 52.54 | 7 |
| ATOM | 2905 | CA | VAL | D | 65 | 47.125 | 59.190 | 143.589 | 1.00 | 52.40 | 6 |
| ATOM | 2906 | CB | VAL | D | 65 | 46.357 | 60.472 | 143.341 | 1.00 | 52.04 | 6 |
| ATOM | 2907 | CG1 | VAL | D | 65 | 47.193 | 61.419 | 142.502 | 1.00 | 52.15 | 6 |
| ATOM | 2908 | CG2 | VAL | D | 65 | 45.076 | 60.159 | 142.633 | 1.00 | 52.36 | 6 |
| ATOM | 2909 | C | VAL | D | 65 | 48.324 | 59.474 | 144.487 | 1.00 | 52.53 | 6 |
| ATOM | 2910 | O | VAL | D | 65 | 49.448 | 59.577 | 144.001 | 1.00 | 52.55 | 8 |
| ATOM | 2911 | N | LEU | D | 66 | 48.082 | 59.588 | 145.790 | 1.00 | 52.55 | 7 |
| ATOM | 2912 | CA | LEU | D | 66 | 49.143 | 59.858 | 146.743 | 1.00 | 53.00 | 6 |
| ATOM | 2913 | CB | LEU | D | 66 | 48.532 | 60.018 | 148.107 | 1.00 | 52.74 | 6 |
| ATOM | 2914 | CG | LEU | D | 66 | 47.829 | 61.338 | 148.317 | 1.00 | 53.72 | 6 |
| ATOM | 2915 | CD1 | LEU | D | 66 | 46.841 | 61.194 | 149.482 | 1.00 | 55.52 | 6 |
| ATOM | 2916 | CD2 | LEU | D | 66 | 48.835 | 62.454 | 148.564 | 1.00 | 52.65 | 6 |
| ATOM | 2917 | C | LEU | D | 66 | 50.176 | 58.735 | 146.799 | 1.00 | 53.53 | 6 |
| ATOM | 2918 | O | LEU | D | 66 | 51.393 | 58.957 | 146.875 | 1.00 | 53.43 | 8 |
| ATOM | 2919 | N | LEU | D | 67 | 49.665 | 57.513 | 146.770 | 1.00 | 53.94 | 7 |
| ATOM | 2920 | CA | LEU | D | 67 | 50.513 | 56.359 | 146.841 | 1.00 | 54.00 | 6 |
| ATOM | 2921 | CB | LEU | D | 67 | 49.676 | 55.106 | 147.103 | 1.00 | 54.17 | 6 |
| ATOM | 2922 | CG | LEU | D | 67 | 48.995 | 55.003 | 148.479 | 1.00 | 54.11 | 6 |
| ATOM | 2923 | CD1 | LEU | D | 67 | 47.983 | 53.882 | 148.478 | 1.00 | 54.74 | 6 |
| ATOM | 2924 | CD2 | LEU | D | 67 | 49.991 | 54.797 | 149.624 | 1.00 | 54.00 | 6 |
| ATOM | 2925 | C | LEU | D | 67 | 51.307 | 56.268 | 145.558 | 1.00 | 54.02 | 6 |
| ATOM | 2926 | O | LEU | D | 67 | 52.473 | 55.913 | 145.612 | 1.00 | 54.06 | 8 |
| ATOM | 2927 | N | LYS | D | 68 | 50.679 | 56.622 | 144.428 | 1.00 | 54.02 | 7 |
| ATOM | 2928 | CA | LYS | D | 68 | 51.336 | 56.647 | 143.118 | 1.00 | 54.25 | 6 |
| ATOM | 2929 | CB | LYS | D | 68 | 50.390 | 57.142 | 142.022 | 1.00 | 54.43 | 6 |
| ATOM | 2930 | CG | LYS | D | 68 | 49.465 | 56.086 | 141.426 | 1.00 | 55.79 | 6 |
| ATOM | 2931 | CD | LYS | D | 68 | 48.256 | 56.748 | 140.659 | 1.00 | 56.44 | 6 |
| ATOM | 2932 | CE | LYS | D | 68 | 47.367 | 55.737 | 139.825 | 1.00 | 57.51 | 6 |
| ATOM | 2933 | NZ | LYS | D | 68 | 46.472 | 54.817 | 140.634 | 1.00 | 57.53 | 7 |
| ATOM | 2934 | C | LYS | D | 68 | 52.526 | 57.565 | 143.160 | 1.00 | 53.49 | 6 |
| ATOM | 2935 | O | LYS | D | 68 | 53.503 | 57.319 | 142.492 | 1.00 | 53.46 | 8 |
| ATOM | 2936 | N | HIS | D | 69 | 52.438 | 58.625 | 143.952 | 1.00 | 53.09 | 7 |
| ATOM | 2937 | CA | HIS | D | 69 | 53.504 | 59.614 | 144.009 | 1.00 | 52.93 | 6 |
| ATOM | 2938 | CB | HIS | D | 69 | 52.931 | 61.029 | 143.973 | 1.00 | 53.08 | 6 |
| ATOM | 2939 | CG | HIS | D | 69 | 52.352 | 61.391 | 142.650 | 1.00 | 53.21 | 6 |
| ATOM | 2940 | ND1 | HIS | D | 69 | 53.114 | 61.461 | 141.506 | 1.00 | 53.80 | 7 |
| ATOM | 2941 | CE1 | HIS | D | 69 | 52.343 | 61.772 | 140.481 | 1.00 | 53.87 | 6 |
| ATOM | 2942 | NE2 | HIS | D | 69 | 51.104 | 61.892 | 140.919 | 1.00 | 54.69 | 7 |
| ATOM | 2943 | CD2 | HIS | D | 69 | 51.083 | 61.660 | 142.274 | 1.00 | 54.11 | 6 |
| ATOM | 2944 | C | HIS | D | 69 | 54.387 | 59.398 | 145.225 | 1.00 | 52.81 | 6 |
| ATOM | 2945 | O | HIS | D | 69 | 55.193 | 60.258 | 145.610 | 1.00 | 52.71 | 8 |
| ATOM | 2946 | N | GLY | D | 70 | 54.204 | 58.237 | 145.835 | 1.00 | 52.60 | 7 |
| ATOM | 2947 | CA | GLY | D | 70 | 55.108 | 57.749 | 146.853 | 1.00 | 52.10 | 6 |

TABLE 1-continued

| ATOM | 2948 | C   | GLY | D | 70 | 54.890 | 58.330 | 148.222 | 1.00 | 51.92 | 6 |
|------|------|-----|-----|---|----|--------|--------|---------|------|-------|---|
| ATOM | 2949 | O   | GLY | D | 70 | 55.850 | 58.600 | 148.922 | 1.00 | 52.00 | 8 |
| ATOM | 2950 | N   | ALA | D | 71 | 53.635 | 58.531 | 148.615 | 1.00 | 51.78 | 7 |
| ATOM | 2951 | CA  | ALA | D | 71 | 53.336 | 58.858 | 150.004 | 1.00 | 51.36 | 6 |
| ATOM | 2952 | CB  | ALA | D | 71 | 51.844 | 59.052 | 150.195 | 1.00 | 51.20 | 6 |
| ATOM | 2953 | C   | ALA | D | 71 | 53.832 | 57.700 | 150.858 | 1.00 | 51.12 | 6 |
| ATOM | 2954 | O   | ALA | D | 71 | 53.669 | 56.542 | 150.476 | 1.00 | 51.47 | 8 |
| ATOM | 2955 | N   | ASP | D | 72 | 54.465 | 57.997 | 151.987 | 1.00 | 50.60 | 7 |
| ATOM | 2956 | CA  | ASP | D | 72 | 54.756 | 56.961 | 152.970 | 1.00 | 50.14 | 6 |
| ATOM | 2957 | CB  | ASP | D | 72 | 55.608 | 57.529 | 154.093 | 1.00 | 50.09 | 6 |
| ATOM | 2958 | CG  | ASP | D | 72 | 55.697 | 56.599 | 155.271 | 1.00 | 51.04 | 6 |
| ATOM | 2959 | OD1 | ASP | D | 72 | 54.796 | 55.751 | 155.420 | 1.00 | 52.00 | 8 |
| ATOM | 2960 | OD2 | ASP | D | 72 | 56.671 | 56.693 | 156.045 | 1.00 | 52.95 | 8 |
| ATOM | 2961 | C   | ASP | D | 72 | 53.450 | 56.360 | 153.535 | 1.00 | 49.61 | 6 |
| ATOM | 2962 | O   | ASP | D | 72 | 52.676 | 57.051 | 154.208 | 1.00 | 49.73 | 8 |
| ATOM | 2963 | N   | VAL | D | 73 | 53.217 | 55.077 | 153.266 | 1.00 | 48.82 | 7 |
| ATOM | 2964 | CA  | VAL | D | 73 | 51.958 | 54.439 | 153.652 | 1.00 | 48.30 | 6 |
| ATOM | 2965 | CB  | VAL | D | 73 | 51.732 | 53.077 | 152.950 | 1.00 | 48.21 | 6 |
| ATOM | 2966 | CG1 | VAL | D | 73 | 52.632 | 52.002 | 153.532 | 1.00 | 47.33 | 6 |
| ATOM | 2967 | CG2 | VAL | D | 73 | 50.278 | 52.653 | 153.073 | 1.00 | 47.25 | 6 |
| ATOM | 2968 | C   | VAL | D | 73 | 51.809 | 54.244 | 155.158 | 1.00 | 48.27 | 6 |
| ATOM | 2969 | O   | VAL | D | 73 | 50.706 | 54.279 | 155.681 | 1.00 | 48.46 | 8 |
| ATOM | 2970 | N   | ASN | D | 74 | 52.915 | 54.013 | 155.848 | 1.00 | 48.08 | 7 |
| ATOM | 2971 | CA  | ASN | D | 74 | 52.874 | 53.768 | 157.288 | 1.00 | 47.92 | 6 |
| ATOM | 2972 | CB  | ASN | D | 74 | 53.873 | 52.686 | 157.667 | 1.00 | 48.30 | 6 |
| ATOM | 2973 | CG  | ASN | D | 74 | 53.529 | 51.373 | 157.083 | 1.00 | 48.84 | 6 |
| ATOM | 2974 | OD1 | ASN | D | 74 | 52.379 | 50.958 | 157.106 | 1.00 | 51.13 | 8 |
| ATOM | 2975 | ND2 | ASN | D | 74 | 54.521 | 50.702 | 156.540 | 1.00 | 49.72 | 7 |
| ATOM | 2976 | C   | ASN | D | 74 | 53.184 | 55.019 | 158.102 | 1.00 | 47.63 | 6 |
| ATOM | 2977 | O   | ASN | D | 74 | 53.726 | 54.936 | 159.221 | 1.00 | 47.50 | 8 |
| ATOM | 2978 | N   | ALA | D | 75 | 52.866 | 56.178 | 157.540 | 1.00 | 46.96 | 7 |
| ATOM | 2979 | CA  | ALA | D | 75 | 53.193 | 57.397 | 158.215 | 1.00 | 46.80 | 6 |
| ATOM | 2980 | CB  | ALA | D | 75 | 52.831 | 58.567 | 157.342 | 1.00 | 46.83 | 6 |
| ATOM | 2981 | C   | ALA | D | 75 | 52.403 | 57.393 | 159.513 | 1.00 | 46.91 | 6 |
| ATOM | 2982 | O   | ALA | D | 75 | 51.207 | 57.064 | 159.490 | 1.00 | 47.21 | 8 |
| ATOM | 2983 | N   | HIS | D | 76 | 53.077 | 57.688 | 160.633 | 1.00 | 46.60 | 7 |
| ATOM | 2984 | CA  | HIS | D | 76 | 52.419 | 57.883 | 161.926 | 1.00 | 46.36 | 6 |
| ATOM | 2985 | CB  | HIS | D | 76 | 53.392 | 57.508 | 163.031 | 1.00 | 46.65 | 6 |
| ATOM | 2986 | CG  | HIS | D | 76 | 53.740 | 56.055 | 163.071 | 1.00 | 48.58 | 6 |
| ATOM | 2987 | ND1 | HIS | D | 76 | 53.021 | 55.135 | 163.807 | 1.00 | 50.60 | 7 |
| ATOM | 2988 | CE1 | HIS | D | 76 | 53.551 | 53.933 | 163.661 | 1.00 | 49.68 | 6 |
| ATOM | 2989 | NE2 | HIS | D | 76 | 54.590 | 54.038 | 162.854 | 1.00 | 51.06 | 7 |
| ATOM | 2990 | CD2 | HIS | D | 76 | 54.733 | 55.356 | 162.474 | 1.00 | 50.44 | 6 |
| ATOM | 2991 | C   | HIS | D | 76 | 52.033 | 59.364 | 162.068 | 1.00 | 45.97 | 6 |
| ATOM | 2992 | O   | HIS | D | 76 | 52.771 | 60.222 | 161.613 | 1.00 | 45.86 | 8 |
| ATOM | 2993 | N   | ASP | D | 77 | 50.885 | 59.690 | 162.667 | 1.00 | 45.68 | 7 |
| ATOM | 2994 | CA  | ASP | D | 77 | 50.619 | 61.100 | 163.054 | 1.00 | 45.23 | 6 |
| ATOM | 2995 | CB  | ASP | D | 77 | 49.129 | 61.412 | 163.245 | 1.00 | 45.55 | 6 |
| ATOM | 2996 | CG  | ASP | D | 77 | 48.507 | 60.627 | 164.409 | 1.00 | 48.44 | 6 |
| ATOM | 2997 | OD1 | ASP | D | 77 | 49.190 | 59.684 | 164.885 | 1.00 | 51.41 | 8 |
| ATOM | 2998 | OD2 | ASP | D | 77 | 47.347 | 60.922 | 164.848 | 1.00 | 50.65 | 8 |
| ATOM | 2999 | C   | ASP | D | 77 | 51.371 | 61.240 | 164.346 | 1.00 | 44.37 | 6 |
| ATOM | 3000 | O   | ASP | D | 77 | 52.162 | 60.369 | 164.667 | 1.00 | 44.16 | 8 |
| ATOM | 3001 | N   | ASN | D | 78 | 51.156 | 62.292 | 165.118 | 1.00 | 43.90 | 7 |
| ATOM | 3002 | CA  | ASN | D | 78 | 51.989 | 62.401 | 166.343 | 1.00 | 43.50 | 6 |
| ATOM | 3003 | CB  | ASN | D | 78 | 52.547 | 63.819 | 166.645 | 1.00 | 43.72 | 6 |
| ATOM | 3004 | CG  | ASN | D | 78 | 51.574 | 64.922 | 166.295 | 1.00 | 45.22 | 6 |
| ATOM | 3005 | OD1 | ASN | D | 78 | 51.854 | 66.108 | 166.466 | 1.00 | 44.24 | 8 |
| ATOM | 3006 | ND2 | ASN | D | 78 | 50.399 | 64.528 | 165.812 | 1.00 | 49.16 | 7 |
| ATOM | 3007 | C   | ASN | D | 78 | 51.416 | 61.709 | 167.552 | 1.00 | 42.45 | 6 |
| ATOM | 3008 | O   | ASN | D | 78 | 52.060 | 61.656 | 168.579 | 1.00 | 42.53 | 8 |
| ATOM | 3009 | N   | ASP | D | 79 | 50.233 | 61.139 | 167.389 | 1.00 | 41.68 | 7 |
| ATOM | 3010 | CA  | ASP | D | 79 | 49.670 | 60.209 | 168.346 | 1.00 | 41.40 | 6 |
| ATOM | 3011 | CB  | ASP | D | 79 | 48.182 | 60.472 | 168.500 | 1.00 | 41.62 | 6 |
| ATOM | 3012 | CG  | ASP | D | 79 | 47.888 | 61.535 | 169.535 | 1.00 | 43.66 | 6 |
| ATOM | 3013 | OD1 | ASP | D | 79 | 48.727 | 61.741 | 170.429 | 1.00 | 45.21 | 8 |
| ATOM | 3014 | OD2 | ASP | D | 79 | 46.810 | 62.165 | 169.477 | 1.00 | 47.28 | 8 |
| ATOM | 3015 | C   | ASP | D | 79 | 49.899 | 58.770 | 167.903 | 1.00 | 41.08 | 6 |
| ATOM | 3016 | O   | ASP | D | 79 | 49.467 | 57.831 | 168.576 | 1.00 | 41.15 | 8 |
| ATOM | 3017 | N   | GLY | D | 80 | 50.552 | 58.601 | 166.752 | 1.00 | 40.54 | 7 |
| ATOM | 3018 | CA  | GLY | D | 80 | 50.996 | 57.294 | 166.299 | 1.00 | 39.71 | 6 |
| ATOM | 3019 | C   | GLY | D | 80 | 50.060 | 56.566 | 165.382 | 1.00 | 39.20 | 6 |
| ATOM | 3020 | O   | GLY | D | 80 | 50.347 | 55.449 | 164.991 | 1.00 | 39.64 | 8 |
| ATOM | 3021 | N   | SER | D | 81 | 48.940 | 57.176 | 165.033 | 1.00 | 38.75 | 7 |
| ATOM | 3022 | CA  | SER | D | 81 | 47.964 | 56.516 | 164.162 | 1.00 | 38.59 | 6 |
| ATOM | 3023 | CB  | SER | D | 81 | 46.602 | 57.193 | 164.241 | 1.00 | 39.27 | 6 |
| ATOM | 3024 | OG  | SER | D | 81 | 46.353 | 57.795 | 165.520 | 1.00 | 41.92 | 8 |
| ATOM | 3025 | C   | SER | D | 81 | 48.420 | 56.583 | 162.738 | 1.00 | 37.93 | 6 |
| ATOM | 3026 | O   | SER | D | 81 | 48.828 | 57.630 | 162.270 | 1.00 | 37.74 | 8 |
| ATOM | 3027 | N   | THR | D | 82 | 48.364 | 55.453 | 162.055 | 1.00 | 37.77 | 7 |

TABLE 1-continued

| | | | | | | | | | | |
|---|---|---|---|---|---|---|---|---|---|---|
| ATOM | 3028 | CA | THR | D | 82 | 48.639 | 55.399 | 160.623 | 1.00 | 37.54 | 6 |
| ATOM | 3029 | CB | THR | D | 82 | 49.116 | 54.041 | 160.249 | 1.00 | 37.08 | 6 |
| ATOM | 3030 | OG1 | THR | D | 82 | 47.991 | 53.158 | 160.272 | 1.00 | 37.19 | 8 |
| ATOM | 3031 | CG2 | THR | D | 82 | 50.154 | 53.580 | 161.237 | 1.00 | 36.45 | 6 |
| ATOM | 3032 | C | THR | D | 82 | 47.351 | 55.645 | 159.815 | 1.00 | 38.09 | 6 |
| ATOM | 3033 | O | THR | D | 82 | 46.215 | 55.645 | 160.374 | 1.00 | 38.23 | 8 |
| ATOM | 3034 | N | PRO | D | 83 | 47.498 | 55.881 | 158.495 | 1.00 | 38.05 | 7 |
| ATOM | 3035 | CA | PRO | D | 83 | 46.265 | 55.952 | 157.700 | 1.00 | 38.02 | 6 |
| ATOM | 3036 | CB | PRO | D | 83 | 46.782 | 56.078 | 156.272 | 1.00 | 38.07 | 6 |
| ATOM | 3037 | CG | PRO | D | 83 | 48.092 | 56.784 | 156.453 | 1.00 | 38.03 | 6 |
| ATOM | 3038 | CD | PRO | D | 83 | 48.691 | 56.149 | 157.677 | 1.00 | 37.77 | 6 |
| ATOM | 3039 | C | PRO | D | 83 | 45.423 | 54.697 | 157.886 | 1.00 | 37.86 | 6 |
| ATOM | 3040 | O | PRO | D | 83 | 44.215 | 54.808 | 158.095 | 1.00 | 37.83 | 8 |
| ATOM | 3041 | N | LEU | D | 84 | 46.067 | 53.529 | 157.879 | 1.00 | 37.61 | 7 |
| ATOM | 3042 | CA | LEU | D | 84 | 45.374 | 52.289 | 158.223 | 1.00 | 37.48 | 6 |
| ATOM | 3043 | CB | LEU | D | 84 | 46.339 | 51.132 | 158.394 | 1.00 | 37.41 | 6 |
| ATOM | 3044 | CG | LEU | D | 84 | 45.679 | 49.761 | 158.573 | 1.00 | 36.97 | 6 |
| ATOM | 3045 | CD1 | LEU | D | 84 | 44.628 | 49.434 | 157.529 | 1.00 | 35.15 | 6 |
| ATOM | 3046 | CD2 | LEU | D | 84 | 46.764 | 48.672 | 158.576 | 1.00 | 39.04 | 6 |
| ATOM | 3047 | C | LEU | D | 84 | 44.486 | 52.396 | 159.459 | 1.00 | 37.59 | 6 |
| ATOM | 3048 | O | LEU | D | 84 | 43.285 | 52.115 | 159.363 | 1.00 | 37.85 | 8 |
| ATOM | 3049 | N | HIS | D | 85 | 45.037 | 52.822 | 160.599 | 1.00 | 37.28 | 7 |
| ATOM | 3050 | CA | HIS | D | 85 | 44.171 | 53.056 | 161.778 | 1.00 | 37.54 | 6 |
| ATOM | 3051 | CB | HIS | D | 85 | 44.882 | 53.735 | 162.947 | 1.00 | 38.21 | 6 |
| ATOM | 3052 | CG | HIS | D | 85 | 46.001 | 52.936 | 163.544 | 1.00 | 40.87 | 6 |
| ATOM | 3053 | ND1 | HIS | D | 85 | 47.314 | 53.057 | 163.124 | 1.00 | 42.17 | 7 |
| ATOM | 3054 | CE1 | HIS | D | 85 | 48.077 | 52.245 | 163.835 | 1.00 | 42.82 | 6 |
| ATOM | 3055 | NE2 | HIS | D | 85 | 47.311 | 51.603 | 164.703 | 1.00 | 43.90 | 7 |
| ATOM | 3056 | CD2 | HIS | D | 85 | 46.009 | 52.026 | 164.550 | 1.00 | 43.00 | 6 |
| ATOM | 3057 | C | HIS | D | 85 | 42.971 | 53.908 | 161.408 | 1.00 | 36.73 | 6 |
| ATOM | 3058 | O | HIS | D | 85 | 41.835 | 53.550 | 161.669 | 1.00 | 36.06 | 8 |
| ATOM | 3059 | N | LEU | D | 86 | 43.227 | 55.034 | 160.771 | 1.00 | 36.74 | 7 |
| ATOM | 3060 | CA | LEU | D | 86 | 42.134 | 55.950 | 160.516 | 1.00 | 36.96 | 6 |
| ATOM | 3061 | CB | LEU | D | 86 | 42.615 | 57.268 | 159.872 | 1.00 | 36.99 | 6 |
| ATOM | 3062 | CG | LEU | D | 86 | 42.840 | 58.501 | 160.779 | 1.00 | 34.96 | 6 |
| ATOM | 3063 | CD1 | LEU | D | 86 | 43.116 | 58.165 | 162.216 | 1.00 | 32.53 | 6 |
| ATOM | 3064 | CD2 | LEU | D | 86 | 43.955 | 59.356 | 160.230 | 1.00 | 34.13 | 6 |
| ATOM | 3065 | C | LEU | D | 86 | 41.052 | 55.243 | 159.721 | 1.00 | 37.09 | 6 |
| ATOM | 3066 | O | LEU | D | 86 | 39.871 | 55.271 | 160.120 | 1.00 | 37.43 | 8 |
| ATOM | 3067 | N | ALA | D | 87 | 41.448 | 54.557 | 158.650 | 1.00 | 37.16 | 7 |
| ATOM | 3068 | CA | ALA | D | 87 | 40.444 | 53.946 | 157.763 | 1.00 | 37.64 | 6 |
| ATOM | 3069 | CB | ALA | D | 87 | 41.076 | 53.314 | 156.536 | 1.00 | 37.78 | 6 |
| ATOM | 3070 | C | ALA | D | 87 | 39.651 | 52.921 | 158.551 | 1.00 | 37.69 | 6 |
| ATOM | 3071 | O | ALA | D | 87 | 38.411 | 52.815 | 158.411 | 1.00 | 37.37 | 8 |
| ATOM | 3072 | N | ALA | D | 88 | 40.376 | 52.201 | 159.410 | 1.00 | 37.56 | 7 |
| ATOM | 3073 | CA | ALA | D | 88 | 39.749 | 51.188 | 160.243 | 1.00 | 37.61 | 6 |
| ATOM | 3074 | CB | ALA | D | 88 | 40.781 | 50.387 | 161.050 | 1.00 | 37.41 | 6 |
| ATOM | 3075 | C | ALA | D | 88 | 38.714 | 51.846 | 161.149 | 1.00 | 37.40 | 6 |
| ATOM | 3076 | O | ALA | D | 88 | 37.527 | 51.485 | 161.095 | 1.00 | 38.05 | 8 |
| ATOM | 3077 | N | LEU | D | 89 | 39.139 | 52.833 | 161.931 | 1.00 | 36.74 | 7 |
| ATOM | 3078 | CA | LEU | D | 89 | 38.235 | 53.494 | 162.842 | 1.00 | 36.75 | 6 |
| ATOM | 3079 | CB | LEU | D | 89 | 38.909 | 54.685 | 163.482 | 1.00 | 36.79 | 6 |
| ATOM | 3080 | CG | LEU | D | 89 | 38.059 | 55.434 | 164.505 | 1.00 | 36.19 | 6 |
| ATOM | 3081 | CD1 | LEU | D | 89 | 37.824 | 54.647 | 165.793 | 1.00 | 34.74 | 6 |
| ATOM | 3082 | CD2 | LEU | D | 89 | 38.754 | 56.719 | 164.804 | 1.00 | 36.48 | 6 |
| ATOM | 3083 | C | LEU | D | 89 | 36.952 | 53.951 | 162.170 | 1.00 | 37.38 | 6 |
| ATOM | 3084 | O | LEU | D | 89 | 35.858 | 53.746 | 162.709 | 1.00 | 37.43 | 8 |
| ATOM | 3085 | N | PHE | D | 90 | 37.081 | 54.544 | 160.986 | 1.00 | 37.87 | 7 |
| ATOM | 3086 | CA | PHE | D | 90 | 35.917 | 55.046 | 160.280 | 1.00 | 38.27 | 6 |
| ATOM | 3087 | CB | PHE | D | 90 | 36.303 | 56.278 | 159.496 | 1.00 | 38.20 | 6 |
| ATOM | 3088 | CG | PHE | D | 90 | 36.814 | 57.400 | 160.359 | 1.00 | 39.63 | 6 |
| ATOM | 3089 | CD1 | PHE | D | 90 | 38.054 | 57.992 | 160.105 | 1.00 | 40.65 | 6 |
| ATOM | 3090 | CE1 | PHE | D | 90 | 38.531 | 59.042 | 160.897 | 1.00 | 39.96 | 6 |
| ATOM | 3091 | CZ | PHE | D | 90 | 37.777 | 59.493 | 161.969 | 1.00 | 39.62 | 6 |
| ATOM | 3092 | CE2 | PHE | D | 90 | 36.535 | 58.909 | 162.241 | 1.00 | 39.71 | 6 |
| ATOM | 3093 | CD2 | PHE | D | 90 | 36.063 | 57.869 | 161.436 | 1.00 | 40.30 | 6 |
| ATOM | 3094 | C | PHE | D | 90 | 35.244 | 54.016 | 159.380 | 1.00 | 38.64 | 6 |
| ATOM | 3095 | O | PHE | D | 90 | 34.197 | 54.301 | 158.790 | 1.00 | 39.21 | 8 |
| ATOM | 3096 | N | GLY | D | 91 | 35.836 | 52.828 | 159.274 | 1.00 | 38.84 | 7 |
| ATOM | 3097 | CA | GLY | D | 91 | 35.289 | 51.769 | 158.433 | 1.00 | 39.45 | 6 |
| ATOM | 3098 | C | GLY | D | 91 | 35.266 | 52.052 | 156.937 | 1.00 | 40.00 | 6 |
| ATOM | 3099 | O | GLY | D | 91 | 34.398 | 51.577 | 156.229 | 1.00 | 39.86 | 8 |
| ATOM | 3100 | N | HIS | D | 92 | 36.220 | 52.834 | 156.461 | 1.00 | 40.94 | 7 |
| ATOM | 3101 | CA | HIS | D | 92 | 36.468 | 52.984 | 155.037 | 1.00 | 42.19 | 6 |
| ATOM | 3102 | CB | HIS | D | 92 | 37.366 | 54.189 | 154.806 | 1.00 | 42.71 | 6 |
| ATOM | 3103 | CG | HIS | D | 92 | 36.897 | 55.458 | 155.462 | 1.00 | 43.31 | 6 |
| ATOM | 3104 | ND1 | HIS | D | 92 | 35.574 | 55.849 | 155.490 | 1.00 | 43.59 | 7 |
| ATOM | 3105 | CE1 | HIS | D | 92 | 35.477 | 57.024 | 156.089 | 1.00 | 42.74 | 6 |
| ATOM | 3106 | NE2 | HIS | D | 92 | 36.690 | 57.417 | 156.436 | 1.00 | 41.57 | 7 |
| ATOM | 3107 | CD2 | HIS | D | 92 | 37.595 | 56.458 | 156.059 | 1.00 | 42.53 | 6 |

TABLE 1-continued

| | | | | | | | | | |
|---|---|---|---|---|---|---|---|---|---|
| ATOM | 3108 | C | HIS | D | 92 | 37.166 | 51.737 | 154.460 | 1.00 | 42.99 | 6 |
| ATOM | 3109 | O | HIS | D | 92 | 38.397 | 51.701 | 154.299 | 1.00 | 42.57 | 8 |
| ATOM | 3110 | N | LEU | D | 93 | 36.351 | 50.727 | 154.156 | 1.00 | 44.14 | 7 |
| ATOM | 3111 | CA | LEU | D | 93 | 36.795 | 49.395 | 153.731 | 1.00 | 45.21 | 6 |
| ATOM | 3112 | CB | LEU | D | 93 | 35.558 | 48.545 | 153.413 | 1.00 | 44.98 | 6 |
| ATOM | 3113 | CG | LEU | D | 93 | 34.916 | 47.793 | 154.584 | 1.00 | 46.49 | 6 |
| ATOM | 3114 | CD1 | LEU | D | 93 | 35.654 | 46.509 | 154.779 | 1.00 | 48.48 | 6 |
| ATOM | 3115 | CD2 | LEU | D | 93 | 34.850 | 48.546 | 155.950 | 1.00 | 47.77 | 6 |
| ATOM | 3116 | C | LEU | D | 93 | 37.727 | 49.446 | 152.516 | 1.00 | 45.79 | 6 |
| ATOM | 3117 | O | LEU | D | 93 | 38.927 | 49.136 | 152.619 | 1.00 | 45.73 | 8 |
| ATOM | 3118 | N | GLU | D | 94 | 37.168 | 49.864 | 151.379 | 1.00 | 46.38 | 7 |
| ATOM | 3119 | CA | GLU | D | 94 | 37.913 | 49.977 | 150.137 | 1.00 | 47.32 | 6 |
| ATOM | 3120 | CB | GLU | D | 94 | 37.209 | 50.875 | 149.123 | 1.00 | 47.87 | 6 |
| ATOM | 3121 | CG | GLU | D | 94 | 35.773 | 50.480 | 148.792 | 1.00 | 50.66 | 6 |
| ATOM | 3122 | CD | GLU | D | 94 | 34.732 | 51.000 | 149.811 | 1.00 | 54.51 | 6 |
| ATOM | 3123 | OE1 | GLU | D | 94 | 35.085 | 51.411 | 150.978 | 1.00 | 55.30 | 8 |
| ATOM | 3124 | OE2 | GLU | D | 94 | 33.541 | 50.987 | 149.409 | 1.00 | 54.82 | 8 |
| ATOM | 3125 | C | GLU | D | 94 | 39.265 | 50.566 | 150.401 | 1.00 | 47.27 | 6 |
| ATOM | 3126 | O | GLU | D | 94 | 40.253 | 50.051 | 149.909 | 1.00 | 47.63 | 8 |
| ATOM | 3127 | N | ILE | D | 95 | 39.325 | 51.642 | 151.181 | 1.00 | 47.25 | 7 |
| ATOM | 3128 | CA | ILE | D | 95 | 40.631 | 52.247 | 151.471 | 1.00 | 46.95 | 6 |
| ATOM | 3129 | CB | ILE | D | 95 | 40.528 | 53.622 | 152.125 | 1.00 | 46.49 | 6 |
| ATOM | 3130 | CG1 | ILE | D | 95 | 39.704 | 54.544 | 151.232 | 1.00 | 47.00 | 6 |
| ATOM | 3131 | CD | ILE | D | 95 | 40.035 | 56.039 | 151.322 | 1.00 | 48.34 | 6 |
| ATOM | 3132 | CG2 | ILE | D | 95 | 41.903 | 54.159 | 152.380 | 1.00 | 44.86 | 6 |
| ATOM | 3133 | C | ILE | D | 95 | 41.566 | 51.319 | 152.273 | 1.00 | 47.05 | 6 |
| ATOM | 3134 | O | ILE | D | 95 | 42.729 | 51.117 | 151.899 | 1.00 | 46.91 | 8 |
| ATOM | 3135 | N | VAL | D | 96 | 41.055 | 50.742 | 153.354 | 1.00 | 46.95 | 7 |
| ATOM | 3136 | CA | VAL | D | 96 | 41.851 | 49.807 | 154.114 | 1.00 | 47.05 | 6 |
| ATOM | 3137 | CB | VAL | D | 96 | 41.031 | 49.076 | 155.184 | 1.00 | 46.86 | 6 |
| ATOM | 3138 | CG1 | VAL | D | 96 | 41.793 | 47.913 | 155.710 | 1.00 | 46.56 | 6 |
| ATOM | 3139 | CG2 | VAL | D | 96 | 40.733 | 49.989 | 156.328 | 1.00 | 47.17 | 6 |
| ATOM | 3140 | C | VAL | D | 96 | 42.474 | 48.807 | 153.144 | 1.00 | 47.44 | 6 |
| ATOM | 3141 | O | VAL | D | 96 | 43.675 | 48.499 | 153.229 | 1.00 | 47.52 | 8 |
| ATOM | 3142 | N | GLU | D | 97 | 41.671 | 48.319 | 152.199 | 1.00 | 47.60 | 7 |
| ATOM | 3143 | CA | GLU | D | 97 | 42.181 | 47.344 | 151.253 | 1.00 | 47.52 | 6 |
| ATOM | 3144 | CB | GLU | D | 97 | 41.073 | 46.733 | 150.430 | 1.00 | 47.27 | 6 |
| ATOM | 3145 | CG | GLU | D | 97 | 41.194 | 45.235 | 150.425 | 1.00 | 50.37 | 6 |
| ATOM | 3146 | CD | GLU | D | 97 | 39.832 | 44.502 | 150.587 | 1.00 | 55.38 | 6 |
| ATOM | 3147 | OE1 | GLU | D | 97 | 38.785 | 45.211 | 150.696 | 1.00 | 56.20 | 8 |
| ATOM | 3148 | OE2 | GLU | D | 97 | 39.812 | 43.220 | 150.609 | 1.00 | 55.45 | 8 |
| ATOM | 3149 | C | GLU | D | 97 | 43.302 | 47.945 | 150.411 | 1.00 | 47.00 | 6 |
| ATOM | 3150 | O | GLU | D | 97 | 44.446 | 47.523 | 150.532 | 1.00 | 47.32 | 8 |
| ATOM | 3151 | N | VAL | D | 98 | 43.021 | 48.975 | 149.628 | 1.00 | 46.38 | 7 |
| ATOM | 3152 | CA | VAL | D | 98 | 44.094 | 49.545 | 148.812 | 1.00 | 46.13 | 6 |
| ATOM | 3153 | CB | VAL | D | 98 | 43.635 | 50.735 | 147.907 | 1.00 | 45.79 | 6 |
| ATOM | 3154 | CG1 | VAL | D | 98 | 42.442 | 51.371 | 148.476 | 1.00 | 45.71 | 6 |
| ATOM | 3155 | CG2 | VAL | D | 98 | 44.743 | 51.749 | 147.692 | 1.00 | 44.99 | 6 |
| ATOM | 3156 | C | VAL | D | 98 | 45.351 | 49.845 | 149.643 | 1.00 | 46.05 | 6 |
| ATOM | 3157 | O | VAL | D | 98 | 46.478 | 49.618 | 149.170 | 1.00 | 46.27 | 8 |
| ATOM | 3158 | N | LEU | D | 99 | 45.166 | 50.314 | 150.876 | 1.00 | 45.49 | 7 |
| ATOM | 3159 | CA | LEU | D | 99 | 46.320 | 50.560 | 151.757 | 1.00 | 45.07 | 6 |
| ATOM | 3160 | CB | LEU | D | 99 | 45.876 | 51.144 | 153.102 | 1.00 | 44.73 | 6 |
| ATOM | 3161 | CG | LEU | D | 99 | 45.508 | 52.622 | 153.075 | 1.00 | 43.54 | 6 |
| ATOM | 3162 | CD1 | LEU | D | 99 | 44.580 | 52.958 | 154.231 | 1.00 | 44.41 | 6 |
| ATOM | 3163 | CD2 | LEU | D | 99 | 46.762 | 53.445 | 153.158 | 1.00 | 42.12 | 6 |
| ATOM | 3164 | C | LEU | D | 99 | 47.149 | 49.283 | 151.958 | 1.00 | 44.90 | 6 |
| ATOM | 3165 | O | LEU | D | 99 | 48.377 | 49.258 | 151.774 | 1.00 | 44.16 | 8 |
| ATOM | 3166 | N | LEU | D | 100 | 46.442 | 48.219 | 152.305 | 1.00 | 44.97 | 7 |
| ATOM | 3167 | CA | LEU | D | 100 | 47.074 | 46.956 | 152.548 | 1.00 | 45.14 | 6 |
| ATOM | 3168 | CB | LEU | D | 100 | 46.018 | 45.915 | 152.916 | 1.00 | 44.84 | 6 |
| ATOM | 3169 | CG | LEU | D | 100 | 45.452 | 46.176 | 154.310 | 1.00 | 44.24 | 6 |
| ATOM | 3170 | CD1 | LEU | D | 100 | 44.266 | 45.300 | 154.603 | 1.00 | 43.26 | 6 |
| ATOM | 3171 | CD2 | LEU | D | 100 | 46.552 | 46.013 | 155.385 | 1.00 | 43.69 | 6 |
| ATOM | 3172 | C | LEU | D | 100 | 47.826 | 46.599 | 151.301 | 1.00 | 45.54 | 6 |
| ATOM | 3173 | O | LEU | D | 100 | 49.012 | 46.298 | 151.363 | 1.00 | 44.84 | 8 |
| ATOM | 3174 | N | LYS | D | 101 | 47.117 | 46.699 | 150.177 | 1.00 | 46.62 | 7 |
| ATOM | 3175 | CA | LYS | D | 101 | 47.627 | 46.356 | 148.877 | 1.00 | 47.97 | 6 |
| ATOM | 3176 | CB | LYS | D | 101 | 46.657 | 46.811 | 147.780 | 1.00 | 48.24 | 6 |
| ATOM | 3177 | CG | LYS | D | 101 | 46.956 | 46.186 | 146.374 | 1.00 | 51.29 | 6 |
| ATOM | 3178 | CD | LYS | D | 101 | 46.738 | 47.169 | 145.188 | 1.00 | 54.07 | 6 |
| ATOM | 3179 | CE | LYS | D | 101 | 45.236 | 47.457 | 144.939 | 1.00 | 56.15 | 6 |
| ATOM | 3180 | NZ | LYS | D | 101 | 44.935 | 48.939 | 144.795 | 1.00 | 57.79 | 7 |
| ATOM | 3181 | C | LYS | D | 101 | 48.960 | 47.041 | 148.710 | 1.00 | 48.35 | 6 |
| ATOM | 3182 | O | LYS | D | 101 | 49.917 | 46.452 | 148.233 | 1.00 | 48.54 | 8 |
| ATOM | 3183 | N | HIS | D | 102 | 49.037 | 48.289 | 149.126 | 1.00 | 49.10 | 7 |
| ATOM | 3184 | CA | HIS | D | 102 | 50.278 | 48.997 | 148.973 | 1.00 | 49.83 | 6 |
| ATOM | 3185 | CB | HIS | D | 102 | 50.026 | 50.453 | 148.615 | 1.00 | 50.28 | 6 |
| ATOM | 3186 | CG | HIS | D | 102 | 49.568 | 50.634 | 147.207 | 1.00 | 52.47 | 6 |
| ATOM | 3187 | ND1 | HIS | D | 102 | 49.607 | 51.849 | 146.560 | 1.00 | 54.04 | 7 |

TABLE 1-continued

| | | | | | | | | | |
|---|---|---|---|---|---|---|---|---|---|
| ATOM | 3188 | CE1 | HIS | D | 102 | 49.133 | 51.707 | 145.334 | 1.00 55.43 6 |
| ATOM | 3189 | NE2 | HIS | D | 102 | 48.813 | 50.435 | 145.156 | 1.00 56.22 7 |
| ATOM | 3190 | CD2 | HIS | D | 102 | 49.080 | 49.741 | 146.310 | 1.00 54.07 6 |
| ATOM | 3191 | C | HIS | D | 102 | 51.117 | 48.856 | 150.214 | 1.00 49.85 6 |
| ATOM | 3192 | O | HIS | D | 102 | 51.895 | 49.750 | 150.542 | 1.00 50.07 8 |
| ATOM | 3193 | N | GLY | D | 103 | 50.946 | 47.736 | 150.910 | 1.00 49.92 7 |
| ATOM | 3194 | CA | GLY | D | 103 | 51.864 | 47.331 | 151.990 | 1.00 49.79 6 |
| ATOM | 3195 | C | GLY | D | 103 | 51.776 | 48.053 | 153.329 | 1.00 49.60 6 |
| ATOM | 3196 | O | GLY | D | 103 | 52.767 | 48.136 | 154.057 | 1.00 49.71 8 |
| ATOM | 3197 | N | ALA | D | 104 | 50.594 | 48.585 | 153.643 | 1.00 49.21 7 |
| ATOM | 3198 | CA | ALA | D | 104 | 50.295 | 49.116 | 154.959 | 1.00 48.27 6 |
| ATOM | 3199 | CB | ALA | D | 104 | 48.817 | 49.457 | 155.057 | 1.00 48.43 6 |
| ATOM | 3200 | C | ALA | D | 104 | 50.609 | 48.041 | 155.938 | 1.00 47.70 6 |
| ATOM | 3201 | O | ALA | D | 104 | 50.172 | 46.904 | 155.778 | 1.00 47.90 8 |
| ATOM | 3202 | N | ASP | D | 105 | 51.378 | 48.393 | 156.947 | 1.00 47.30 7 |
| ATOM | 3203 | CA | ASP | D | 105 | 51.674 | 47.449 | 158.009 | 1.00 47.43 6 |
| ATOM | 3204 | CB | ASP | D | 105 | 52.836 | 47.943 | 158.859 | 1.00 47.65 6 |
| ATOM | 3205 | CG | ASP | D | 105 | 53.146 | 46.995 | 159.980 | 1.00 49.35 6 |
| ATOM | 3206 | OD1 | ASP | D | 105 | 52.416 | 45.990 | 160.093 | 1.00 52.31 8 |
| ATOM | 3207 | OD2 | ASP | D | 105 | 54.101 | 47.236 | 160.747 | 1.00 50.89 8 |
| ATOM | 3208 | C | ASP | D | 105 | 50.454 | 47.179 | 158.902 | 1.00 46.81 6 |
| ATOM | 3209 | O | ASP | D | 105 | 50.028 | 48.051 | 159.658 | 1.00 47.03 8 |
| ATOM | 3210 | N | VAL | D | 106 | 49.908 | 45.971 | 158.829 | 1.00 45.98 7 |
| ATOM | 3211 | CA | VAL | D | 106 | 48.718 | 45.650 | 159.603 | 1.00 45.54 6 |
| ATOM | 3212 | CB | VAL | D | 106 | 48.139 | 44.282 | 159.178 | 1.00 45.57 6 |
| ATOM | 3213 | CG1 | VAL | D | 106 | 49.185 | 43.177 | 159.333 | 1.00 45.17 6 |
| ATOM | 3214 | CG2 | VAL | D | 106 | 46.848 | 43.957 | 159.943 | 1.00 44.74 6 |
| ATOM | 3215 | C | VAL | D | 106 | 49.037 | 45.659 | 161.105 | 1.00 45.38 6 |
| ATOM | 3216 | O | VAL | D | 106 | 48.164 | 45.842 | 161.959 | 1.00 46.00 8 |
| ATOM | 3217 | N | ASN | D | 107 | 50.305 | 45.468 | 161.411 | 1.00 44.44 7 |
| ATOM | 3218 | CA | ASN | D | 107 | 50.727 | 45.272 | 162.769 | 1.00 43.82 6 |
| ATOM | 3219 | CB | ASN | D | 107 | 51.978 | 44.409 | 162.790 | 1.00 43.96 6 |
| ATOM | 3220 | CG | ASN | D | 107 | 51.667 | 42.965 | 162.783 | 1.00 43.63 6 |
| ATOM | 3221 | OD1 | ASN | D | 107 | 50.552 | 42.559 | 163.102 | 1.00 45.40 8 |
| ATOM | 3222 | ND2 | ASN | D | 107 | 52.645 | 42.167 | 162.437 | 1.00 42.98 7 |
| ATOM | 3223 | C | ASN | D | 107 | 51.070 | 46.553 | 163.438 | 1.00 43.38 6 |
| ATOM | 3224 | O | ASN | D | 107 | 51.303 | 46.562 | 164.643 | 1.00 43.78 8 |
| ATOM | 3225 | N | ALA | D | 108 | 51.149 | 47.622 | 162.654 | 1.00 42.64 7 |
| ATOM | 3226 | CA | ALA | D | 108 | 51.585 | 48.921 | 163.145 | 1.00 41.86 6 |
| ATOM | 3227 | CB | ALA | D | 108 | 51.520 | 49.926 | 162.033 | 1.00 41.89 6 |
| ATOM | 3228 | C | ALA | D | 108 | 50.684 | 49.337 | 164.275 | 1.00 41.55 6 |
| ATOM | 3229 | O | ALA | D | 108 | 49.448 | 49.162 | 164.186 | 1.00 41.65 8 |
| ATOM | 3230 | N | GLN | D | 109 | 51.286 | 49.864 | 165.344 | 1.00 41.02 7 |
| ATOM | 3231 | CA | GLN | D | 109 | 50.483 | 50.349 | 166.484 | 1.00 40.85 6 |
| ATOM | 3232 | CB | GLN | D | 109 | 50.621 | 49.461 | 167.717 | 1.00 40.51 6 |
| ATOM | 3233 | CG | GLN | D | 109 | 51.932 | 48.751 | 167.878 | 1.00 40.99 6 |
| ATOM | 3234 | CD | GLN | D | 109 | 52.040 | 48.087 | 169.243 | 1.00 41.68 6 |
| ATOM | 3235 | OE1 | GLN | D | 109 | 52.939 | 48.401 | 170.005 | 1.00 42.71 8 |
| ATOM | 3236 | NE2 | GLN | D | 109 | 51.097 | 47.199 | 169.575 | 1.00 42.04 7 |
| ATOM | 3237 | C | GLN | D | 109 | 50.641 | 51.825 | 166.851 | 1.00 40.50 6 |
| ATOM | 3238 | O | GLN | D | 109 | 51.721 | 52.374 | 166.752 | 1.00 40.77 8 |
| ATOM | 3239 | N | ASP | D | 110 | 49.548 | 52.461 | 167.260 | 1.00 40.06 7 |
| ATOM | 3240 | CA | ASP | D | 110 | 49.587 | 53.849 | 167.666 | 1.00 39.99 6 |
| ATOM | 3241 | CB | ASP | D | 110 | 48.196 | 54.441 | 167.600 | 1.00 40.69 6 |
| ATOM | 3242 | CG | ASP | D | 110 | 47.228 | 53.757 | 168.554 | 1.00 42.12 6 |
| ATOM | 3243 | OD1 | ASP | D | 110 | 47.674 | 53.154 | 169.561 | 1.00 42.18 8 |
| ATOM | 3244 | OD2 | ASP | D | 110 | 46.009 | 53.833 | 168.298 | 1.00 44.73 8 |
| ATOM | 3245 | C | ASP | D | 110 | 50.067 | 53.888 | 169.091 | 1.00 39.64 6 |
| ATOM | 3246 | O | ASP | D | 110 | 50.463 | 52.859 | 169.637 | 1.00 39.93 8 |
| ATOM | 3247 | N | LYS | D | 111 | 49.977 | 55.053 | 169.722 | 1.00 39.12 7 |
| ATOM | 3248 | CA | LYS | D | 111 | 50.610 | 55.272 | 171.027 | 1.00 38.69 6 |
| ATOM | 3249 | CB | LYS | D | 111 | 50.677 | 56.767 | 171.365 | 1.00 38.75 6 |
| ATOM | 3250 | CG | LYS | D | 111 | 49.407 | 57.380 | 171.880 | 1.00 38.85 6 |
| ATOM | 3251 | CD | LYS | D | 111 | 49.560 | 58.871 | 172.150 | 1.00 39.40 6 |
| ATOM | 3252 | CE | LYS | D | 111 | 48.660 | 59.273 | 173.329 | 1.00 41.93 6 |
| ATOM | 3253 | NZ | LYS | D | 111 | 48.289 | 60.728 | 173.381 | 1.00 43.00 7 |
| ATOM | 3254 | C | LYS | D | 111 | 49.991 | 54.504 | 172.172 | 1.00 38.32 6 |
| ATOM | 3255 | O | LYS | D | 111 | 50.566 | 54.449 | 173.241 | 1.00 38.35 8 |
| ATOM | 3256 | N | PHE | D | 112 | 48.811 | 53.930 | 171.947 | 1.00 38.20 7 |
| ATOM | 3257 | CA | PHE | D | 112 | 48.149 | 53.047 | 172.912 | 1.00 37.90 6 |
| ATOM | 3258 | CB | PHE | D | 112 | 46.650 | 53.254 | 172.835 | 1.00 37.59 6 |
| ATOM | 3259 | CG | PHE | D | 112 | 46.236 | 54.650 | 173.009 | 1.00 38.01 6 |
| ATOM | 3260 | CD1 | PHE | D | 112 | 45.931 | 55.138 | 174.267 | 1.00 38.14 6 |
| ATOM | 3261 | CE1 | PHE | D | 112 | 45.527 | 56.467 | 174.430 | 1.00 38.84 6 |
| ATOM | 3262 | CZ | PHE | D | 112 | 45.429 | 57.328 | 173.323 | 1.00 38.07 6 |
| ATOM | 3263 | CE2 | PHE | D | 112 | 45.722 | 56.850 | 172.063 | 1.00 38.90 6 |
| ATOM | 3264 | CD2 | PHE | D | 112 | 46.124 | 55.498 | 171.904 | 1.00 39.25 6 |
| ATOM | 3265 | C | PHE | D | 112 | 48.432 | 51.575 | 172.590 | 1.00 37.78 6 |
| ATOM | 3266 | O | PHE | D | 112 | 47.815 | 50.666 | 173.137 | 1.00 37.67 8 |
| ATOM | 3267 | N | GLY | D | 113 | 49.332 | 51.341 | 171.652 | 1.00 37.75 7 |

TABLE 1-continued

| | | | | | | | | | | |
|---|---|---|---|---|---|---|---|---|---|---|
| ATOM | 3268 | CA | GLY | D | 113 | 49.599 | 49.997 | 171.200 | 1.00 | 37.64 | 6 |
| ATOM | 3269 | C | GLY | D | 113 | 48.435 | 49.293 | 170.528 | 1.00 | 37.60 | 6 |
| ATOM | 3270 | O | GLY | D | 113 | 48.449 | 48.061 | 170.443 | 1.00 | 38.12 | 8 |
| ATOM | 3271 | N | LYS | D | 114 | 47.436 | 50.040 | 170.049 | 1.00 | 37.15 | 7 |
| ATOM | 3272 | CA | LYS | D | 114 | 46.343 | 49.433 | 169.285 | 1.00 | 36.68 | 6 |
| ATOM | 3273 | CB | LYS | D | 114 | 45.053 | 50.239 | 169.374 | 1.00 | 36.20 | 6 |
| ATOM | 3274 | CG | LYS | D | 114 | 44.621 | 50.644 | 170.746 | 1.00 | 34.82 | 6 |
| ATOM | 3275 | CD | LYS | D | 114 | 43.126 | 50.756 | 170.808 | 1.00 | 31.61 | 6 |
| ATOM | 3276 | CE | LYS | D | 114 | 42.525 | 49.461 | 171.278 | 1.00 | 30.65 | 6 |
| ATOM | 3277 | NZ | LYS | D | 114 | 42.300 | 49.489 | 172.731 | 1.00 | 31.39 | 7 |
| ATOM | 3278 | C | LYS | D | 114 | 46.728 | 49.385 | 167.835 | 1.00 | 37.20 | 6 |
| ATOM | 3279 | O | LYS | D | 114 | 47.293 | 50.332 | 167.303 | 1.00 | 37.31 | 8 |
| ATOM | 3280 | N | THR | D | 115 | 46.404 | 48.277 | 167.190 | 1.00 | 38.07 | 7 |
| ATOM | 3281 | CA | THR | D | 115 | 46.512 | 48.164 | 165.730 | 1.00 | 38.81 | 6 |
| ATOM | 3282 | CB | THR | D | 115 | 47.098 | 46.797 | 165.282 | 1.00 | 39.00 | 6 |
| ATOM | 3283 | OG1 | THR | D | 115 | 46.073 | 45.782 | 165.327 | 1.00 | 38.89 | 8 |
| ATOM | 3284 | CG2 | THR | D | 115 | 48.278 | 46.395 | 166.150 | 1.00 | 38.82 | 6 |
| ATOM | 3285 | C | THR | D | 115 | 45.126 | 48.293 | 165.082 | 1.00 | 39.25 | 6 |
| ATOM | 3286 | O | THR | D | 115 | 44.063 | 48.239 | 165.761 | 1.00 | 39.14 | 8 |
| ATOM | 3287 | N | ALA | D | 116 | 45.133 | 48.433 | 163.760 | 1.00 | 39.29 | 7 |
| ATOM | 3288 | CA | ALA | D | 116 | 43.871 | 48.480 | 163.051 | 1.00 | 39.43 | 6 |
| ATOM | 3289 | CB | ALA | D | 116 | 44.100 | 48.402 | 161.581 | 1.00 | 39.57 | 6 |
| ATOM | 3290 | C | ALA | D | 116 | 42.962 | 47.341 | 163.529 | 1.00 | 39.35 | 6 |
| ATOM | 3291 | O | ALA | D | 116 | 41.785 | 47.556 | 163.872 | 1.00 | 39.21 | 8 |
| ATOM | 3292 | N | PHE | D | 117 | 43.529 | 46.143 | 163.602 | 1.00 | 39.13 | 7 |
| ATOM | 3293 | CA | PHE | D | 117 | 42.756 | 45.006 | 164.014 | 1.00 | 39.14 | 6 |
| ATOM | 3294 | CB | PHE | D | 117 | 43.622 | 43.785 | 164.124 | 1.00 | 39.19 | 6 |
| ATOM | 3295 | CG | PHE | D | 117 | 42.847 | 42.559 | 164.482 | 1.00 | 39.34 | 6 |
| ATOM | 3296 | CD1 | PHE | D | 117 | 42.051 | 41.926 | 163.530 | 1.00 | 39.36 | 6 |
| ATOM | 3297 | CE1 | PHE | D | 117 | 41.338 | 40.799 | 163.848 | 1.00 | 38.22 | 6 |
| ATOM | 3298 | CZ | PHE | D | 117 | 41.410 | 40.285 | 165.126 | 1.00 | 38.31 | 6 |
| ATOM | 3299 | CE2 | PHE | D | 117 | 42.179 | 40.912 | 166.084 | 1.00 | 37.14 | 6 |
| ATOM | 3300 | CD2 | PHE | D | 117 | 42.885 | 42.050 | 165.766 | 1.00 | 37.40 | 6 |
| ATOM | 3301 | C | PHE | D | 117 | 42.002 | 45.189 | 165.327 | 1.00 | 39.31 | 6 |
| ATOM | 3302 | O | PHE | D | 117 | 40.805 | 44.869 | 165.388 | 1.00 | 39.25 | 8 |
| ATOM | 3303 | N | ASP | D | 118 | 42.676 | 45.687 | 166.369 | 1.00 | 39.30 | 7 |
| ATOM | 3304 | CA | ASP | D | 118 | 41.955 | 45.995 | 167.609 | 1.00 | 39.79 | 6 |
| ATOM | 3305 | CB | ASP | D | 118 | 42.823 | 46.614 | 168.685 | 1.00 | 40.66 | 6 |
| ATOM | 3306 | CG | ASP | D | 118 | 44.248 | 46.129 | 168.638 | 1.00 | 43.93 | 6 |
| ATOM | 3307 | OD1 | ASP | D | 118 | 44.709 | 45.438 | 169.599 | 1.00 | 46.69 | 8 |
| ATOM | 3308 | OD2 | ASP | D | 118 | 44.905 | 46.448 | 167.623 | 1.00 | 46.66 | 8 |
| ATOM | 3309 | C | ASP | D | 118 | 40.834 | 46.964 | 167.314 | 1.00 | 39.28 | 6 |
| ATOM | 3310 | O | ASP | D | 118 | 39.685 | 46.656 | 167.624 | 1.00 | 39.00 | 8 |
| ATOM | 3311 | N | ILE | D | 119 | 41.165 | 48.111 | 166.695 | 1.00 | 38.74 | 7 |
| ATOM | 3312 | CA | ILE | D | 119 | 40.158 | 49.134 | 166.348 | 1.00 | 38.04 | 6 |
| ATOM | 3313 | CB | ILE | D | 119 | 40.655 | 50.167 | 165.331 | 1.00 | 37.88 | 6 |
| ATOM | 3314 | CG1 | ILE | D | 119 | 41.790 | 50.981 | 165.904 | 1.00 | 37.76 | 6 |
| ATOM | 3315 | CD | ILE | D | 119 | 42.035 | 52.231 | 165.105 | 1.00 | 39.40 | 6 |
| ATOM | 3316 | CG2 | ILE | D | 119 | 39.563 | 51.122 | 164.936 | 1.00 | 36.31 | 6 |
| ATOM | 3317 | C | ILE | D | 119 | 38.918 | 48.476 | 165.773 | 1.00 | 38.04 | 6 |
| ATOM | 3318 | O | ILE | D | 119 | 37.818 | 48.756 | 166.251 | 1.00 | 37.85 | 8 |
| ATOM | 3319 | N | SER | D | 120 | 39.102 | 47.594 | 164.783 | 1.00 | 38.01 | 7 |
| ATOM | 3320 | CA | SER | D | 120 | 37.981 | 46.879 | 164.149 | 1.00 | 38.88 | 6 |
| ATOM | 3321 | CB | SER | D | 120 | 38.455 | 45.917 | 163.061 | 1.00 | 38.86 | 6 |
| ATOM | 3322 | OG | SER | D | 120 | 39.324 | 44.953 | 163.615 | 1.00 | 40.23 | 8 |
| ATOM | 3323 | C | SER | D | 120 | 37.163 | 46.086 | 165.152 | 1.00 | 39.11 | 6 |
| ATOM | 3324 | O | SER | D | 120 | 35.920 | 46.130 | 165.142 | 1.00 | 39.19 | 8 |
| ATOM | 3325 | N | ILE | D | 121 | 37.860 | 45.359 | 166.020 | 1.00 | 39.36 | 7 |
| ATOM | 3326 | CA | ILE | D | 121 | 37.187 | 44.658 | 167.108 | 1.00 | 39.54 | 6 |
| ATOM | 3327 | CB | ILE | D | 121 | 38.147 | 43.791 | 167.947 | 1.00 | 39.27 | 6 |
| ATOM | 3328 | CG1 | ILE | D | 121 | 38.940 | 42.817 | 167.067 | 1.00 | 39.46 | 6 |
| ATOM | 3329 | CD | ILE | D | 121 | 38.308 | 41.475 | 166.842 | 1.00 | 39.04 | 6 |
| ATOM | 3330 | CG2 | ILE | D | 121 | 37.380 | 43.063 | 169.017 | 1.00 | 38.50 | 6 |
| ATOM | 3331 | C | ILE | D | 121 | 36.497 | 45.648 | 168.042 | 1.00 | 40.04 | 6 |
| ATOM | 3332 | O | ILE | D | 121 | 35.374 | 45.421 | 168.424 | 1.00 | 40.19 | 8 |
| ATOM | 3333 | N | ASP | D | 122 | 37.172 | 46.742 | 168.390 | 1.00 | 40.72 | 7 |
| ATOM | 3334 | CA | ASP | D | 122 | 36.672 | 47.688 | 169.376 | 1.00 | 41.41 | 6 |
| ATOM | 3335 | CB | ASP | D | 122 | 37.685 | 48.782 | 169.650 | 1.00 | 41.82 | 6 |
| ATOM | 3336 | CG | ASP | D | 122 | 38.892 | 48.278 | 170.407 | 1.00 | 44.06 | 6 |
| ATOM | 3337 | OD1 | ASP | D | 122 | 38.835 | 47.186 | 171.051 | 1.00 | 45.13 | 8 |
| ATOM | 3338 | OD2 | ASP | D | 122 | 39.911 | 48.993 | 170.342 | 1.00 | 46.51 | 8 |
| ATOM | 3339 | C | ASP | D | 122 | 35.407 | 48.339 | 168.934 | 1.00 | 41.66 | 6 |
| ATOM | 3340 | O | ASP | D | 122 | 34.514 | 48.571 | 169.741 | 1.00 | 42.06 | 8 |
| ATOM | 3341 | N | ASN | D | 123 | 35.295 | 48.665 | 167.662 | 1.00 | 42.04 | 7 |
| ATOM | 3342 | CA | ASN | D | 123 | 34.003 | 49.166 | 167.261 | 1.00 | 42.54 | 6 |
| ATOM | 3343 | CB | ASN | D | 123 | 34.075 | 50.565 | 166.638 | 1.00 | 42.09 | 6 |
| ATOM | 3344 | CG | ASN | D | 123 | 35.046 | 50.646 | 165.537 | 1.00 | 41.28 | 6 |
| ATOM | 3345 | OD1 | ASN | D | 123 | 35.365 | 49.636 | 164.930 | 1.00 | 41.88 | 8 |
| ATOM | 3346 | ND2 | ASN | D | 123 | 35.524 | 51.844 | 165.249 | 1.00 | 39.46 | 7 |
| ATOM | 3347 | C | ASN | D | 123 | 33.222 | 48.132 | 166.464 | 1.00 | 43.06 | 6 |

TABLE 1-continued

| | | | | | | | | | | |
|---|---|---|---|---|---|---|---|---|---|---|
| ATOM | 3348 | O | ASN | D | 123 | 32.422 | 48.466 | 165.602 | 1.00 | 43.33 | 8 |
| ATOM | 3349 | N | GLY | D | 124 | 33.466 | 46.867 | 166.789 | 1.00 | 43.87 | 7 |
| ATOM | 3350 | CA | GLY | D | 124 | 32.633 | 45.741 | 166.348 | 1.00 | 45.09 | 6 |
| ATOM | 3351 | C | GLY | D | 124 | 32.368 | 45.593 | 164.858 | 1.00 | 45.73 | 6 |
| ATOM | 3352 | O | GLY | D | 124 | 31.375 | 45.019 | 164.455 | 1.00 | 45.73 | 8 |
| ATOM | 3353 | N | ASN | D | 125 | 33.251 | 46.128 | 164.038 | 1.00 | 46.74 | 7 |
| ATOM | 3354 | CA | ASN | D | 125 | 33.127 | 45.991 | 162.611 | 1.00 | 47.72 | 6 |
| ATOM | 3355 | CB | ASN | D | 125 | 33.801 | 47.166 | 161.910 | 1.00 | 47.53 | 6 |
| ATOM | 3356 | CG | ASN | D | 125 | 33.739 | 47.066 | 160.416 | 1.00 | 46.64 | 6 |
| ATOM | 3357 | OD1 | ASN | D | 125 | 33.200 | 46.121 | 159.872 | 1.00 | 46.94 | 8 |
| ATOM | 3358 | ND2 | ASN | D | 125 | 34.294 | 48.047 | 159.741 | 1.00 | 46.95 | 7 |
| ATOM | 3359 | C | ASN | D | 125 | 33.784 | 44.701 | 162.215 | 1.00 | 48.87 | 6 |
| ATOM | 3360 | O | ASN | D | 125 | 34.970 | 44.667 | 161.901 | 1.00 | 49.09 | 8 |
| ATOM | 3361 | N | GLU | D | 126 | 32.992 | 43.639 | 162.238 | 1.00 | 50.50 | 7 |
| ATOM | 3362 | CA | GLU | D | 126 | 33.447 | 42.277 | 161.980 | 1.00 | 52.59 | 6 |
| ATOM | 3363 | CB | GLU | D | 126 | 32.290 | 41.321 | 162.268 | 1.00 | 52.18 | 6 |
| ATOM | 3364 | CG | GLU | D | 126 | 32.679 | 39.846 | 162.309 | 1.00 | 54.34 | 6 |
| ATOM | 3365 | CD | GLU | D | 126 | 31.454 | 38.932 | 162.234 | 1.00 | 55.49 | 6 |
| ATOM | 3366 | OE1 | GLU | D | 126 | 31.509 | 37.855 | 161.569 | 1.00 | 58.43 | 8 |
| ATOM | 3367 | OE2 | GLU | D | 126 | 30.416 | 39.306 | 162.841 | 1.00 | 59.24 | 8 |
| ATOM | 3368 | C | GLU | D | 126 | 33.951 | 42.045 | 160.550 | 1.00 | 52.89 | 6 |
| ATOM | 3369 | O | GLU | D | 126 | 34.895 | 41.287 | 160.333 | 1.00 | 53.13 | 8 |
| ATOM | 3370 | N | ASP | D | 127 | 33.294 | 42.676 | 159.578 | 1.00 | 53.67 | 7 |
| ATOM | 3371 | CA | ASP | D | 127 | 33.741 | 42.651 | 158.185 | 1.00 | 54.21 | 6 |
| ATOM | 3372 | CB | ASP | D | 127 | 32.923 | 43.612 | 157.337 | 1.00 | 54.22 | 6 |
| ATOM | 3373 | CG | ASP | D | 127 | 31.630 | 43.013 | 156.867 | 1.00 | 55.59 | 6 |
| ATOM | 3374 | OD1 | ASP | D | 127 | 31.512 | 41.772 | 156.897 | 1.00 | 58.23 | 8 |
| ATOM | 3375 | OD2 | ASP | D | 127 | 30.722 | 43.770 | 156.457 | 1.00 | 56.87 | 8 |
| ATOM | 3376 | C | ASP | D | 127 | 35.191 | 43.043 | 158.060 | 1.00 | 54.52 | 6 |
| ATOM | 3377 | O | ASP | D | 127 | 35.989 | 42.266 | 157.555 | 1.00 | 55.01 | 8 |
| ATOM | 3378 | N | LEU | D | 128 | 35.516 | 44.253 | 158.515 | 1.00 | 54.66 | 7 |
| ATOM | 3379 | CA | LEU | D | 128 | 36.875 | 44.754 | 158.558 | 1.00 | 54.89 | 6 |
| ATOM | 3380 | CB | LEU | D | 128 | 36.942 | 46.009 | 159.399 | 1.00 | 55.14 | 6 |
| ATOM | 3381 | CG | LEU | D | 128 | 38.054 | 47.049 | 159.209 | 1.00 | 55.58 | 6 |
| ATOM | 3382 | CD1 | LEU | D | 128 | 38.414 | 47.709 | 160.527 | 1.00 | 54.76 | 6 |
| ATOM | 3383 | CD2 | LEU | D | 128 | 39.286 | 46.495 | 158.561 | 1.00 | 56.13 | 6 |
| ATOM | 3384 | C | LEU | D | 128 | 37.792 | 43.755 | 159.206 | 1.00 | 55.21 | 6 |
| ATOM | 3385 | O | LEU | D | 128 | 38.806 | 43.390 | 158.628 | 1.00 | 55.31 | 8 |
| ATOM | 3386 | N | ALA | D | 129 | 37.438 | 43.323 | 160.413 | 1.00 | 55.68 | 7 |
| ATOM | 3387 | CA | ALA | D | 129 | 38.233 | 42.348 | 161.158 | 1.00 | 56.33 | 6 |
| ATOM | 3388 | CB | ALA | D | 129 | 37.463 | 41.856 | 162.340 | 1.00 | 56.44 | 6 |
| ATOM | 3389 | C | ALA | D | 129 | 38.666 | 41.181 | 160.294 | 1.00 | 56.73 | 6 |
| ATOM | 3390 | O | ALA | D | 129 | 39.834 | 40.849 | 160.229 | 1.00 | 56.57 | 8 |
| ATOM | 3391 | N | GLU | D | 130 | 37.697 | 40.595 | 159.612 | 1.00 | 57.71 | 7 |
| ATOM | 3392 | CA | GLU | D | 130 | 37.891 | 39.482 | 158.699 | 1.00 | 58.84 | 6 |
| ATOM | 3393 | CB | GLU | D | 130 | 36.549 | 39.088 | 158.086 | 1.00 | 58.91 | 6 |
| ATOM | 3394 | CG | GLU | D | 130 | 36.326 | 37.580 | 157.875 | 1.00 | 60.78 | 6 |
| ATOM | 3395 | CD | GLU | D | 130 | 34.915 | 37.246 | 157.329 | 1.00 | 61.28 | 6 |
| ATOM | 3396 | OE1 | GLU | D | 130 | 34.605 | 36.036 | 157.168 | 1.00 | 63.77 | 8 |
| ATOM | 3397 | OE2 | GLU | D | 130 | 34.114 | 38.185 | 157.060 | 1.00 | 63.59 | 8 |
| ATOM | 3398 | C | GLU | D | 130 | 38.815 | 39.850 | 157.574 | 1.00 | 58.34 | 6 |
| ATOM | 3399 | O | GLU | D | 130 | 39.571 | 39.031 | 157.107 | 1.00 | 58.65 | 8 |
| ATOM | 3400 | N | ILE | D | 131 | 38.750 | 41.073 | 157.098 | 1.00 | 58.35 | 7 |
| ATOM | 3401 | CA | ILE | D | 131 | 39.672 | 41.412 | 156.042 | 1.00 | 58.43 | 6 |
| ATOM | 3402 | CB | ILE | D | 131 | 39.202 | 42.551 | 155.099 | 1.00 | 58.03 | 6 |
| ATOM | 3403 | CG1 | ILE | D | 131 | 40.244 | 43.640 | 155.041 | 1.00 | 57.11 | 6 |
| ATOM | 3404 | CD | ILE | D | 131 | 40.041 | 44.549 | 153.922 | 1.00 | 57.22 | 6 |
| ATOM | 3405 | CG2 | ILE | D | 131 | 37.883 | 43.136 | 155.513 | 1.00 | 57.47 | 6 |
| ATOM | 3406 | C | ILE | D | 131 | 41.077 | 41.609 | 156.579 | 1.00 | 58.96 | 6 |
| ATOM | 3407 | O | ILE | D | 131 | 42.036 | 41.410 | 155.845 | 1.00 | 59.08 | 8 |
| ATOM | 3408 | N | LEU | D | 132 | 41.200 | 41.967 | 157.857 | 1.00 | 59.64 | 7 |
| ATOM | 3409 | CA | LEU | D | 132 | 42.525 | 42.078 | 158.485 | 1.00 | 60.48 | 6 |
| ATOM | 3410 | CB | LEU | D | 132 | 42.537 | 43.048 | 159.664 | 1.00 | 59.77 | 6 |
| ATOM | 3411 | CG | LEU | D | 132 | 42.123 | 44.505 | 159.427 | 1.00 | 58.68 | 6 |
| ATOM | 3412 | CD1 | LEU | D | 132 | 41.962 | 45.279 | 160.734 | 1.00 | 56.21 | 6 |
| ATOM | 3413 | CD2 | LEU | D | 132 | 43.092 | 45.215 | 158.517 | 1.00 | 58.25 | 6 |
| ATOM | 3414 | C | LEU | D | 132 | 43.106 | 40.728 | 158.915 | 1.00 | 61.74 | 6 |
| ATOM | 3415 | O | LEU | D | 132 | 44.325 | 40.564 | 158.889 | 1.00 | 61.96 | 8 |
| ATOM | 3416 | N | GLN | D | 133 | 42.252 | 39.769 | 159.297 | 1.00 | 62.98 | 7 |
| ATOM | 3417 | CA | GLN | D | 133 | 42.714 | 38.421 | 159.632 | 1.00 | 64.24 | 6 |
| ATOM | 3418 | CB | GLN | D | 133 | 41.629 | 37.568 | 160.269 | 1.00 | 63.46 | 6 |
| ATOM | 3419 | CG | GLN | D | 133 | 40.606 | 38.347 | 161.010 | 1.00 | 63.49 | 6 |
| ATOM | 3420 | CD | GLN | D | 133 | 40.125 | 37.696 | 162.295 | 1.00 | 62.49 | 6 |
| ATOM | 3421 | OE1 | GLN | D | 133 | 38.944 | 37.366 | 162.422 | 1.00 | 61.70 | 8 |
| ATOM | 3422 | NE2 | GLN | D | 133 | 41.025 | 37.559 | 163.274 | 1.00 | 61.16 | 7 |
| ATOM | 3423 | C | GLN | D | 133 | 43.196 | 37.722 | 158.391 | 1.00 | 65.87 | 6 |
| ATOM | 3424 | O | GLN | D | 133 | 44.056 | 36.862 | 158.462 | 1.00 | 66.34 | 8 |
| ATOM | 3425 | N | LYS | D | 134 | 42.637 | 38.098 | 157.247 | 1.00 | 67.88 | 7 |
| ATOM | 3426 | CA | LYS | D | 134 | 42.958 | 37.479 | 155.968 | 1.00 | 69.45 | 6 |
| ATOM | 3427 | CB | LYS | D | 134 | 41.982 | 37.949 | 154.899 | 1.00 | 69.50 | 6 |

TABLE 1-continued

| ATOM | 3428 | CG | LYS | D | 134 | 40.880 | 36.954 | 154.655 | 1.00 | 69.74 | 6 |
|---|---|---|---|---|---|---|---|---|---|---|---|
| ATOM | 3429 | CD | LYS | D | 134 | 40.247 | 37.167 | 153.282 | 1.00 | 70.46 | 6 |
| ATOM | 3430 | CE | LYS | D | 134 | 39.081 | 36.219 | 153.101 | 1.00 | 69.53 | 6 |
| ATOM | 3431 | NZ | LYS | D | 134 | 38.315 | 36.185 | 154.378 | 1.00 | 68.46 | 7 |
| ATOM | 3432 | C | LYS | D | 134 | 44.380 | 37.758 | 155.516 | 1.00 | 70.59 | 6 |
| ATOM | 3433 | O | LYS | D | 134 | 44.776 | 37.378 | 154.419 | 1.00 | 71.05 | 8 |
| ATOM | 3434 | N | LEU | D | 135 | 45.161 | 38.419 | 156.352 | 1.00 | 71.76 | 7 |
| ATOM | 3435 | CA | LEU | D | 135 | 46.517 | 38.729 | 155.952 | 1.00 | 73.04 | 6 |
| ATOM | 3436 | CB | LEU | D | 135 | 46.817 | 40.200 | 156.190 | 1.00 | 72.80 | 6 |
| ATOM | 3437 | CG | LEU | D | 135 | 45.845 | 41.222 | 155.624 | 1.00 | 73.19 | 6 |
| ATOM | 3438 | CD1 | LEU | D | 135 | 46.683 | 42.401 | 155.235 | 1.00 | 73.35 | 6 |
| ATOM | 3439 | CD2 | LEU | D | 135 | 45.045 | 40.723 | 154.417 | 1.00 | 73.25 | 6 |
| ATOM | 3440 | C | LEU | D | 135 | 47.585 | 37.880 | 156.630 | 1.00 | 73.90 | 6 |
| ATOM | 3441 | O | LEU | D | 135 | 47.401 | 37.401 | 157.750 | 1.00 | 74.12 | 8 |
| ATOM | 3442 | N | ASN | D | 136 | 48.698 | 37.697 | 155.917 | 1.00 | 74.85 | 7 |
| ATOM | 3443 | CA | ASN | D | 136 | 49.983 | 37.279 | 156.506 | 1.00 | 75.36 | 6 |
| ATOM | 3444 | CB | ASN | D | 136 | 51.157 | 37.643 | 155.572 | 1.00 | 75.34 | 6 |
| ATOM | 3445 | CG | ASN | D | 136 | 51.405 | 36.607 | 154.495 | 1.00 | 75.68 | 6 |
| ATOM | 3446 | OD1 | ASN | D | 136 | 52.547 | 36.392 | 154.085 | 1.00 | 76.30 | 8 |
| ATOM | 3447 | ND2 | ASN | D | 136 | 50.343 | 35.961 | 154.026 | 1.00 | 76.17 | 7 |
| ATOM | 3448 | C | ASN | D | 136 | 50.223 | 37.945 | 157.869 | 1.00 | 75.50 | 6 |
| ATOM | 3449 | O | ASN | D | 136 | 50.143 | 39.172 | 158.017 | 1.00 | 75.57 | 8 |
| ATOM | 3450 | OXT | ASN | D | 136 | 50.494 | 37.277 | 158.867 | 1.00 | 75.61 | 8 |
| ATOM | 3451 | O | HOH | W | 1 | 39.138 | 62.572 | 162.958 | 1.00 | 35.50 | 8 |
| ATOM | 3452 | O | HOH | W | 2 | 23.650 | 56.588 | 178.179 | 1.00 | 14.86 | 8 |
| ATOM | 3453 | O | HOH | W | 3 | 29.968 | 72.539 | 172.433 | 1.00 | 39.04 | 8 |
| ATOM | 3454 | O | HOH | W | 4 | 15.687 | 58.071 | 156.392 | 1.00 | 42.72 | 8 |
| ATOM | 3455 | O | HOH | W | 5 | 53.222 | 71.911 | 156.097 | 1.00 | 17.44 | 8 |
| ATOM | 3456 | O | HOH | W | 7 | 7.516 | 45.583 | 169.214 | 1.00 | 27.95 | 8 |
| ATOM | 3457 | O | HOH | W | 8 | 21.763 | 70.506 | 166.534 | 1.00 | 52.40 | 8 |
| ATOM | 3458 | O | HOH | W | 9 | 40.935 | 72.205 | 154.010 | 1.00 | 52.17 | 8 |
| ATOM | 3459 | O | HOH | W | 10 | 25.966 | 55.823 | 176.389 | 1.00 | 33.09 | 8 |
| ATOM | 3460 | O | HOH | W | 11 | 22.985 | 68.007 | 186.404 | 1.00 | 31.73 | 8 |
| ATOM | 3461 | O | HOH | W | 12 | 19.448 | 80.405 | 148.664 | 1.00 | 55.55 | 8 |
| ATOM | 3462 | O | HOH | W | 13 | 45.407 | 70.720 | 157.818 | 1.00 | 51.51 | 8 |
| ATOM | 3463 | O | HOH | W | 14 | 63.737 | 34.018 | 250.378 | 1.00 | 32.05 | 8 |
| ATOM | 3464 | O | HOH | W | 15 | 47.212 | 38.556 | 218.411 | 1.00 | 49.21 | 8 |
| ATOM | 3465 | O | HOH | W | 16 | 15.743 | 67.512 | 164.830 | 1.00 | 48.95 | 8 |
| ATOM | 3466 | O | HOH | W | 17 | 22.476 | 54.851 | 168.024 | 1.00 | 38.77 | 8 |
| ATOM | 3467 | O | HOH | W | 18 | 41.039 | 72.232 | 147.406 | 1.00 | 42.02 | 8 |
| ATOM | 3468 | O | HOH | W | 19 | 19.457 | 49.799 | 183.166 | 1.00 | 51.67 | 8 |
| ATOM | 3469 | O | HOH | W | 20 | 50.654 | 61.154 | 152.546 | 1.00 | 50.46 | 8 |
| ATOM | 3470 | O | HOH | W | 21 | 49.970 | 57.246 | 176.606 | 1.00 | 41.58 | 8 |
| ATOM | 3471 | O | HOH | W | 22 | 15.170 | 61.276 | 178.334 | 1.00 | 54.81 | 8 |
| ATOM | 3472 | O | HOH | W | 23 | 50.212 | 50.934 | 189.517 | 1.00 | 60.63 | 8 |
| ATOM | 3473 | O | HOH | W | 24 | 21.739 | 52.101 | 175.735 | 1.00 | 60.72 | 8 |
| ATOM | 3474 | O | HOH | W | 25 | 33.393 | 54.787 | 148.401 | 1.00 | 52.56 | 8 |
| ATOM | 3475 | O | HOH | W | 26 | 15.340 | 61.743 | 143.921 | 1.00 | 71.13 | 8 |
| ATOM | 3476 | O | HOH | W | 27 | 45.833 | 67.108 | 136.296 | 1.00 | 58.98 | 8 |
| ATOM | 3477 | O3 | GOL | W | 50 | 44.951 | 55.236 | 166.054 | 1.00 | 42.03 | 8 |
| ATOM | 3478 | C3 | GOL | W | 50 | 43.576 | 55.492 | 166.281 | 1.00 | 44.24 | 6 |
| ATOM | 3479 | C2 | GOL | W | 50 | 43.379 | 55.849 | 167.742 | 1.00 | 46.17 | 6 |
| ATOM | 3480 | O2 | GOL | W | 50 | 43.678 | 54.769 | 168.615 | 1.00 | 45.85 | 8 |
| ATOM | 3481 | C1 | GOL | W | 50 | 41.926 | 56.188 | 167.959 | 1.00 | 47.57 | 6 |
| ATOM | 3482 | O1 | GOL | W | 50 | 41.639 | 55.649 | 169.238 | 1.00 | 52.52 | 8 |

The invention claimed is:

1. A crystal of a CC2-LZ domain of mammalian Nuclear factor kappa B Essential Modulator (NEMO), comprising at least one ankyrin 1D5 polypeptide having the sequence set forth in SEQ ID NO:5 and at least one CC2-LZ domain of mammalian NEMO, wherein the CC2-LZ domain comprises the amino acid sequence as set forth in SEQ ID NO:3 or SEQ ID NO:4, wherein the crystal has the following unit cell parameters:
a=b=63.5±5 Å;
c=437.5±5 Å; and
α=β=γ=90°;
and the crystal has a space group $P4_32_12$.

2. The crystal of claim 1, wherein the crystallographic coordinates are as described in Table 1.

3. The crystal of claim 1, wherein the at least one ankyrin 1D5 polypeptide stabilizes the complex.

4. The crystal of claim 1, wherein the three-dimensional structure is obtained by X-ray diffraction, and the three-dimensional structure is as shown in FIGS. 2 and 3.

5. The crystal of claim 1, wherein the CC2-LZ domain having the amino acid sequence set forth in SEQ ID NO:3 comprises the mutation Val66Pro (V66P) and/or the mutation Phe55Ala (F55A), which mutations correspond to Val316Pro (V316P) and Phe305Ala (F305A) relative to the murine NEMO protein sequence set forth in SEQ ID NO:1.

6. The crystal of claim 1, wherein the CC2-LZ domain having the amino acid sequence set forth in SEQ ID NO:4 comprises the mutation Ala66Pro (A66P) and/or the mutation Phe55Ala (F55A), which mutations correspond to Ala323Pro (A323P) and Phe312Ala (F312A) relative to the human NEMO protein sequence set forth in SEQ ID NO:2.

7. A method of crystallizing an CC2-LZ domain of mammalian NEMO, comprising the following steps:
incubating at least one ankyrin 1D5 polypeptide having the sequence, set forth in SEQ ID NO:5 and an CC2-LZ domain comprising an amino acid sequence as set forth in SEQ ID NO:3 or SEQ ID NO:4; and
co-crystallizing the ankyrin CC2-LZ protein complex by growing crystals in a reservoir solution comprising 10% polyethylene glycol 40000, 5% isopropanol, 100 mM Na Hepes pH7.5, or a reservoir solution comprising 5% 2-methyl-2,4-pentadiol, 5% ethanol, 100 mM Na Hepes pH7.5, by vapour diffusion at 18-20° C. for more than 36 hours,
seeding with microcrystals, and
allowing growth for a few days to reach a size of 300×150× 20 μm.

8. A crystal produced by the method of claim 7.

* * * * *

UNITED STATES PATENT AND TRADEMARK OFFICE
CERTIFICATE OF CORRECTION

PATENT NO. : 8,440,790 B2
APPLICATION NO. : 12/735671
DATED : May 14, 2013
INVENTOR(S) : Fabrice Agou et al.

Page 1 of 1

It is certified that error appears in the above-identified patent and that said Letters Patent is hereby corrected as shown below:

Title Page, Item (75) Inventors Address, after Stephane Duquerroy: "Paris" should be --Saint Ouen--.

Signed and Sealed this
Sixteenth Day of July, 2013

Teresa Stanek Rea
*Acting Director of the United States Patent and Trademark Office*